(12) United States Patent
Jung et al.

(10) Patent No.: US 12,209,083 B2
(45) Date of Patent: Jan. 28, 2025

(54) POLYCYCLIC COMPOUND AND ORGANIC LIGHT EMITTING DIODE COMPRISING SAME

(71) Applicant: LG CHEM, LTD., Seoul (KR)

(72) Inventors: Min Woo Jung, Daejeon (KR); Dong Hoon Lee, Daejeon (KR); Boonjae Jang, Daejeon (KR); Jungha Lee, Daejeon (KR); Su Jin Han, Daejeon (KR); Seulchan Park, Daejeon (KR); Sunghyun Hwang, Daejeon (KR)

(73) Assignee: LG Chem, Ltd., Seoul (KR)

( * ) Notice: Subject to any disclaimer, the term of this patent is extended or adjusted under 35 U.S.C. 154(b) by 675 days.

(21) Appl. No.: 17/054,687

(22) PCT Filed: Jul. 4, 2019

(86) PCT No.: PCT/KR2019/008191
§ 371 (c)(1),
(2) Date: Nov. 11, 2020

(87) PCT Pub. No.: WO2020/009492
PCT Pub. Date: Jan. 9, 2020

(65) Prior Publication Data
US 2021/0078992 A1    Mar. 18, 2021

(30) Foreign Application Priority Data
Jul. 5, 2018   (KR) .................. 10-2018-0078358

(51) Int. Cl.
*C07D 417/14* (2006.01)
*C07D 413/14* (2006.01)
(Continued)

(52) U.S. Cl.
CPC ......... *C07D 417/14* (2013.01); *C07D 413/14* (2013.01); *H10K 85/656* (2023.02);
(Continued)

(58) Field of Classification Search
CPC .. C07D 417/14; C07D 413/14; C07D 209/82; C07D 251/24; C07D 277/62; H10K 85/656; H10K 85/6572; H10K 85/631
See application file for complete search history.

(56) References Cited

U.S. PATENT DOCUMENTS

| | | |
|---|---|---|
| 2013/0048956 A1 | 2/2013 | Balaganesan et al. |
| 2018/0040829 A1 | 2/2018 | Lee et al. |
| 2019/0165282 A1 | 5/2019 | Parham et al. |

FOREIGN PATENT DOCUMENTS

| | | |
|---|---|---|
| KR | 20100075079 A | 7/2010 |
| KR | 1020130022391 A | 3/2013 |

(Continued)

*Primary Examiner* — Jenna N Chandhok
(74) *Attorney, Agent, or Firm* — Bryan Cave Leighton Paisner LLP

(57) ABSTRACT

The present specification provides a compound represented by Formula 1 and an organic light emitting device including the same. The compound is used for an organic material layer of the organic light emitting device.

[Formula 1]

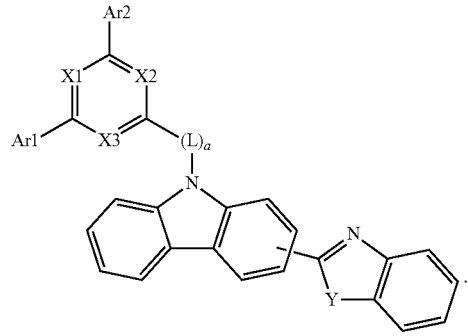

6 Claims, 1 Drawing Sheet

(51) Int. Cl.
    *H10K 50/16*         (2023.01)
    *H10K 50/17*         (2023.01)
    *H10K 85/60*         (2023.01)

(52) U.S. Cl.
    CPC ......... *H10K 85/6572* (2023.02); *H10K 50/16* (2023.02); *H10K 50/171* (2023.02)

(56) References Cited

FOREIGN PATENT DOCUMENTS

| | | | |
|---|---|---|---|
| KR | 20130118269 | A | 10/2013 |
| KR | 20140004005 | A | 1/2014 |
| KR | 20170003502 | A | 1/2017 |
| KR | 20170030427 | A | 3/2017 |
| KR | 1741415 | B1 | 5/2017 |
| WO | 2010126270 | A1 | 11/2010 |
| WO | 2017178311 | A1 | 10/2017 |

[Figure 1]
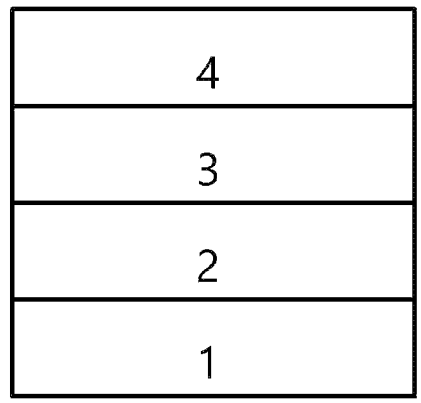
[Figure 2]
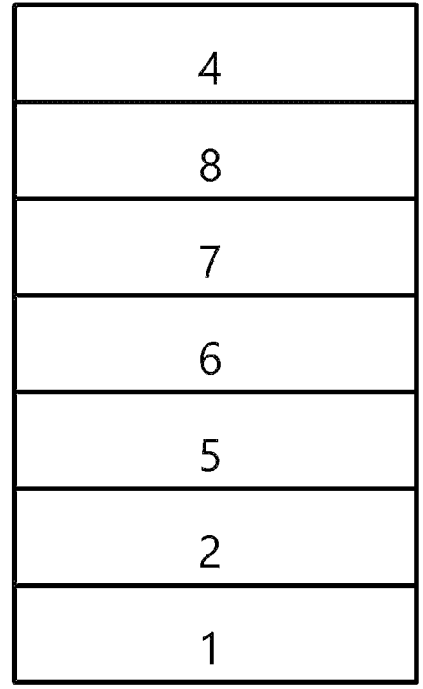

POLYCYCLIC COMPOUND AND ORGANIC LIGHT EMITTING DIODE COMPRISING SAME

The present application is a National Stage Application of International Application No. PCT/KR2019/008191 filed on Jul. 4, 2019, which claims priority to and the benefit of Korean Patent Application No. 10-2018-0078358 filed in the Korean Intellectual Property Office on Jul. 5, 2018, the entire contents of which are incorporated herein by reference.

TECHNICAL FIELD

The present specification relates to a polycyclic compound and an organic light emitting device including the same.

BACKGROUND ART

In the present specification, an organic light emitting device is a light emitting device using an organic semiconductor material, and requires an exchange of holes and/or electrons between electrodes and organic semiconductor materials. The organic light emitting device may be roughly divided into the following two light emitting devices depending on the operation principle. The first organic light emitting device is a light emitting device in which an exciton is formed in an organic material layer by a photon that flows from an external light source to the device, the exciton is separated into electrons and holes, and the electrons and the holes are each transferred to the different electrodes and used as a current source (voltage source). The second organic light emitting device is a light emitting device in which holes and/or electrons are injected into organic semiconductor material layers forming an interface with an electrode by applying a voltage or current to two or more electrodes, and the device is operated by the injected electrons and holes.

In general, an organic light emitting phenomenon refers to a phenomenon in which electric energy is converted into light energy by using an organic material. An organic light emitting device using the organic light emitting phenomenon usually has a structure including a positive electrode, a negative electrode, and an organic material layer interposed therebetween. Here, the organic material layer in many cases has a multi-layered structure composed of different materials in order to improve the efficiency and stability of the organic light emitting device, and for example, may be composed of a hole injection layer, a hole transport layer, a light emitting layer, an electron transport layer, an electron injection layer, and the like. In such a structure of the organic light emitting device, if a voltage is applied between the two electrodes, holes are injected from the positive electrode into the organic material layer and electrons are injected from the negative electrode into the organic material layer, and when the injected holes and electrons meet each other, an exciton is formed, and light is emitted when the exciton falls down again to a ground state. Such an organic light emitting device has been known to have characteristics such as self-emission, high brightness, high efficiency, a low driving voltage, a wide viewing angle, and high contrast.

In an organic light emitting device, materials used as an organic material layer may be classified into a light emitting material and a charge transport material, for example, a hole injection material, a hole transport material, an electron transport material, an electron injection material, and the like, depending on the function. The light emitting materials include blue, green, and red light emitting materials according to the light emitting color, and yellow and orange light emitting materials required for implementing a much better natural color.

Furthermore, a host/dopant system may be used as a light emitting material for the purpose of enhancing color purity and light emitting efficiency through energy transfer. The principle is that when a small amount of dopant which has a smaller energy bandgap and better light emitting efficiency than those of a host mainly constituting a light emitting layer is mixed with the light emitting layer, the excitons generated by the host are transported to the dopant to emit light with high efficiency. In this case, it is possible to obtain light with a desired wavelength according to the type of dopant used because the wavelength of the host moves to the wavelength range of the dopant.

In order to fully exhibit the above-described excellent characteristics of the organic light emitting device, materials constituting an organic material layer in the device, for example, a hole injection material, a hole transport material, a light emitting material, an electron transport material, an electron injection material, and the like need to be supported by stable and efficient materials, so that there is a continuous need for developing a new material.

DETAILED DESCRIPTION OF INVENTION

Technical Problem

The present specification describes a polycyclic compound and an organic light emitting device including the same.

Technical Solution

An exemplary embodiment of the present specification provides a compound represented by the following Formula 1.

[Formula 1]

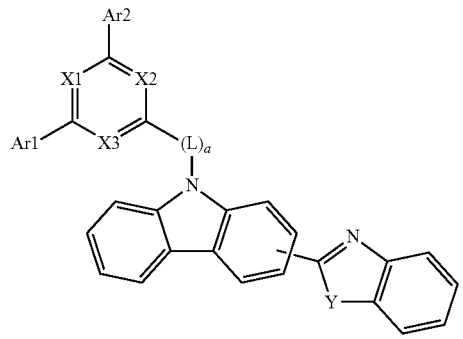

In Formula 1, at least two of X1 to X3 are N, and the rest is CR,

R is hydrogen; deuterium; a substituted or unsubstituted alkyl group; a substituted or unsubstituted aryl group; or a substituted or unsubstituted heterocyclic group, Ar1 and Ar2 are each independently a substituted or unsubstituted aryl group; or a substituted or unsubstituted heterocyclic group, Y is O or S, L is a direct bond; or a substituted or unsubstituted arylene group, a is 1 or 2, and Ls in the parenthesis are the same as or different from each other provided that a is 2.

Further, an exemplary embodiment of the present specification provides an organic light emitting device including: a first electrode; a second electrode provided to face the first electrode; and an organic material layer having one or more layers provided between the first electrode and the second electrode, in which the one or more layers of the organic material layer include the compound.

Advantageous Effects

The compound described in the present specification may be used as a material for an organic material layer of an organic light emitting device. A compound according to at least one exemplary embodiment may improve a service life characteristic in an organic light emitting device. In particular, the compound described in the present specification may be used as a material for a light emitting layer, an electron transport layer, an electron injection layer, and the like.

BRIEF DESCRIPTION OF DRAWINGS

FIG. 1 illustrates an example of an organic light emitting device composed of a substrate 1, a positive electrode 2, a light emitting layer 3, and a negative electrode 4.

FIG. 2 illustrates an example of an organic light emitting device composed of a substrate 1, a positive electrode 2, a hole injection layer 5, a hole transport layer 6, a light emitting layer 7, an electron transport layer 8, and a negative electrode 4.

EXPLANATION OF REFERENCE NUMERALS AND SYMBOLS

1: Substrate
2: Positive electrode
3: Light emitting layer
4: Negative electrode
5: Hole injection layer
6: Hole transport layer
7: Light emitting layer
8: Electron transport layer

BEST MODE

Hereinafter, the present specification will be described in more detail.

The present specification provides the compound represented by Formula 1. When the compound represented by Formula 1 is used for an organic material layer of an organic light emitting device, the efficiency of the organic light emitting device is improved.

When one part "includes" one constituent element in the present specification, unless otherwise specifically described, this does not mean that another constituent element is excluded, but means that another constituent element may be further included.

When one member is disposed "on" another member in the present specification, this includes not only a case where the one member is brought into contact with another member, but also a case where still another member is present between the two members.

Examples of the substituents in the present specification will be described below, but are not limited thereto.

The term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In the present specification, the term "substituted or unsubstituted" means being substituted with one or two or more substituents selected from the group consisting of deuterium; a halogen group; a cyano group; a substituted or unsubstituted alkyl group; a substituted or unsubstituted cycloalkyl group; a substituted or unsubstituted arylamine group; a substituted or unsubstituted aryl group; and a substituted or unsubstituted heterocyclic group or being substituted with a substituent to which two or more substituents are linked among the substituents exemplified above, or having no substituent. For example, "the substituent to which two or more substituents are linked" may be a biphenyl group. That is, the biphenyl group may also be an aryl group, and may be interpreted as a substituent to which two phenyl groups are linked.

Examples of the substituents will be described below, but are not limited thereto.

In the present specification, examples of a halogen group include fluorine (F), chlorine (Cl), bromine (Br) or iodine (I).

In the present specification, the alkyl group may be straight-chained or branched, and the number of carbon atoms thereof is not particularly limited, but is preferably 1 to 60. According to an exemplary embodiment, the number of carbon atoms of the alkyl group is 1 to 30. According to another exemplary embodiment, the number of carbon atoms of the alkyl group is 1 to 20. According to still another exemplary embodiment, the number of carbon atoms of the alkyl group is 1 to 10. Specific examples of the alkyl group include a methyl group, an ethyl group, an n-propyl group, an isopropyl group, an n-butyl group, an isobutyl group, a tert-butyl group, an n-pentyl group, an n-hexyl group, an n-heptyl group, an n-octyl group, and the like, but are not limited thereto.

In the present specification, a cycloalkyl group is not particularly limited, but has preferably 3 to 60 carbon atoms, and according to an exemplary embodiment, the number of carbon atoms of the cycloalkyl group is 3 to 30. According to another exemplary embodiment, the number of carbon atoms of the cycloalkyl group is 3 to 20. According to still another exemplary embodiment, the number of carbon atoms of the cycloalkyl group is 3 to 6. Specific examples thereof include a cyclopropyl group, a cyclobutyl group, a cyclopentyl group, a cyclohexyl group, a cycloheptyl group, a cyclooctyl group, and the like, but are not limited thereto.

In the present specification, examples of an arylamine group include a substituted or unsubstituted monoarylamine group, a substituted or unsubstituted diarylamine group, or a substituted or unsubstituted triarylamine group. The aryl group in the arylamine group may be a monocyclic aryl group or a polycyclic aryl group. The arylamine group including the two or more aryl groups may include a monocyclic aryl group, a polycyclic aryl group, or both a monocyclic aryl group and a polycyclic aryl group.

Specific examples of the arylamine group include a phenylamine group, a naphthylamine group, a biphenylamine group, an anthracenylamine group, a 3-methyl-phenylamine group, a 4-methyl-naphthylamine group, a 2-methyl-biphenylamine group, a 9-methyl-anthracenylamine group, a diphenylamine group, a phenylnaphthylamine group, a biphenylphenylamine group, and the like, but are not limited thereto.

In the present specification, an aryl group is not particularly limited, but has preferably 6 to 60 carbon atoms, and may be a monocyclic aryl group or a polycyclic aryl group. According to an exemplary embodiment, the number of carbon atoms of the aryl group is 6 to 30. According to an exemplary embodiment, the number of carbon atoms of the aryl group is 6 to 20. Examples of the monocyclic aryl group include a phenyl group, a biphenyl group, a terphenyl group, and the like, but are not limited thereto. Examples of the polycyclic aryl group include a naphthyl group, an anthracenyl group, a phenanthrenyl group, a pyrenyl group, a perylenyl group, a triphenylene group, a chrysenyl group, a fluorenyl group, and the like, but are not limited thereto.

In the present specification, a fluorenyl group may be substituted, and two substituents may be bonded to each other to form a spiro structure.

When the fluorenyl group is substituted, the substituent may be a substituted fluorenyl group such as a spiro fluorenyl group such as

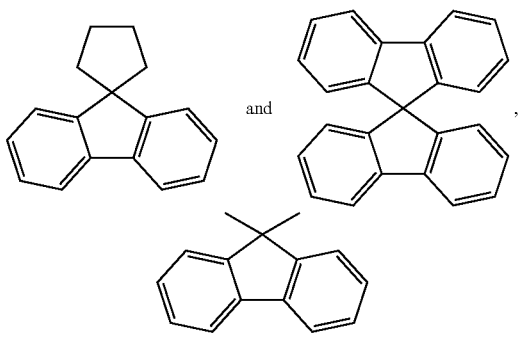

(a 9,9-dimethylfluorenyl group), and

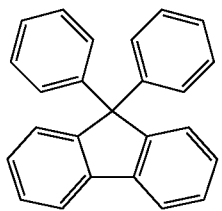 [SMILES: c1ccc(C2(c3ccccc3)c3ccccc3-c3ccccc32)cc1]

(a 9,9-diphenylfluorenyl group). However, the substituent is not limited thereto.

In the present specification, a heterocyclic group is a cyclic group including one or more of N, O, P, S, Si, and Se as a heteroatom, and the number of carbon atoms thereof is not particularly limited, but is preferably 2 to 60. According to an exemplary embodiment, the number of carbon atoms of the heterocyclic group is 2 to 30. Examples of the heterocyclic group include a pyridyl group, a pyrrole group, a pyrimidyl group, a pyridazinyl group, a furanyl group, a thiophenyl group, an imidazole group, a pyrazole group, a dibenzofuranyl group, a dibenzothiophenyl group, and the like, but are not limited thereto.

In the present specification, the above-described description on the heterocyclic group may be applied to a heteroaryl group except for an aromatic heteroaryl group.

In the present specification, the "adjacent" group may mean a substituent substituted with an atom directly linked to an atom in which the corresponding substituent is substituted, a substituent disposed to be sterically closest to the corresponding substituent, or another substituent substituted with an atom in which the corresponding substituent is substituted. For example, two substituents substituted at the ortho position in a benzene ring and two substituents substituted with the same carbon in an aliphatic ring may be interpreted as groups which are "adjacent" to each other.

In the present specification, in a substituted or unsubstituted ring formed by bonding adjacent groups, the "ring" means a hydrocarbon ring; or a hetero ring.

In the present specification, a hydrocarbon ring may be an aromatic ring, an aliphatic ring, or a fused ring of the aromatic ring and the aliphatic ring, and may be selected from the examples of the cycloalkyl group or the aryl group, except for the hydrocarbon ring which is not monovalent.

In the present specification, the description on the aryl group may be applied to an aromatic hydrocarbon ring except for a monovalent aromatic hydrocarbon ring.

In the present specification, a hetero ring includes one or more atoms other than carbon, that is, one or more heteroatoms, and specifically, the heteroatom may include one or more atoms selected from the group consisting of N, O, P, S, Si, Se, and the like. The hetero ring may be monocyclic or polycyclic, may be an aromatic ring, an aliphatic ring, or a fused ring of the aromatic ring and the aliphatic ring, and the aromatic hetero ring may be selected from the examples of the heteroaryl group, except for the aromatic hetero ring which is not monovalent.

According to an exemplary embodiment of the present specification, at least two of X1 to X3 are N, and the rest is CR.

According to an exemplary embodiment of the present specification, X1 and X3 are N.

According to an exemplary embodiment of the present specification, X1 and X2 are N.

According to an exemplary embodiment of the present specification, X2 and X3 are N.

According to an exemplary embodiment of the present specification, X1 to X3 are N.

According to an exemplary embodiment of the present specification, R is hydrogen; deuterium; a substituted or unsubstituted alkyl group; a substituted or unsubstituted aryl group; or a substituted or unsubstituted heterocyclic group.

According to an exemplary embodiment of the present specification, R is hydrogen; deuterium; a substituted or unsubstituted alkyl group having 1 to 30 carbon atoms; a substituted or unsubstituted aryl group having 6 to 30 carbon atoms; or a substituted or unsubstituted heterocyclic group having 2 to 30 carbon atoms.

According to an exemplary embodiment of the present specification, R is hydrogen; or deuterium.

According to an exemplary embodiment of the present specification, Ar1 and Ar2 are each independently a substituted or unsubstituted aryl group; or a substituted or unsubstituted heterocyclic group.

According to an exemplary embodiment of the present specification, Ar1 and Ar2 are each independently a substituted or unsubstituted aryl group having 6 to 60 carbon atoms; or a substituted or unsubstituted heterocyclic group having 2 to 60 carbon atoms.

According to an exemplary embodiment of the present specification, Ar1 and Ar2 are each independently a substituted or unsubstituted aryl group having 6 to 30 carbon atoms; or a substituted or unsubstituted heterocyclic group having 2 to 30 carbon atoms.

According to an exemplary embodiment of the present specification, Ar1 and Ar2 are each independently a substituted or unsubstituted aryl group having 6 to 15 carbon atoms; or a substituted or unsubstituted heterocyclic group having 2 to 15 carbon atoms.

According to an exemplary embodiment of the present specification, Formula 1 may be represented by the following Formula 2.

[Formula 2]

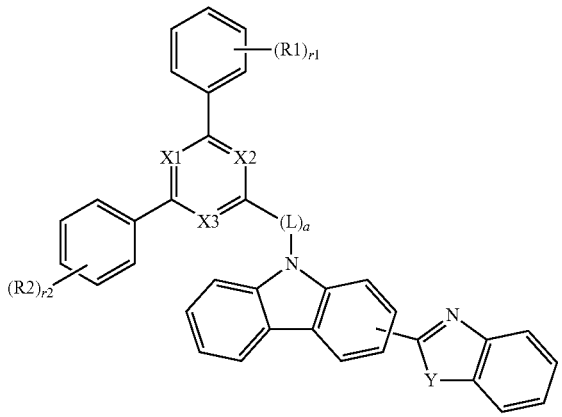

In Formula 2, X1 to X3, L, a, and Y are the same as definitions in Formula 1,

R1 and R2 are each independently hydrogen; deuterium; a substituted or unsubstituted phenyl group; or a substituted or unsubstituted naphthyl group, or are each bonded to an adjacent group to form a substituted or unsubstituted ring, r1 and r2 are each independently an integer from 1 to 5, and when r1 and r2 are each 2 or more, structures in the parenthesis are the same as or different from each other.

According to an exemplary embodiment of the present specification, R1 and R2 are each independently hydrogen; deuterium; a phenyl group; or a naphthyl group.

According to an exemplary embodiment of the present specification, R1 and R2 are each independently hydrogen; or a phenyl group.

According to an exemplary embodiment of the present specification, adjacent R1s are bonded to each other to form a substituted or unsubstituted ring.

According to an exemplary embodiment of the present specification, adjacent R1s are bonded to each other to form a substituted or unsubstituted hydrocarbon ring; or a substituted or unsubstituted hetero ring.

According to an exemplary embodiment of the present specification, adjacent R1s are bonded to each other to form a substituted or unsubstituted benzene; a substituted or unsubstituted naphthalene; a substituted or unsubstituted indene; a substituted or unsubstituted dihydroindene; a substituted or unsubstituted dihydrophenanthrene; a substituted or unsubstituted benzofuran; or a substituted or unsubstituted benzothiophene.

According to an exemplary embodiment of the present specification, Ar1 and Ar2 are each independently a substituted or unsubstituted phenyl group; a substituted or unsubstituted biphenyl group; a substituted or unsubstituted terphenyl group; a substituted or unsubstituted naphthyl group; a substituted or unsubstituted anthracenyl group; a substituted or unsubstituted phenanthrenyl group; a substituted or unsubstituted pyrenyl group; a substituted or unsubstituted perylenyl group; a substituted or unsubstituted triphenylene group; a substituted or unsubstituted chrysenyl group; a substituted or unsubstituted fluorenyl group; a substituted or unsubstituted dibenzothiophene group; or a substituted or unsubstituted dibenzofuran group.

According to an exemplary embodiment of the present specification, Ar1 and Ar2 are the same as each other.

According to an exemplary embodiment of the present specification, Ar1 and Ar2 are different from each other.

According to an exemplary embodiment of the present specification, L is a direct bond, or a substituted or unsubstituted arylene group having 6 to 30 carbon atoms.

According to an exemplary embodiment of the present specification, L is a direct bond, or a substituted or unsubstituted arylene group having 6 to 15 carbon atoms.

According to an exemplary embodiment of the present specification, L is a direct bond; a substituted or unsubstituted phenylene group; a substituted or unsubstituted biphenylene group; a substituted or unsubstituted naphthalene group; a substituted or unsubstituted anthracenylene group; a substituted or unsubstituted divalent phenanthrene group; a substituted or unsubstituted divalent triphenylene group; or a substituted or unsubstituted divalent fluorene group.

According to an exemplary embodiment of the present specification, L is a direct bond; a substituted or unsubstituted phenylene group; a substituted or unsubstituted biphenylene group; or a substituted or unsubstituted naphthalene group.

According to an exemplary embodiment of the present specification, a is 1 or 2.

According to an exemplary embodiment of the present specification, a is 1.

According to an exemplary embodiment of the present specification, a is 2.

According to an exemplary embodiment of the present specification, Y is O or S.

According to an exemplary embodiment of the present specification, Y is O.

According to an exemplary embodiment of the present specification, Y is S.

According to an exemplary embodiment of the present specification, Formula 1 is represented by any one of the following structures.

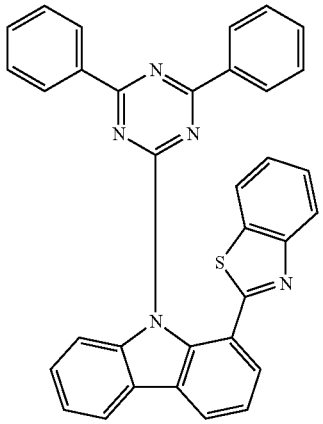

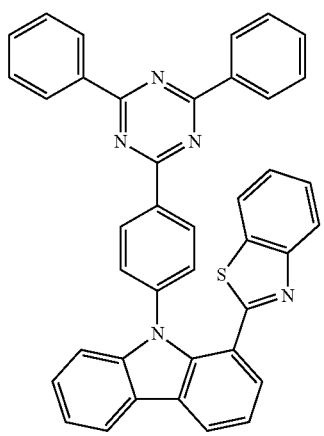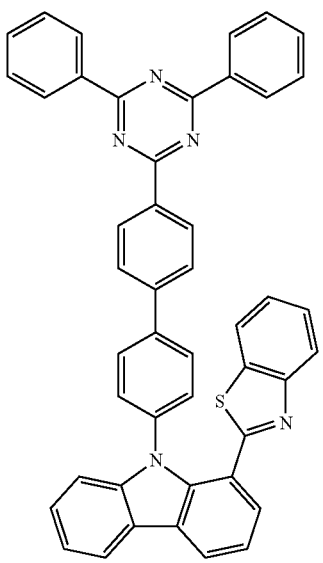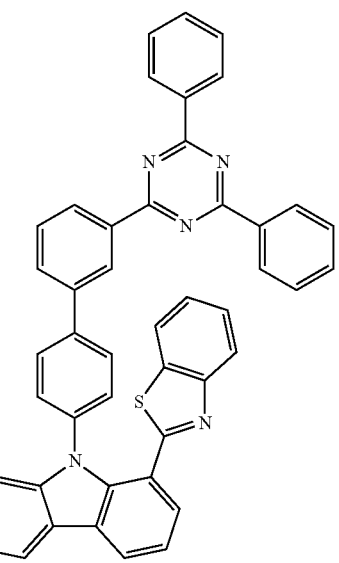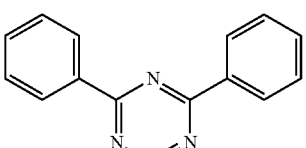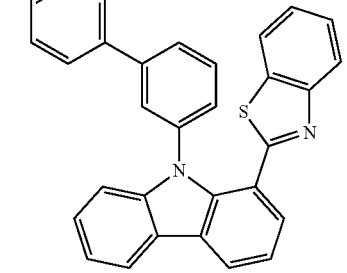

-continued
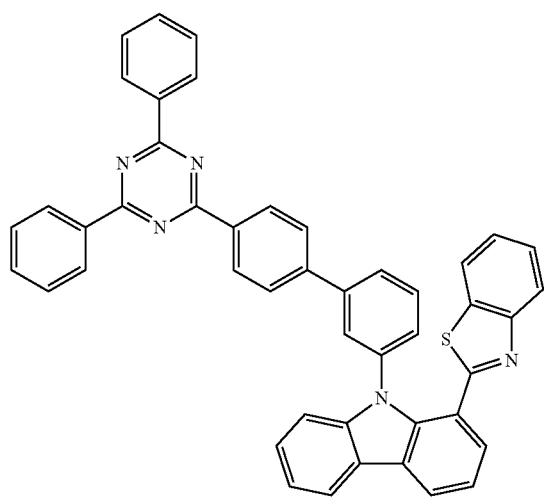
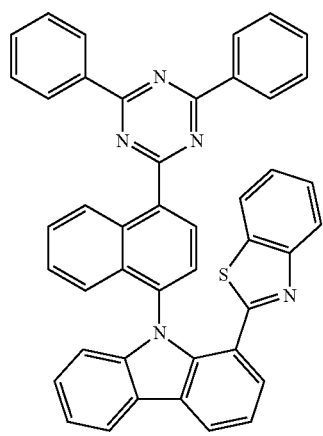
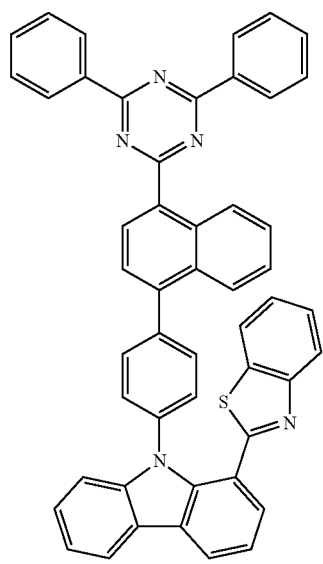
-continued
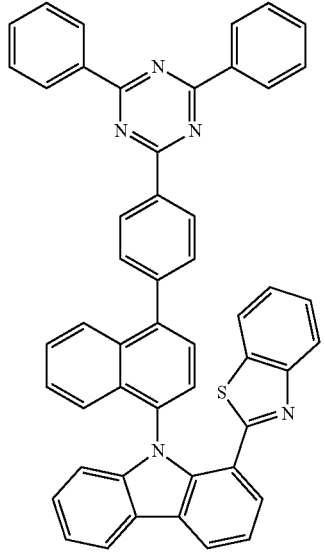
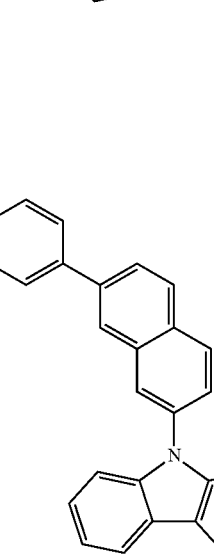
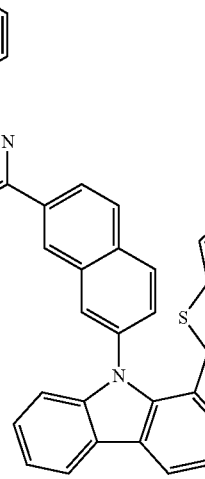

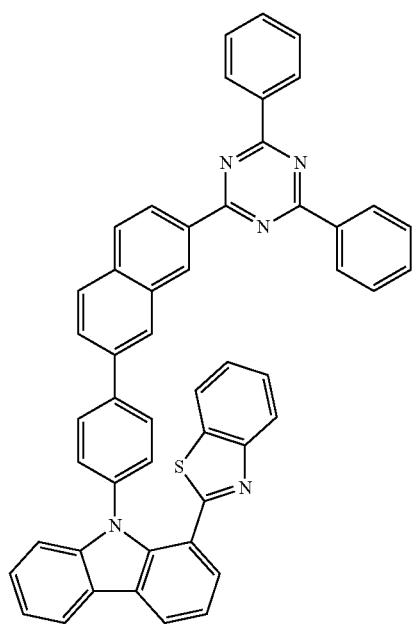
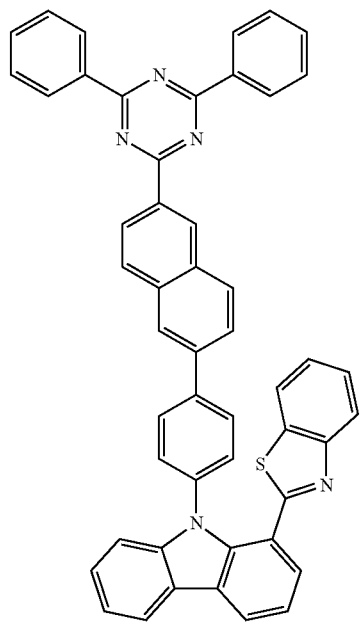

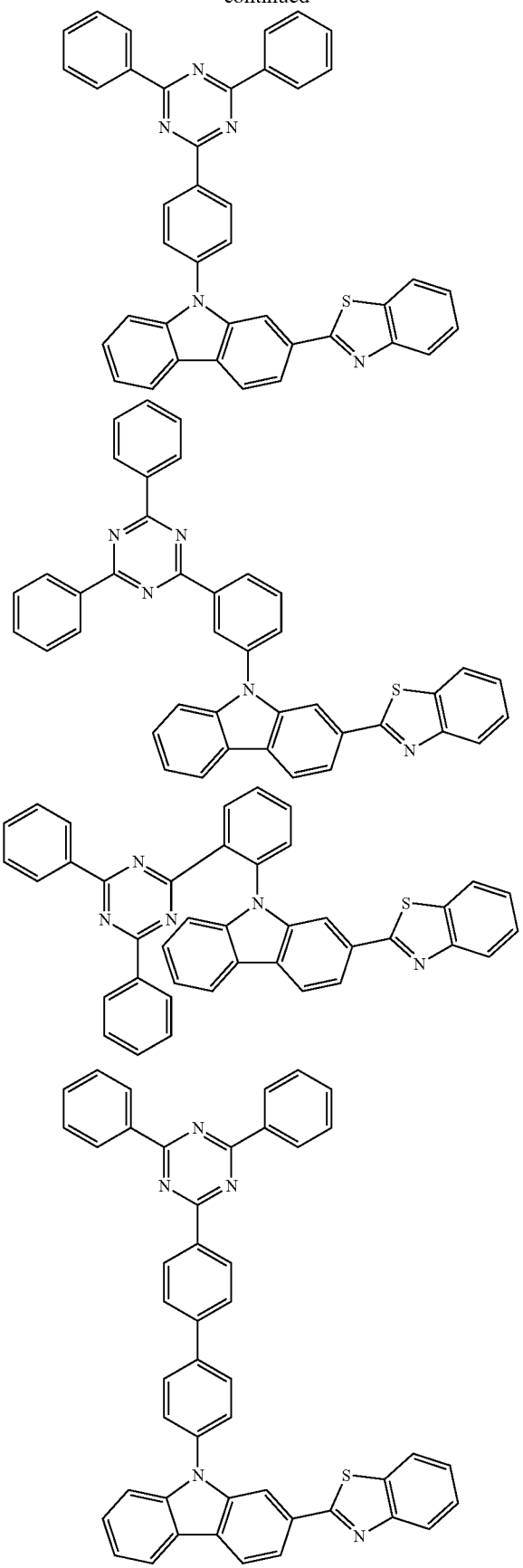
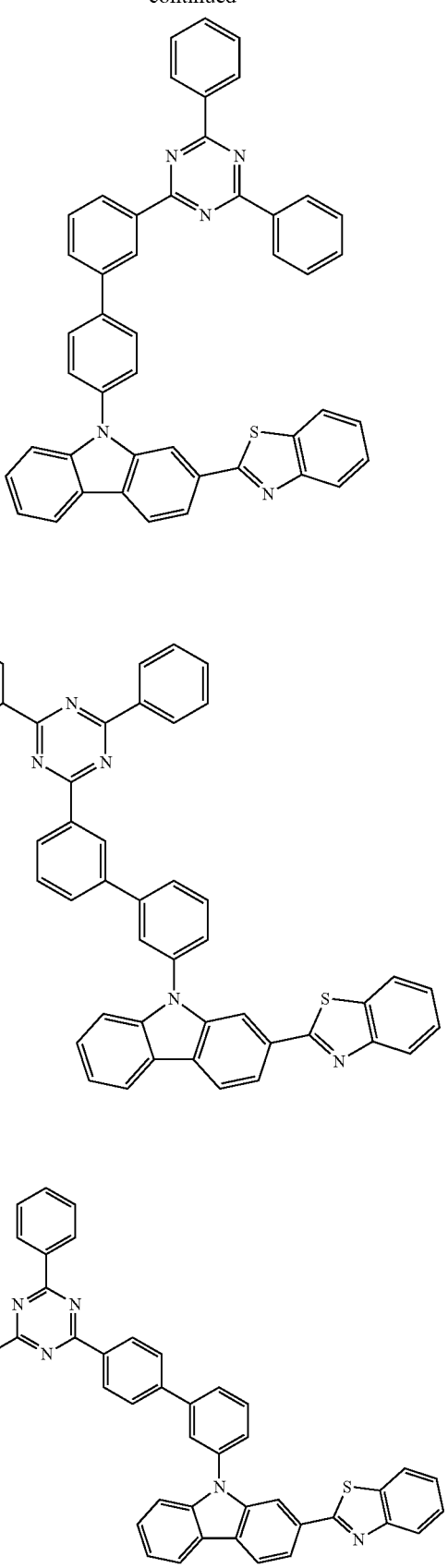

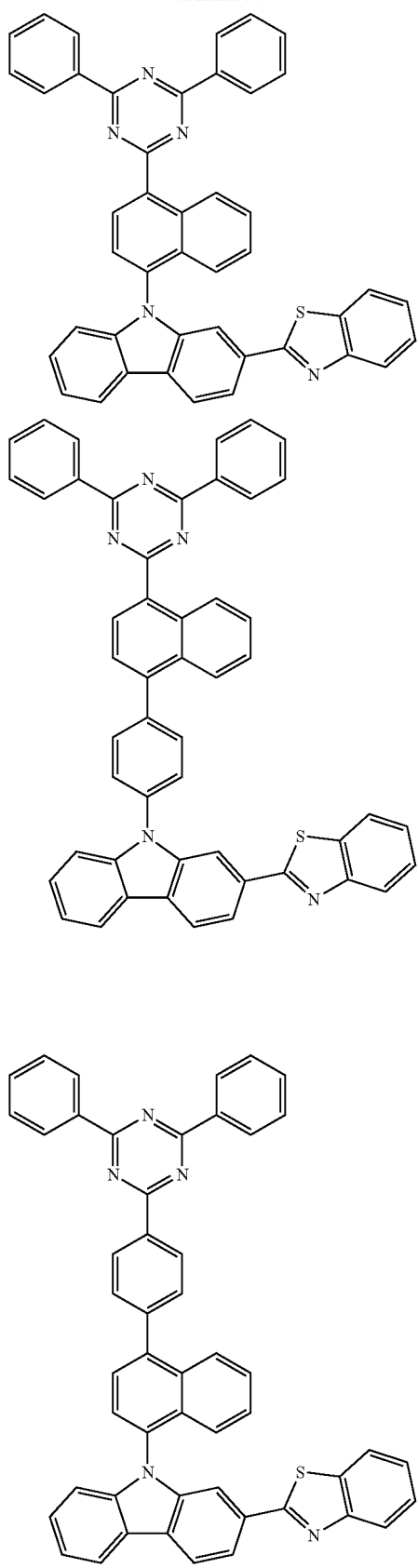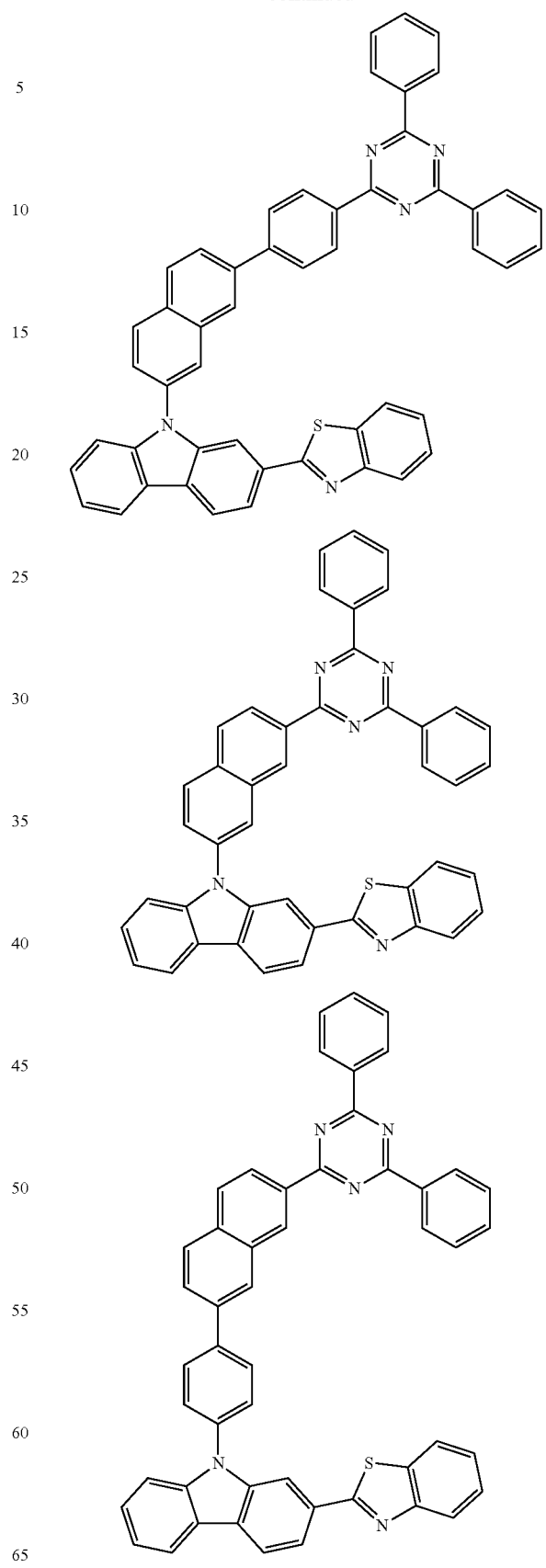

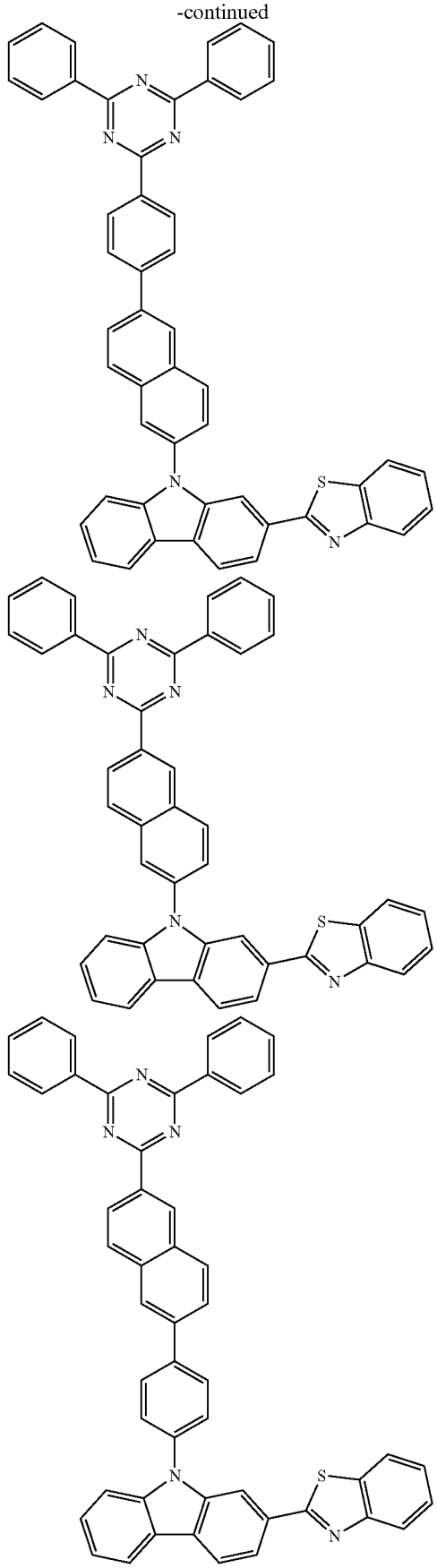
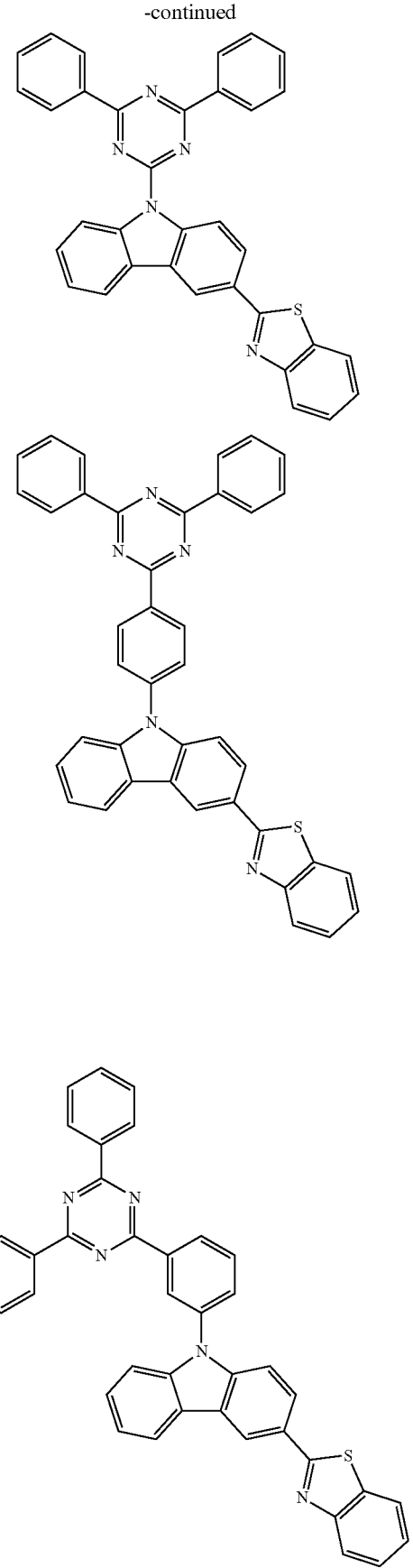

-continued
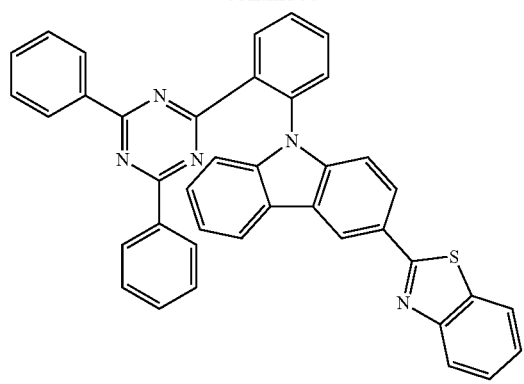
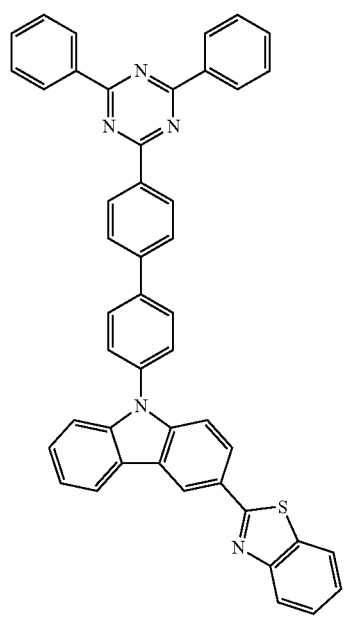
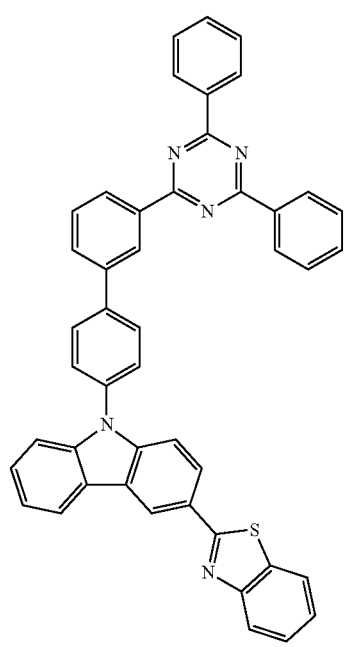
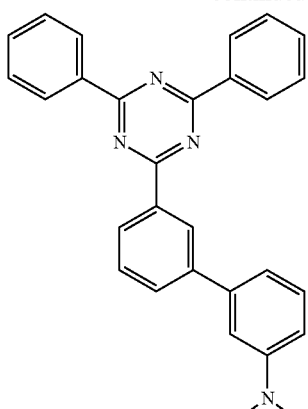
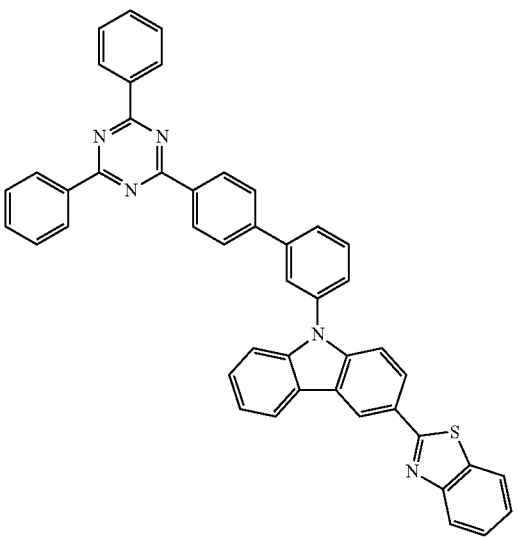

23
-continued
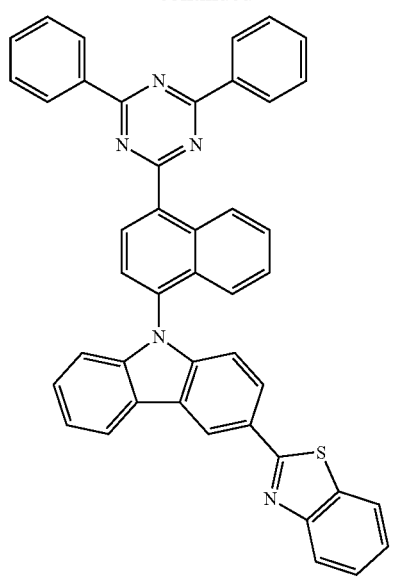
24
-continued
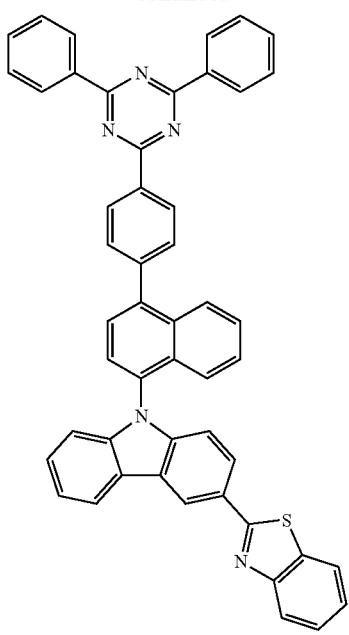

-continued
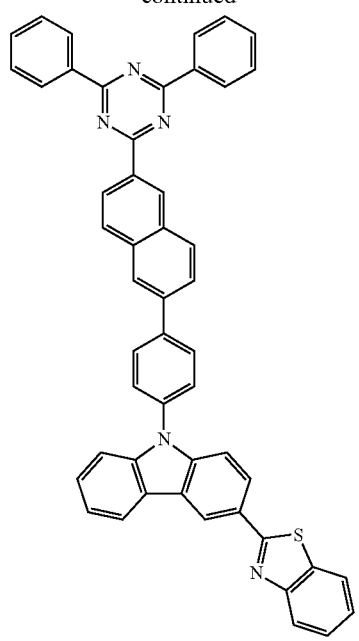
-continued
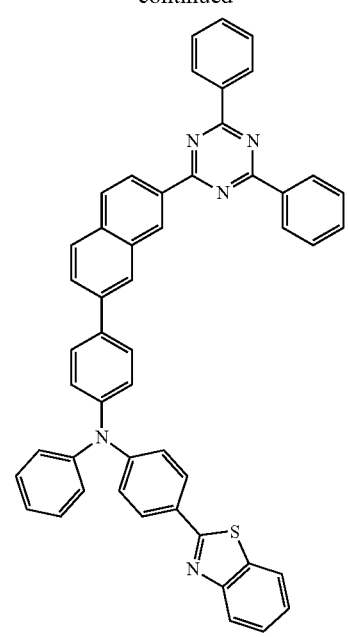
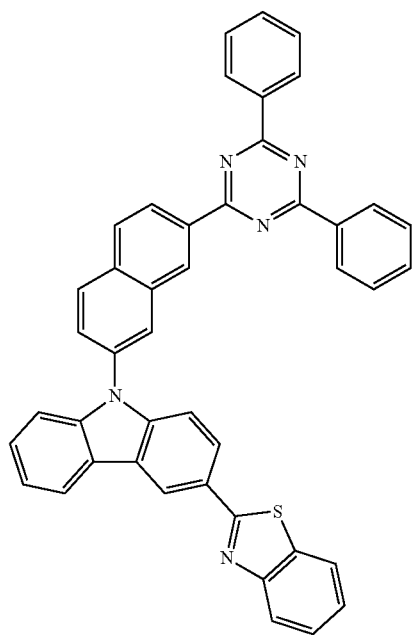
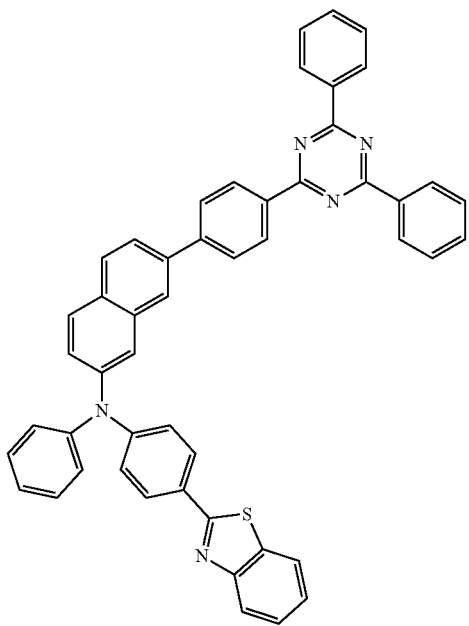

27
-continued
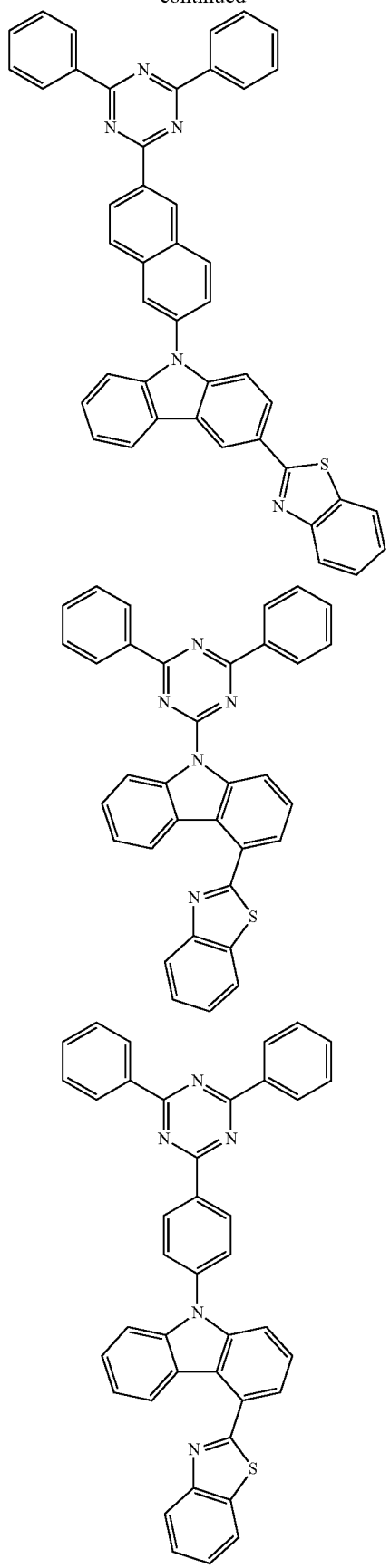
28
-continued
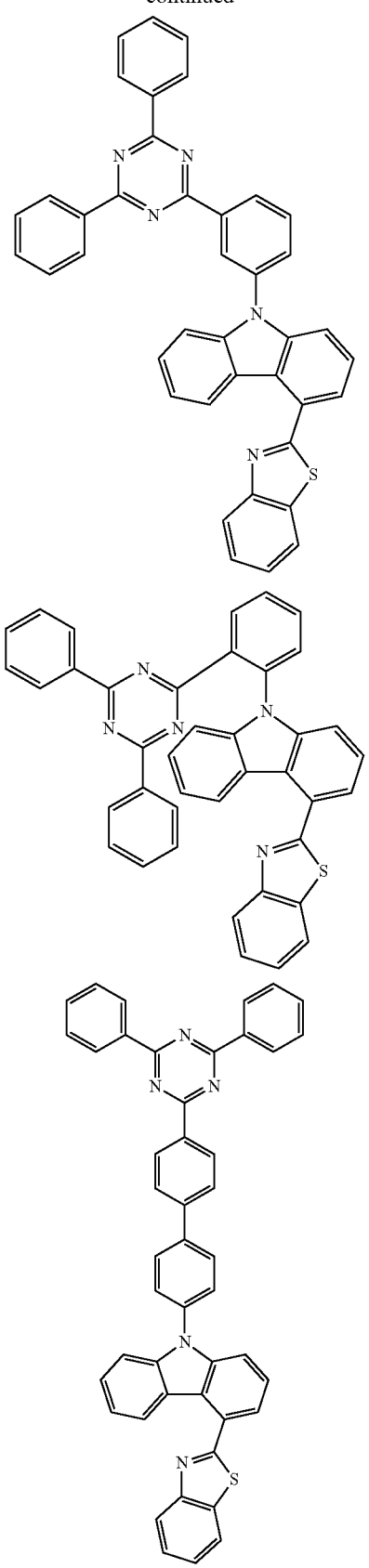

29
-continued
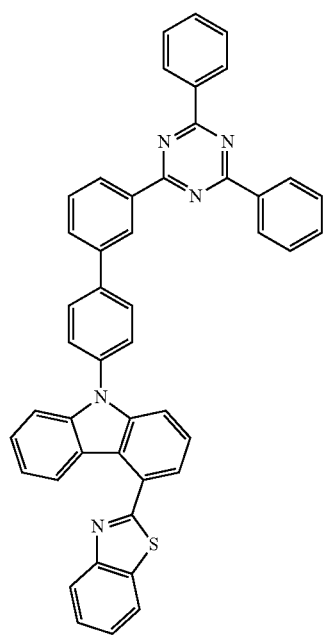
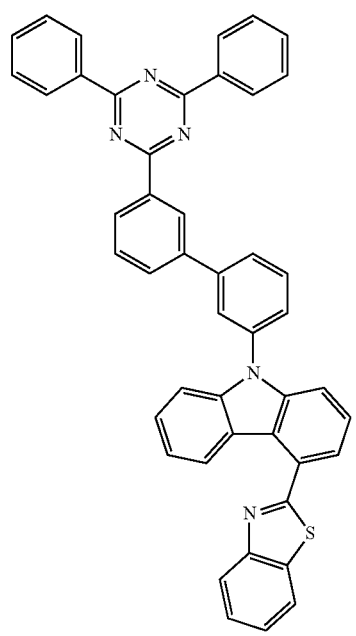
30
-continued
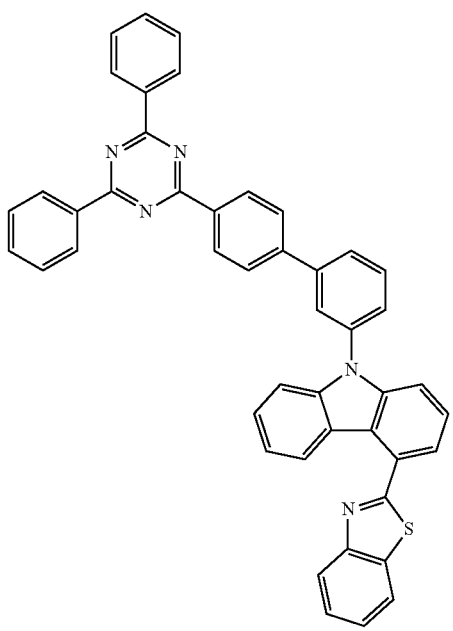

31
-continued
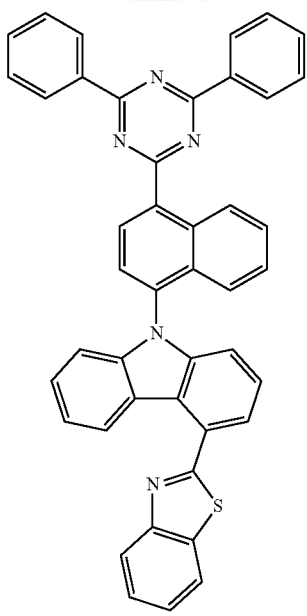
32
-continued
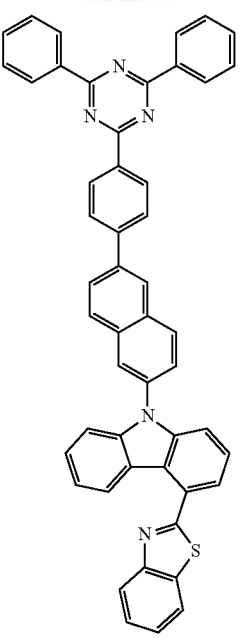
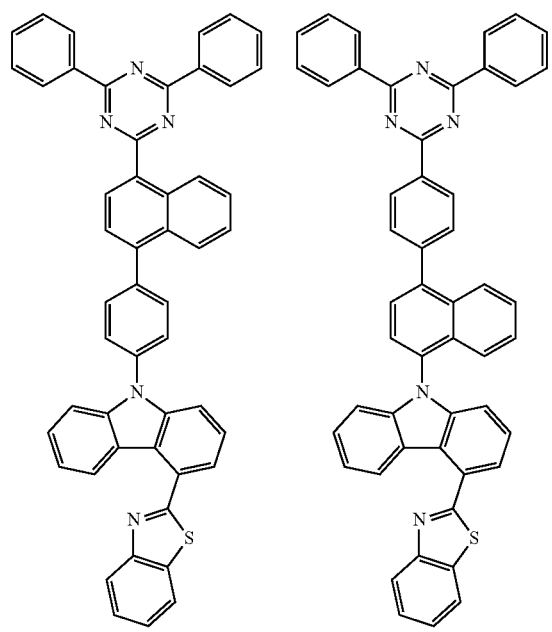
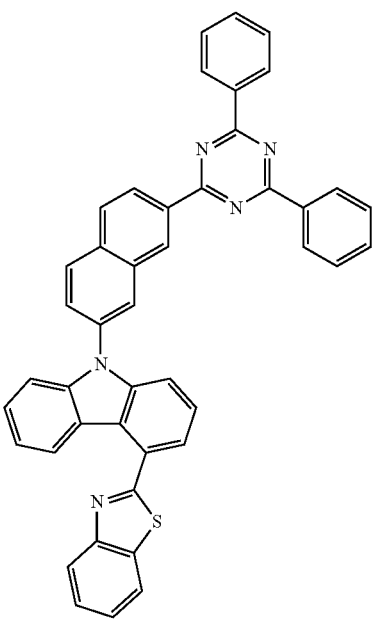

33
-continued
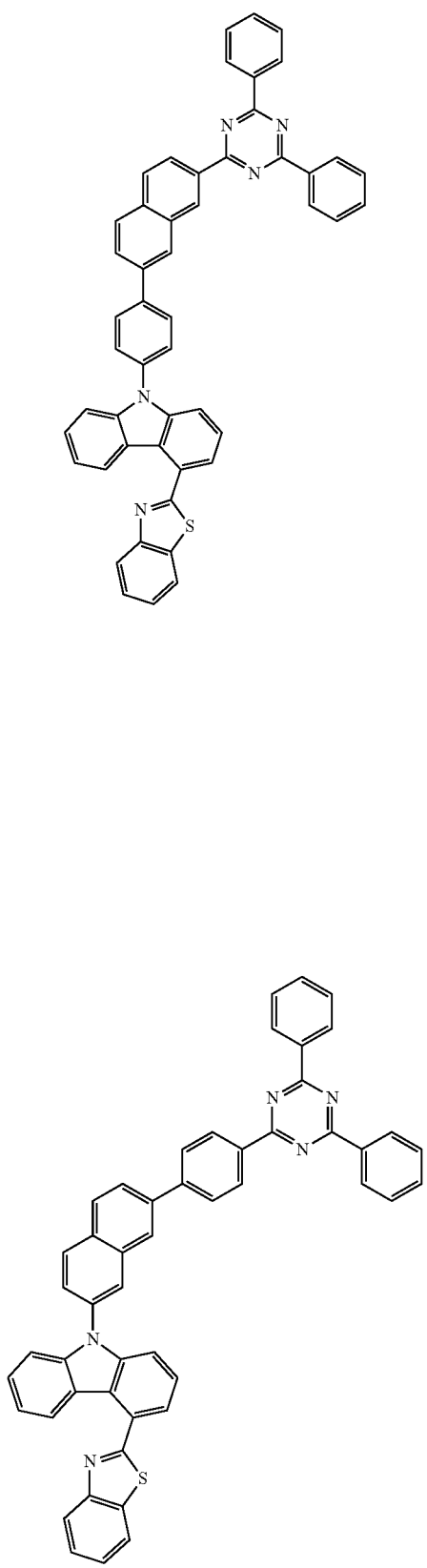
34
-continued
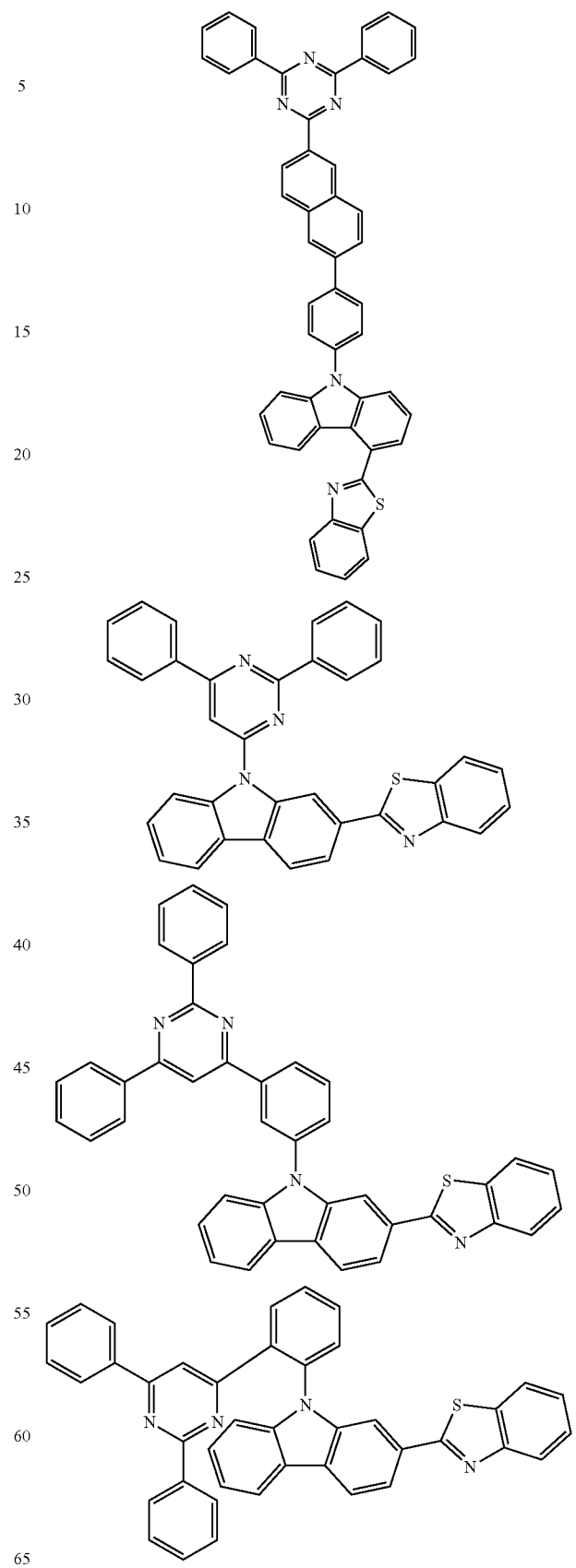

-continued
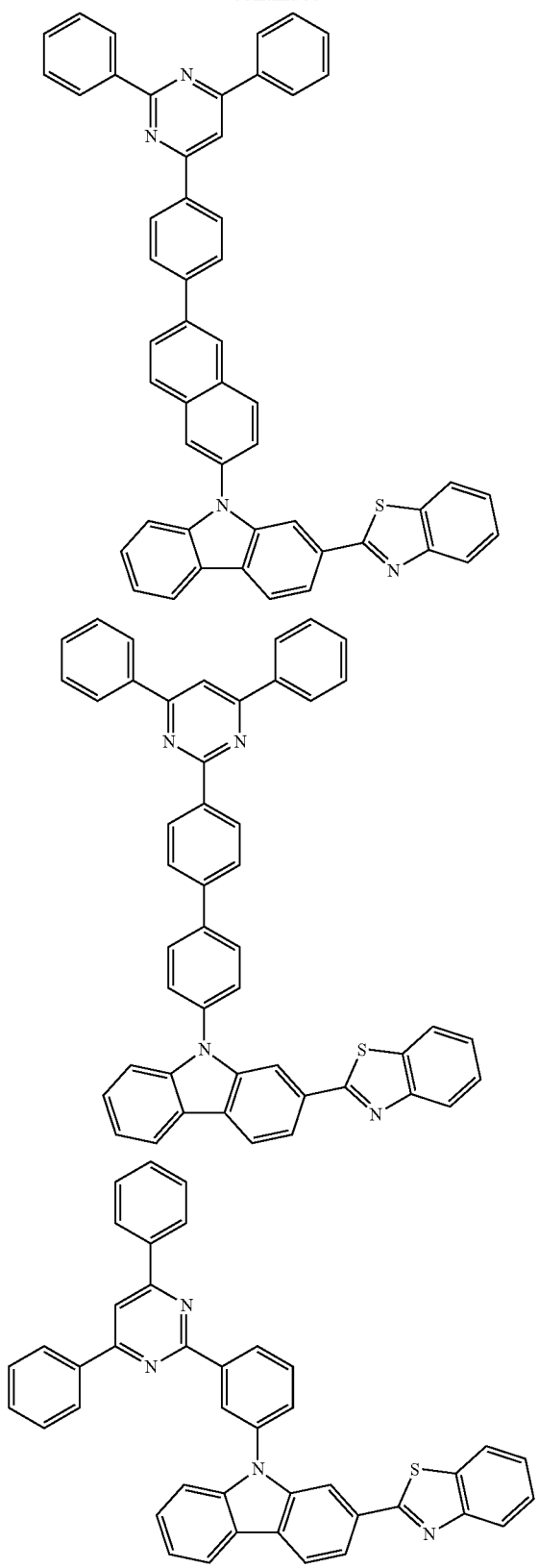
-continued
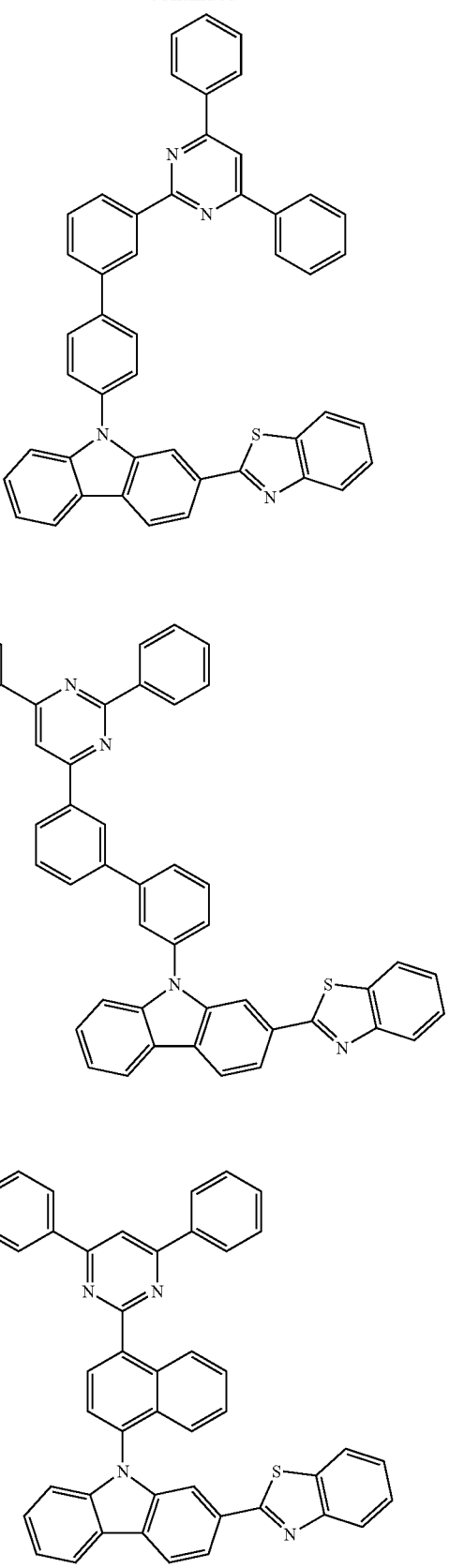

37
-continued
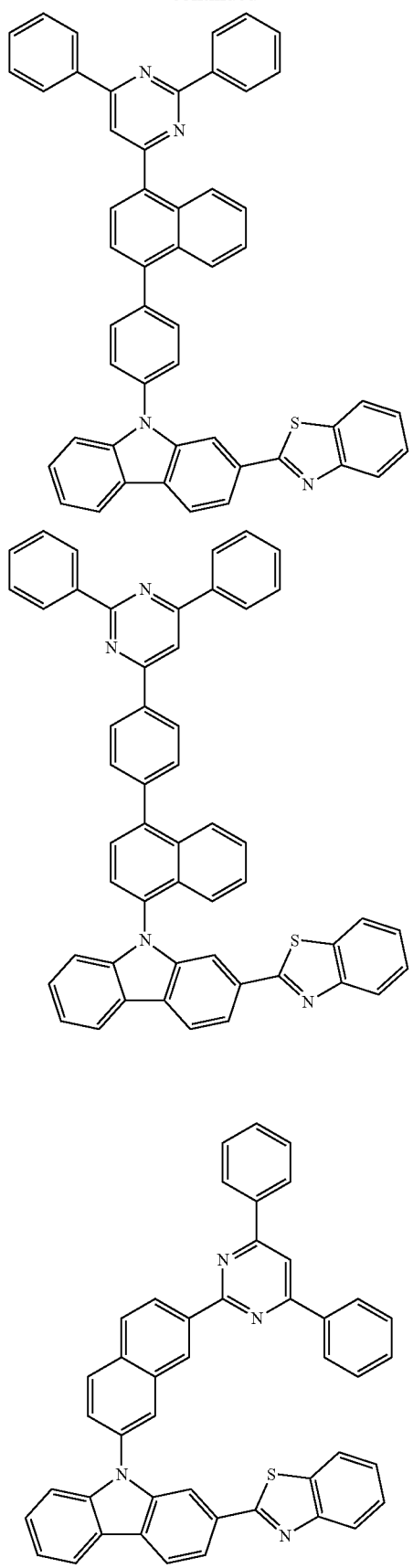
38
-continued
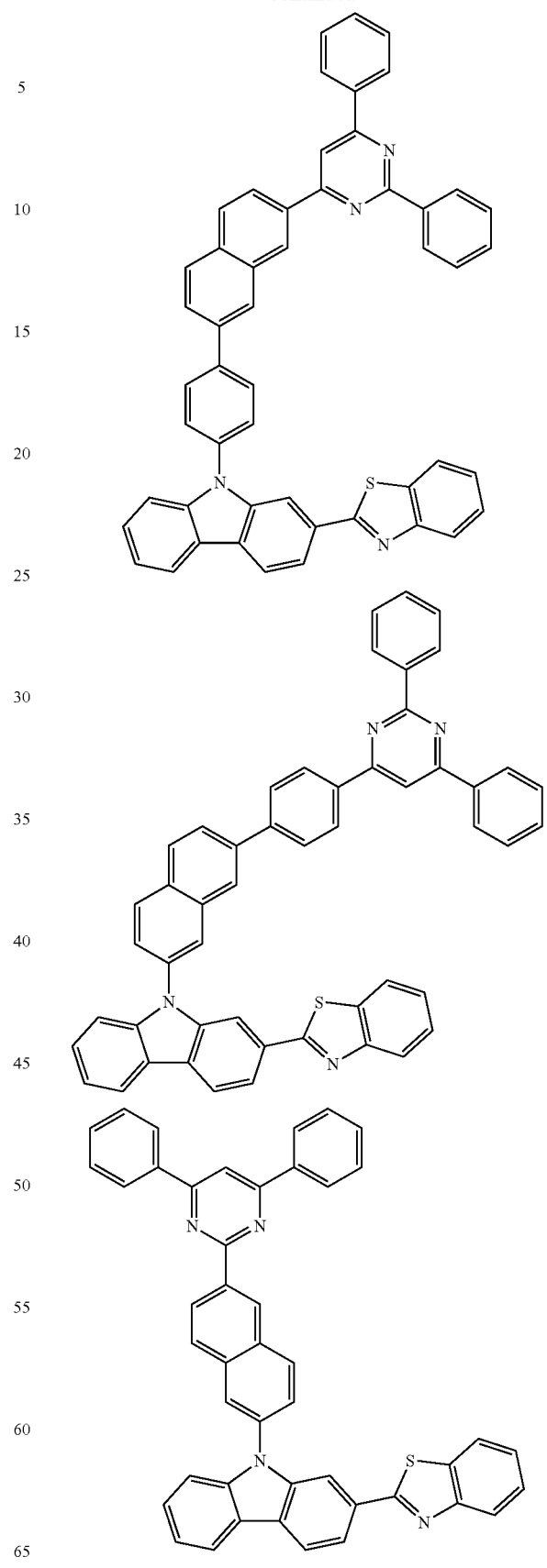

-continued
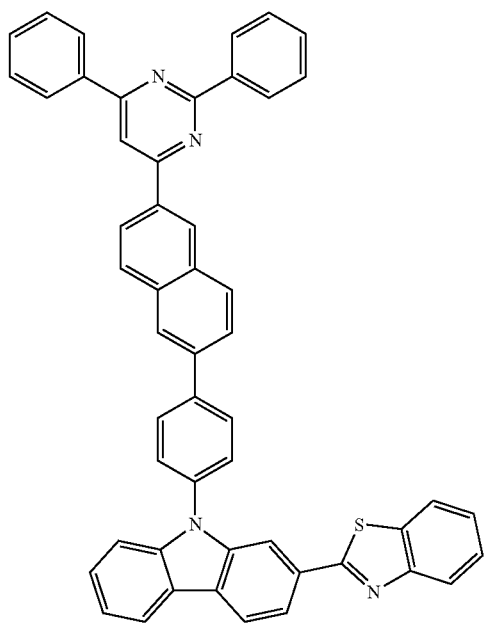
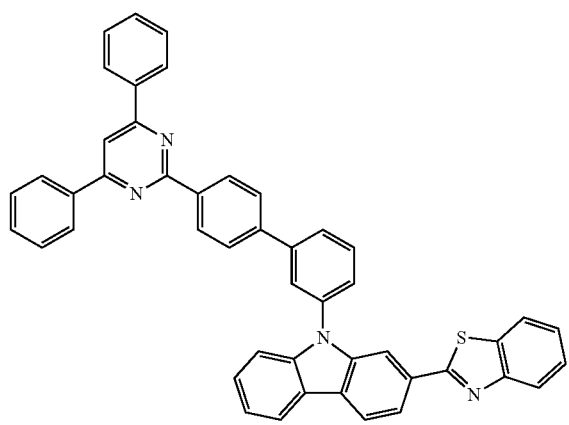 [SMILES: c1ccc(-c2cc(-c3ccccc3)nc(-c3ccc(-c4cccc(-n5c6ccccc6c6ccc(-c7nc8ccccc8o7)cc65)c4)cc3)n2)cc1]
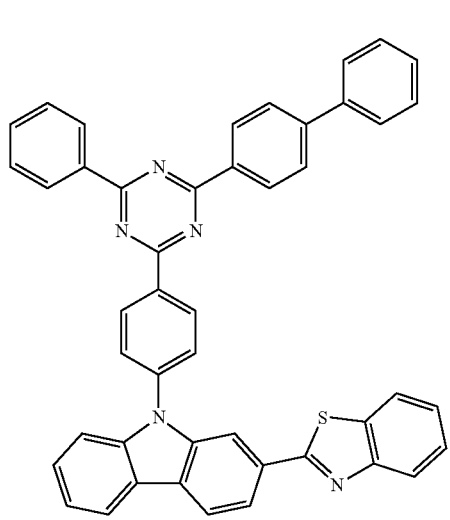
-continued
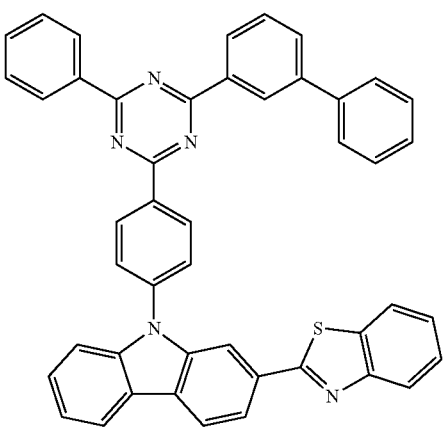
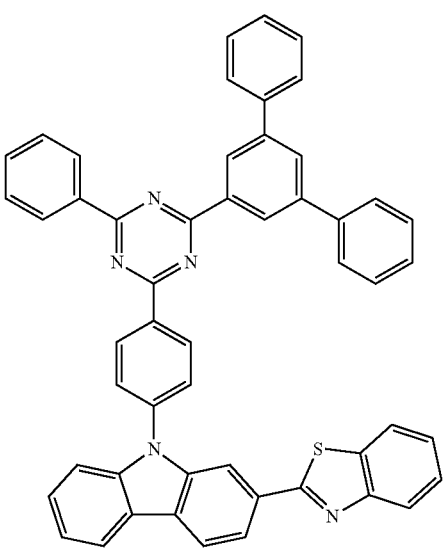
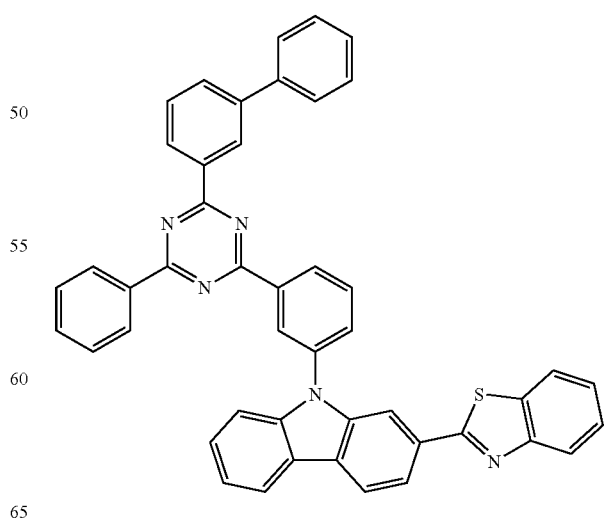

-continued
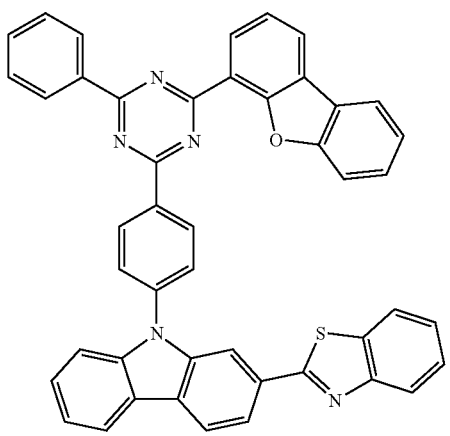
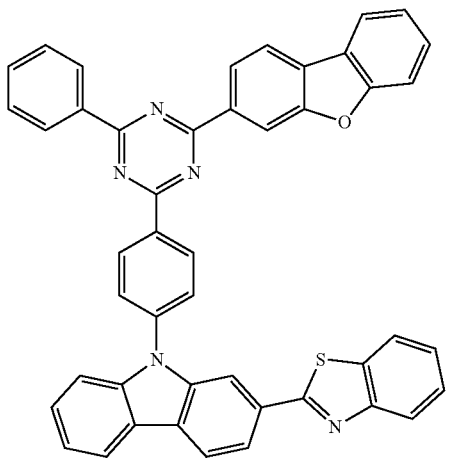
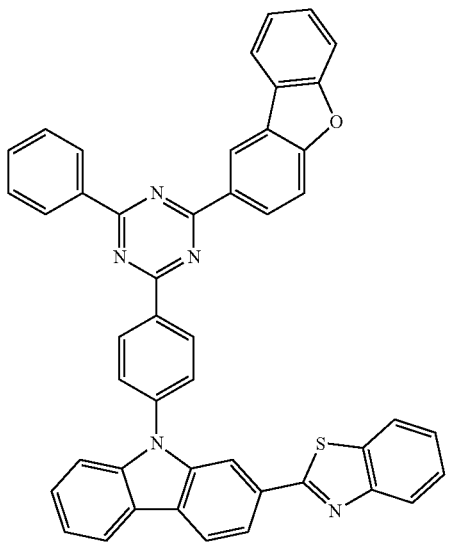
-continued
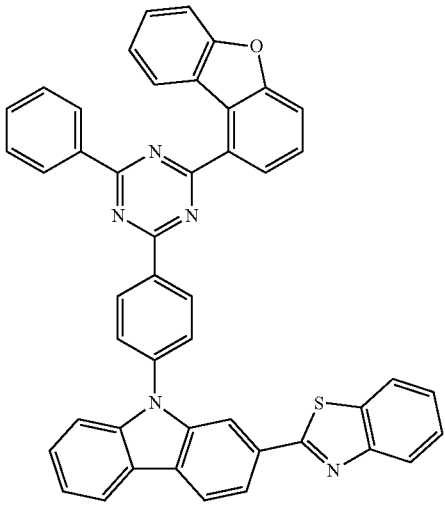
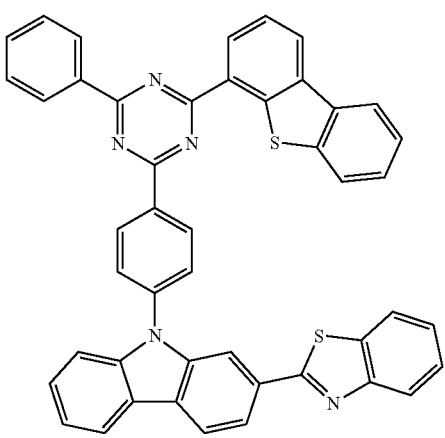
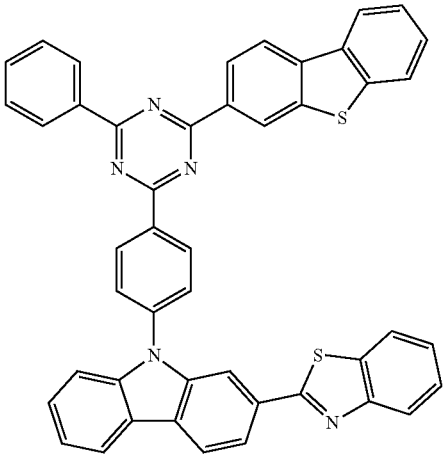

-continued
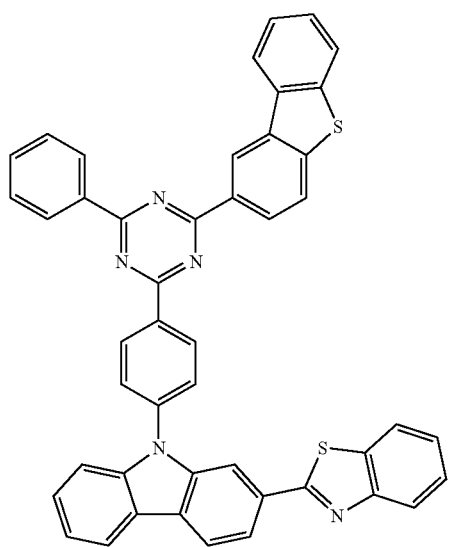
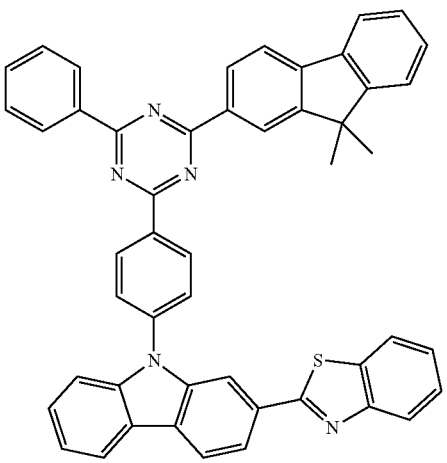
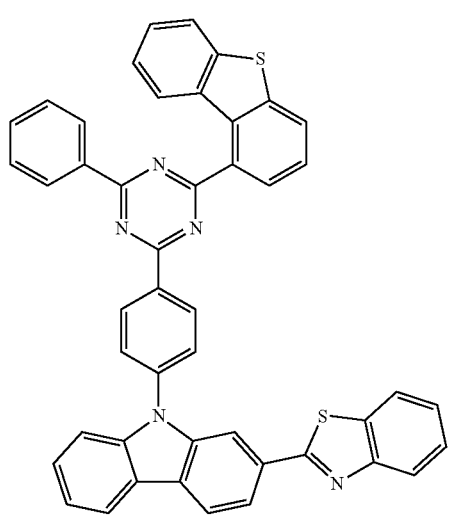
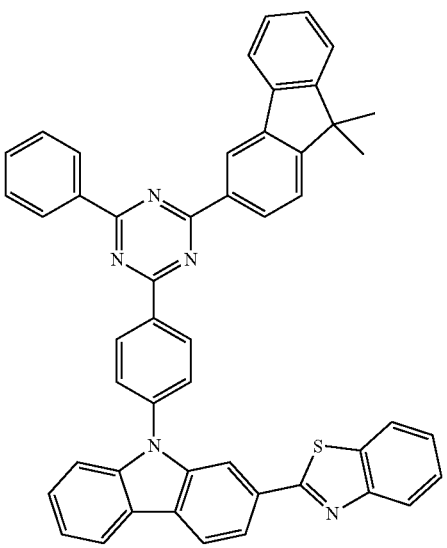
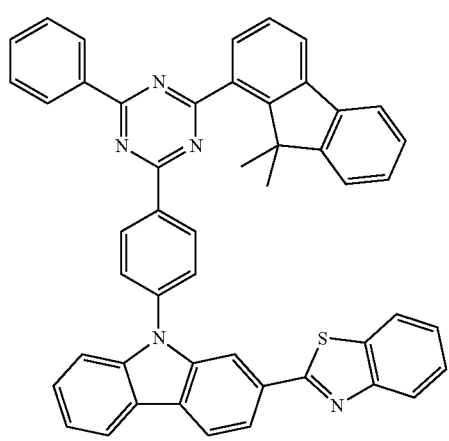
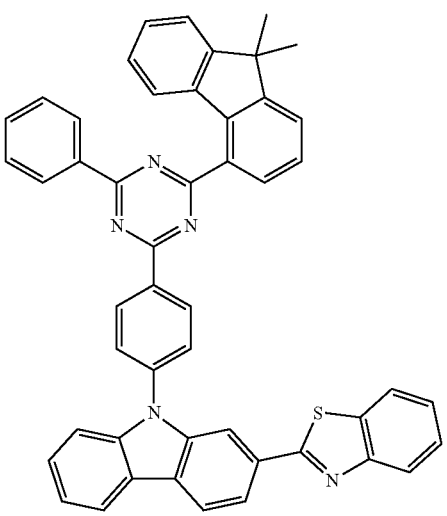

-continued
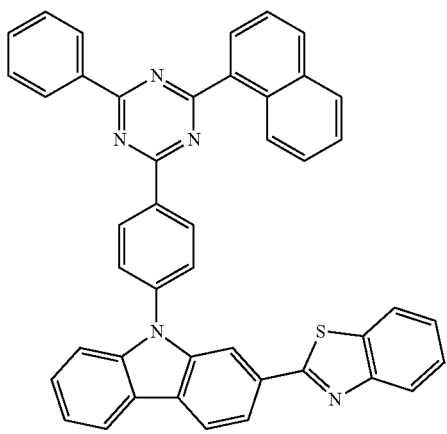
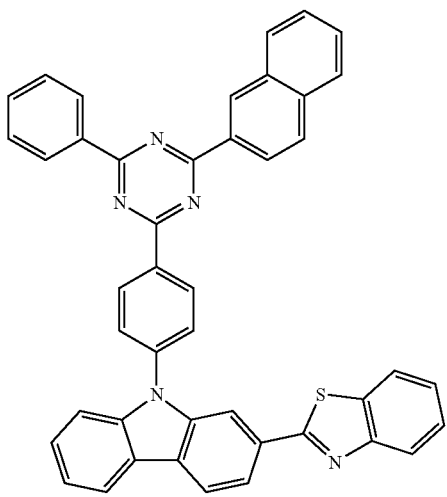
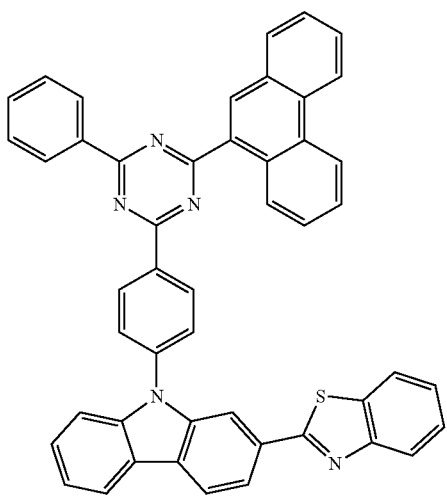
-continued
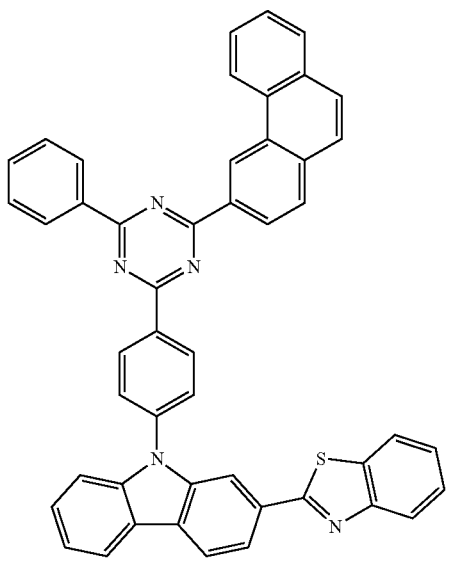
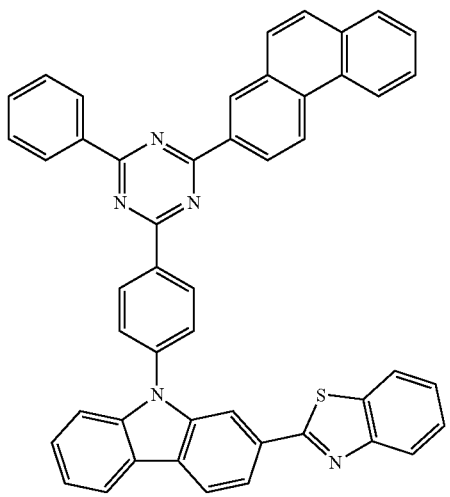
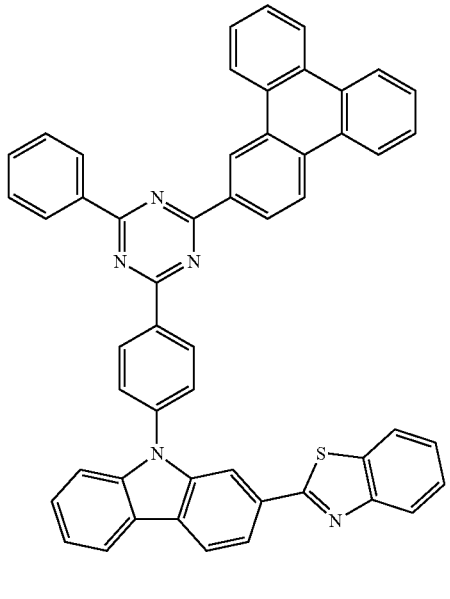

-continued
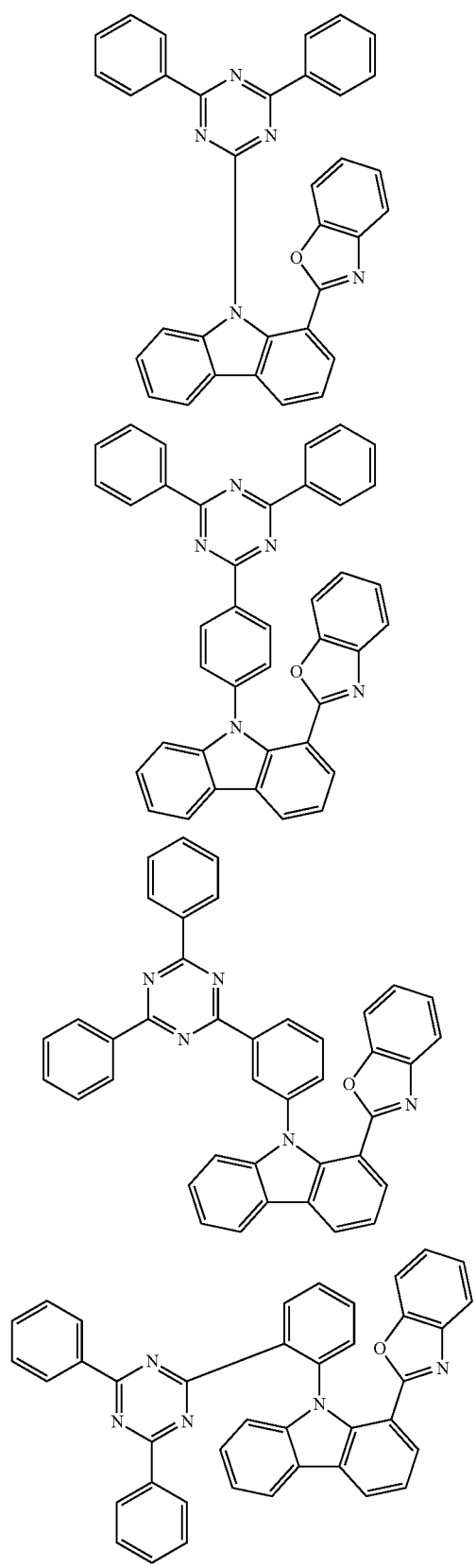
-continued
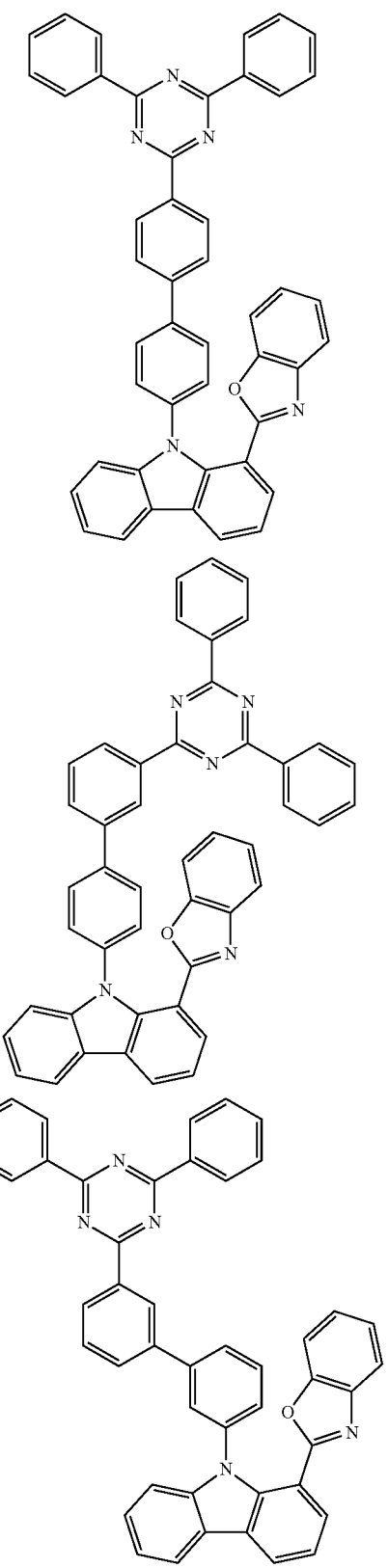

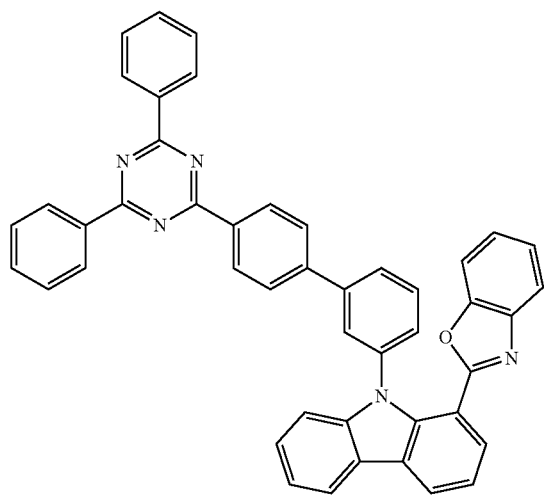
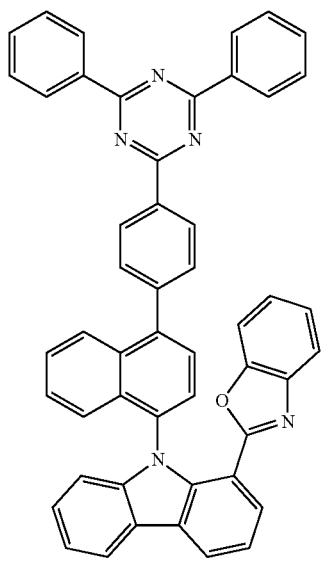
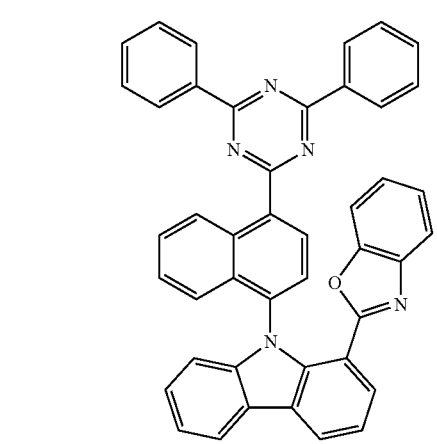
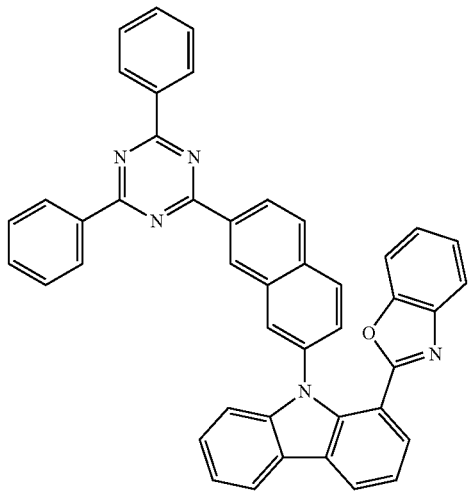
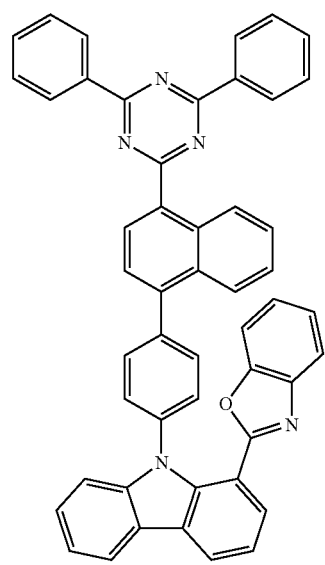

51
-continued
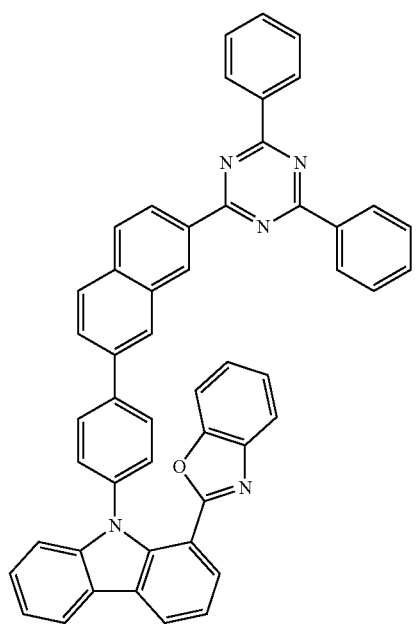
52
-continued
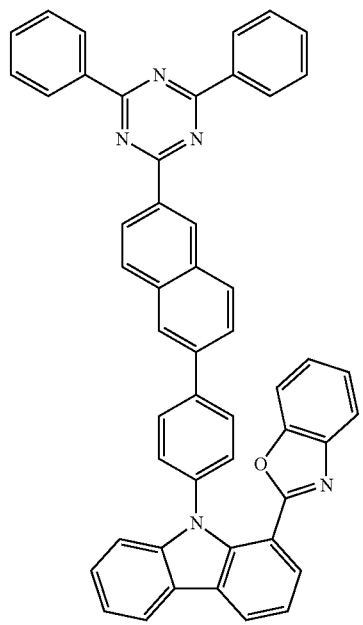
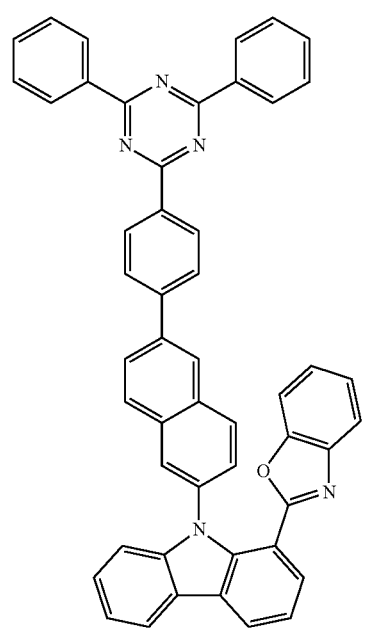

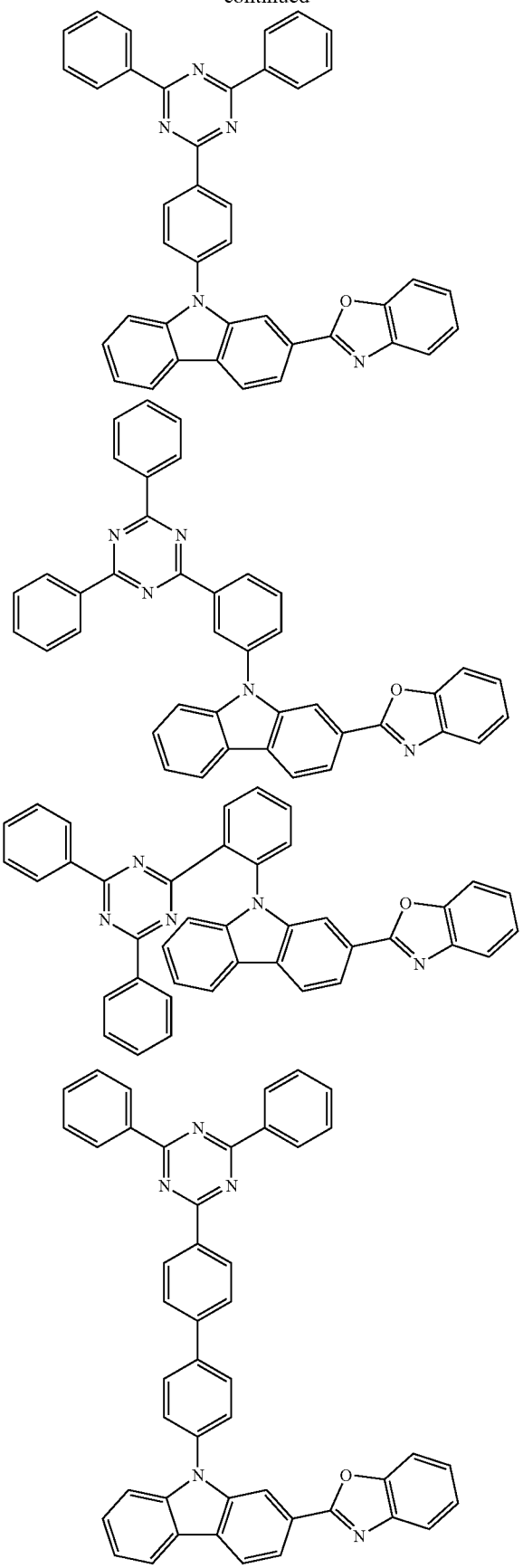
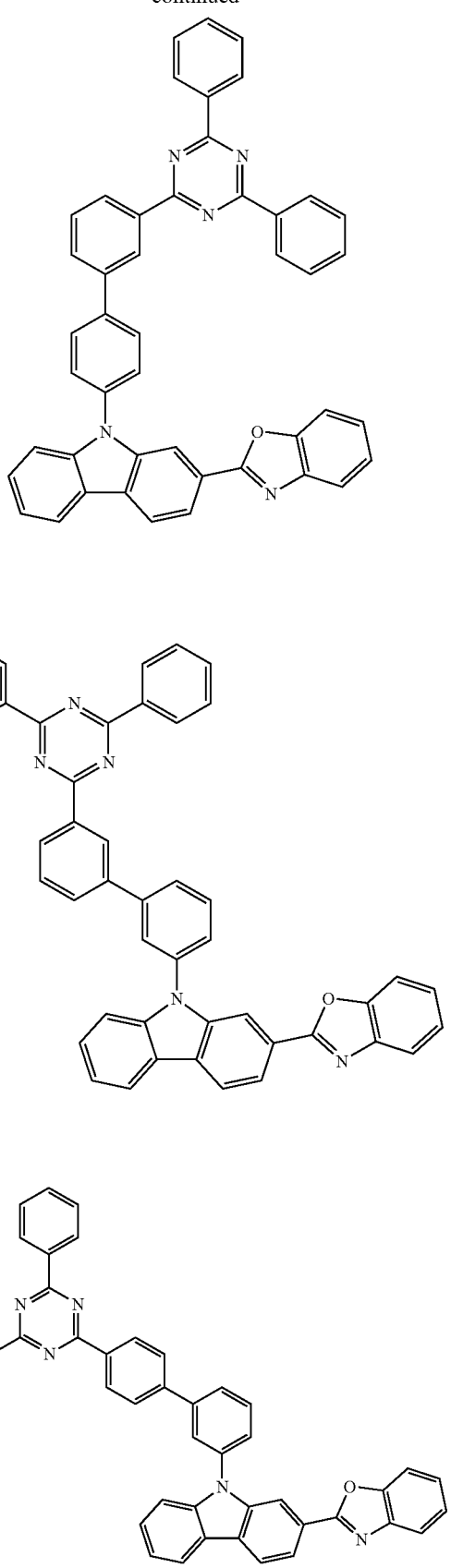

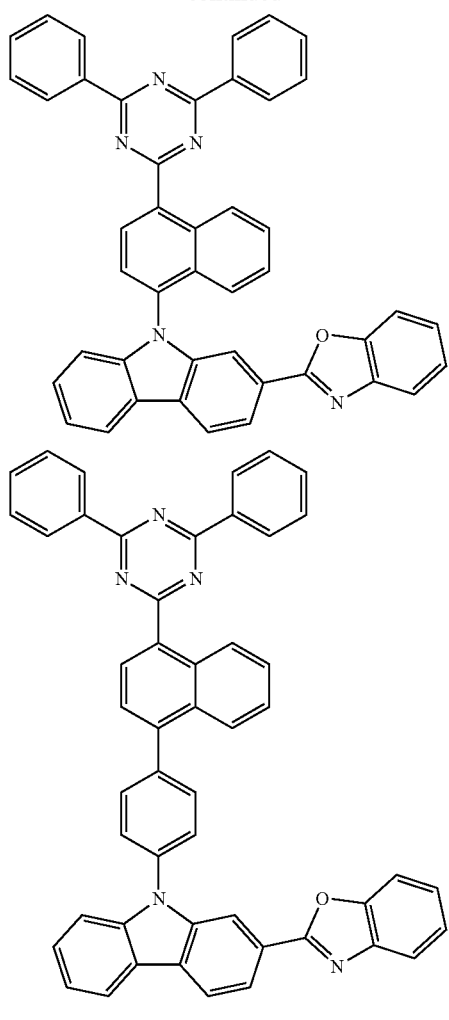
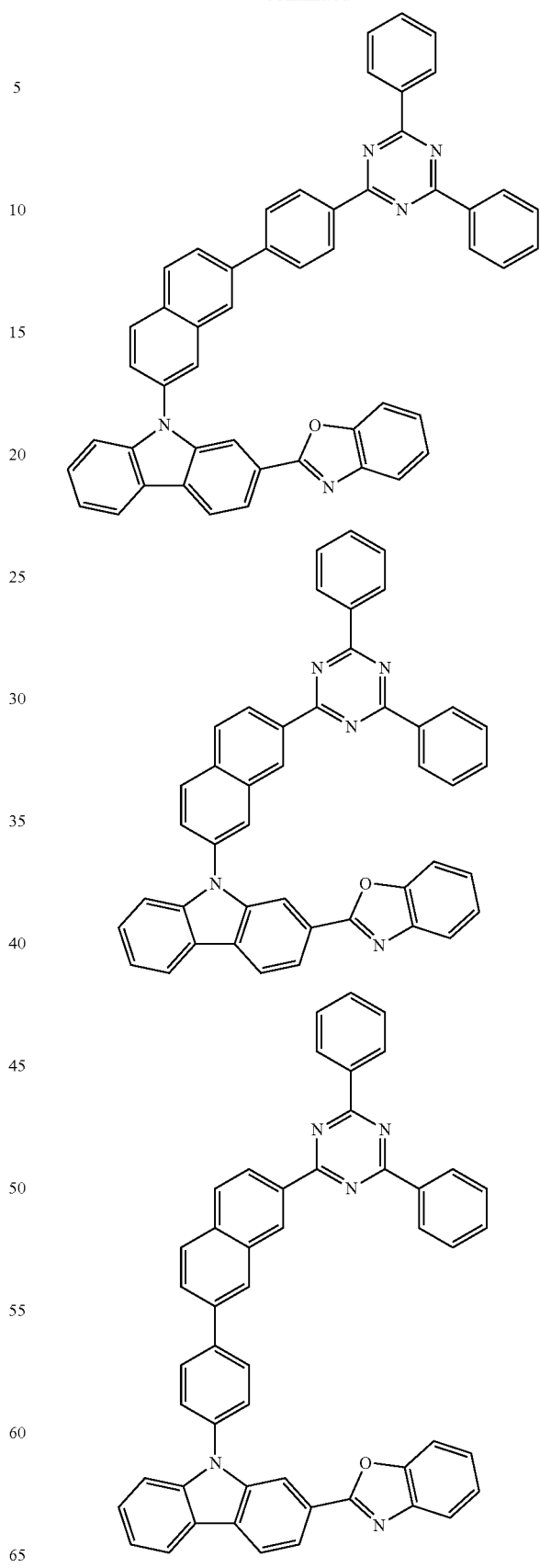

57
-continued
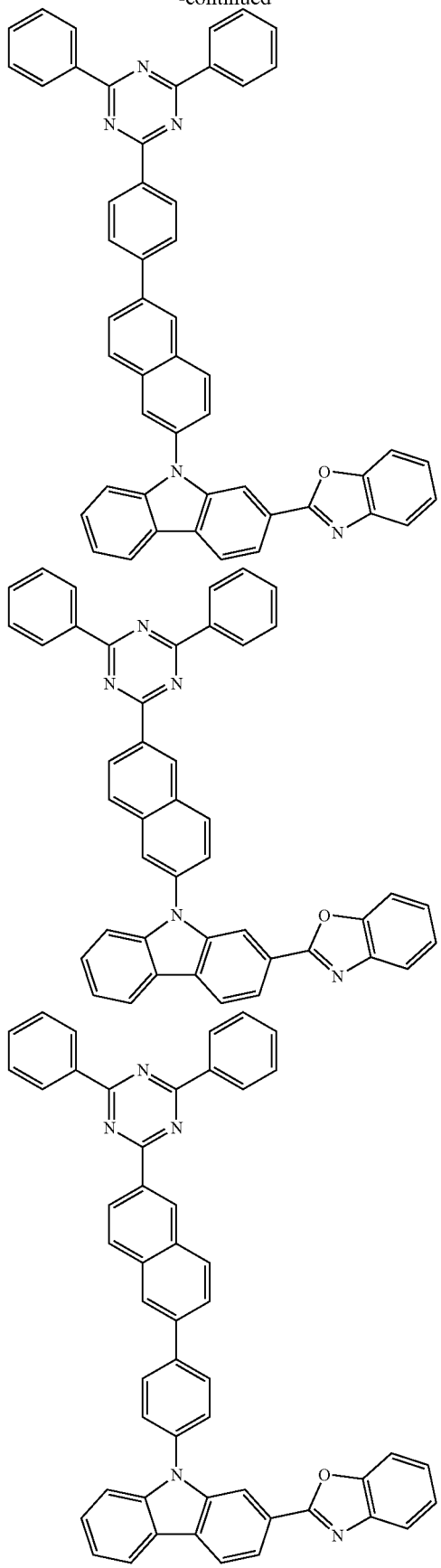
58
-continued
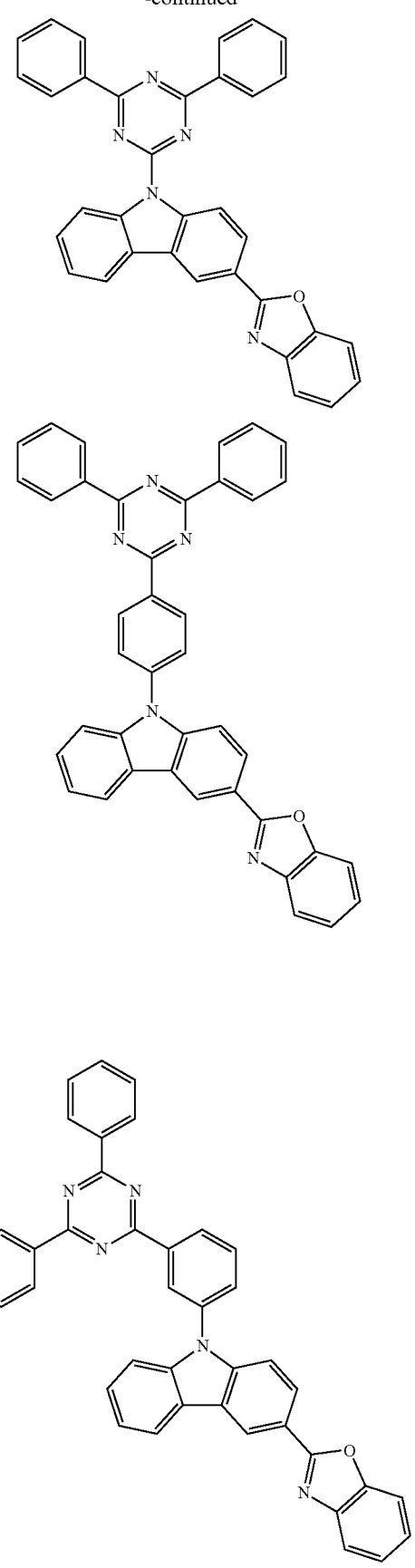

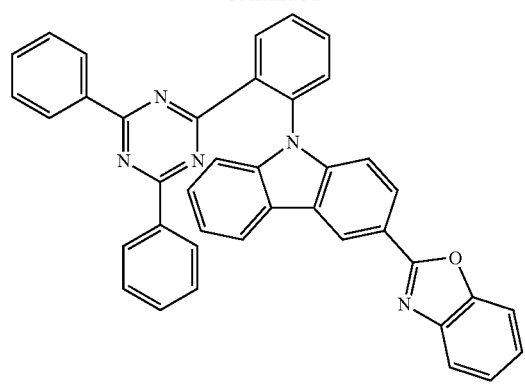
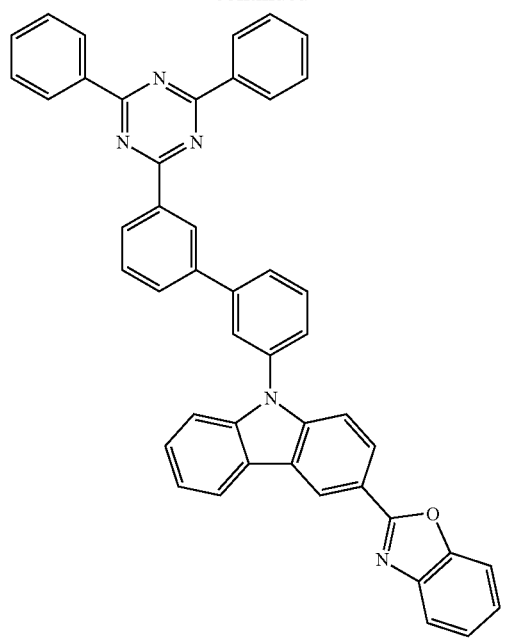
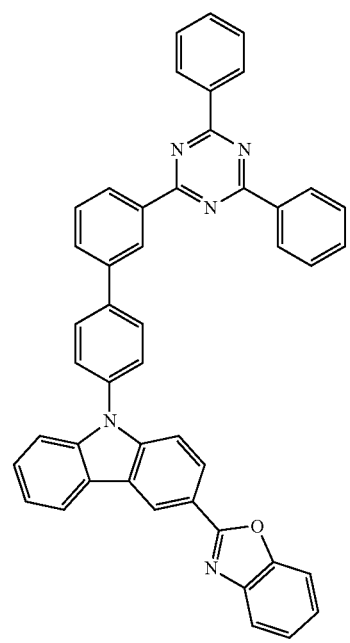
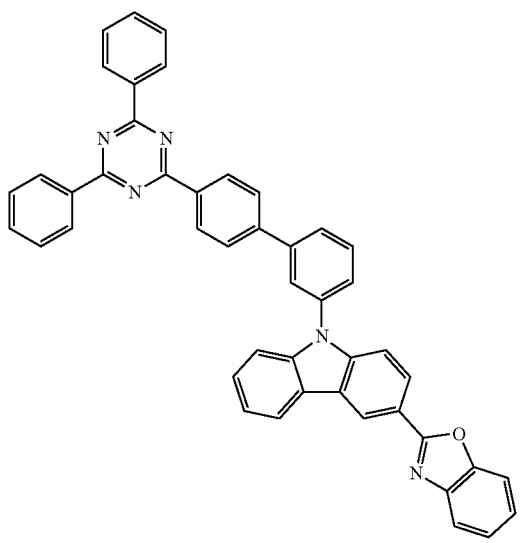

61
-continued
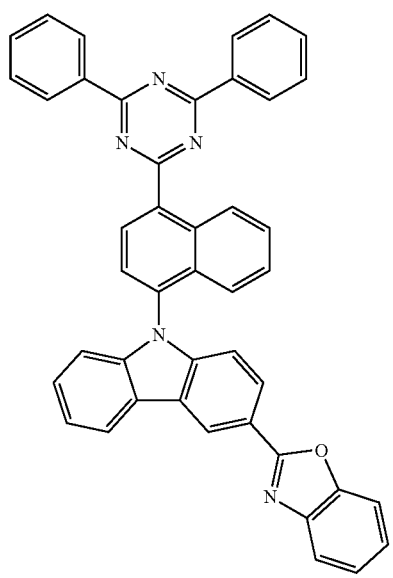
62
-continued
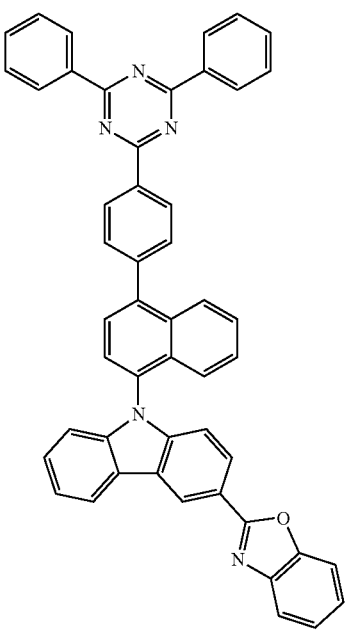
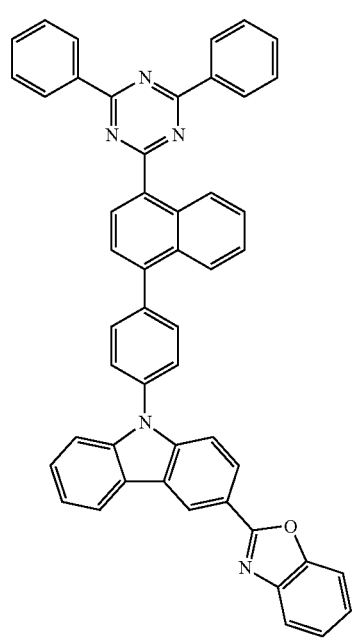
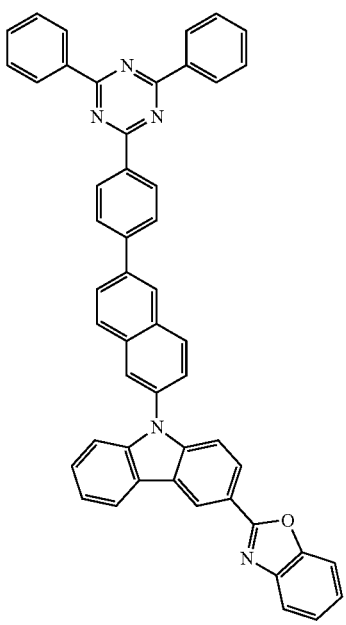

63
-continued
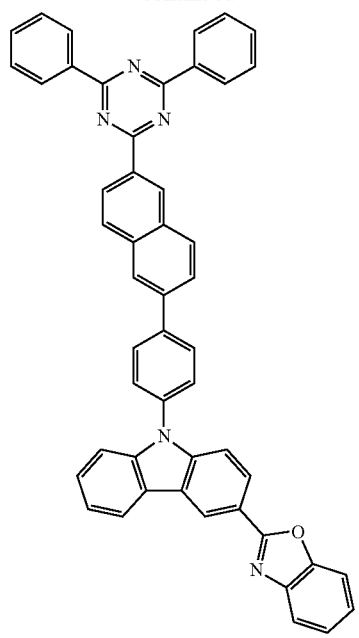
64
-continued
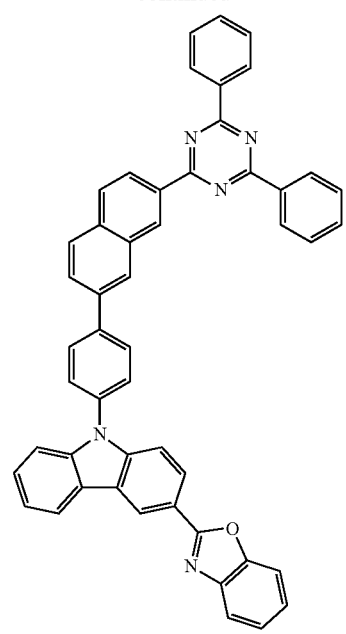
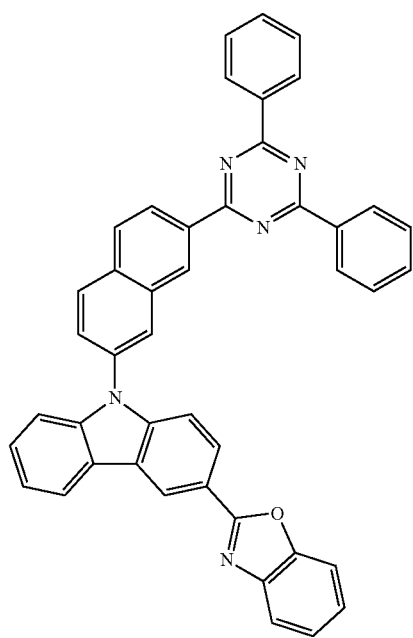
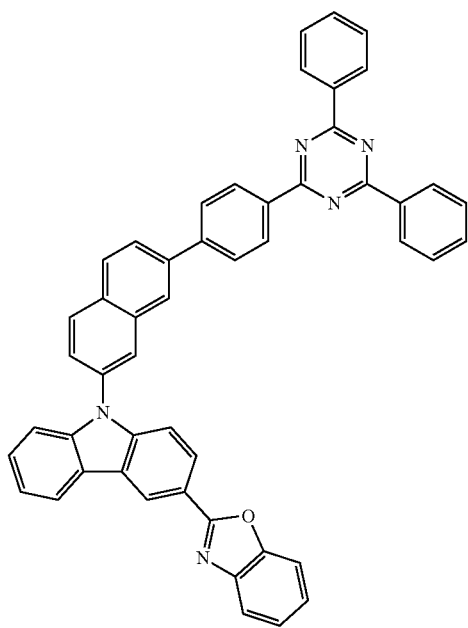

-continued
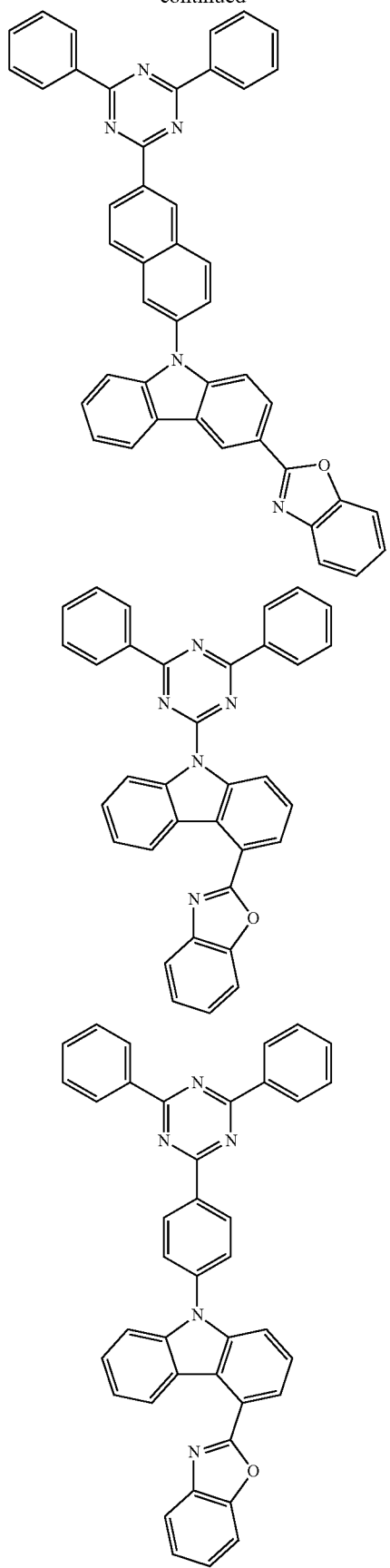
-continued
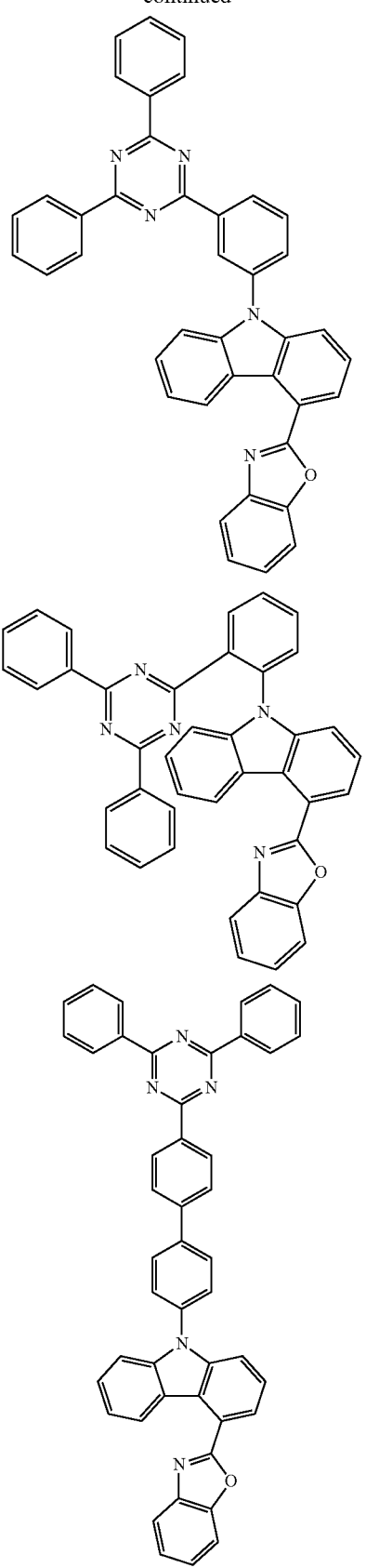

67
-continued
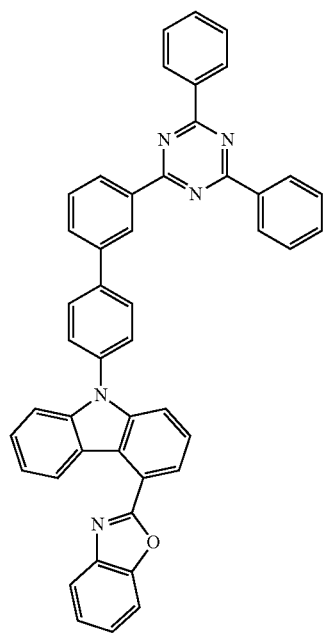
68
-continued
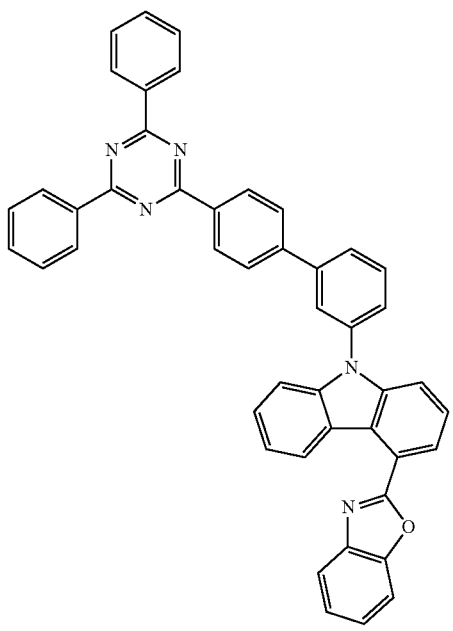
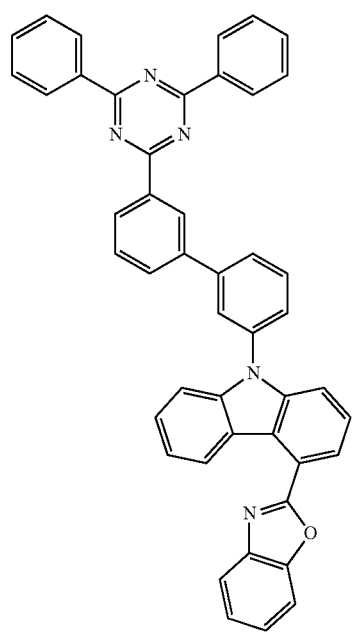
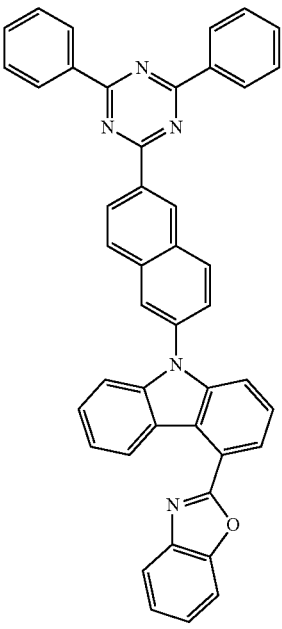

69
-continued
70
-continued
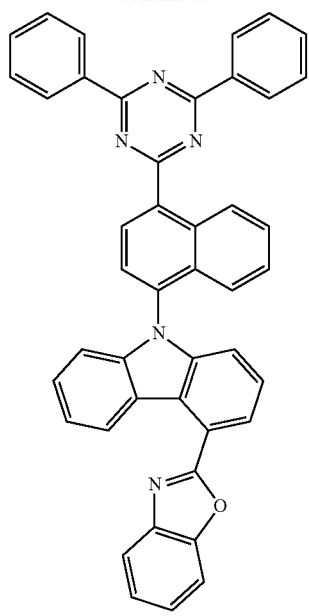
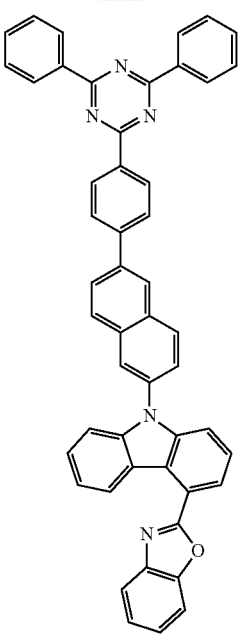
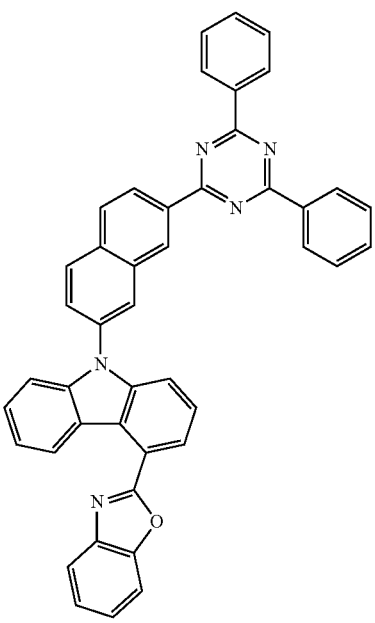

71
-continued
72
-continued
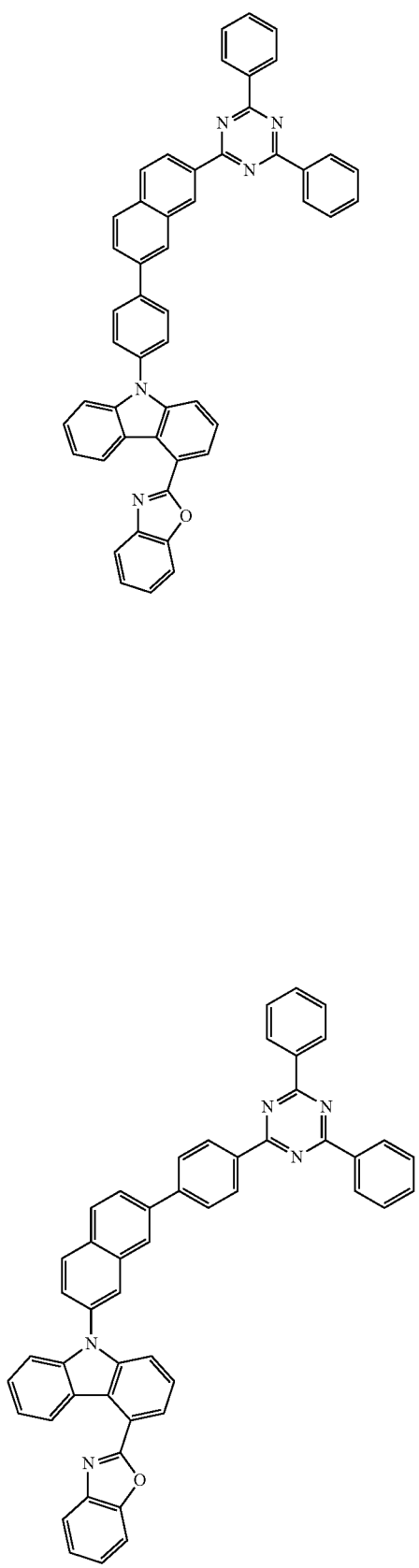
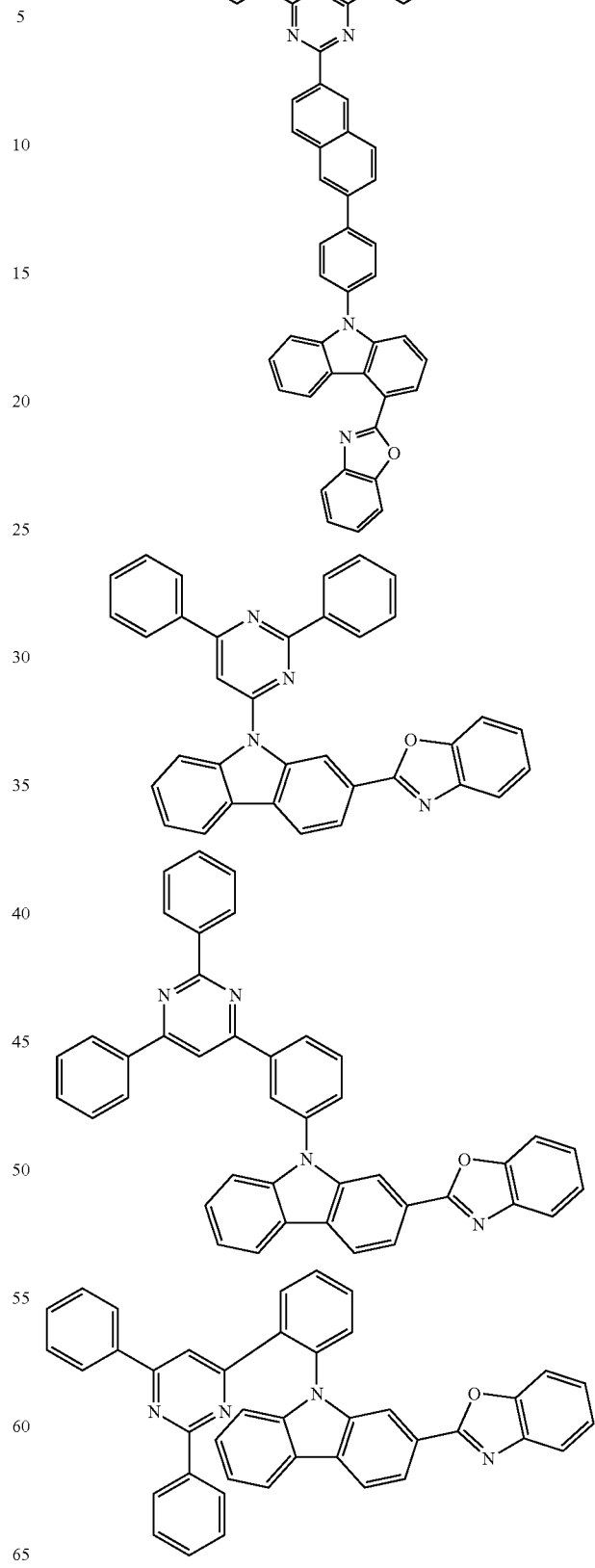

73
-continued
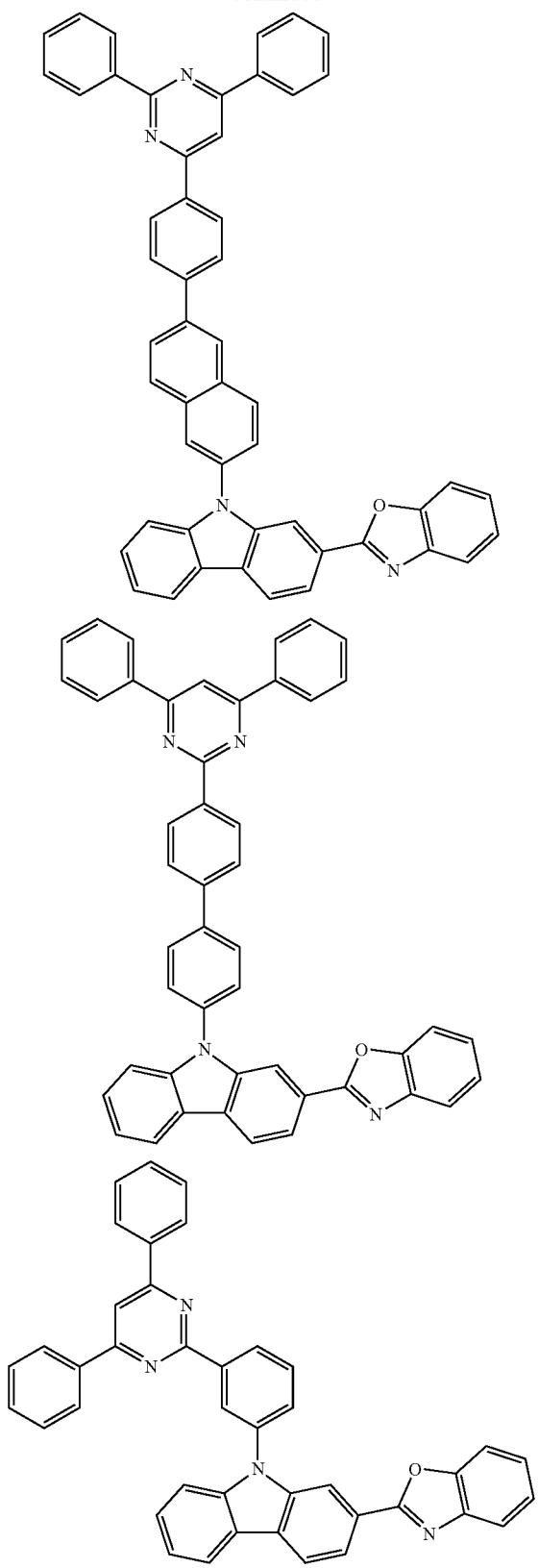
74
-continued
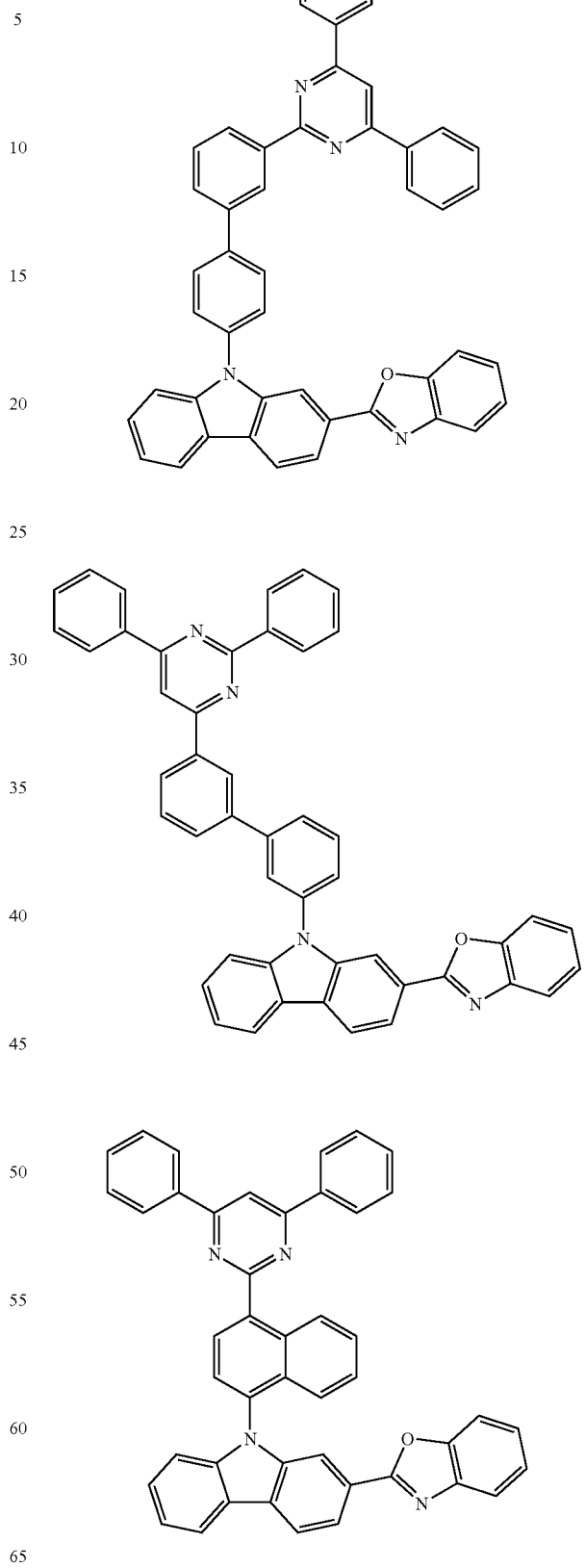

75
-continued
76
-continued
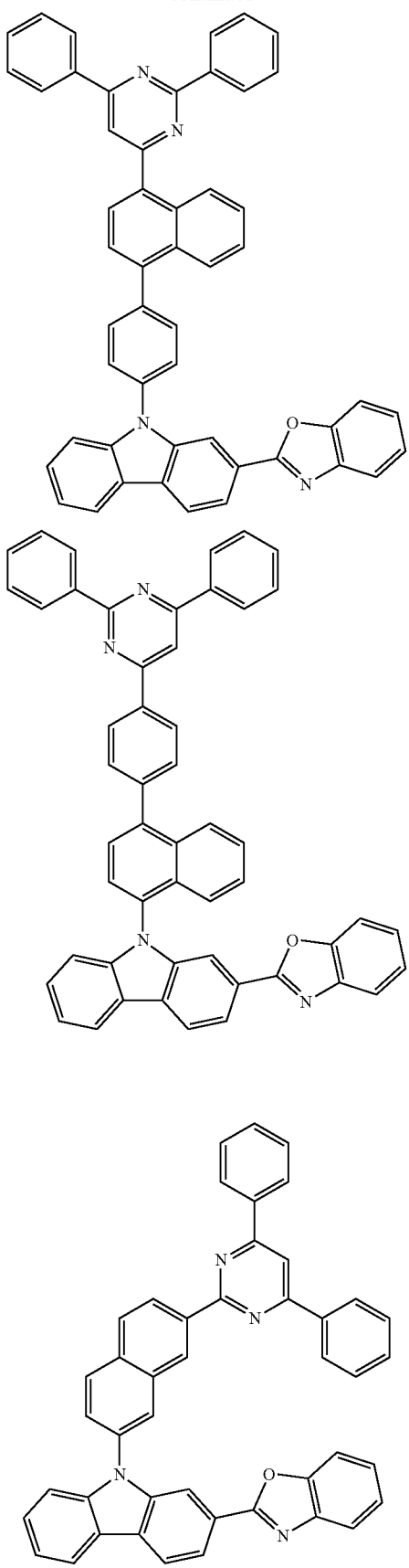
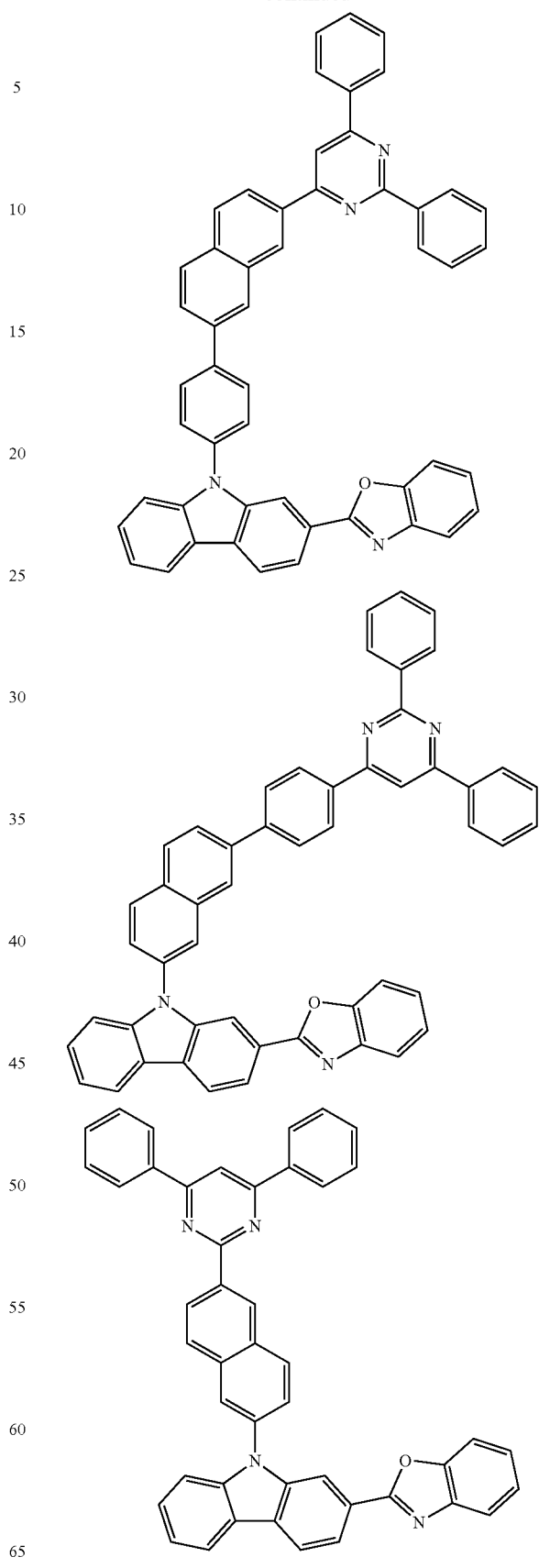

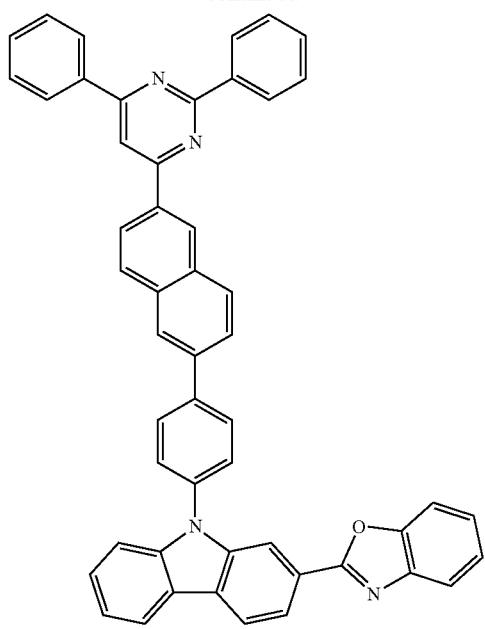
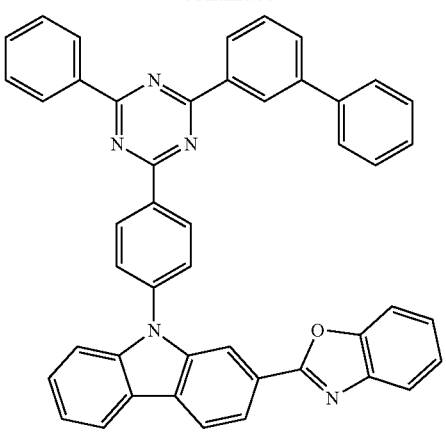

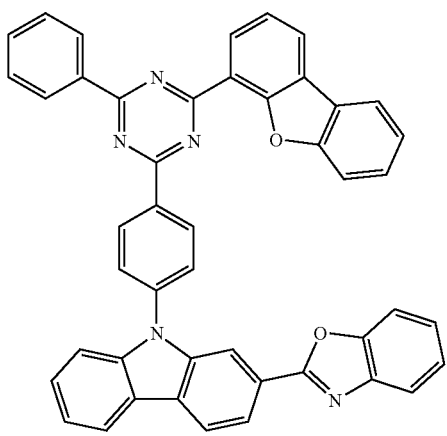
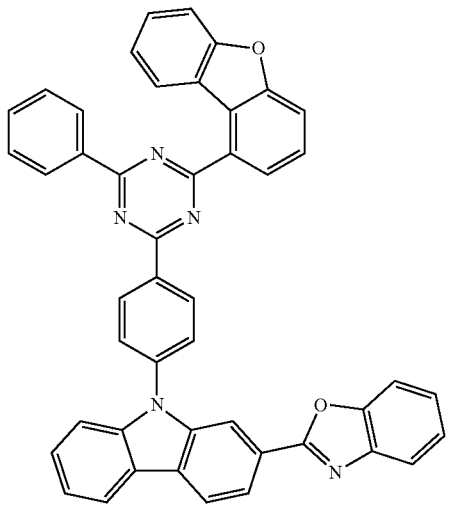
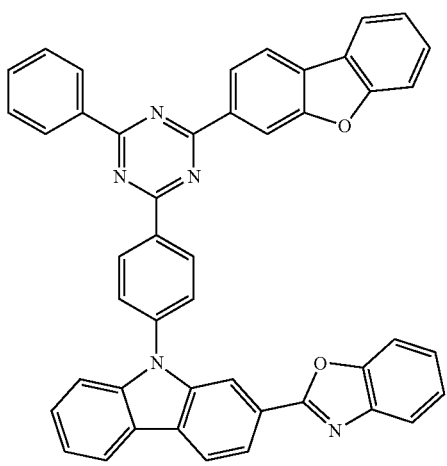
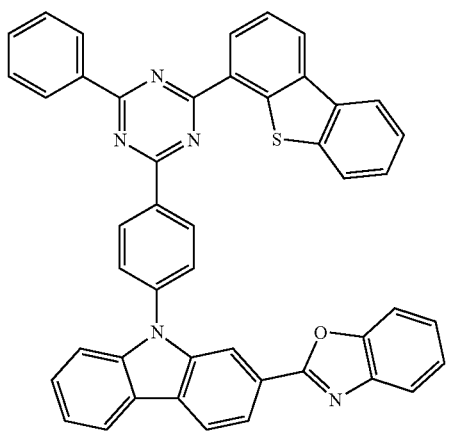
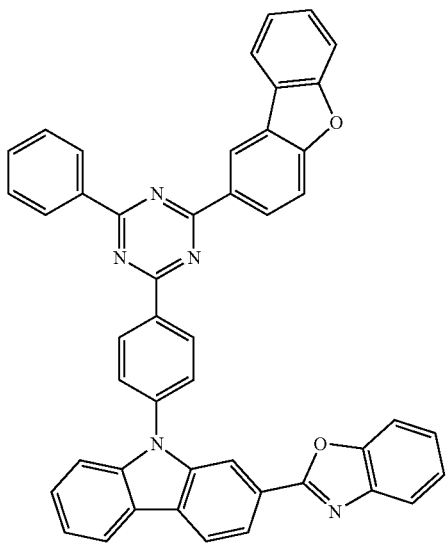
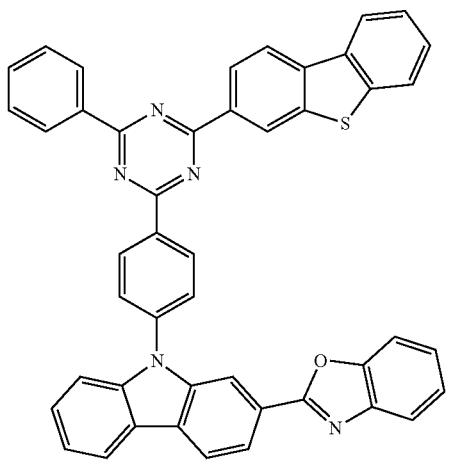

-continued
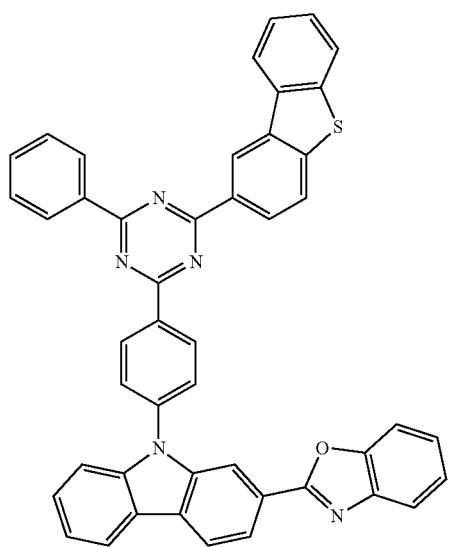
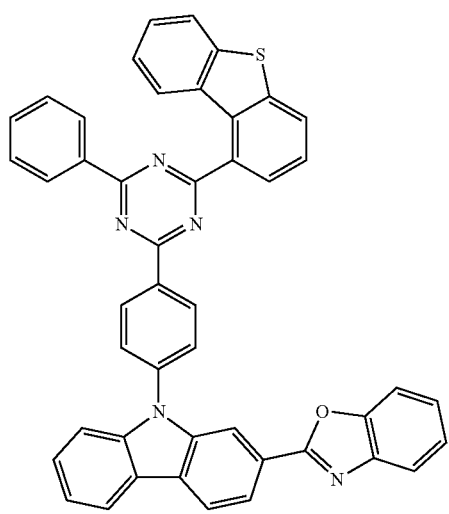
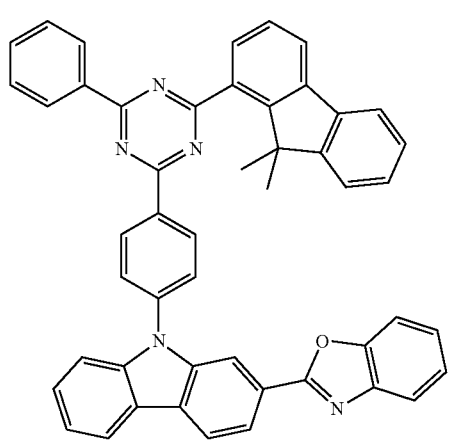
-continued
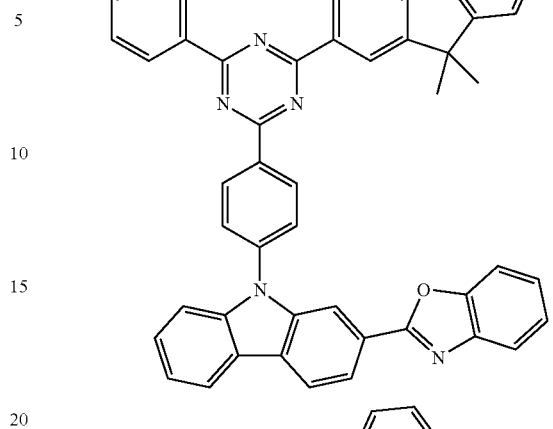
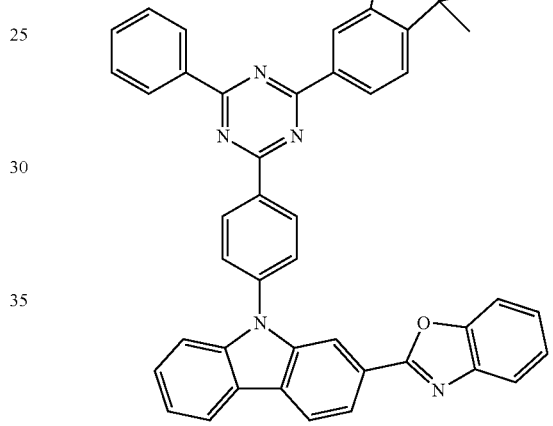
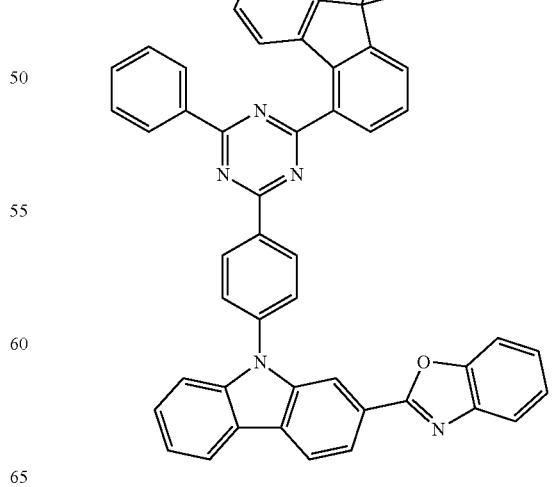

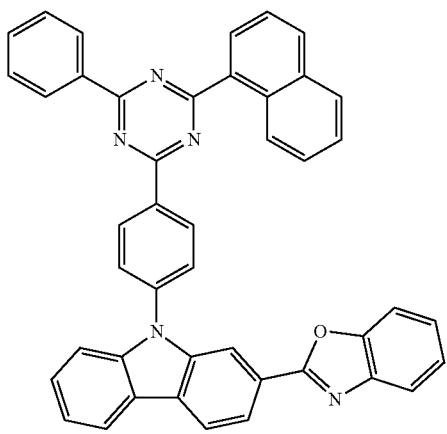
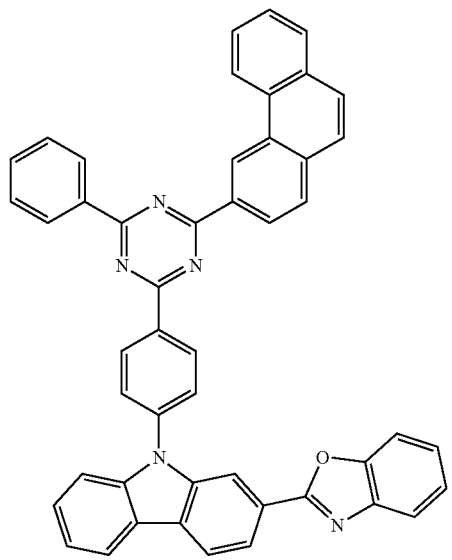
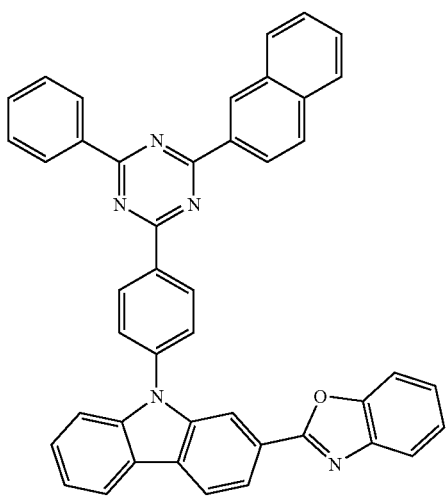
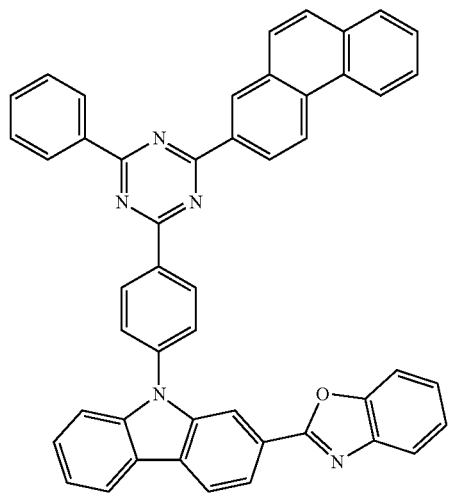
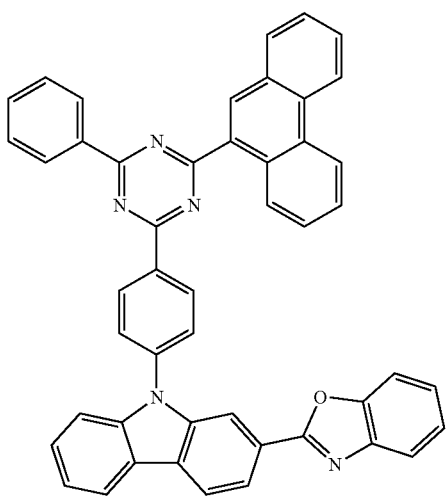
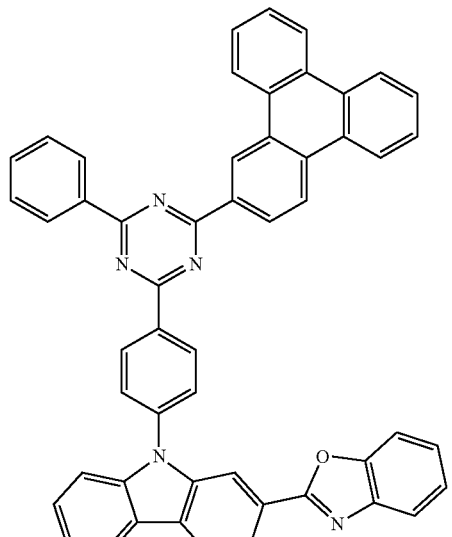
The compound of Formula 1 according to an exemplary embodiment of the present specification may be prepared by a preparation method to be described below.

A conjugation length and an energy bandgap of a compound are closely associated with each other. Specifically, the longer a conjugation length of a compound is, the smaller a bandgap is.

In the present invention, various substituents may be introduced into the core structure as described above to synthesize compounds having various energy bandgaps. Further, in the present invention, various substituents may be introduced into the core structure having the structure as described above to adjust the HOMO and LUMO energy levels of a compound.

In addition, various substituents may be introduced into the core structure having the structure as described above to synthesize a compound having inherent characteristics of the introduced substituent. For example, a substituent mainly used for a hole injection layer material, a material for transporting holes, a light emitting layer material, and an electron transport layer material, which are used for manufacturing an organic light emitting device, may be introduced into the core structure to synthesize a material which satisfies conditions required for each organic material layer.

Further, the organic light emitting device according to the present invention is an organic light emitting device including: a first electrode; a second electrode provided to face the first electrode; and an organic material layer having one or more layers provided between the first electrode and the second electrode, in which one or more layers of the organic material layer include the compound of Formula 1.

The organic light emitting device of the present invention may be manufactured by typical preparation methods and materials of an organic light emitting device, except that the above-described compound is used to form an organic material layer having one or more layers.

The compound may be formed as an organic material layer by not only a vacuum deposition method, but also a solution application method when an organic light emitting device is manufactured. Here, the solution application method means spin coating, dip coating, inkjet printing, screen printing, a spray method, roll coating, and the like, but is not limited thereto.

The organic material layer of the organic light emitting device of the present invention may be composed of a single-layered structure, but may also be composed of a multi-layered structure in which organic material layers each having two or more layers are stacked. For example, the organic light emitting device of the present invention may have a structure including a hole injection layer, a hole transport layer, an electron blocking layer, a light emitting layer, an electron transport layer, an electron injection layer, and the like, as organic material layers. However, the structure of the organic light emitting device is not limited thereto, and may include a fewer number of organic material layers.

In the organic light emitting device of the present invention, the organic material layer may include an electron transport layer or an electron injection layer, and the electron transport layer or the electron injection layer may include the compound represented by Formula 1.

In another exemplary embodiment, the organic material layer includes a light emitting layer, and the light emitting layer includes the compound represented by Formula 1.

According to still another exemplary embodiment, the organic material layer includes a light emitting layer, and the light emitting layer may include the compound represented by Formula 1 as a host of the light emitting layer.

In yet another exemplary embodiment, the organic material layer including the compound represented by Formula 1 may include the compound represented by Formula 1 as a host, further include a fluorescent host or a phosphorescent host, and include another organic compound, a metal or a metal compound as a dopant.

As still yet another example, the organic material layer including the compound represented by Formula 1 may include the compound represented by Formula 1 as a host, further include a fluorescent host or a phosphorescent host, and may use an iridium (Ir)-based dopant together.

In an exemplary embodiment of the present specification, the first electrode is a positive electrode, and the second electrode is a negative electrode.

According to another exemplary embodiment, the first electrode is a negative electrode, and the second electrode is a positive electrode.

The organic light emitting device may have, for example, the stacking structure described below, but the stacking structure is not limited thereto.

(1) Positive electrode/Hole transport layer/Light emitting layer/Negative electrode (2) Positive electrode/Hole injection layer/Hole transport layer/Light emitting layer/Negative electrode (3) Positive electrode/Hole injection layer/Hole buffer layer/Hole transport layer/Light emitting layer/Negative electrode (4) Positive electrode/Hole transport layer/Light emitting layer/Electron transport layer/Negative electrode (5) Positive electrode/Hole transport layer/Light emitting layer/Electron transport layer/Electron injection layer/Negative electrode (6) Positive electrode/Hole injection layer/Hole transport layer/Light emitting layer/Electron transport layer/Negative electrode (7) Positive electrode/Hole injection layer/Hole transport layer/Light emitting layer/Electron transport layer/Electron injection layer/Negative electrode (8) Positive electrode/Hole injection layer/Hole buffer layer/Hole transport layer/Light emitting layer/Electron transport layer/Negative electrode (9) Positive electrode/Hole injection layer/Hole buffer layer/Hole transport layer/Light emitting layer/Electron transport layer/Electron injection layer/Negative electrode

(10) Positive electrode/Hole transport layer/Electron blocking layer/Light emitting layer/Electron transport layer/Negative electrode

(11) Positive electrode/Hole transport layer/Electron blocking layer/Light emitting layer/Electron transport layer/Electron injection layer/Negative electrode

(12) Positive electrode/Hole injection layer/Hole transport layer/Electron blocking layer/Light emitting layer/Electron transport layer/Negative electrode

(13) Positive electrode/Hole injection layer/Hole transport layer/Electron blocking layer/Light emitting layer/Electron transport layer/Electron injection layer/Negative electrode

(14) Positive electrode/Hole transport layer/Light emitting layer/Hole blocking layer/Electron transport layer/Negative electrode

(15) Positive electrode/Hole transport layer/Light emitting layer/Hole blocking layer/Electron transport layer/Electron injection layer/Negative electrode

(16) Positive electrode/Hole injection layer/Hole transport layer/Light emitting layer/Hole blocking layer/Electron transport layer/Negative electrode

(17) Positive electrode/Hole injection layer/Hole transport layer/Light emitting layer/Hole blocking layer/Electron transport layer/Electron injection layer/Negative electrode

(18) Positive electrode/Hole injection layer/Hole transport layer/Light emitting layer/Layer which simultaneously injects and transports electrons/Negative electrode The structure of the organic light emitting device of the present invention may have structures illustrated in FIGS. 1 and 2, but is not limited thereto.

FIG. 1 exemplifies the structure of an organic light emitting device in which a positive electrode 2, a light emitting layer 3, and a negative electrode 4 are sequentially stacked on a substrate 1. In the structure described above, the compound may be included in the light emitting layer 3.

FIG. 2 exemplifies the structure of an organic light emitting device in which a positive electrode 2, a hole injection layer 5, a hole transport layer 6, a light emitting layer 7, an electron transport layer 8, and a negative electrode 4 are sequentially stacked on a substrate 1. In the structure described above, the compound may be included in the light emitting layer 7 or the electron transport layer 8.

For example, the organic light emitting device according to the present invention may be manufactured by depositing a metal or a metal oxide having conductivity, or an alloy thereof on a substrate to form a positive electrode, forming an organic material layer including a hole injection layer, a hole transport layer, an electron blocking layer, a light emitting layer, and an electron transport layer thereon, and then depositing a material, which may be used as a negative electrode, thereon, by using a physical vapor deposition (PVD) method such as sputtering or e-beam evaporation. In addition to the method described above, an organic light emitting device may also be made by sequentially depositing a negative electrode material, an organic material layer, and a positive electrode material on a substrate.

The organic material layer may have a multi-layered structure including a hole injection layer, a hole transport layer, an electron blocking layer, a light emitting layer, and an electron transport layer, and the like, but is not limited thereto and may have a single-layered structure. Further, the organic material layer may be manufactured as a fewer number of layers by a method such as a solvent process, for example, spin coating, dip coating, doctor blading, screen printing, inkjet printing, or a thermal transfer method, using various polymer materials, instead of a deposition method.

As the positive electrode material, materials having a high work function are usually preferred so as to facilitate the injection of holes into an organic material layer. Specific examples of the positive electrode material which may be used in the present invention include: a metal such as vanadium, chromium, copper, zinc, and gold, or an alloy thereof; a metal oxide such as zinc oxide, indium oxide, indium tin oxide (ITO), and indium zinc oxide (IZO); a combination of a metal and an oxide, such as ZnO:Al or SnO$_2$:Sb; a conductive polymer such as poly(3-methylthiophene), poly[3,4-(ethylene-1,2-dioxy)thiophene] (PEDOT), polypyrrole, and polyaniline; and the like, but are not limited thereto.

As the negative electrode material, materials having a low work function are usually preferred so as to facilitate the injection of electrons into an organic material layer. Specific examples of the negative electrode material include: a metal such as magnesium, calcium, sodium, potassium, titanium, indium, yttrium, lithium, gadolinium, aluminum, silver, tin, and lead, or an alloy thereof; a multi-layer structured material, such as LiF/Al or LiO$_2$/Al; and the like, but are not limited thereto.

The hole injection material is a material which may proficiently accept holes from a positive electrode at low voltage, and the highest occupied molecular orbital (HOMO) of the hole injection material is preferably a value between the work function of the positive electrode material and the HOMO of the neighboring organic material layer. Specific examples of the hole injection material include metal porphyrin, oligothiophene, arylamine-based organic materials, hexanitrile hexaazatriphenylene-based organic materials, quinacridone-based organic materials, perylene-based organic materials, anthraquinone, polyaniline-based and polythiophene-based conductive polymers, and the like, but are not limited thereto.

The hole transport material is suitably a material having high hole mobility which may accept holes from a positive electrode or a hole injection layer and transfer the holes to a light emitting layer. Specific examples thereof include arylamine-based organic materials, conductive polymers, block copolymers having both conjugated portions and non-conjugated portions, and the like, but are not limited thereto.

An electron blocking layer may be provided between a hole transport layer and a light emitting layer. For the electron blocking layer, the above-described compound or a material known in the art may be used.

The light emitting layer may emit red, green, or blue light, and may be composed of a phosphorescent material or a fluorescent material. The light emitting material is a material which may receive holes and electrons from a hole transport layer and an electron transport layer, respectively, and combine the holes and the electrons to emit light in a visible ray region, and is preferably a material having good quantum efficiency to fluorescence or phosphorescence. Specific examples thereof include: 8-hydroxy-quinoline aluminum complexes (Alq$_3$); carbazole-based compounds; dimerized styryl compounds; BAlq; 10-hydroxybenzoquinoline-metal compounds; benzoxazole-based, benzothiazole-based and benzimidazole-based compounds; poly(p-phenylenevinylene) (PPV)-based polymers; spiro compounds; polyfluorene; rubrene; and the like, but are not limited thereto.

Examples of the host material of the light emitting layer include fused aromatic ring derivatives, or hetero ring-containing compounds, and the like. Specifically, examples of the fused aromatic ring derivatives include anthracene derivatives, pyrene derivatives, naphthalene derivatives, pentacene derivatives, phenanthrene compounds, fluoranthene compounds, and the like, and examples of the hetero ring-containing compounds include carbazole derivatives, dibenzofuran derivatives, ladder-type furan compounds, pyrimidine derivatives, and the like, but the examples thereof are not limited thereto.

Examples of an iridium-based complex used as a dopant of the light emitting layer include compounds described below, but are not limited thereto.

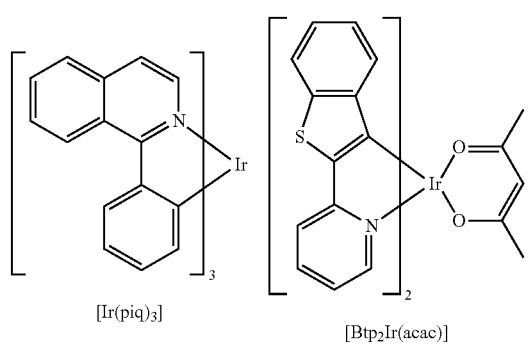

[Ir(piq)$_3$]   [Btp$_2$Ir(acac)]

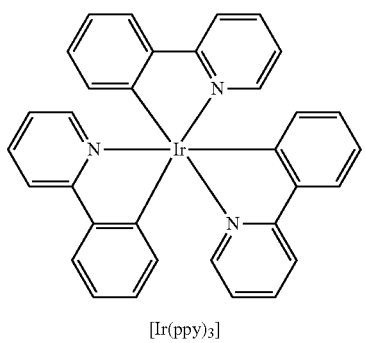

[Ir(ppy)₃]

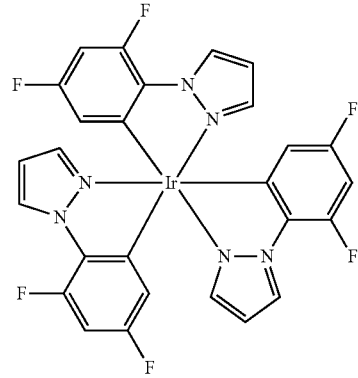

[Ir(dfppz)₃]

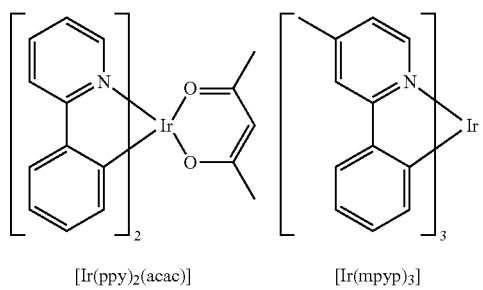

[Ir(ppy)₂(acac)]     [Ir(mpyp)₃]

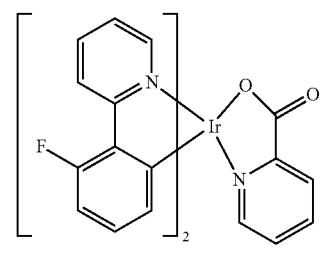

[F₂Irpic]

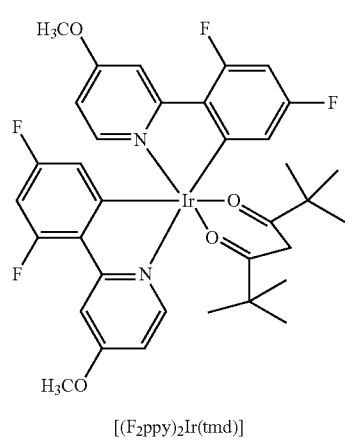

[(F₂ppy)₂Ir(tmd)]

The electron transport material is suitably a material having high electron mobility which may proficiently accept electrons from a negative electrode and transfer the electrons to a light emitting layer. Specific examples thereof include: Al complexes of 8-hydroxyquinoline; complexes including Alq₃; organic radical compounds; hydroxyflavone-metal complexes; and the like, but are not limited thereto.

The hole blocking layer is a layer which blocks holes from reaching a negative electrode, and may be generally formed under the same conditions as those of the hole injection layer. Specific examples thereof include oxadiazole derivatives or triazole derivatives, phenanthroline derivatives, BCP, aluminum complexes, and the like, but are not limited thereto.

The organic light emitting device according to the present invention may be a top emission type, a bottom emission type, or a dual emission type according to the material to be used.

A core structure may be prepared, as in the following reaction formula, for the compound represented by Formula 1 of the present specification. The substituent may be bonded by a method known in the art, and the type and position of the substituent and the number of substituents may be changed according to the technology known in the art.

MODE FOR INVENTION

Hereinafter, the present specification will be described in more detail through Examples. However, the following Examples are provided only for exemplifying the present specification, but are not intended to limit the present specification.

PREPARATION EXAMPLES

[Preparation Example 1] Preparation of Intermediates 1 to 5

1) Preparation of Intermediate 1 (sub 1)

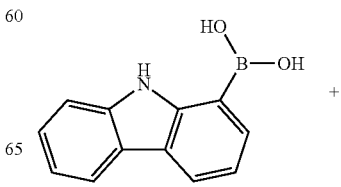

+

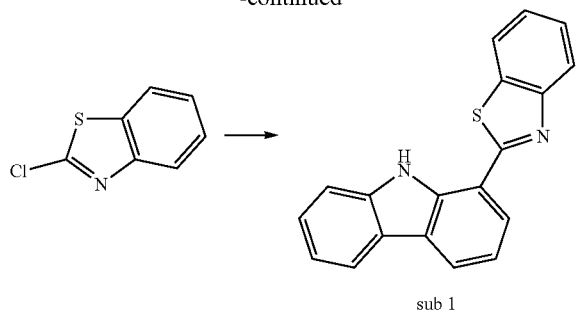

sub 1

(9H-carbazol-1-yl)boronic acid (50.0 g, 236.9 mmol) and 2-chlorobenzo[d]thiazole (40.0 g, 236.9 mmol) were put into 500 ml of tetrahydrofuran and the resulting mixture was stirred and refluxed in a nitrogen atmosphere. Thereafter, potassium carbonate (98.2 g, 710.6 mmol) was dissolved in 200 ml of water, the resulting solution was introduced thereinto, the resulting mixture was sufficiently stirred, and then tetrakistriphenyl-phosphinopalladium (8.2 g, 3 mol %) was introduced thereinto. After the reaction for 12 hours, the temperature of the mixture was lowered to room temperature, the organic layer and the aqueous layer were separated, and then the organic layer was distilled under reduced pressure. The distillate was extracted with chloroform and water, and then the organic layer was dried by using magnesium sulfate. Thereafter, the organic layer was dried, and then sub 1 (45.5 g, 64%) was prepared through recrystallization with ethanol.

MS: [M+H]+=301

2) Preparation of Intermediate 2 (sub 2)

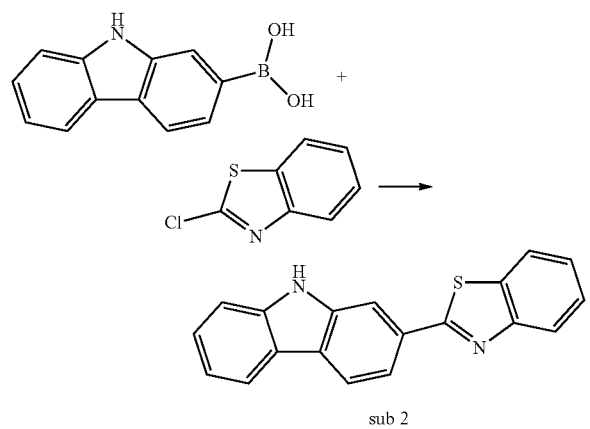

sub 2

(9H-carbazol-2-yl)boronic acid (50.0 g, 236.9 mmol) and 2-chlorobenzo[d]thiazole (40.0 g, 236.9 mmol) were put into 500 ml of tetrahydrofuran and the resulting mixture was stirred and refluxed in a nitrogen atmosphere. Thereafter, potassium carbonate (98.2 g, 710.6 mmol) was dissolved in 200 ml of water, the resulting solution was introduced thereinto, the resulting mixture was sufficiently stirred, and then tetrakistriphenyl-phosphinopalladium (8.2 g, 3 mol %) was introduced thereinto. After the reaction for 12 hours, the temperature of the mixture was lowered to room temperature, the organic layer and the aqueous layer were separated, and then the organic layer was distilled under reduced pressure. The distillate was extracted with chloroform and water, and then the organic layer was dried by using magnesium sulfate. Thereafter, the organic layer was dried, and then sub 2 (51.2 g, 72%) was prepared through recrystallization with ethanol.

MS: [M+H]+=301

3) Preparation of Intermediate 3 (sub 3)

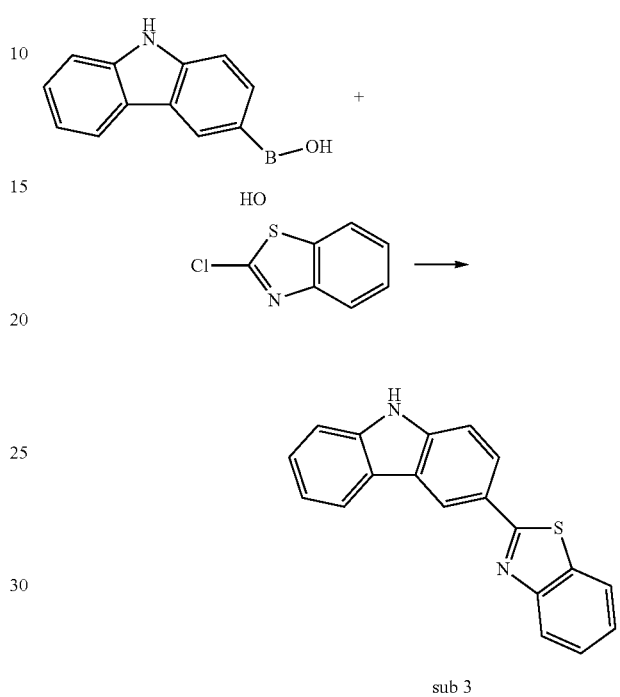

sub 3

(9H-carbazol-3-yl)boronic acid (50.0 g, 236.9 mmol) and 2-chlorobenzo[d]thiazole (40.0 g, 236.9 mmol) were put into 500 ml of tetrahydrofuran and the resulting mixture was stirred and refluxed in a nitrogen atmosphere. Thereafter, potassium carbonate (98.2 g, 710.6 mmol) was dissolved in 200 ml of water, the resulting solution was introduced thereinto, the resulting mixture was sufficiently stirred, and then tetrakistriphenyl-phosphinopalladium (8.2 g, 3 mol %) was introduced thereinto. After the reaction for 12 hours, the temperature of the mixture was lowered to room temperature, the organic layer and the aqueous layer were separated, and then the organic layer was distilled under reduced pressure. The distillate was extracted with chloroform and water, and then the organic layer was dried by using magnesium sulfate. Thereafter, the organic layer was dried, and then sub 3 (40.5 g, 57%) was prepared through recrystallization with ethanol.

MS: [M+H]+=301

4) Preparation of Intermediate 4 (sub 4)

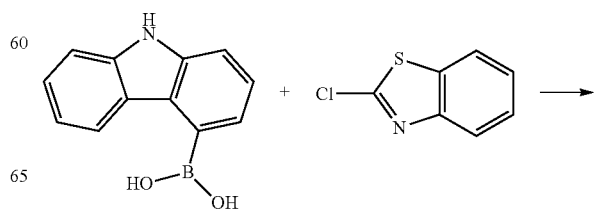

-continued

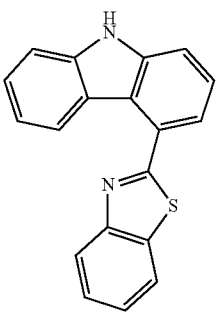

sub 4

(9H-carbazol-4-yl)boronic acid (50.0 g, 236.9 mmol) and 2-chlorobenzo[d]thiazole (40.0 g, 236.9 mmol) were put into 500 ml of tetrahydrofuran and the resulting mixture was stirred and refluxed in a nitrogen atmosphere. Thereafter, potassium carbonate (98.2 g, 710.6 mmol) was dissolved in 200 ml of water, the resulting solution was introduced thereinto, the resulting mixture was sufficiently stirred, and then tetrakistriphenyl-phosphinopalladium (8.2 g, 3 mol %) was introduced thereinto. After the reaction for 12 hours, the temperature of the mixture was lowered to room temperature, the organic layer and the aqueous layer were separated, and then the organic layer was distilled under reduced pressure. The distillate was extracted with chloroform and water, and then the organic layer was dried by using magnesium sulfate. Thereafter, the organic layer was dried, and then sub 4 (44.8 g, 63%) was prepared through recrystallization with ethanol.

MS: [M+H]+=301

5) Preparation of Intermediate 5 (sub 5)

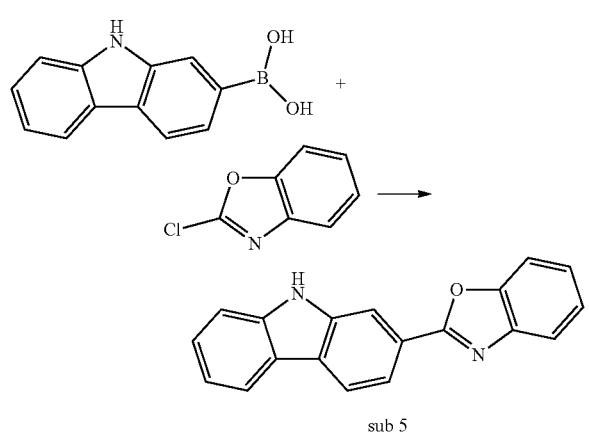

sub 5

(9H-carbazol-2-yl)boronic acid (50.0 g, 236.9 mmol) and 2-chlorobenzo[d]oxazole (36.2 g, 236.9 mmol) were put into 500 ml of tetrahydrofuran and the resulting mixture was stirred and refluxed in a nitrogen atmosphere. Thereafter, potassium carbonate (98.2 g, 710.6 mmol) was dissolved in 200 ml of water, the resulting solution was introduced thereinto, the resulting mixture was sufficiently stirred, and then tetrakistriphenyl-phosphinopalladium (8.2 g, 3 mol %) was introduced thereinto. After the reaction for 12 hours, the temperature of the mixture was lowered to room temperature, the organic layer and the aqueous layer were separated, and then the organic layer was distilled under reduced pressure. The distillate was extracted with chloroform and water, and then the organic layer was dried by using magnesium sulfate. Thereafter, the organic layer was dried, and then sub 5 (31.6 g, 47%) was prepared through recrystallization with ethanol.

MS: [M+H]+=285

[Preparation Example 2] Preparation of Compounds 1 to 14

1) Preparation of Compound 1

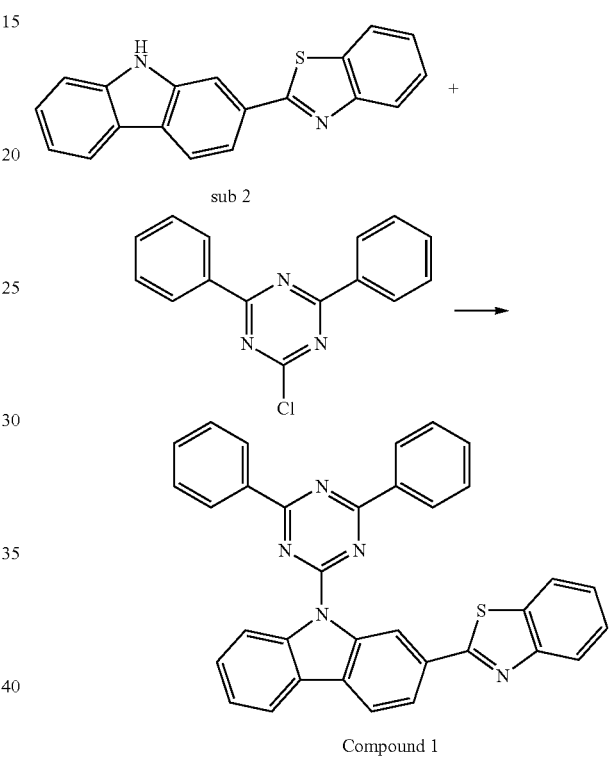

Compound 1

The compound sub 2 (20.0 g, 66.7 mmol) and 2-chloro-4,6-diphenyl-1,3,5-triazine (17.8 g, 66.7 mmol) were introduced into and dissolved in 200 mL of xylene, sodium tertiary-butoxide (18.4 g, 133.3 mmol) was added thereto, and the resulting mixture was warmed. Bis(tri tertiary-butylphosphine)palladium (1.0 g, 3 mol %) was introduced thereinto, and the resulting mixture was refluxed and stirred for 12 hours. When the reaction was completed, the temperature of the mixture was lowered to room temperature, and then the produced solid was filtered. After the solid was dissolved in 700 mL of chloroform and washed twice with water, the organic layer was separated, anhydrous magnesium sulfate was added thereto, the resulting mixture was stirred and then filtered, and the filtrate was distilled under reduced pressure. The concentrated compound was purified through recrystallization using chloroform and ethyl acetate to prepare a pale green solid Compound 1 (7.4 g, 21%).

MS: [M+H]+=532

2) Preparation of Compound 2

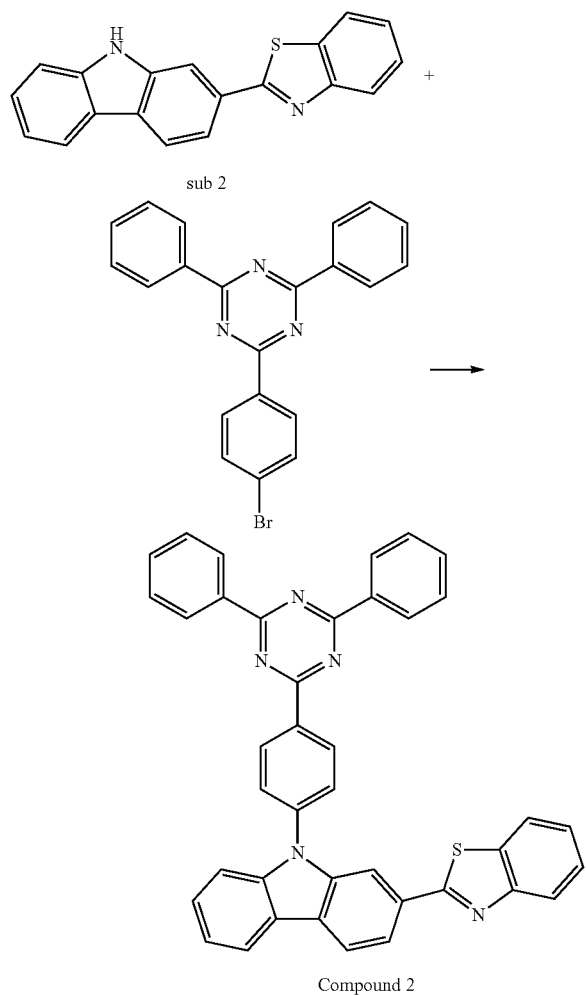

Compound 2

The compound sub 2 (20.0 g, 66.7 mmol) and 2-(4-bromophenyl)-4,6-diphenyl-1,3,5-triazine (25.8 g, 66.7 mmol) were introduced into and dissolved in 200 mL of xylene, sodium tertiary-butoxide (18.4 g, 133.3 mmol) was added thereto, and the resulting mixture was warmed. Bis(tri tertiary-butylphosphine)palladium (1.0 g, 3 mol %) was introduced thereinto, and the resulting mixture was refluxed and stirred for 12 hours. When the reaction was completed, the temperature of the mixture was lowered to room temperature, and then the produced solid was filtered. After the solid was dissolved in 700 mL of chloroform and washed twice with water, the organic layer was separated, anhydrous magnesium sulfate was added thereto, the resulting mixture was stirred and then filtered, and the filtrate was distilled under reduced pressure. The concentrated compound was purified through recrystallization using chloroform and ethyl acetate to prepare a pale green solid Compound 2 (31.2 g, 77%).

MS: [M+H]+=608

3) Preparation of Compound 3

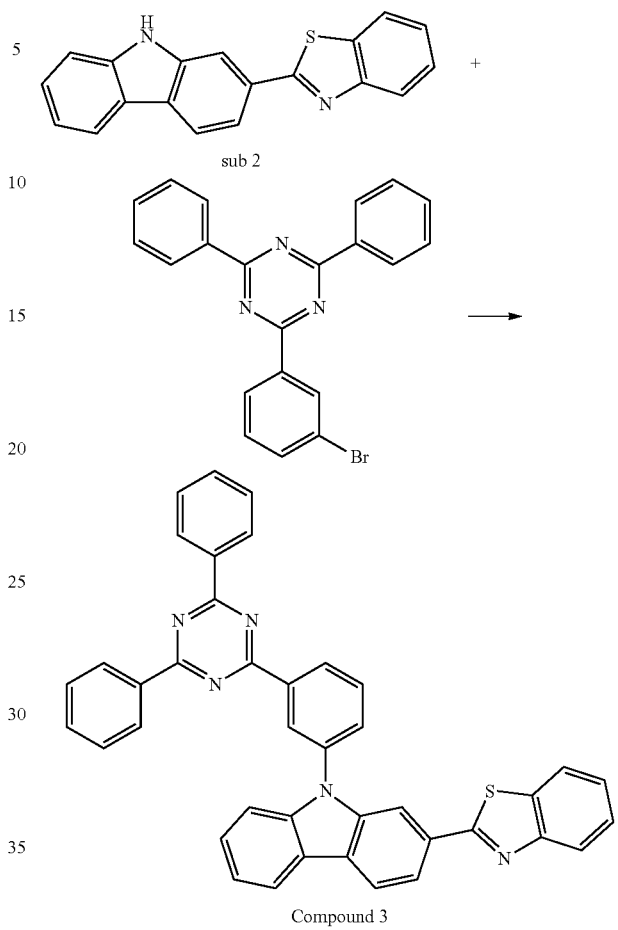

Compound 3

The compound sub 2 (20.0 g, 66.7 mmol) and 2-(3-bromophenyl)-4,6-diphenyl-1,3,5-triazine (25.8 g, 66.7 mmol) were introduced into and dissolved in 200 mL of xylene, sodium tertiary-butoxide (18.4 g, 133.3 mmol) was added thereto, and the resulting mixture was warmed. Bis(tri tertiary-butylphosphine)palladium (1.0 g, 3 mol %) was introduced thereinto, and the resulting mixture was refluxed and stirred for 12 hours. When the reaction was completed, the temperature of the mixture was lowered to room temperature, and then the produced solid was filtered. After the solid was dissolved in 700 mL of chloroform and washed twice with water, the organic layer was separated, anhydrous magnesium sulfate was added thereto, the resulting mixture was stirred and then filtered, and the filtrate was distilled under reduced pressure. The concentrated compound was purified through recrystallization using chloroform and ethyl acetate to prepare a pale green solid Compound 3 (19.8 g, 49%).

MS: [M+H]+=608

4) Preparation of Compound 4

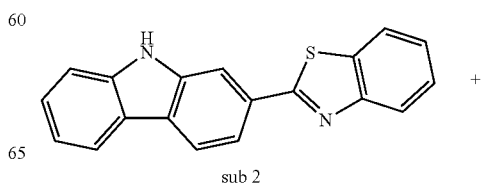

sub 2

-continued

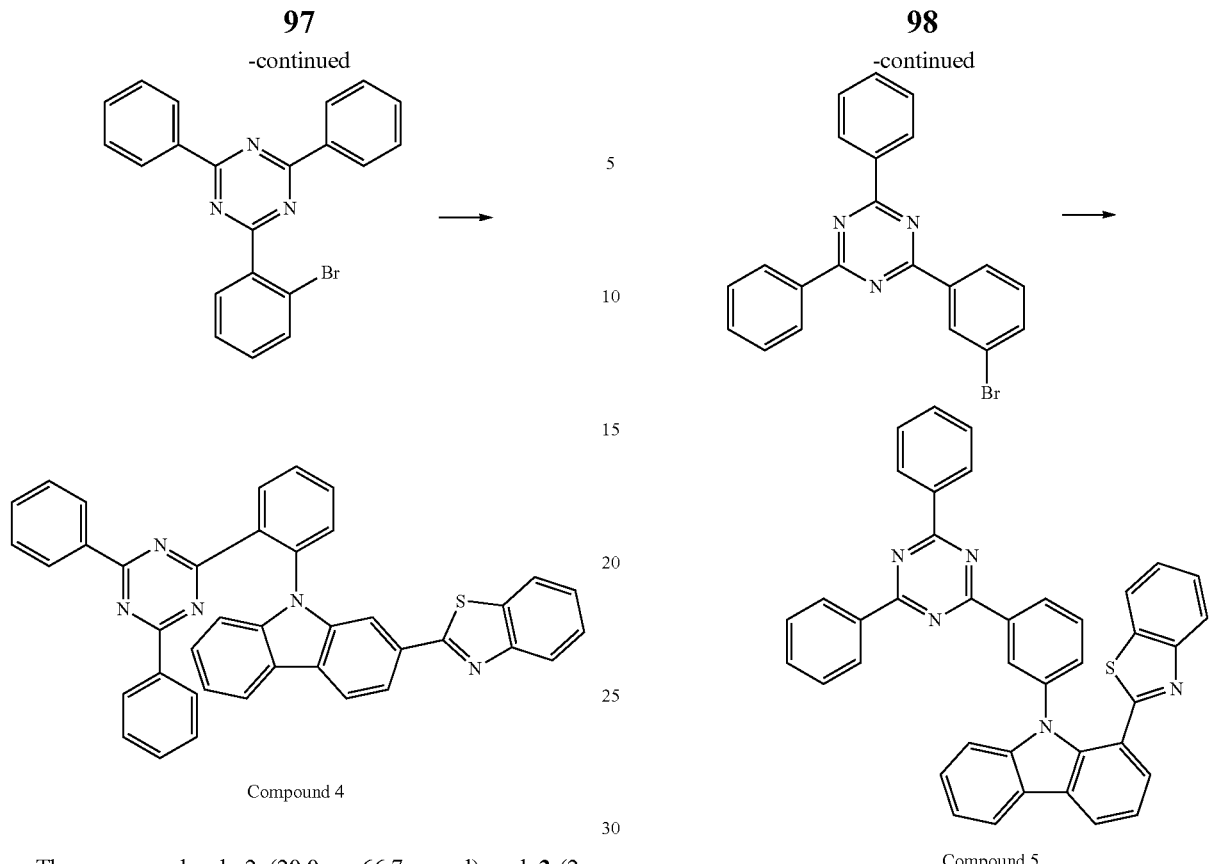

Compound 4

The compound sub 2 (20.0 g, 66.7 mmol) and 2-(2-bromophenyl)-4,6-diphenyl-1,3,5-triazine (25.8 g, 66.7 mmol) were introduced into and dissolved in 200 mL of xylene, sodium tertiary-butoxide (18.4 g, 133.3 mmol) was added thereto, and the resulting mixture was warmed. Bis(tri tertiary-butylphosphine)palladium (1.0 g, 3 mol %) was introduced thereinto, and the resulting mixture was refluxed and stirred for 12 hours. When the reaction was completed, the temperature of the mixture was lowered to room temperature, and then the produced solid was filtered. After the solid was dissolved in 700 mL of chloroform and washed twice with water, the organic layer was separated, anhydrous magnesium sulfate was added thereto, the resulting mixture was stirred and then filtered, and the filtrate was distilled under reduced pressure. The concentrated compound was purified through recrystallization using chloroform and ethyl acetate to prepare a pale green solid Compound 4 (8.9 g, 22%).

MS: [M+H]+=608

5) Preparation of Compound 5

-continued

Compound 5

The compound sub 1 (20.0 g, 66.7 mmol) and 2-(3-bromophenyl)-4,6-diphenyl-1,3,5-triazine (25.8 g, 66.7 mmol) were introduced into and dissolved in 200 mL of xylene, sodium tertiary-butoxide (18.4 g, 133.3 mmol) was added thereto, and the resulting mixture was warmed. Bis(tri tertiary-butylphosphine)palladium (1.0 g, 3 mol %) was introduced thereinto, and the resulting mixture was refluxed and stirred for 12 hours. When the reaction was completed, the temperature of the mixture was lowered to room temperature, and then the produced solid was filtered. After the solid was dissolved in 700 mL of chloroform and washed twice with water, the organic layer was separated, anhydrous magnesium sulfate was added thereto, the resulting mixture was stirred and then filtered, and the filtrate was distilled under reduced pressure. The concentrated compound was purified through recrystallization using chloroform and ethyl acetate to prepare a pale green solid Compound 5 (17.8 g, 44%).

MS: [M+H]+=608

6) Preparation of Compound 6

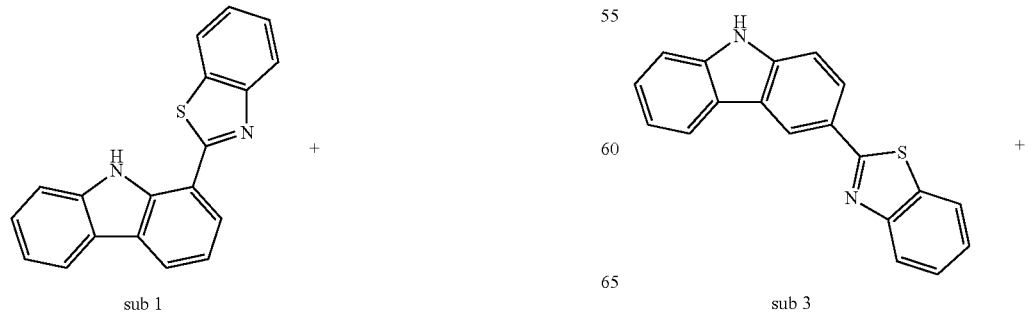

sub 1 sub 3

-continued

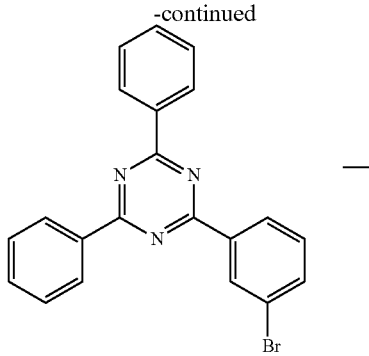

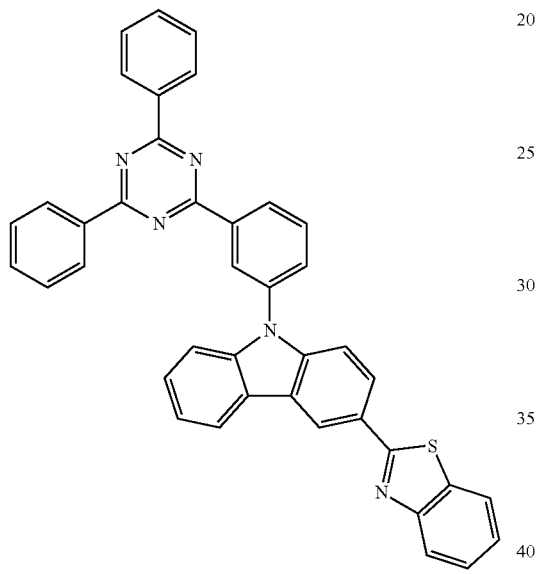

Compound 6

The compound sub 3 (20.0 g, 66.7 mmol) and 2-(3-bromophenyl)-4,6-diphenyl-1,3,5-triazine (25.8 g, 66.7 mmol) were introduced into and dissolved in 200 mL of xylene, sodium tertiary-butoxide (18.4 g, 133.3 mmol) was added thereto, and the resulting mixture was warmed. Bis(tri tertiary-butylphosphine)palladium (1.0 g, 3 mol %) was introduced thereinto, and the resulting mixture was refluxed and stirred for 12 hours. When the reaction was completed, the temperature of the mixture was lowered to room temperature, and then the produced solid was filtered. After the solid was dissolved in 700 mL of chloroform and washed twice with water, the organic layer was separated, anhydrous magnesium sulfate was added thereto, the resulting mixture was stirred and then filtered, and the filtrate was distilled under reduced pressure. The concentrated compound was purified through recrystallization using chloroform and ethyl acetate to prepare a pale green solid Compound 6 (21.4 g, 53%).

MS: [M+H]+=608

7) Preparation of Compound 7

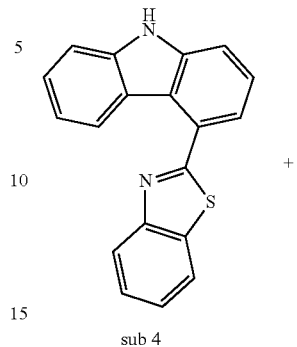

sub 4

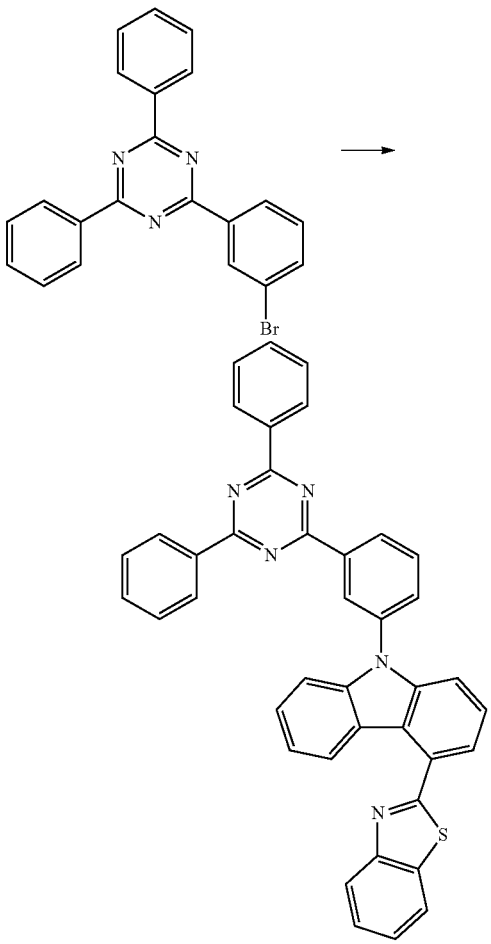

Compound 7

The compound sub 4 (20.0 g, 66.7 mmol) and 2-(3-bromophenyl)-4,6-diphenyl-1,3,5-triazine (25.8 g, 66.7 mmol) were introduced into and dissolved in 200 mL of xylene, sodium tertiary-butoxide (18.4 g, 133.3 mmol) was added thereto, and the resulting mixture was warmed. Bis(tri tertiary-butylphosphine)palladium (1.0 g, 3 mol %) was introduced thereinto, and the resulting mixture was refluxed and stirred for 12 hours. When the reaction was completed, the temperature of the mixture was lowered to room temperature, and then the produced solid was filtered. After the solid was dissolved in 700 mL of chloroform and washed twice with water, the organic layer was separated, anhydrous magnesium sulfate was added thereto, the resulting mixture was stirred and then filtered, and the filtrate was distilled under reduced pressure. The concentrated compound was purified through recrystallization using chloroform and ethyl acetate to prepare a pale green solid Compound 7 (24.3 g, 60%).

MS: [M+H]+=608

8) Preparation of Compound 8

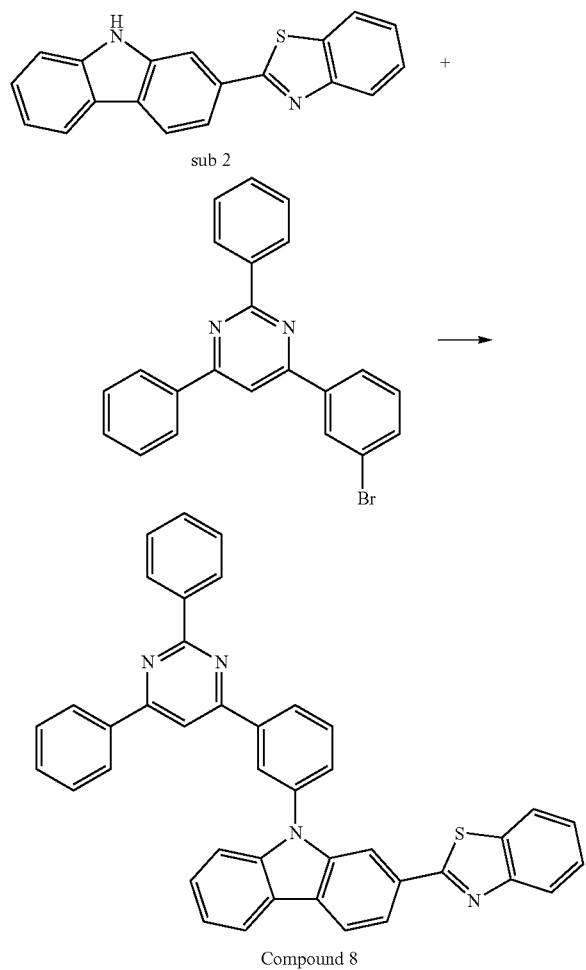

Compound 8

9) Preparation of Compound 9

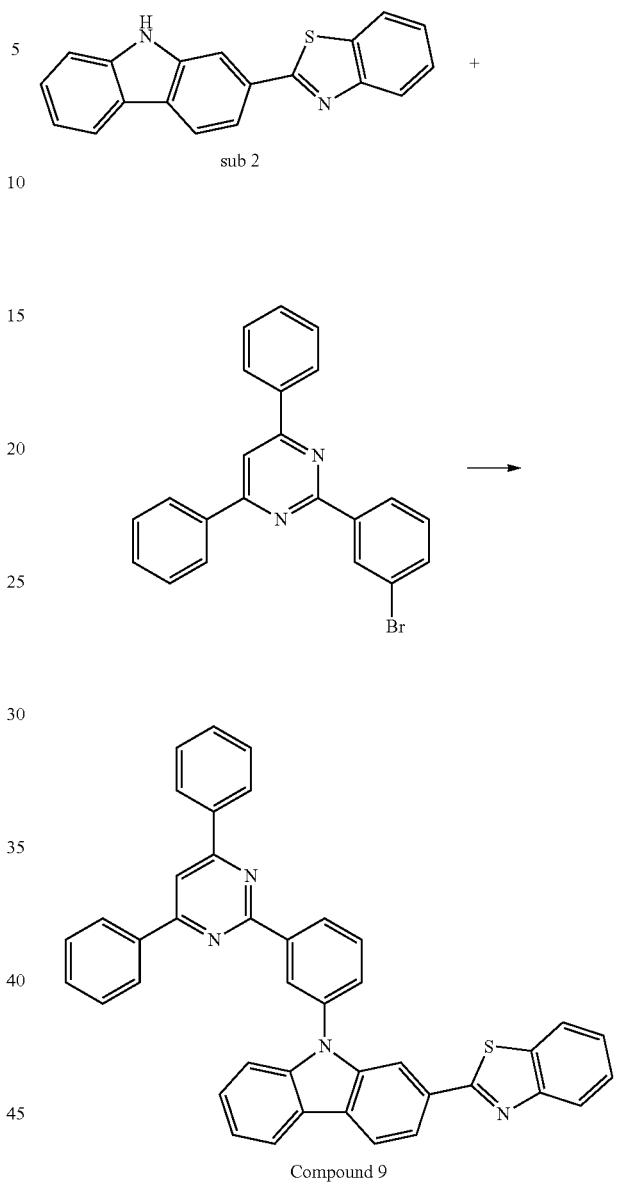

Compound 9

The compound sub 2 (20.0 g, 66.7 mmol) and 4-(3-bromophenyl)-2,6-diphenylpyrimidine (25.8 g, 66.7 mmol) were introduced into and dissolved in 200 mL of xylene, sodium tertiary-butoxide (18.4 g, 133.3 mmol) was added thereto, and the resulting mixture was warmed. Bis(tri tertiary-butylphosphine)palladium (1.0 g, 3 mol %) was introduced thereinto, and the resulting mixture was refluxed and stirred for 12 hours. When the reaction was completed, the temperature of the mixture was lowered to room temperature, and then the produced solid was filtered. After the solid was dissolved in 700 mL of chloroform and washed twice with water, the organic layer was separated, anhydrous magnesium sulfate was added thereto, the resulting mixture was stirred and then filtered, and the filtrate was distilled under reduced pressure. The concentrated compound was purified through recrystallization using chloroform and ethyl acetate to prepare a pale green solid Compound 8 (20.2 g, 50%).

MS: [M+H]+=607

The compound sub 2 (20.0 g, 66.7 mmol) and 2-(3-bromophenyl)-4,6-diphenylpyrimidine (25.8 g, 66.7 mmol) were introduced into and dissolved in 200 mL of xylene, sodium tertiary-butoxide (18.4 g, 133.3 mmol) was added thereto, and the resulting mixture was warmed. Bis(tri tertiary-butylphosphine)palladium (1.0 g, 3 mol %) was introduced thereinto, and the resulting mixture was refluxed and stirred for 12 hours. When the reaction was completed, the temperature of the mixture was lowered to room temperature, and then the produced solid was filtered. After the solid was dissolved in 700 mL of chloroform and washed twice with water, the organic layer was separated, anhydrous magnesium sulfate was added thereto, the resulting mixture was stirred and then filtered, and the filtrate was distilled under reduced pressure. The concentrated compound was purified through recrystallization using chloroform and ethyl acetate to prepare a pale green solid Compound 9 (14.9 g, 37%).

MS: [M+H]+=607

10) Preparation of Compound 10

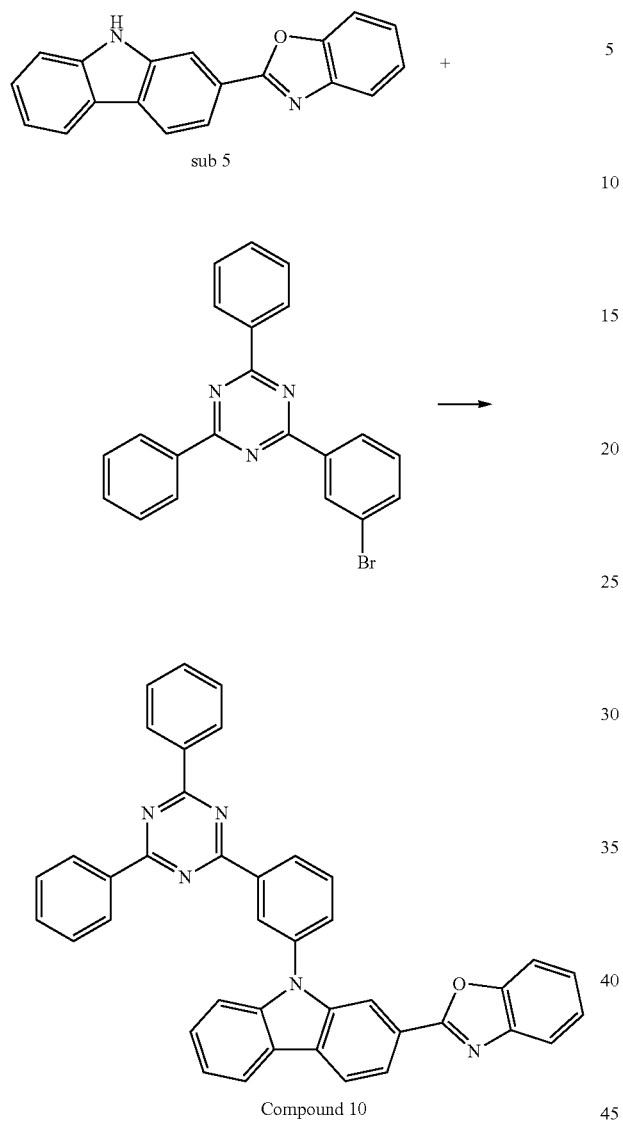

sub 5

Compound 10

11) Preparation of Compound 11

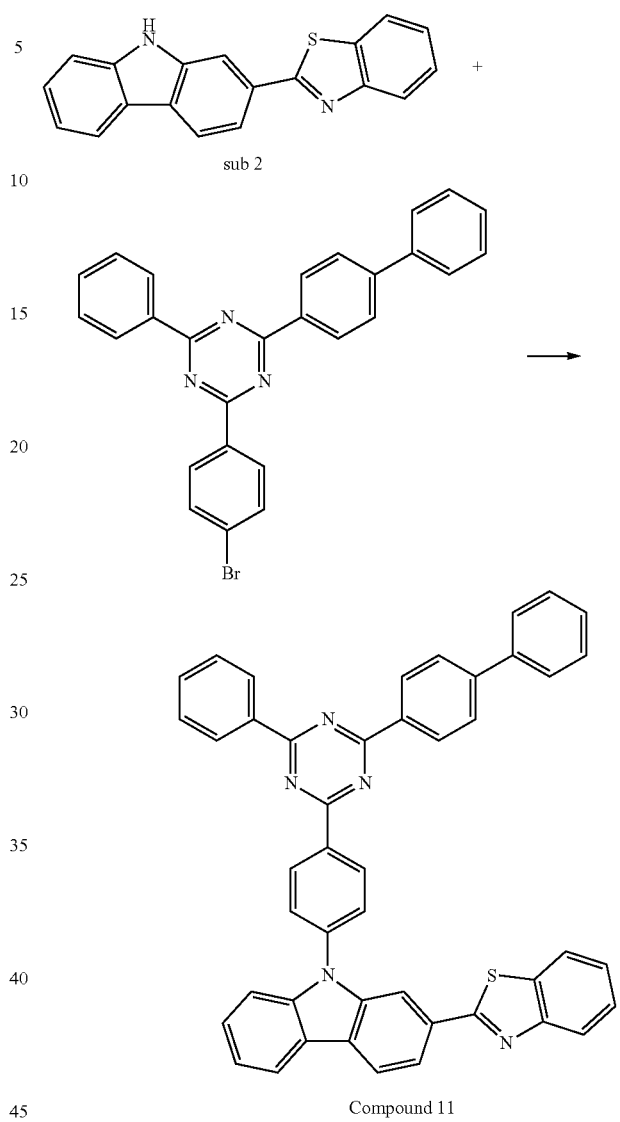

sub 2

Compound 11

The compound sub 5 (20.0 g, 70.4 mmol) and 2-(3-bromophenyl)-4,6-diphenyl-1,3,5-triazine (27.2 g, 70.4 mmol) were introduced into and dissolved in 200 mL of xylene, sodium tertiary-butoxide (19.5 g, 140.8 mmol) was added thereto, and the resulting mixture was warmed. Bis(tri tertiary-butylphosphine)palladium (1.1 g, 3 mol %) was introduced thereinto, and the resulting mixture was refluxed and stirred for 12 hours. When the reaction was completed, the temperature of the mixture was lowered to room temperature, and then the produced solid was filtered. After the solid was dissolved in 800 mL of chloroform and washed twice with water, the organic layer was separated, anhydrous magnesium sulfate was added thereto, the resulting mixture was stirred and then filtered, and the filtrate was distilled under reduced pressure. The concentrated compound was purified through recrystallization using chloroform and ethyl acetate to prepare a pale green solid Compound 10 (18.3 g, 44%).

MS: [M+H]+=592

The compound sub 2 (20.0 g, 66.7 mmol) and 2-([1,1'-biphenyl]-4-yl)-4-(4-bromophenyl)-6-phenyl-1,3,5-triazine (30.9 g, 66.7 mmol) were introduced into and dissolved in 200 mL of xylene, sodium tertiary-butoxide (18.4 g, 133.3 mmol) was added thereto, and the resulting mixture was warmed. Bis(tri tertiary-butylphosphine)palladium (1.0 g, 3 mol %) was introduced thereinto, and the resulting mixture was refluxed and stirred for 12 hours. When the reaction was completed, the temperature of the mixture was lowered to room temperature, and then the produced solid was filtered. After the solid was dissolved in 700 mL of chloroform and washed twice with water, the organic layer was separated, anhydrous magnesium sulfate was added thereto, the resulting mixture was stirred and then filtered, and the filtrate was distilled under reduced pressure. The concentrated compound was purified through recrystallization using chloroform and ethyl acetate to prepare a pale green solid Compound 11 (27.8 g, 61%).

MS: [M+H]+=684

12) Preparation of Compound 12

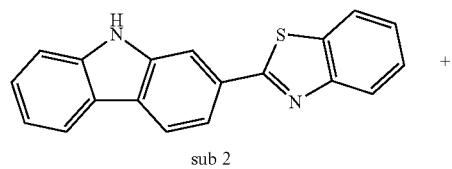

sub 2

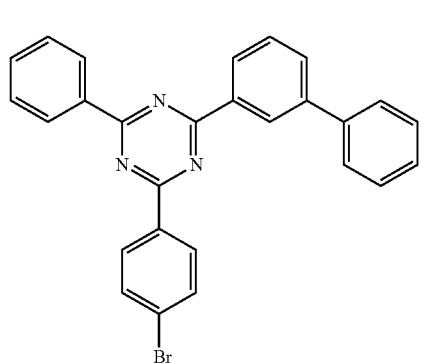

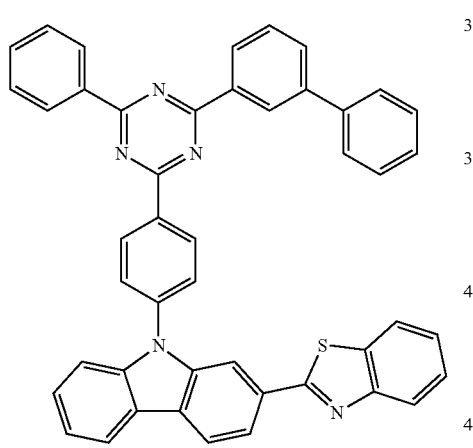

Compound 12

The compound sub 2 (20.0 g, 66.7 mmol) and 2-([1,1'-biphenyl]-3-yl)-4-(4-bromophenyl)-6-phenyl-1,3,5-triazine (30.9 g, 66.7 mmol) were introduced into and dissolved in 200 mL of xylene, sodium tertiary-butoxide (18.4 g, 133.3 mmol) was added thereto, and the resulting mixture was warmed. Bis(tri tertiary-butylphosphine)palladium (1.0 g, 3 mol %) was introduced thereinto, and the resulting mixture was refluxed and stirred for 12 hours. When the reaction was completed, the temperature of the mixture was lowered to room temperature, and then the produced solid was filtered. After the solid was dissolved in 700 mL of chloroform and washed twice with water, the organic layer was separated, anhydrous magnesium sulfate was added thereto, the resulting mixture was stirred and then filtered, and the filtrate was distilled under reduced pressure. The concentrated compound was purified through recrystallization using chloroform and ethyl acetate to prepare a pale green solid Compound 12 (26.4 g, 68%).

MS: [M+H]+=684

13) Preparation of Compound 13

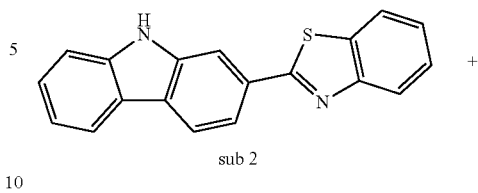

sub 2

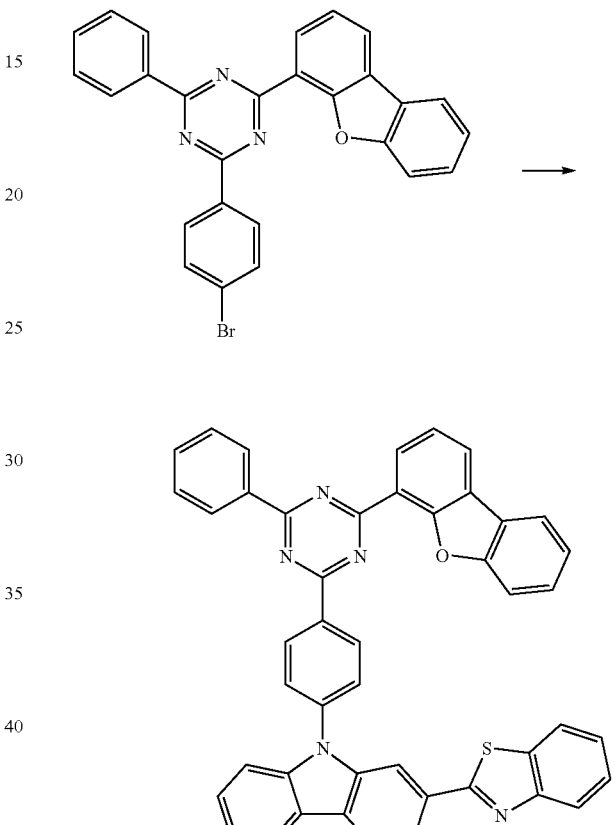

Compound 13

The compound sub 2 (20.0 g, 66.7 mmol) and 2-(4-bromophenyl)-4-(dibenzo[b,d]furan-4-yl)-6-phenyl-1,3,5-triazine (30.9 g, 66.7 mmol) were introduced into and dissolved in 200 mL of xylene, sodium tertiary-butoxide (18.4 g, 133.3 mmol) was added thereto, and the resulting mixture was warmed. Bis(tri tertiary-butylphosphine)palladium (1.0 g, 3 mol %) was introduced thereinto, and the resulting mixture was refluxed and stirred for 12 hours. When the reaction was completed, the temperature of the mixture was lowered to room temperature, and then the produced solid was filtered. After the solid was dissolved in 700 mL of chloroform and washed twice with water, the organic layer was separated, anhydrous magnesium sulfate was added thereto, the resulting mixture was stirred and then filtered, and the filtrate was distilled under reduced pressure. The concentrated compound was purified through recrystallization using chloroform and ethyl acetate to prepare a pale green solid Compound 13 (28.8 g, 62%).

MS: [M+H]+=698

14) Preparation of Compound 14

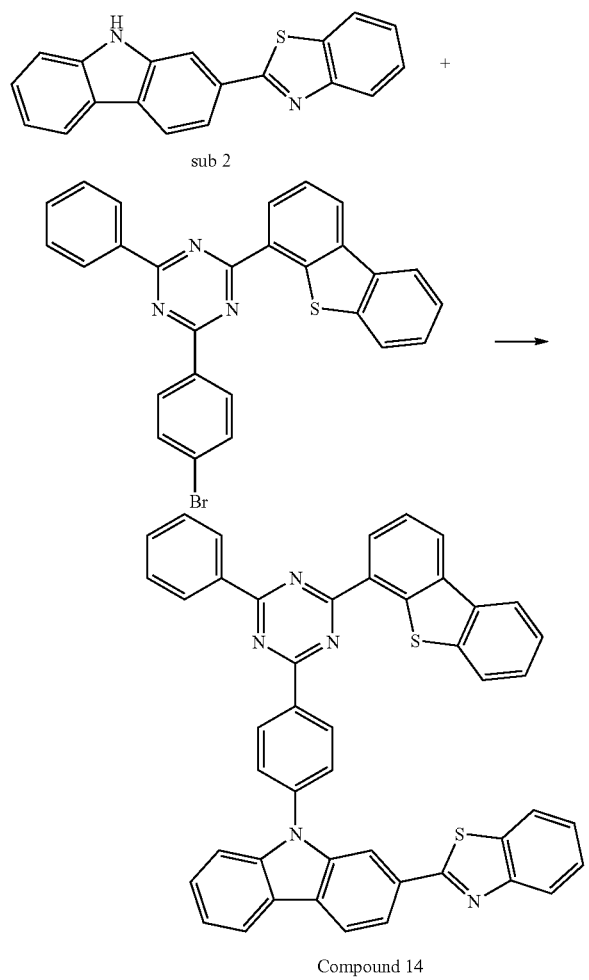

Compound 14

The compound sub 2 (20.0 g, 66.7 mmol) and 2-(4-bromophenyl)-4-(dibenzo[b,d]thiophen-4-yl)-6-phenyl-1,3,5-triazine (30.9 g, 66.7 mmol) were introduced into and dissolved in 200 mL of xylene, sodium tertiary-butoxide (18.4 g, 133.3 mmol) was added thereto, and the resulting mixture was warmed. Bis(tri tertiary-butylphosphine)palladium (1.0 g, 3 mol %) was introduced thereinto, and the resulting mixture was refluxed and stirred for 12 hours. When the reaction was completed, the temperature of the mixture was lowered to room temperature, and then the produced solid was filtered. After the solid was dissolved in 700 mL of chloroform and washed twice with water, the organic layer was separated, anhydrous magnesium sulfate was added thereto, the resulting mixture was stirred and then filtered, and the filtrate was distilled under reduced pressure. The concentrated compound was purified through recrystallization using chloroform and ethyl acetate to prepare a pale green solid Compound 14 (15.2 g, 32%).

MS: [M+H]+=714

Experimental Examples

Experimental Example 1

A glass substrate thinly coated with indium tin oxide (ITO) to have a thickness of 1,300 Å was put into distilled water in which a detergent was dissolved, and ultrasonically washed. In this case, a product manufactured by the Fischer Co., was used as the detergent, and distilled water twice filtered using a filter manufactured by Millipore Co., was used as the distilled water. After the ITO was washed for 30 minutes, ultrasonic washing was repeated twice by using distilled water for 10 minutes. After the washing using distilled water was completed, ultrasonic washing was conducted by using isopropyl alcohol, acetone, and methanol solvents, and the resulting product was dried and then transported to a plasma washing machine. Furthermore, the substrate was cleaned by using oxygen plasma for 5 minutes, and then was transported to a vacuum deposition machine.

The following HI-1 compound was thermally vacuum-deposited to have a thickness of 50 Å on the transparent ITO electrode, which was prepared as described above, thereby forming a hole injection layer. The following HT-1 compound was thermally vacuum-deposited to have a thickness of 250 Å on the hole injection layer, thereby forming a hole transport layer, and the following HT-2 compound was vacuum-deposited to have a thickness of 50 Å on the HT-1 deposition film, thereby forming an electron blocking layer. Compound 1 prepared previously in Preparation Example 2 as a light emitting layer, the following YGH-1 compound, and a phosphorescent dopant YGD-1 were co-deposited at a weight ratio of 44:44:12 on the HT-2 deposition film, thereby forming a light emitting layer having a thickness of 400 Å. The following ET-1 compound was vacuum-deposited to have a thickness of 250 Å on the light emitting layer, thereby forming an electron transport layer, and the following ET-2 compound and Li were vacuum-deposited at a weight ratio of 98:2 on the electron transport layer, thereby forming an electron injection layer having a thickness of 100 Å. Aluminum was deposited to have a thickness of 1,000 Å on the electron injection layer, thereby forming a negative electrode.

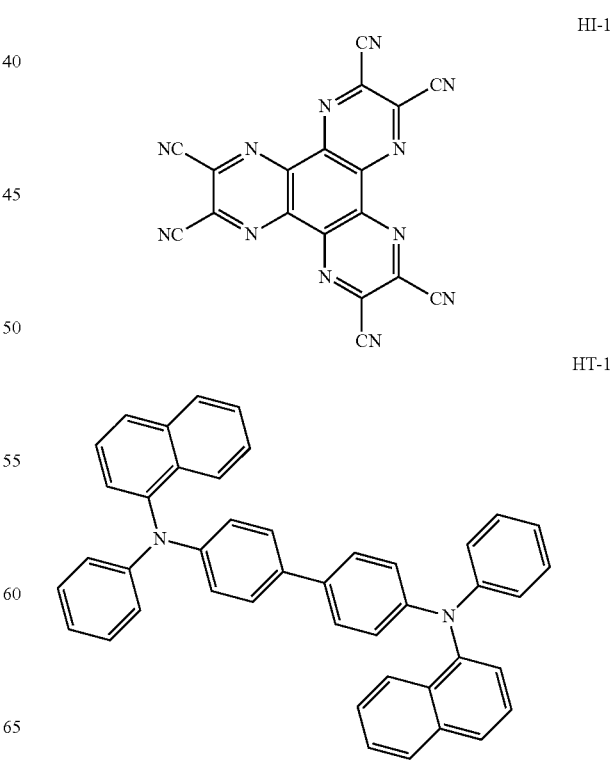

-continued

HT-2
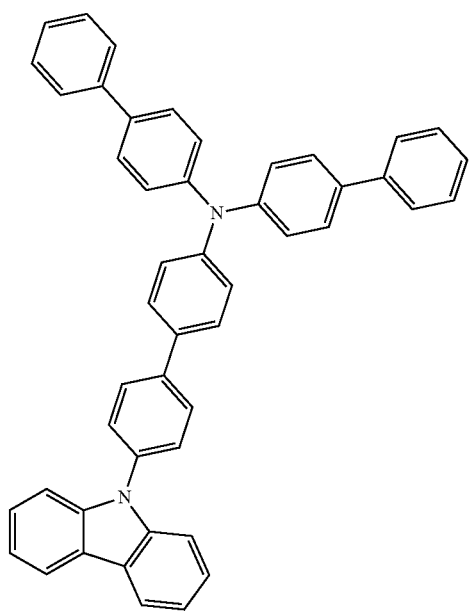

YGH-1
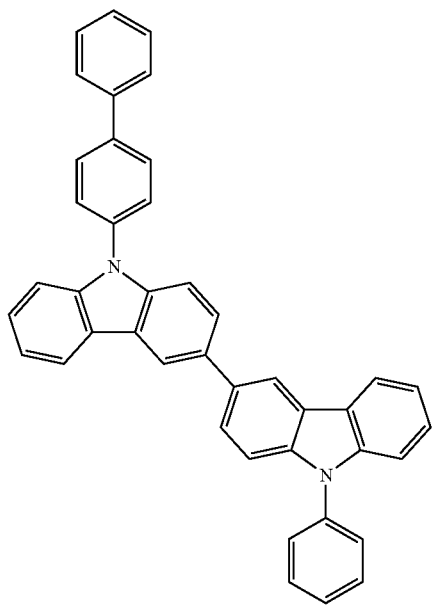

YGD-1
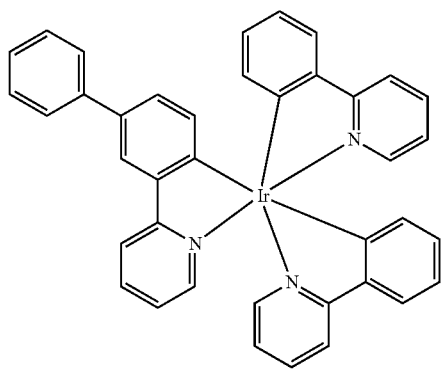

-continued

ET-1
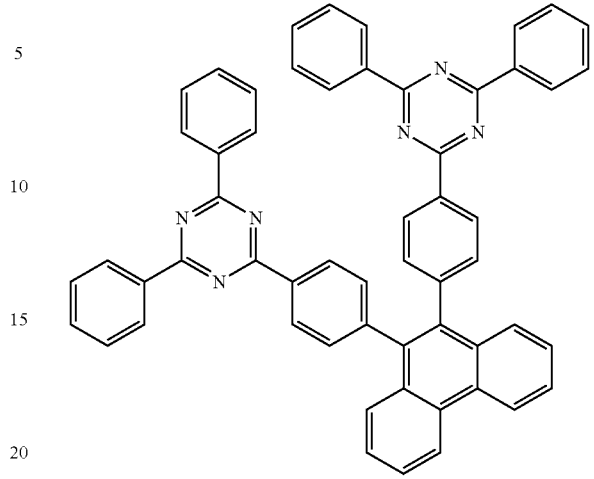

ET-2
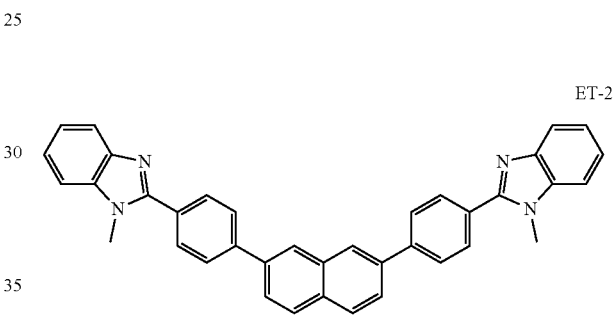

In the aforementioned procedure, the deposition rate of the organic material was maintained at 0.4 to 0.7 Å/sec, the deposition rate of aluminum was maintained at 2 Å/sec, and the degree of vacuum during the deposition was maintained at $5\times10^{-8}$ to $1\times10^{-7}$ torr.

Experimental Examples 2 to 14

Organic light emitting devices were manufactured in the same manner as in Experimental Example 1, except that in Experimental Example 1, the compounds described in the following Table 1 were used instead of Compound 1 in Experimental Example 1.

Comparative Experimental Examples 1 to 3

Organic light emitting devices were manufactured in the same manner as in Experimental Example 1, except that in Experimental Example 1, the compounds described in the following Table 1 were used instead of Compound 1 in Experimental Example 1. CE1 to CE3 Compounds of the following Table 1 were as follows.

CE1

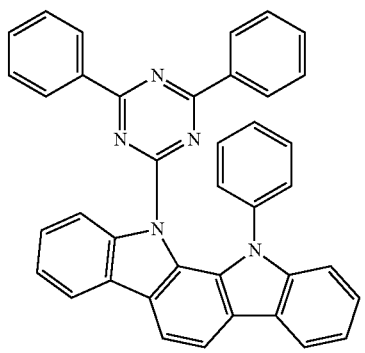

CE2

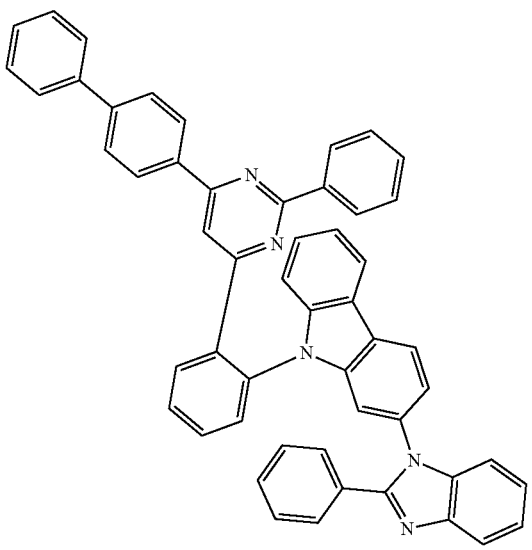

CE3

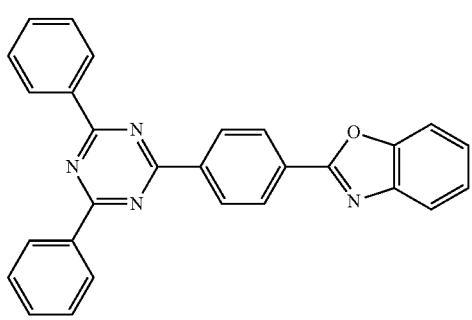

The voltage and efficiency of each of the organic light emitting devices in the Experimental Examples and the Comparative Experimental Examples were measured at a current density of 10 mA/cm², and the service life thereof was measured at a current density of 50 mA/cm², and the results thereof are shown in the following Table 1. In this case, $LT_{95}$ means time taken for the luminance to become 95% as compared to the initial luminance.

TABLE 1

| Compound | Voltage (V) (@10 mA/cm²) | Efficiency (Cd/A) (@10 mA/cm²) | Color coordinate (x, y) | Service life (h) ($LT_{95}$ at 50 mA/cm²) |
|---|---|---|---|---|
| Experimental Example 1 | Compound 1 | 4.4 | 79 | 0.44, 0.54 | 140 |
| Experimental Example 2 | Compound 2 | 4.1 | 82 | 0.46, 0.54 | 135 |
| Experimental Example 3 | Compound 3 | 4.0 | 83 | 0.46, 0.55 | 150 |
| Experimental Example 4 | Compound 4 | 4.1 | 81 | 0.46, 0.54 | 125 |
| Experimental Example 5 | Compound 5 | 4.1 | 81 | 0.46, 0.54 | 115 |
| Experimental Example 6 | Compound 6 | 4.1 | 81 | 0.46, 0.55 | 145 |
| Experimental Example 7 | Compound 7 | 4.0 | 83 | 0.46, 0.54 | 170 |
| Experimental Example 8 | Compound 8 | 4.2 | 83 | 0.46, 0.54 | 120 |
| Experimental Example 9 | Compound 9 | 4.2 | 82 | 0.46, 0.53 | 115 |
| Experimental Example 10 | Compound 10 | 4.1 | 79 | 0.46, 0.54 | 100 |
| Experimental Example 11 | Compound 11 | 4.2 | 82 | 0.46, 0.54 | 162 |
| Experimental Example 12 | Compound 12 | 4.2 | 82 | 0.46, 0.54 | 175 |
| Experimental Example 13 | Compound 13 | 4.3 | 81 | 0.46, 0.53 | 185 |
| Experimental Example 14 | Compound 14 | 4.2 | 81 | 0.46, 0.54 | 190 |
| Comparative Experimental Example 1 | CE1 | 4.5 | 75 | 0.46, 0.54 | 85 |
| Comparative Experimental Example 2 | CE2 | 4.4 | 70 | 0.47, 0.54 | 12 |
| Comparative Experimental Example 3 | CE3 | 4.6 | 55 | 0.48, 0.59 | 10 |

As shown in Table 1, it could be confirmed that when the compound of the present invention was used as a light emitting layer material, characteristics of excellent efficiency and long service life were exhibited as compared to the Comparative Experimental Examples. It is considered that as benzoxazole or benzothiazole was additionally substituted with a carbazoyl substituent, the electronic stability was increased.

What is claimed is:

1. An organic light emitting device comprising:
    a first electrode;
    a second electrode provided to face the first electrode; and
    an organic material layer having one or more layers provided between the first electrode and the second electrode,
    wherein the organic material layer comprises a light emitting layer, and the light emitting layer comprises a combination including a compound represented by Formula 1 and a dopant, wherein the dopant is a green light emitting material:

[Formula 1]

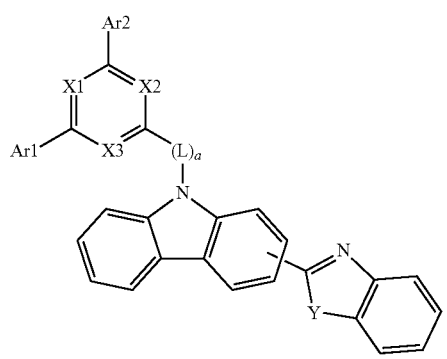

wherein in Formula 1:

at least two of X1 to X3 are N, and any remaining is CR;

R is hydrogen, deuterium, a substituted or unsubstituted alkyl group, a substituted or unsubstituted aryl group, or a substituted or unsubstituted heterocyclic group;

Ar1 and Ar2 are each independently a substituted or unsubstituted aryl group or a substituted or unsubstituted heterocyclic group;

Y is O or S;

L is a phenylene group;

a is 1 or 2; and

Ls in the parenthesis are the same as or different from each other when a is 2.

2. The organic light emitting device of claim 1, wherein Ar1 and Ar2 are each independently a substituted or unsubstituted phenyl group; a substituted or unsubstituted biphenyl group; a substituted or unsubstituted terphenyl group; a substituted or unsubstituted naphthyl group; a substituted or unsubstituted anthracenyl group; a substituted or unsubstituted phenanthrenyl group; a substituted or unsubstituted pyrenyl group; a substituted or unsubstituted perylenyl group; a substituted or unsubstituted triphenylene group; a substituted or unsubstituted chrysenyl group; a substituted or unsubstituted fluorenyl group; a substituted or unsubstituted dibenzothiophene group; or a substituted or unsubstituted dibenzofuran group.

3. The organic light emitting device of claim 1, wherein the compound of Formula 1 is any one of the following compounds:

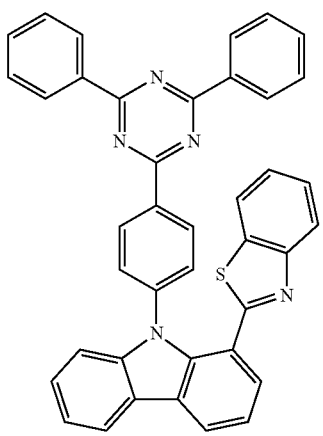

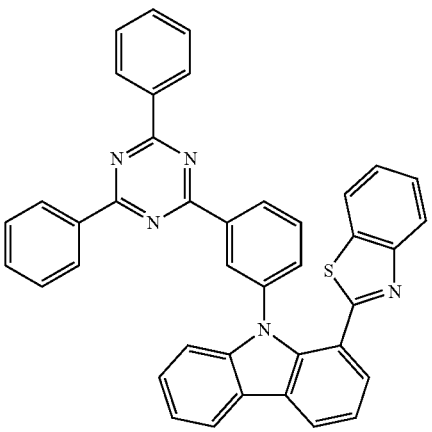

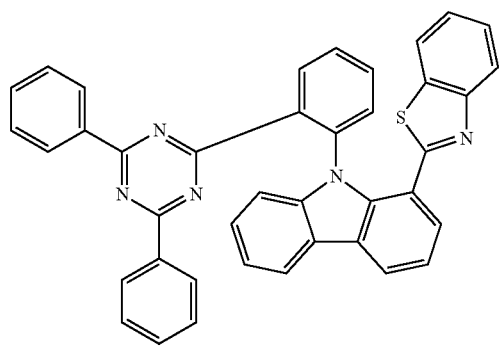

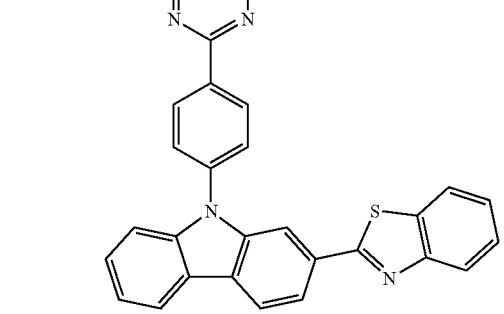

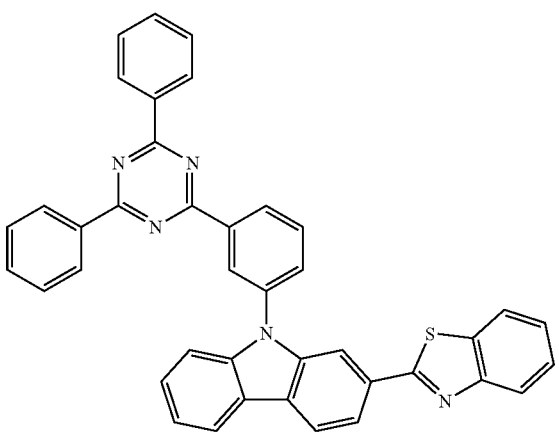 [SMILES: c1ccc(-c2cc(-c3ccccc3)nc(-c3cccc(-n4c5ccccc5c5ccc(-c6nc7ccccc7o6)cc54)c3)n2)cc1]

115
-continued
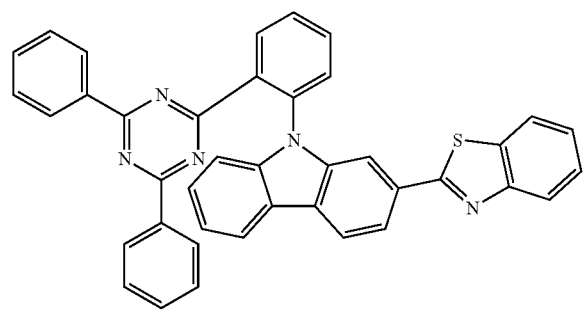
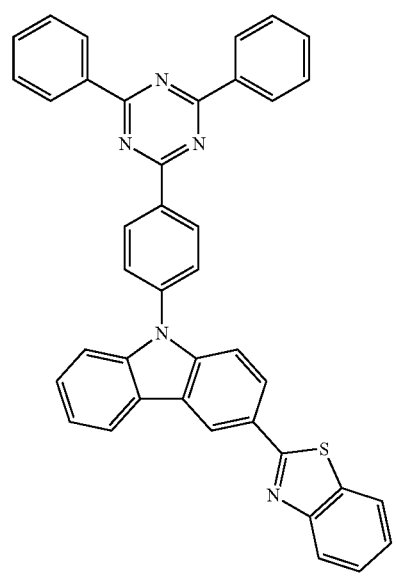
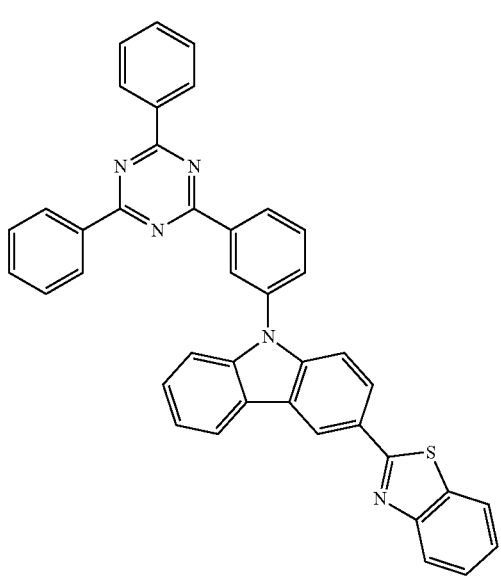
116
-continued
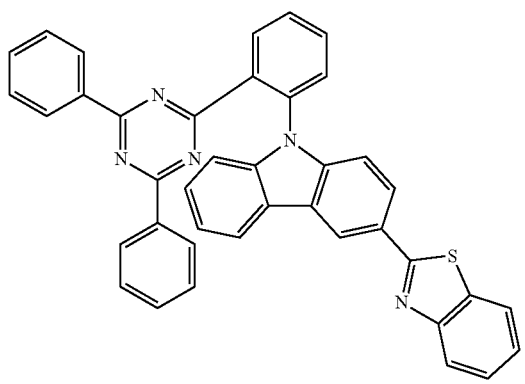
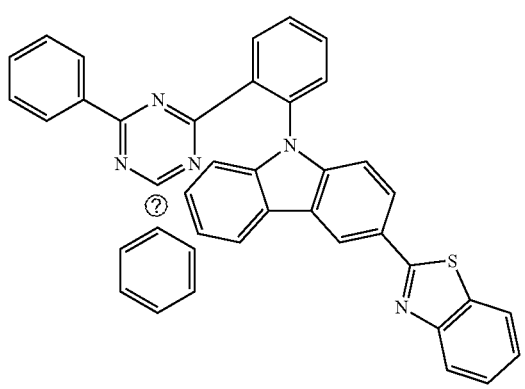
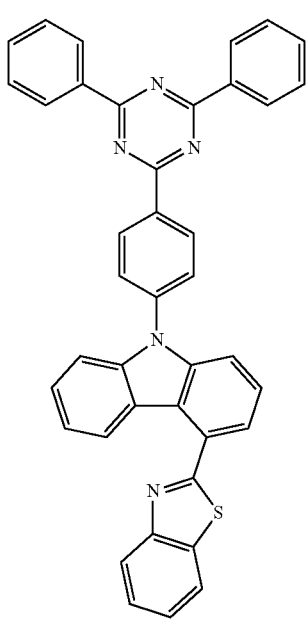

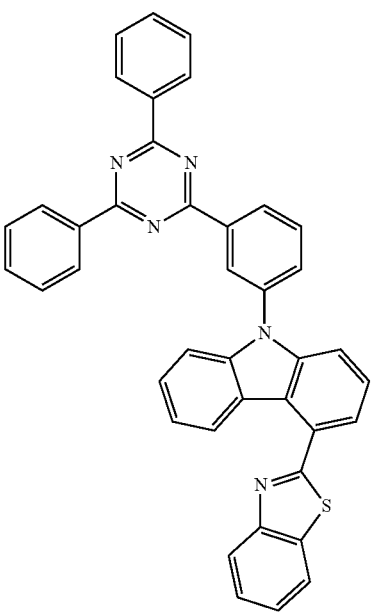
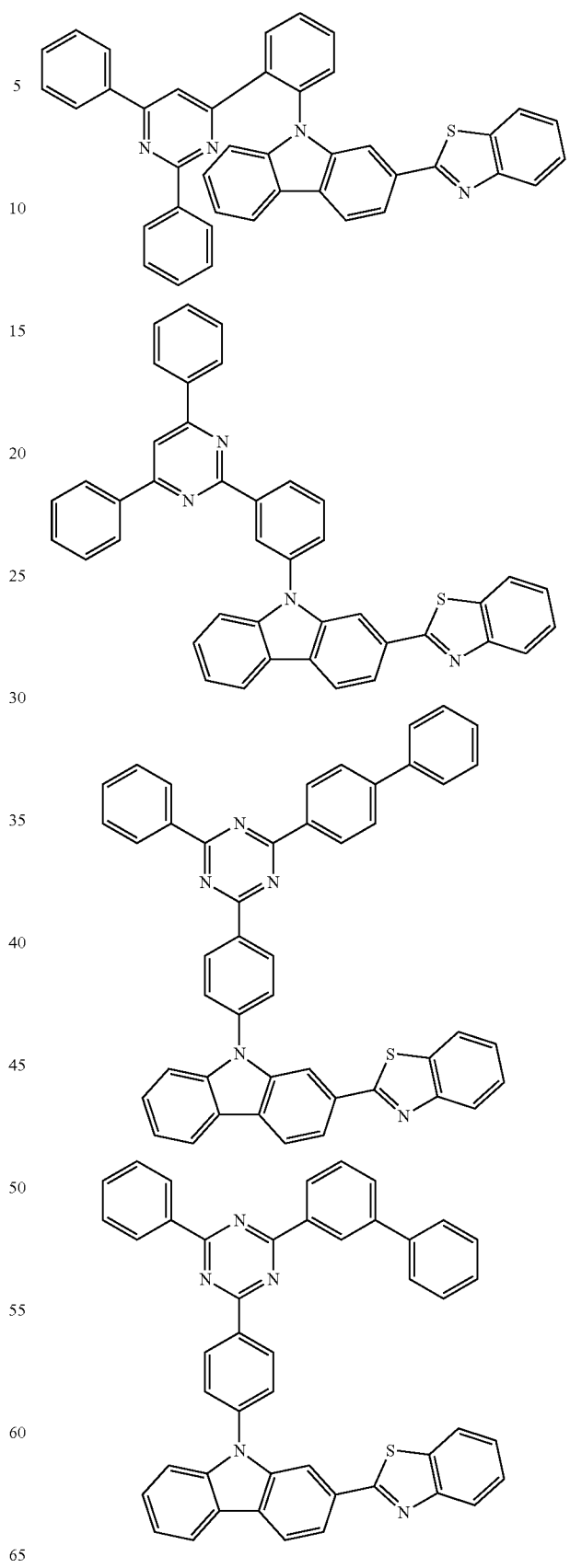

119
-continued
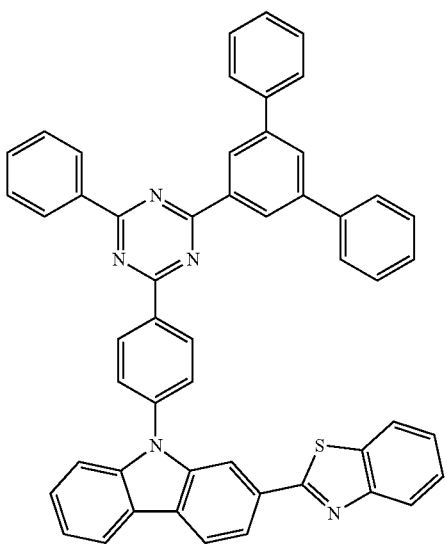
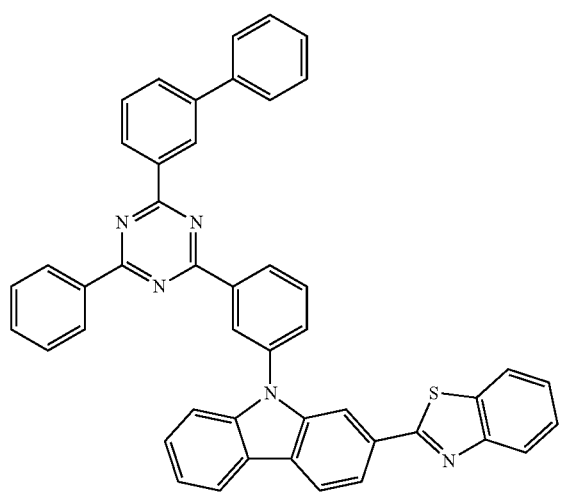
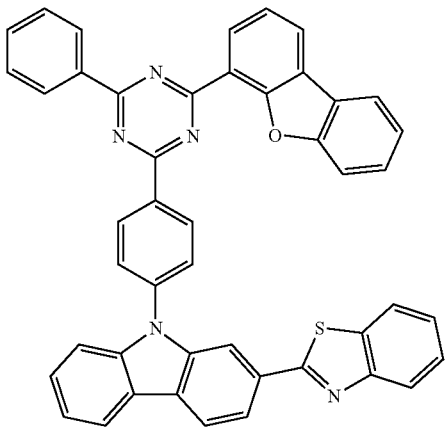
120
-continued
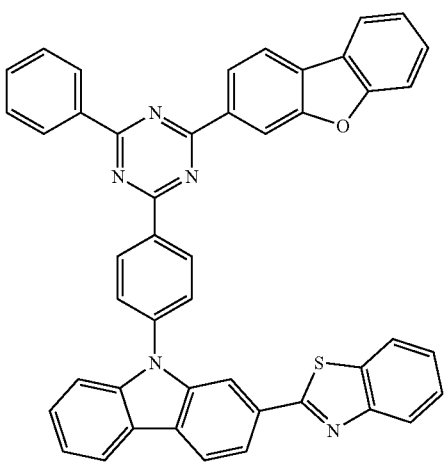
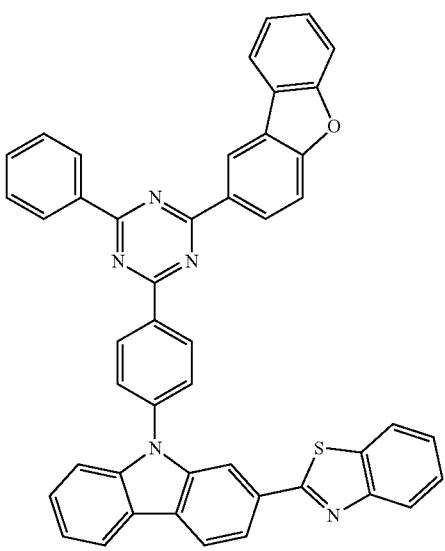
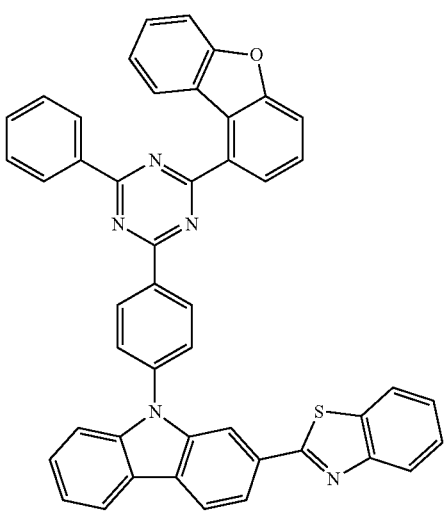

121
-continued
122
-continued
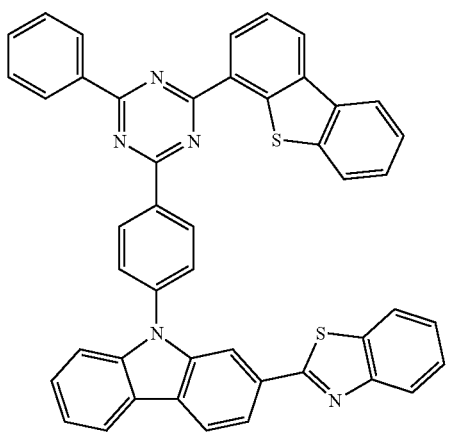
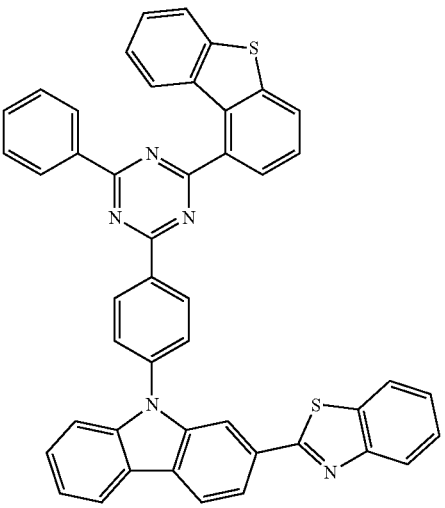

123
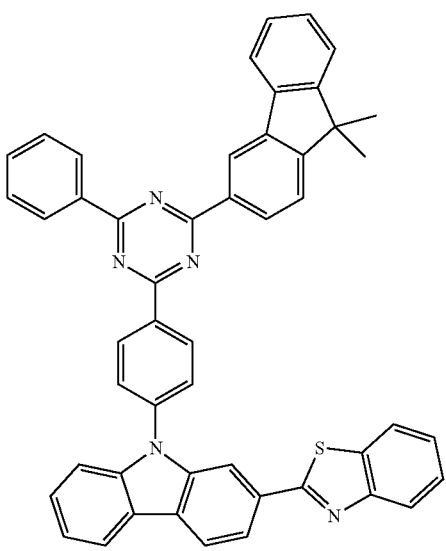
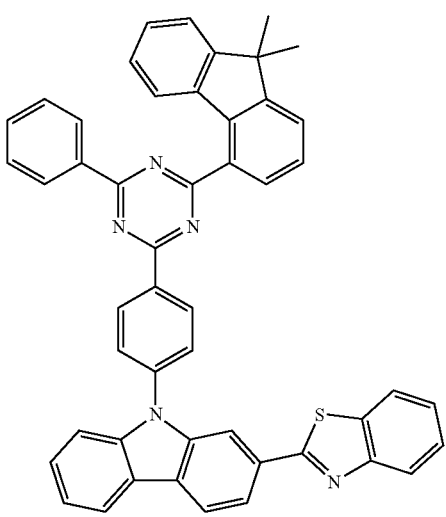
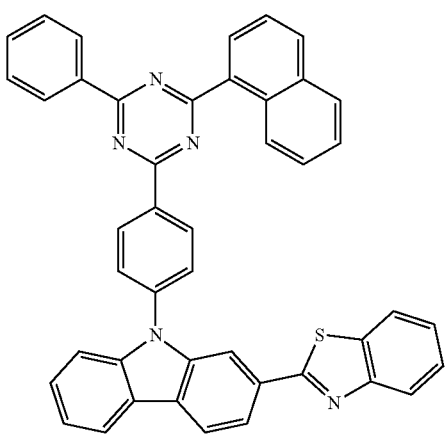
124
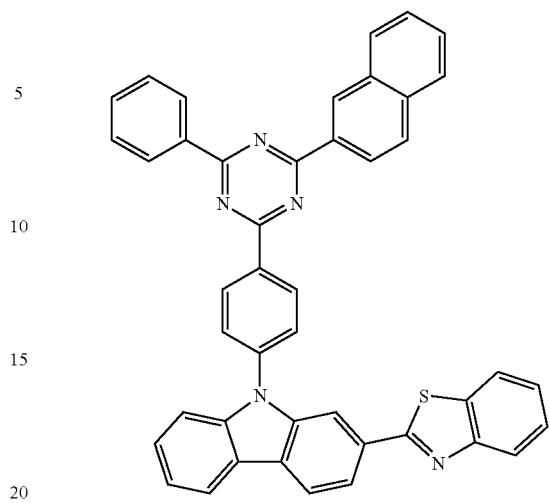
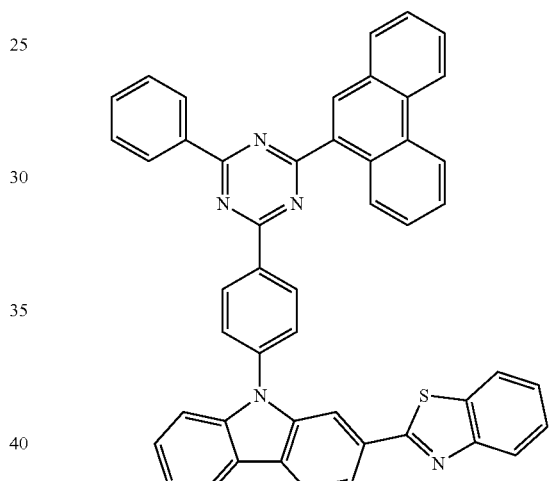
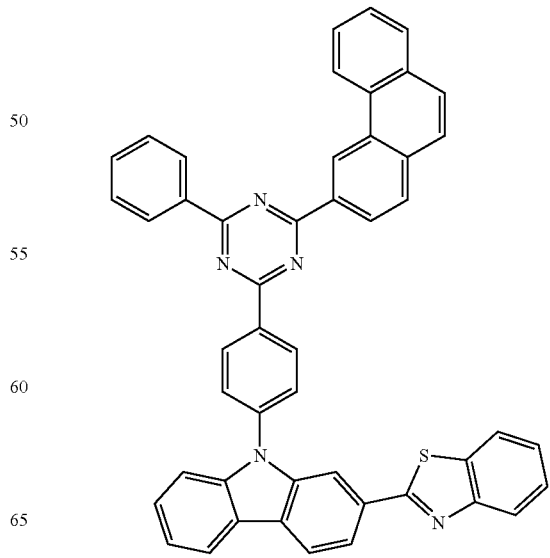

125
-continued
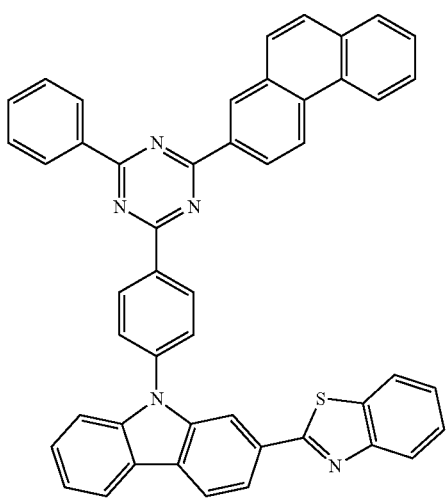
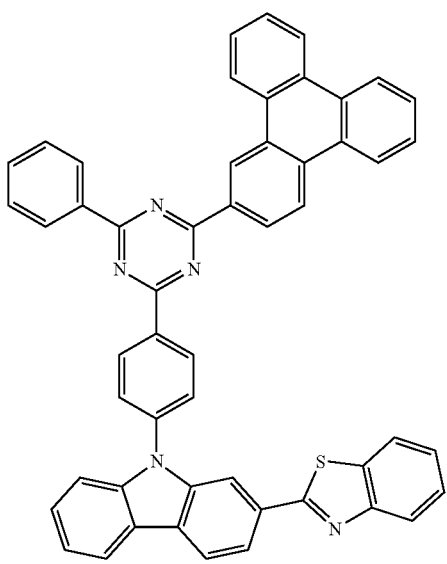
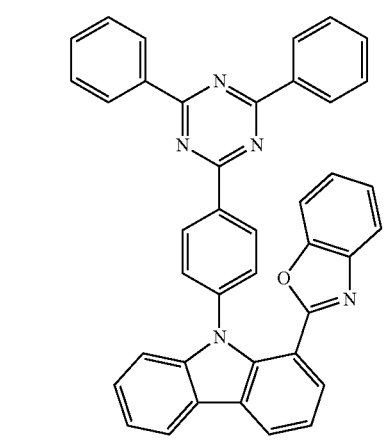
126
-continued
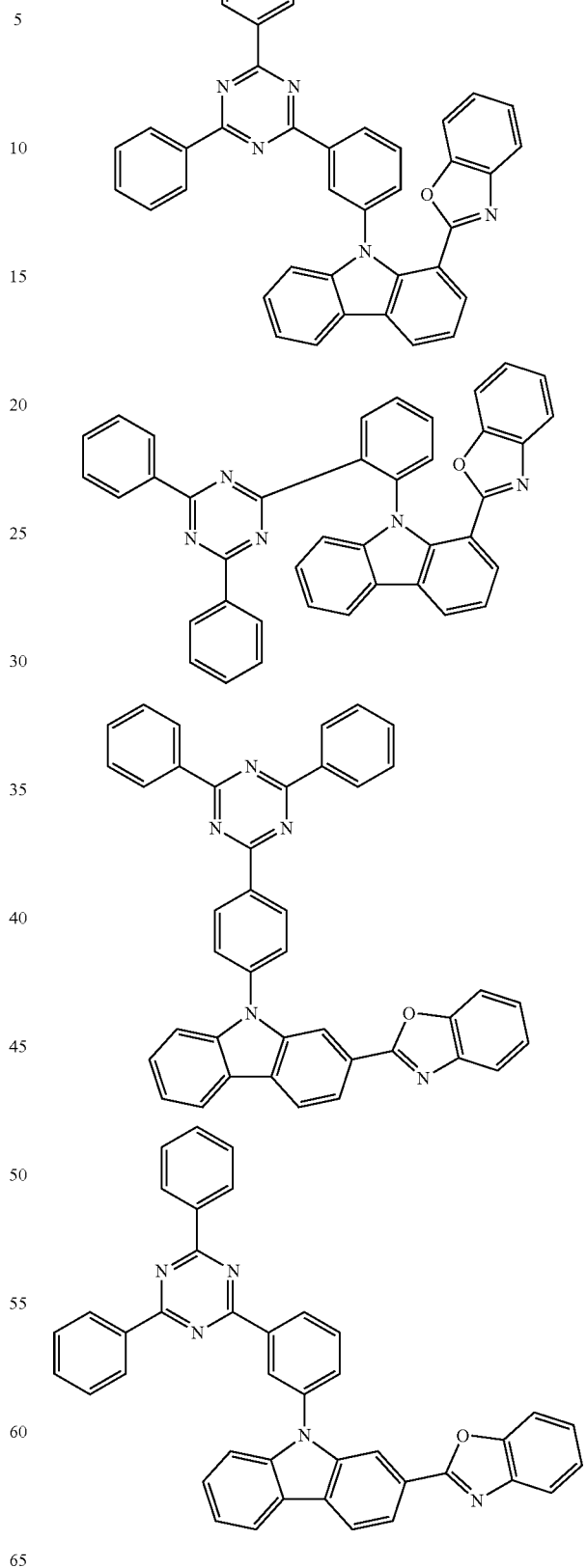

127
-continued
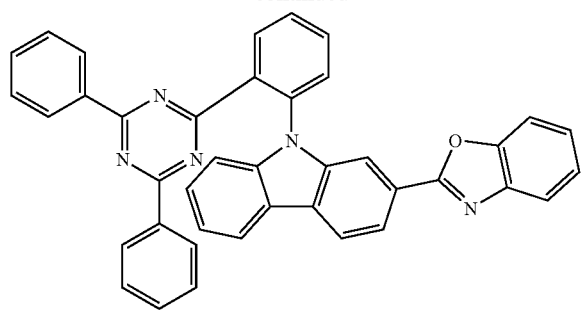
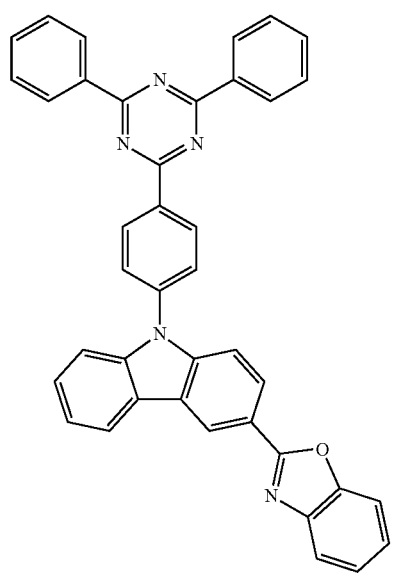
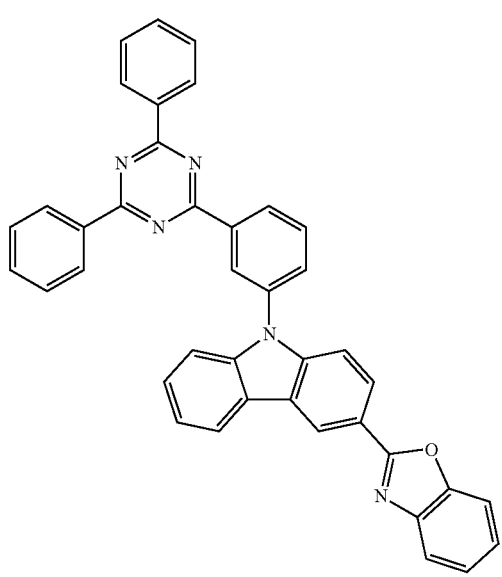
128
-continued
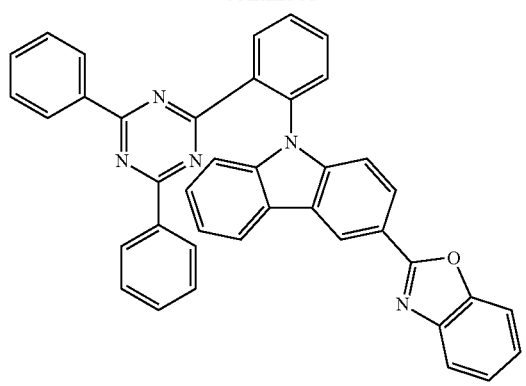
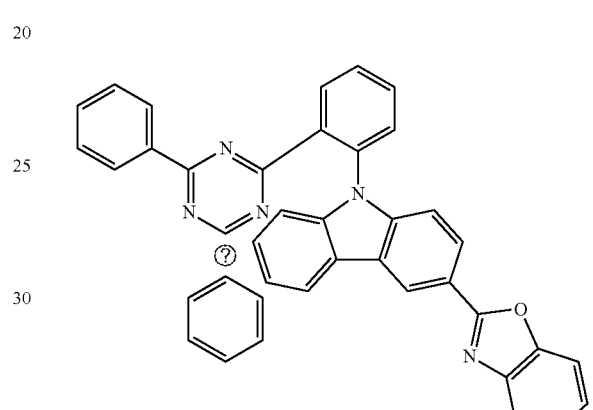
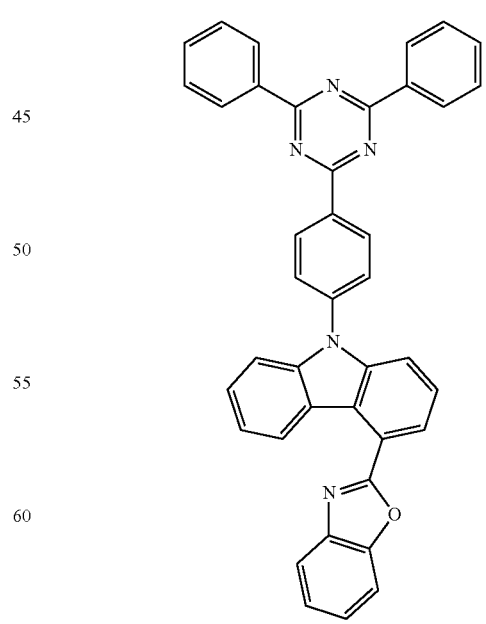

129
-continued
130
-continued
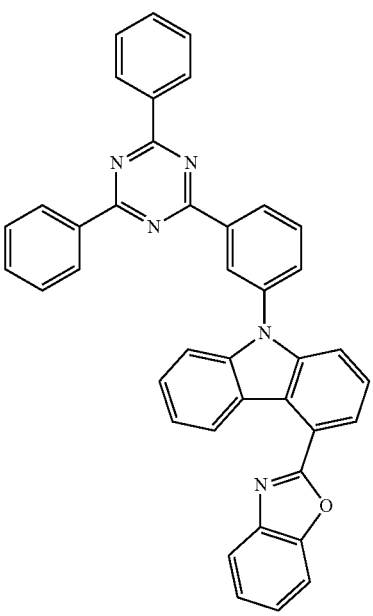
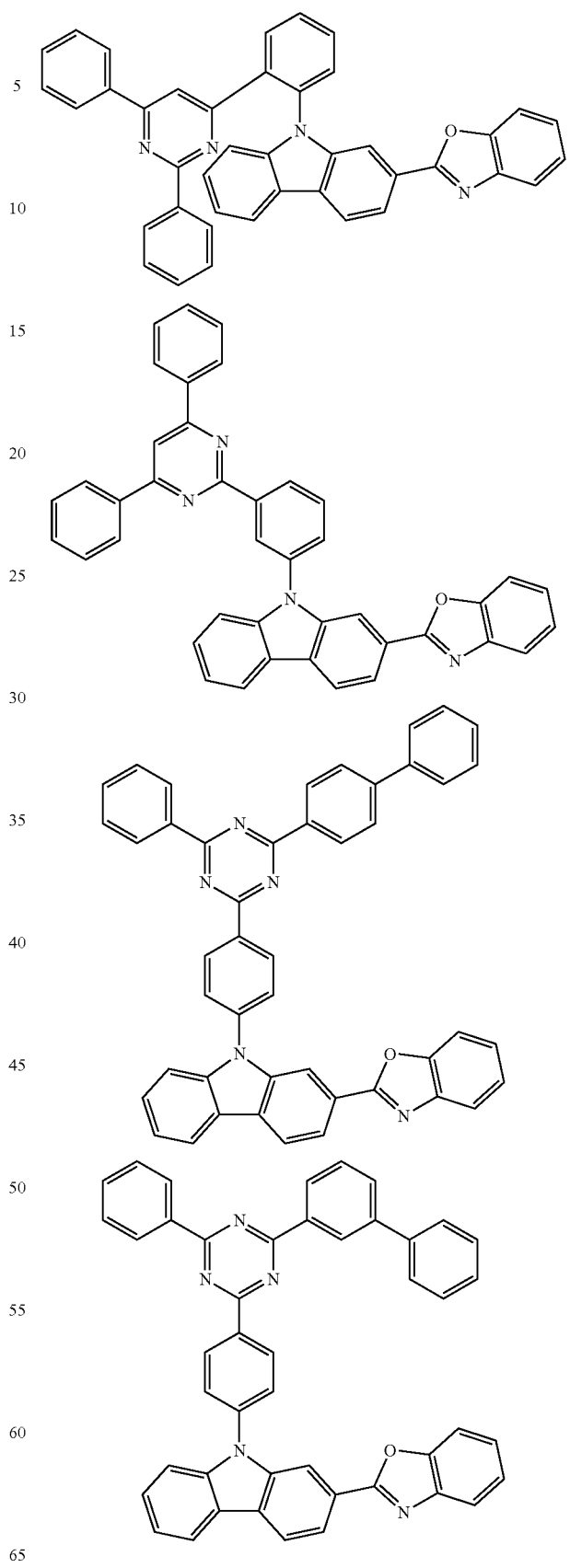

131
-continued
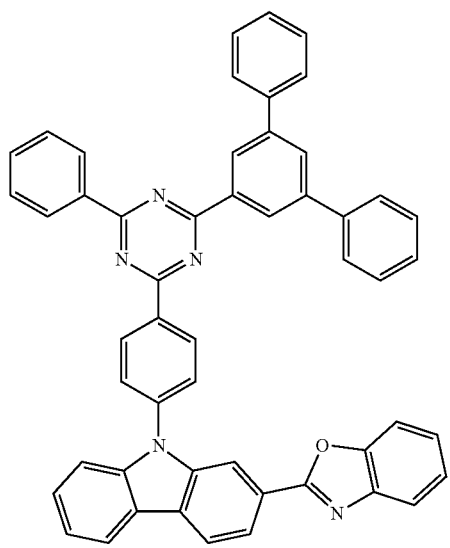
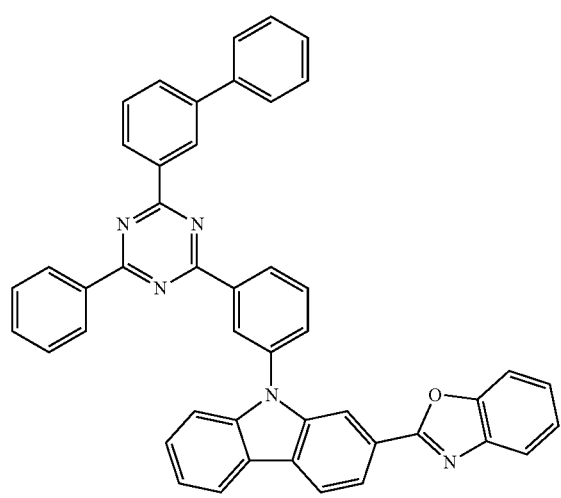
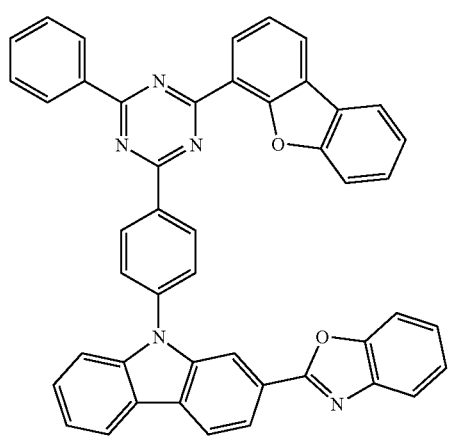
132
-continued
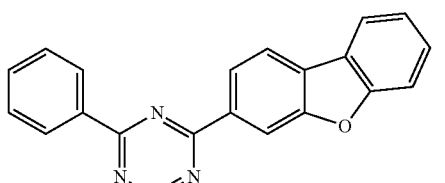
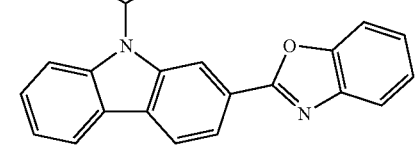
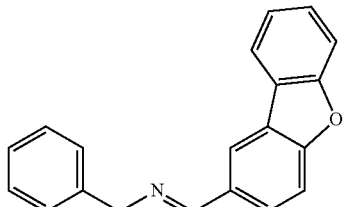
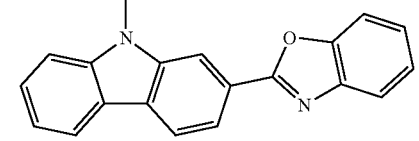
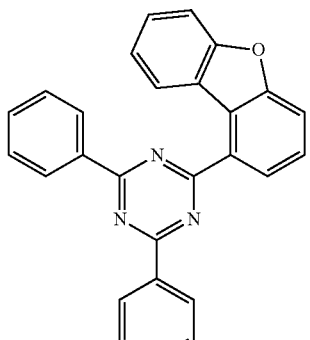
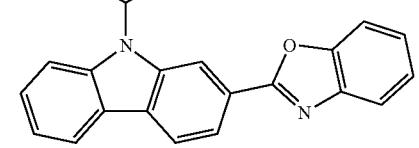

133
-continued
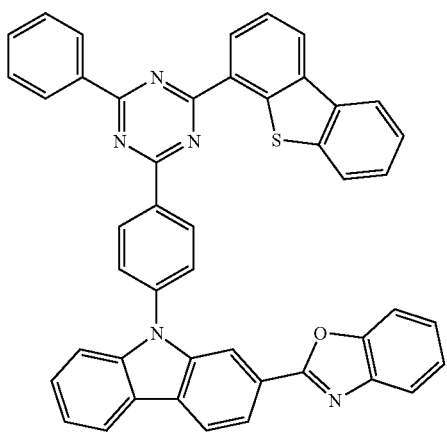
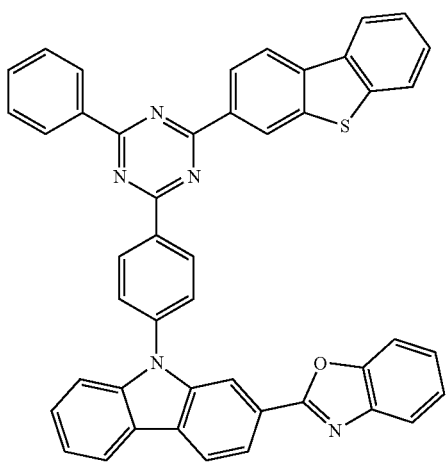
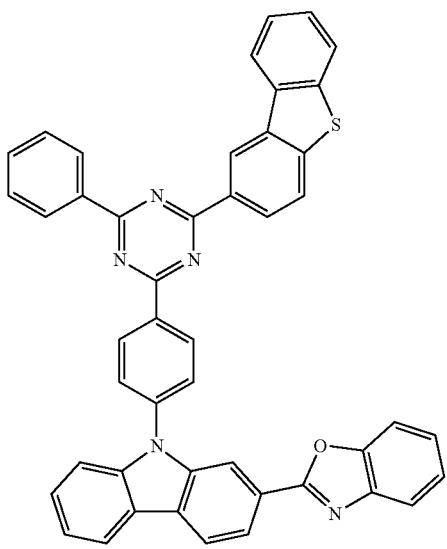
134
-continued
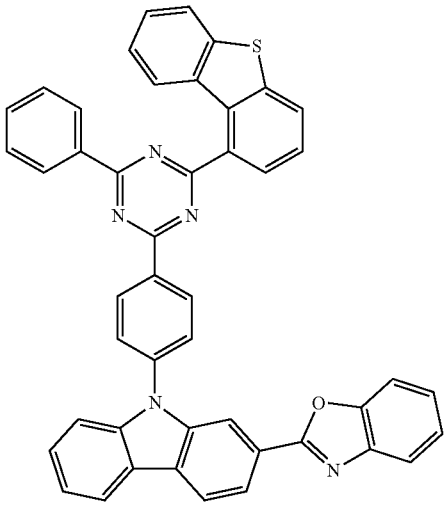
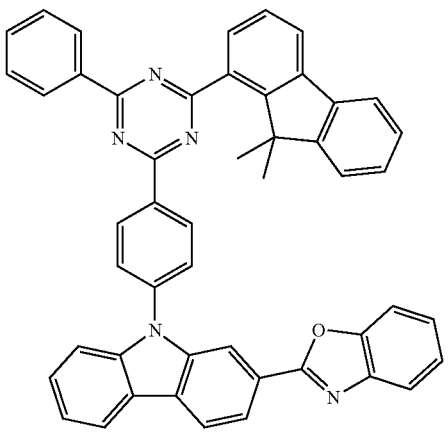
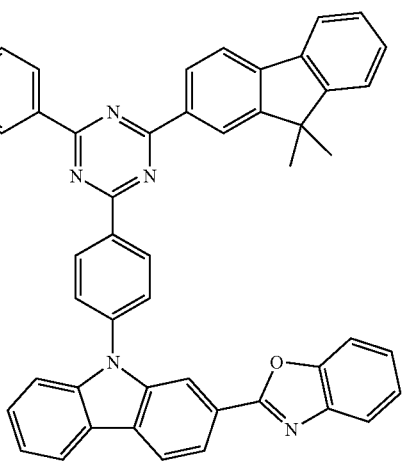

-continued
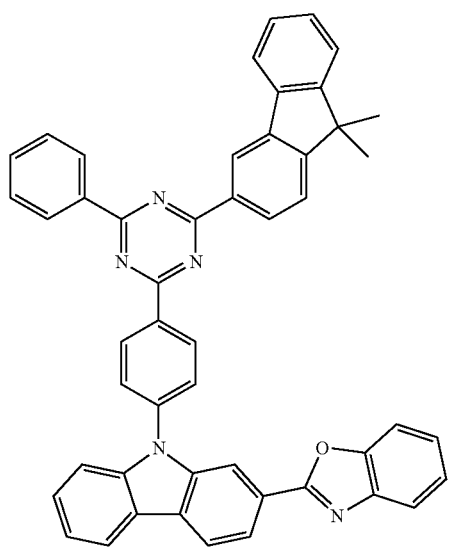
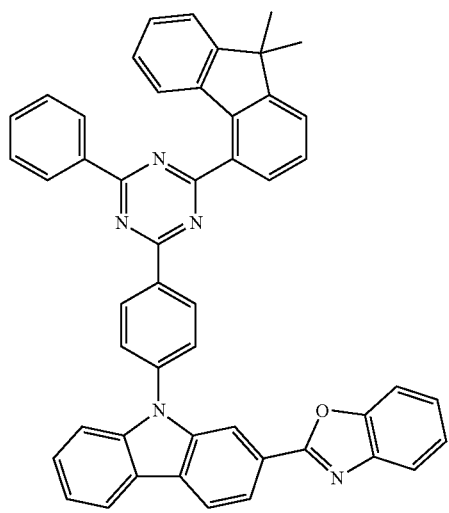
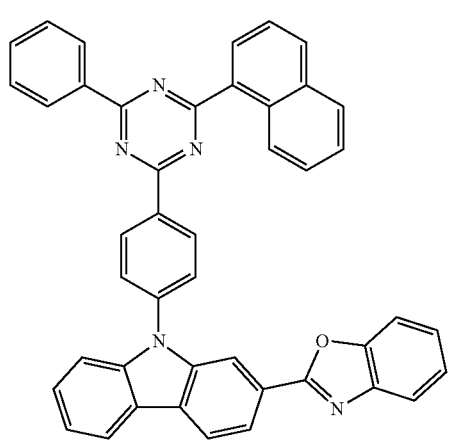
-continued
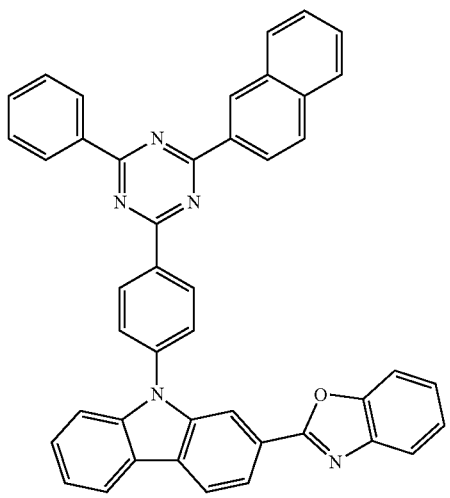
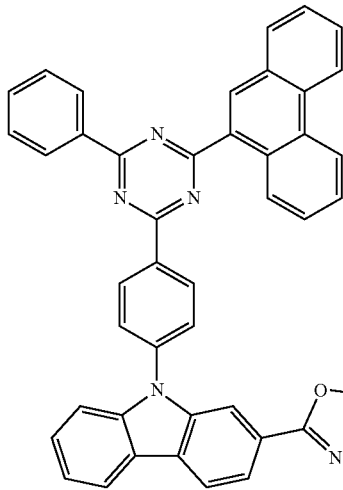
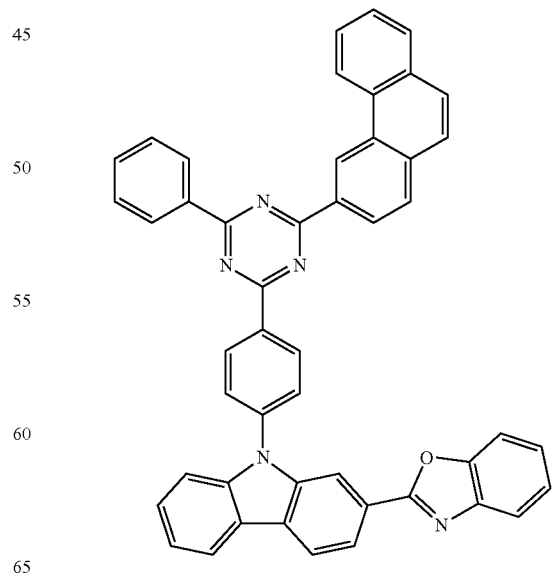

-continued

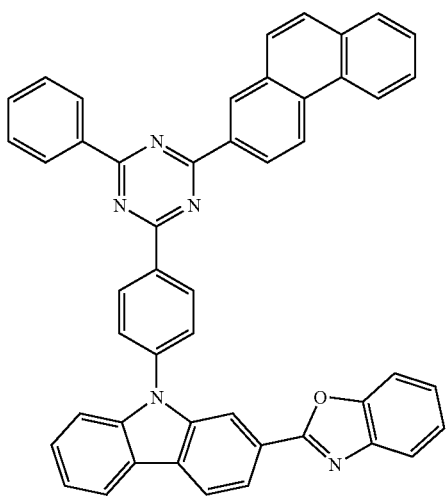

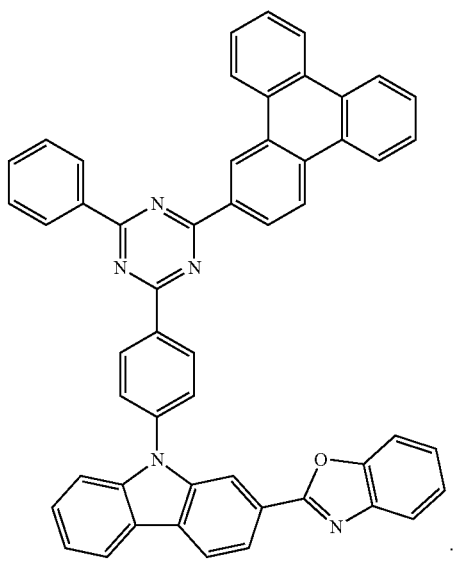

4. An organic light emitting device, comprising:

a first electrode;

a second electrode provided to face the first electrode; and an organic material layer having one or more layers provided between the first electrode and the second electrode, wherein one of the one or more layers of the organic material layer is a light emitting layer comprising a combination including a compound of Formula 1, a fluorescent host or a phosphorescent host, and an iridium (Ir)-based dopant:

[Formula 1]

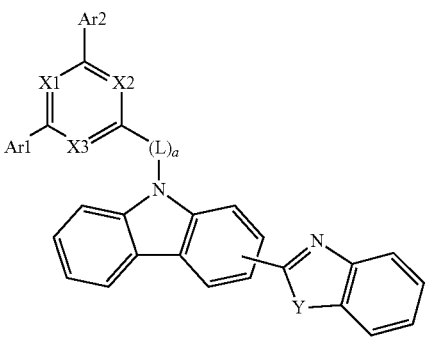

wherein in Formula 1:

at least two of X1 to X3 are N, and any remaining is CR;

R is hydrogen, deuterium, a substituted or unsubstituted alkyl group, a substituted or unsubstituted aryl group, or a substituted or unsubstituted heterocyclic group;

Ar1 and Ar2 are each independently a substituted or unsubstituted aryl group or a substituted or unsubstituted heterocyclic group;

Y is O or S;

L is a substituted or unsubstituted arylene group;

a is 1 or 2; and

Ls in the parenthesis are the same as or different from each other when a is 2.

5. The organic light emitting device of claim 4, wherein the compound of Formula 1 is any one of the following compounds:

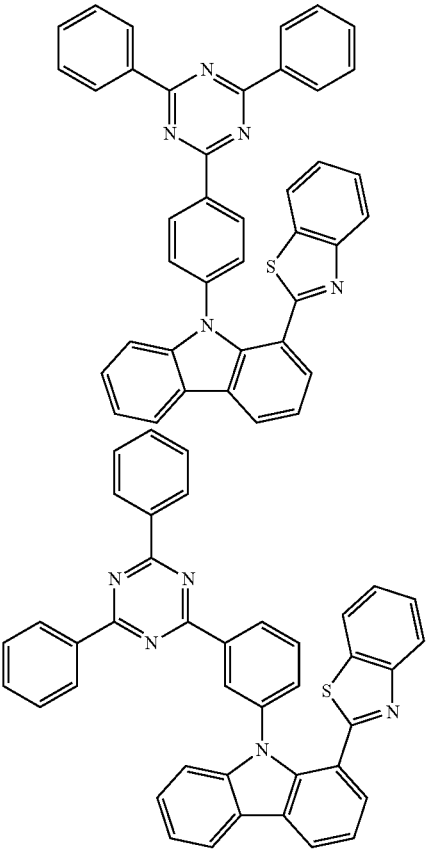

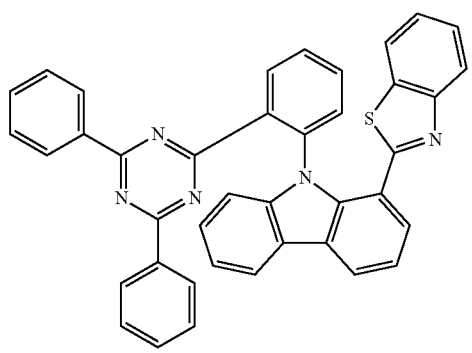
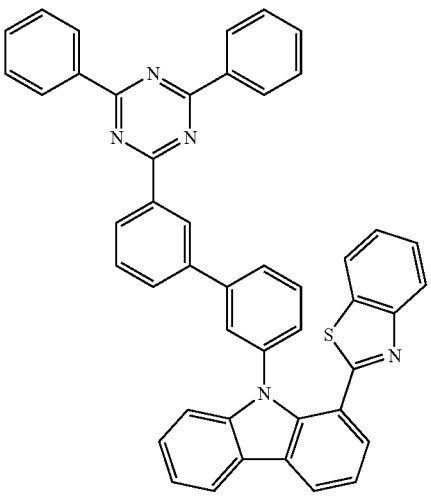
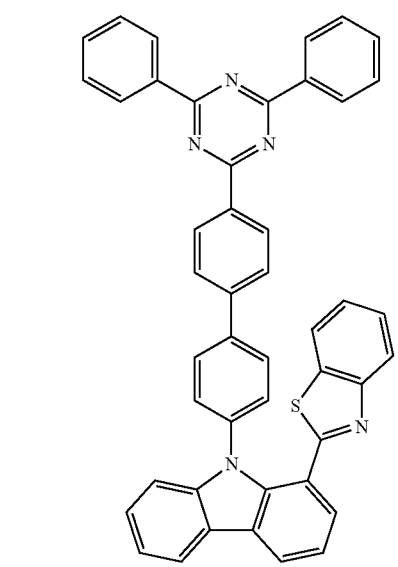
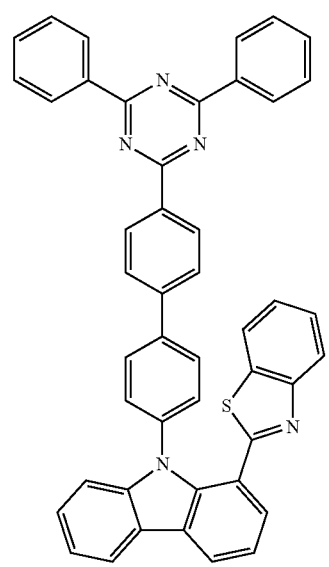
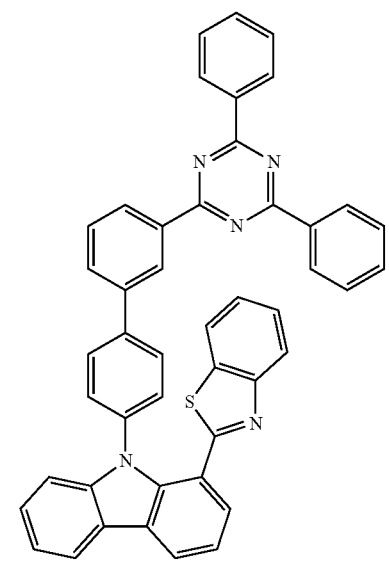
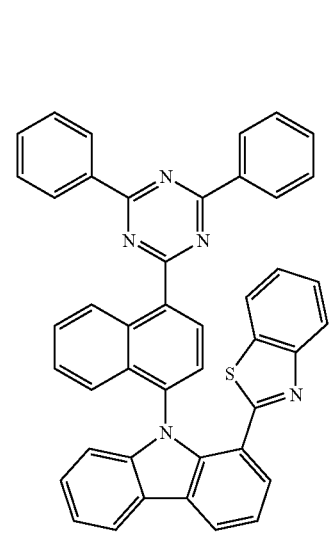

141
-continued
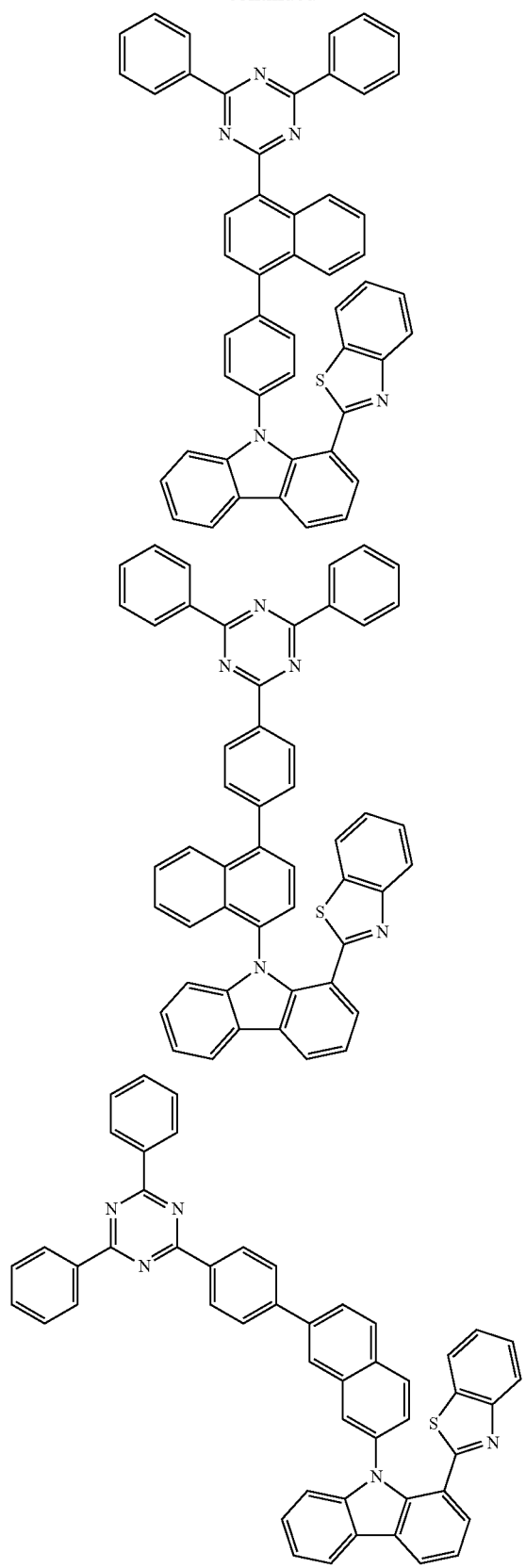
142
-continued
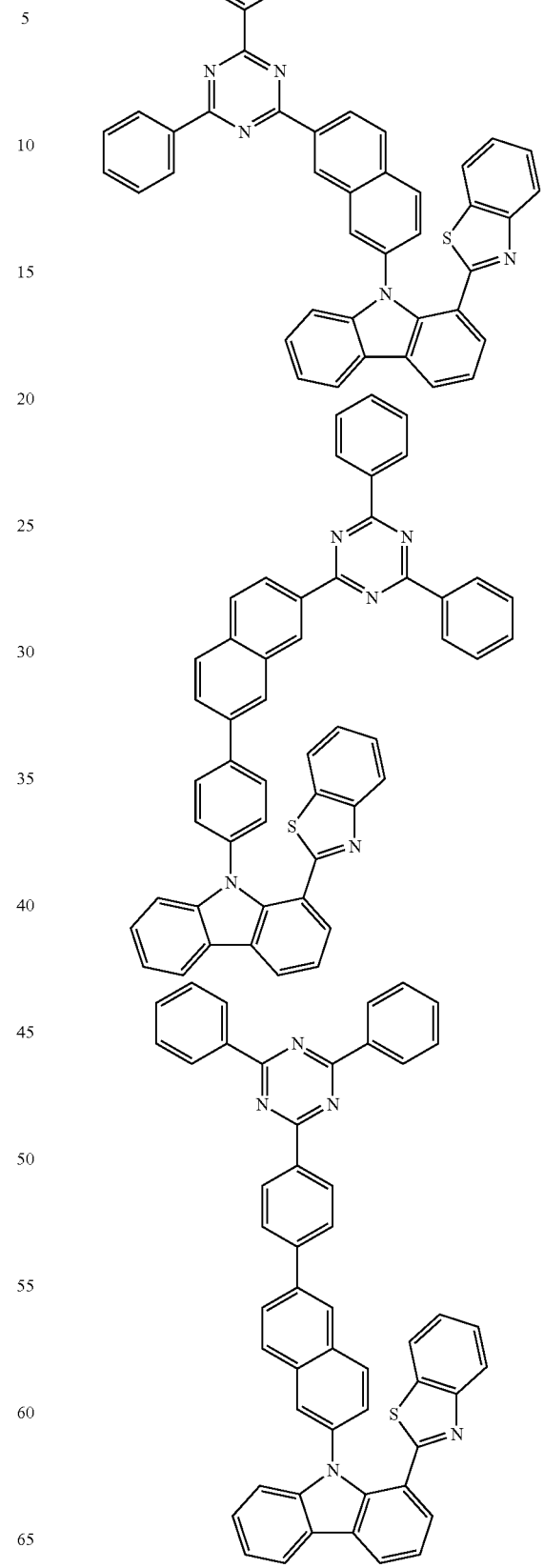

-continued
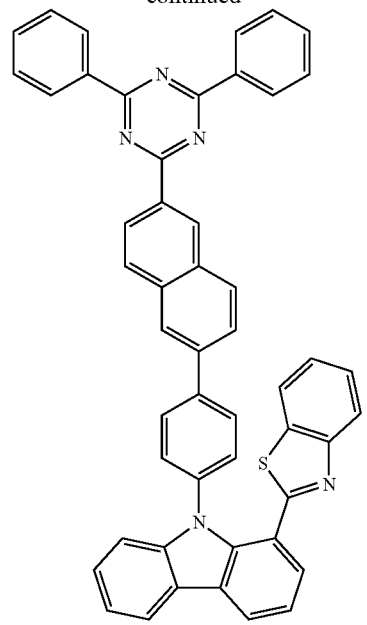
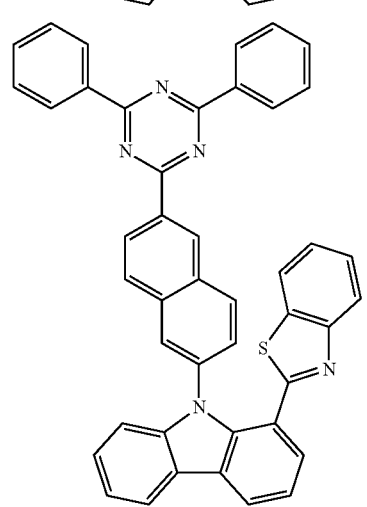
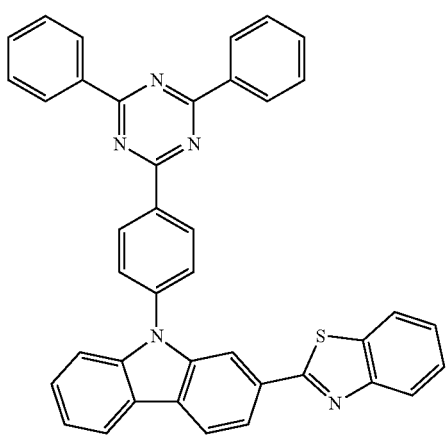
-continued
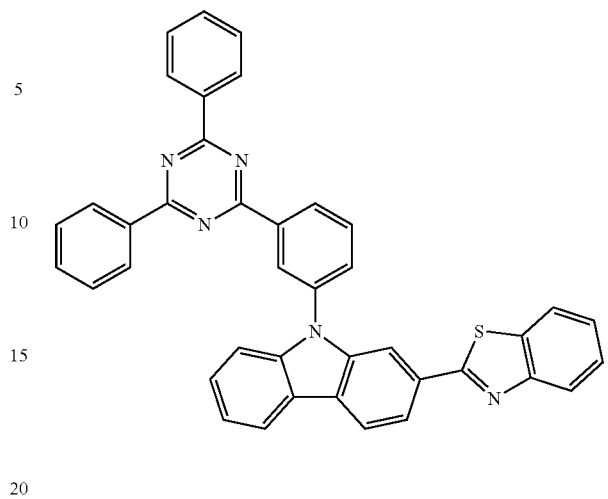
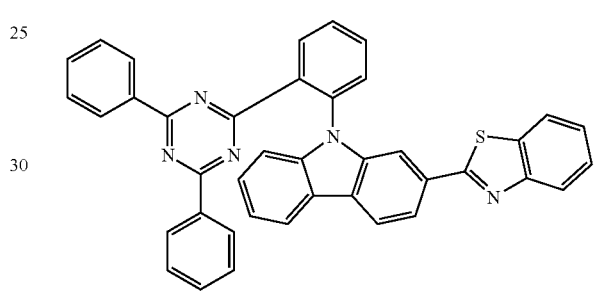
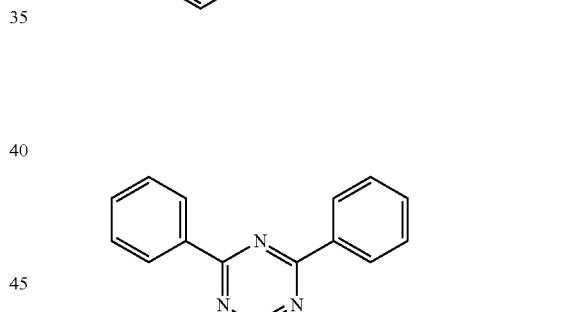
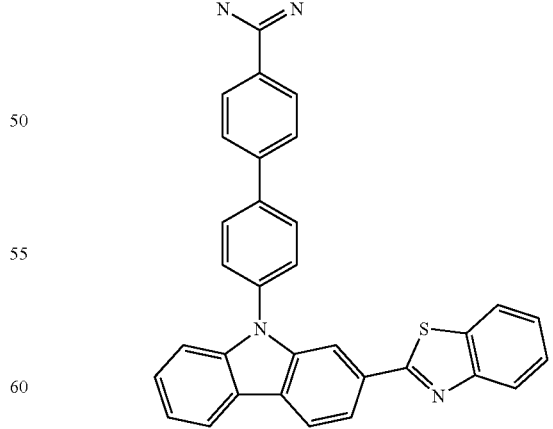

145
-continued
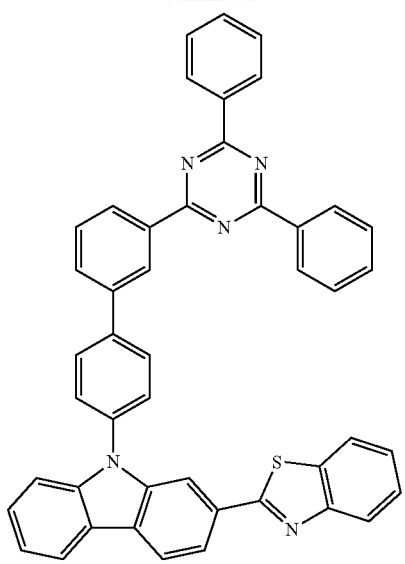
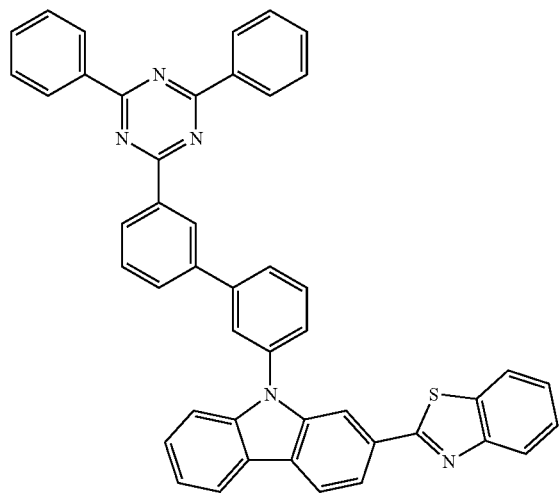
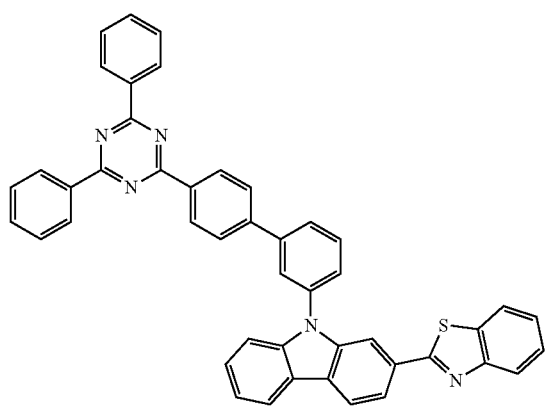
146
-continued
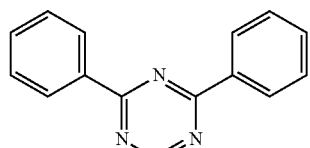
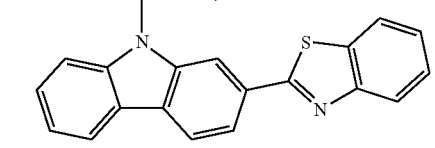
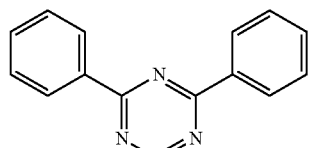
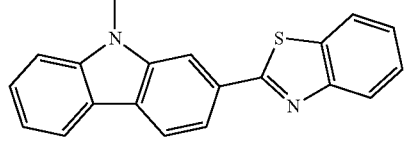
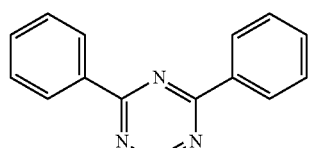
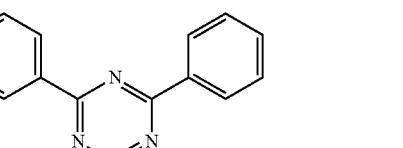
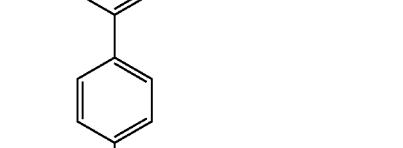
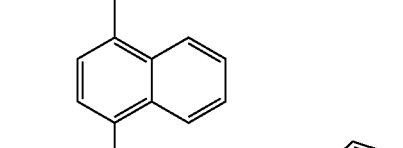
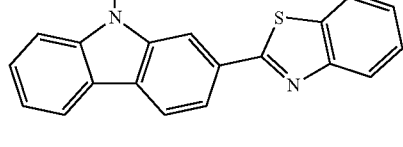

-continued
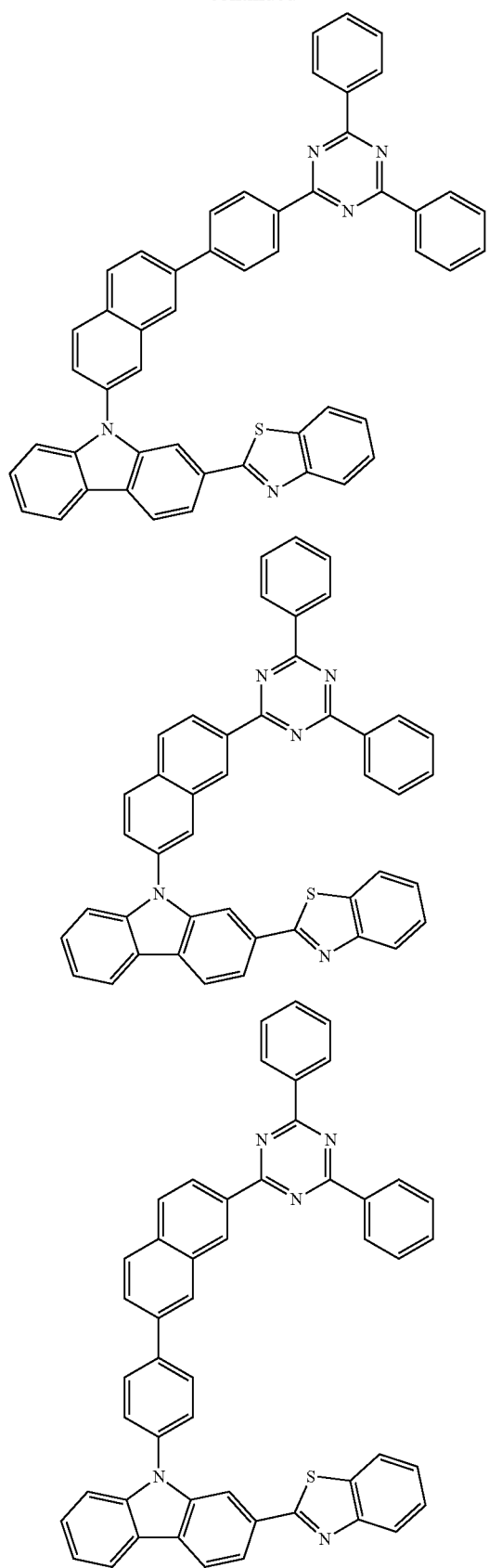
-continued
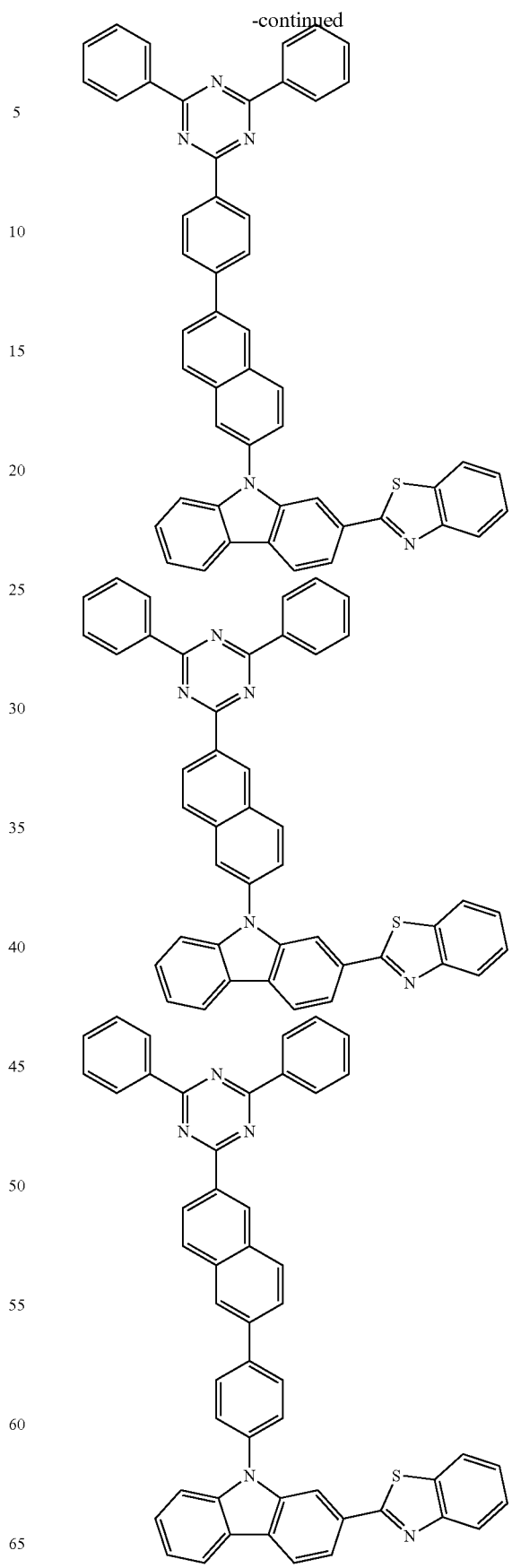

149
-continued
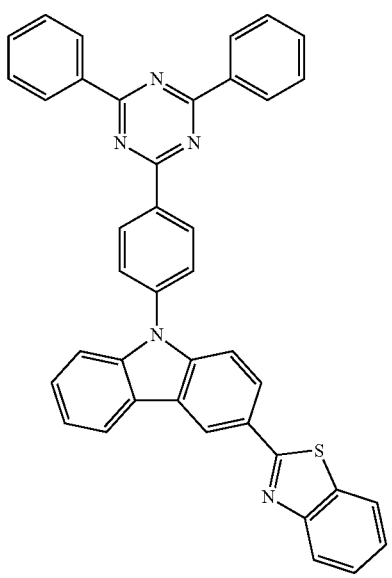
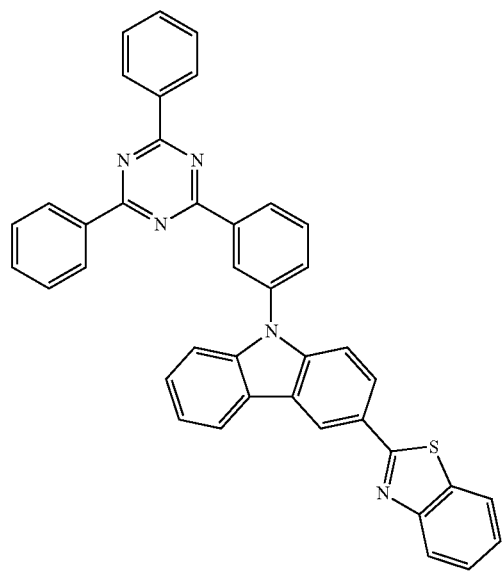
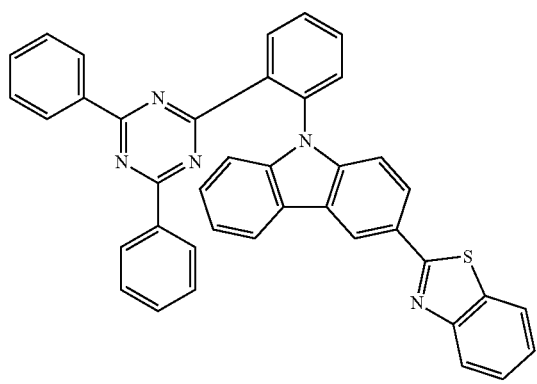
150
-continued
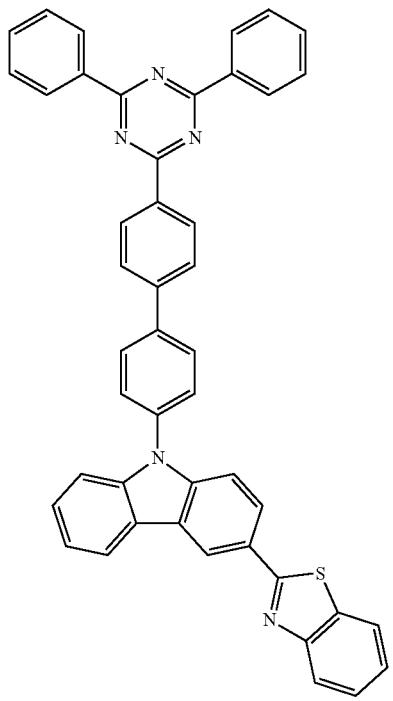
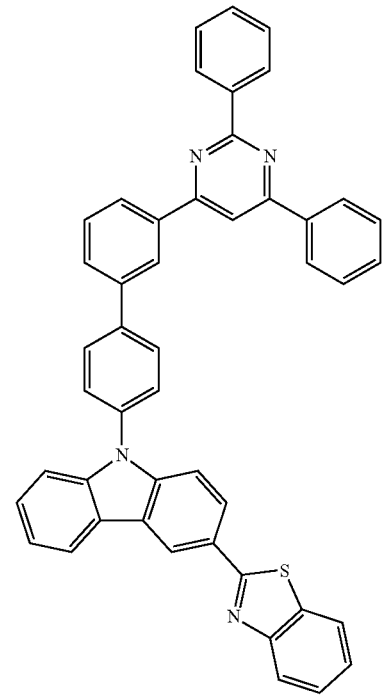

151
-continued
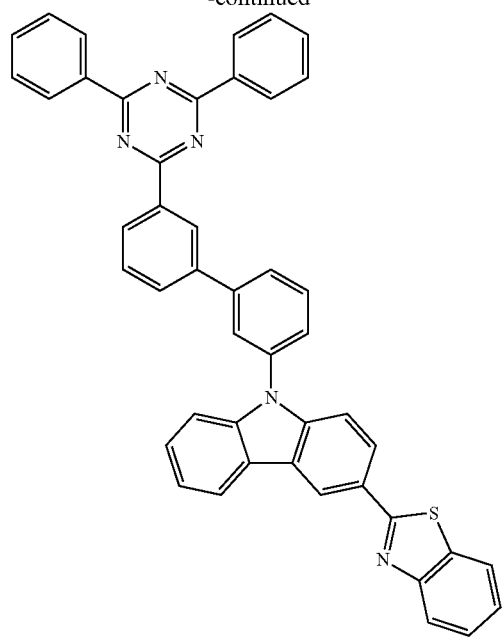
152
-continued
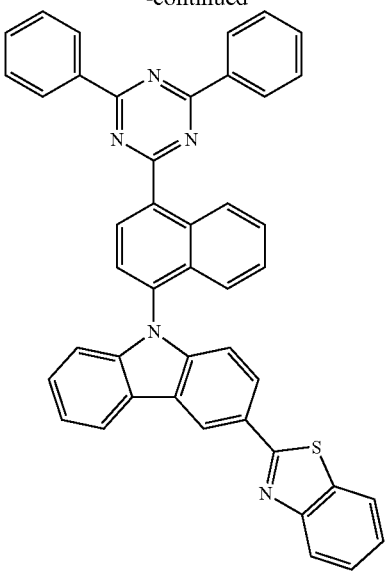
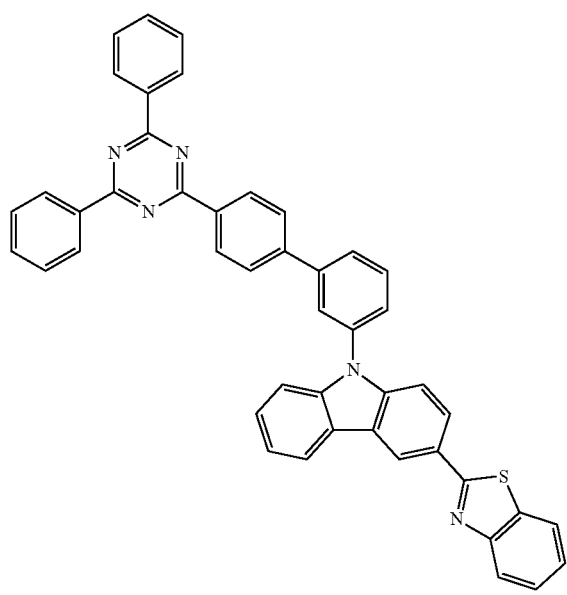
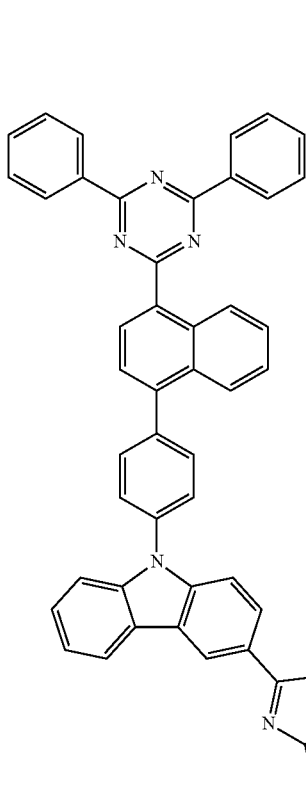

153
-continued
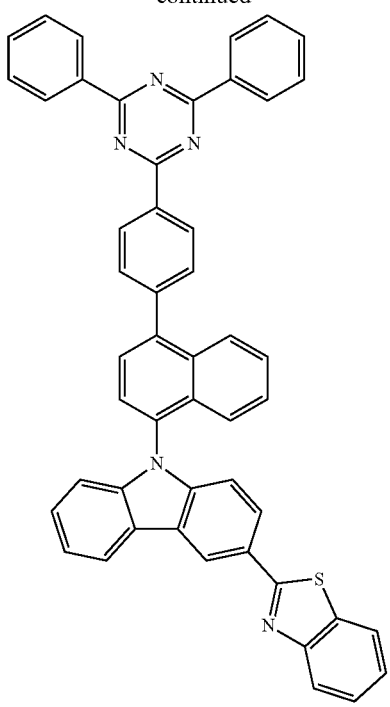
154
-continued
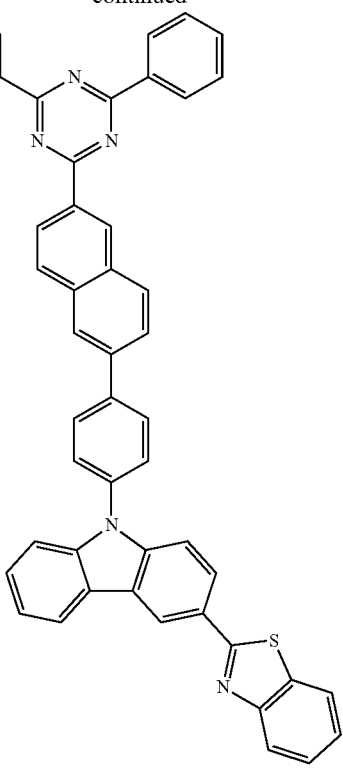
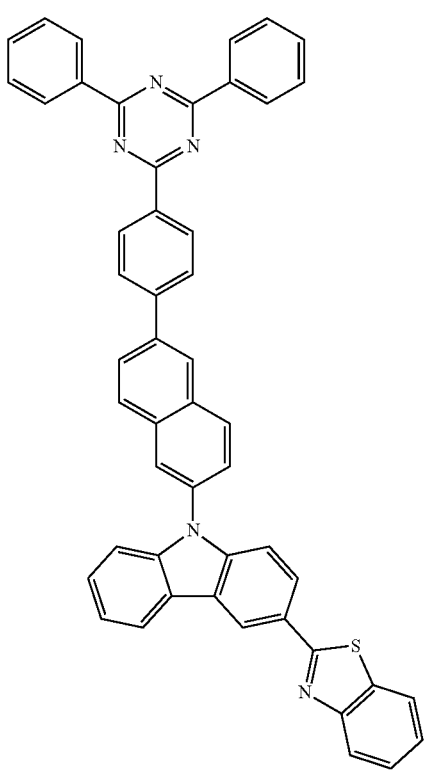

155
-continued
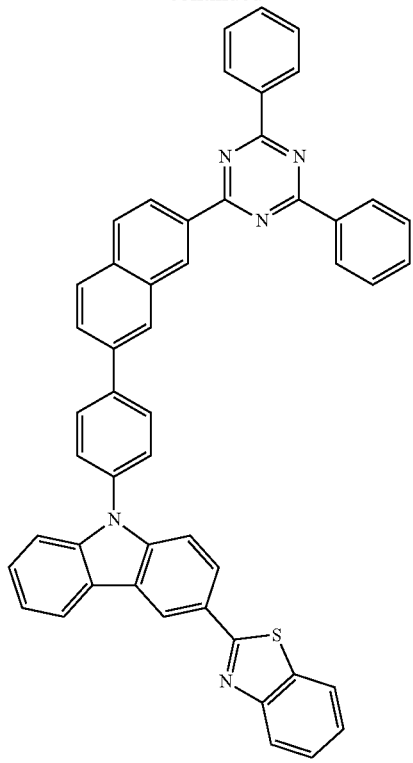
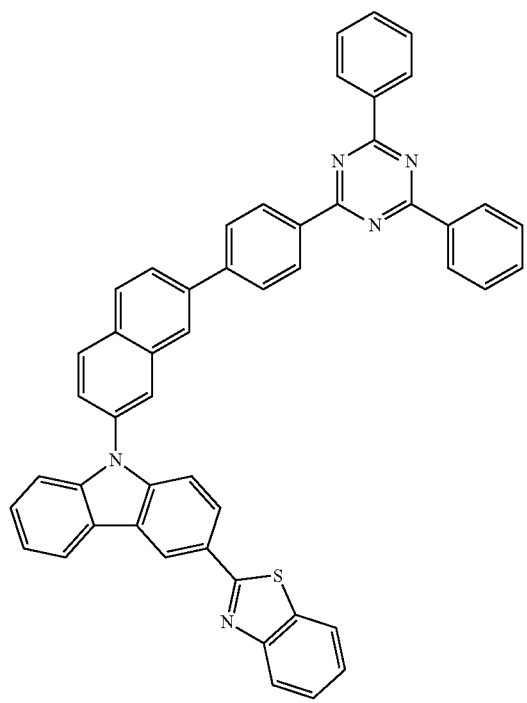
156
-continued
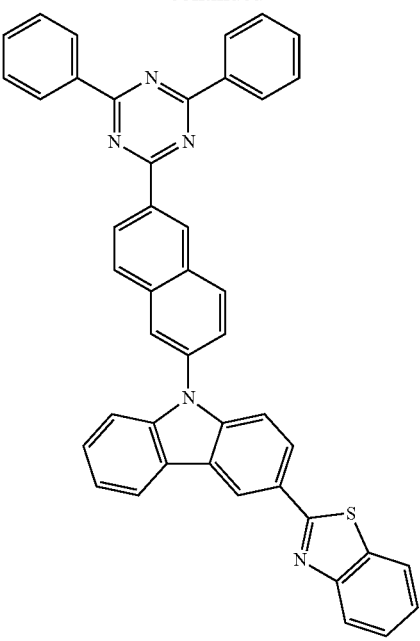
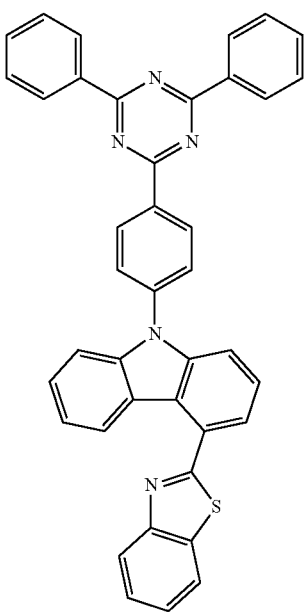

157
-continued
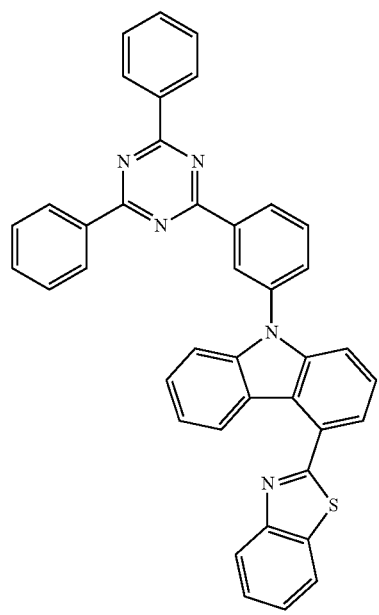
158
-continued
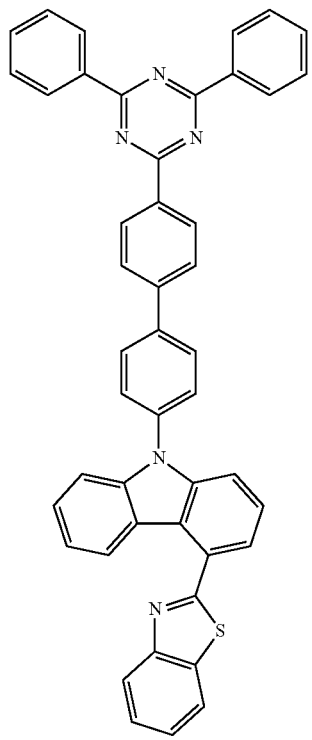
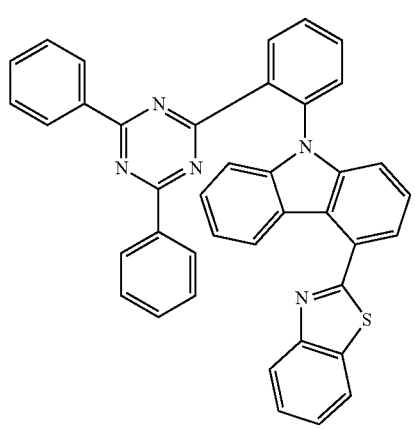
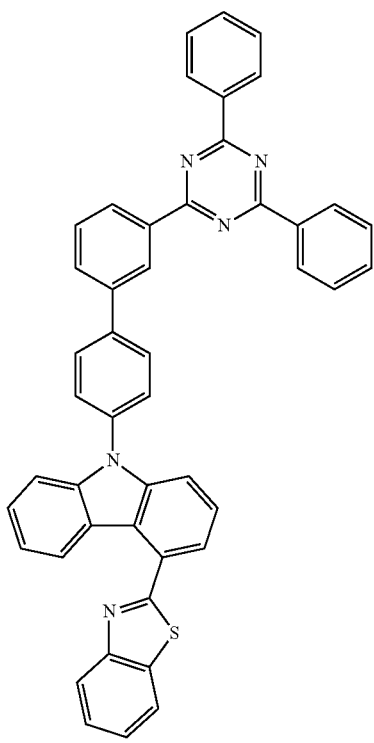

159
-continued
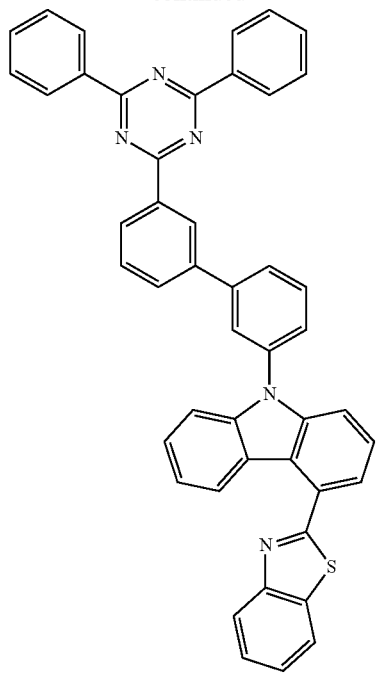
160
-continued
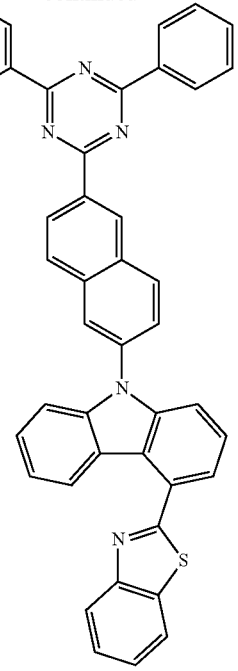
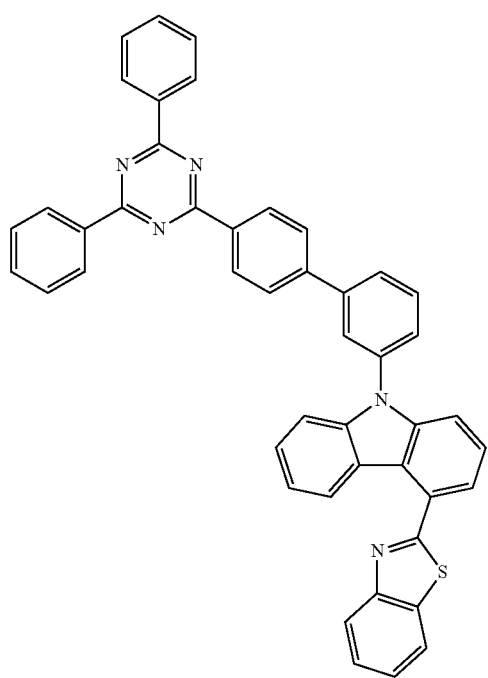
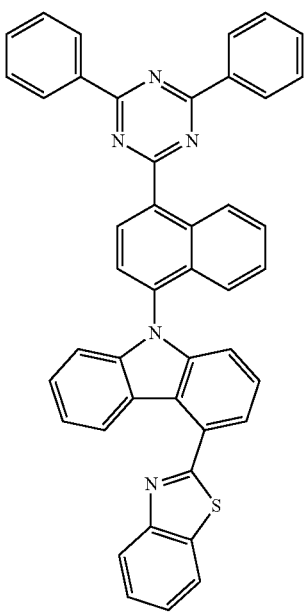

161
-continued
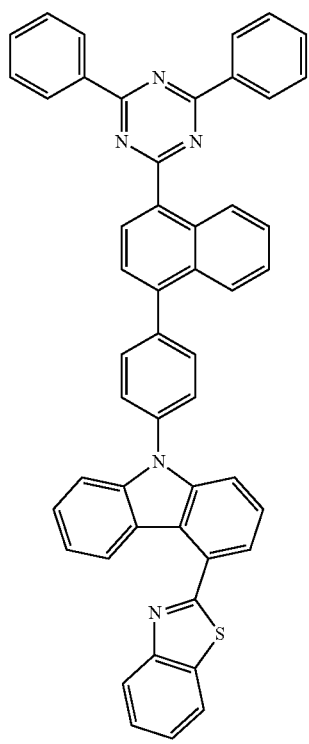
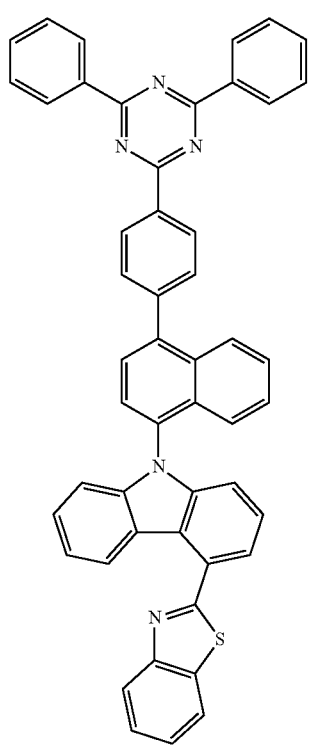
162
-continued
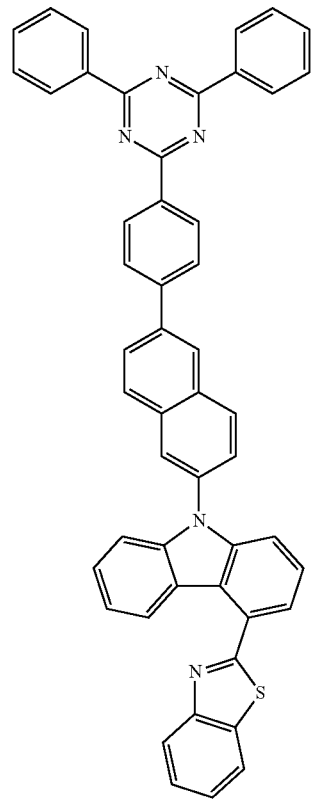
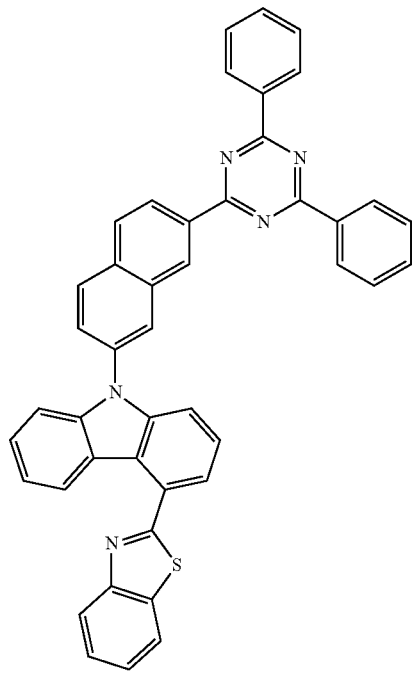

163
-continued
164
-continued
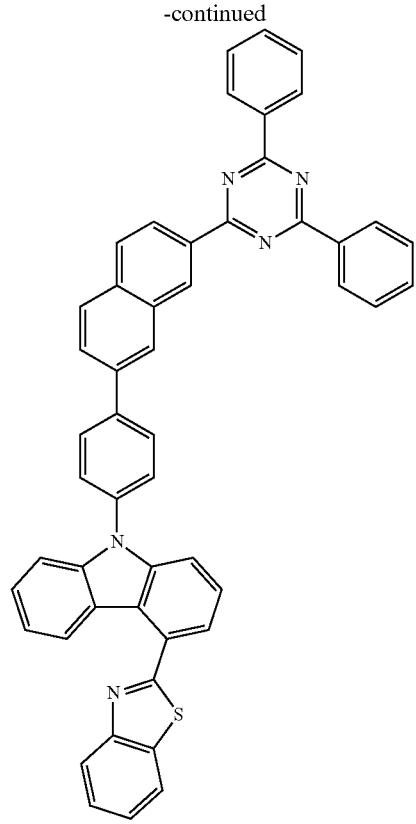
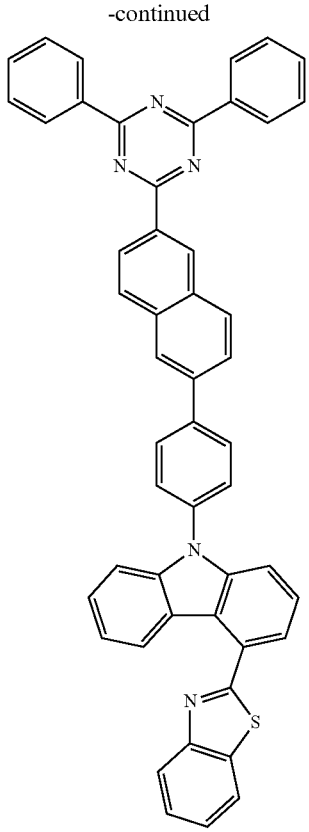
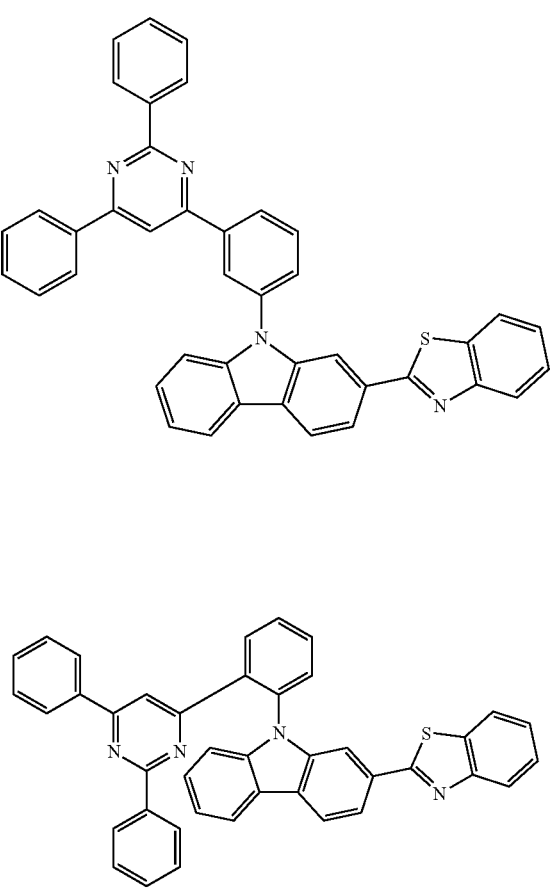

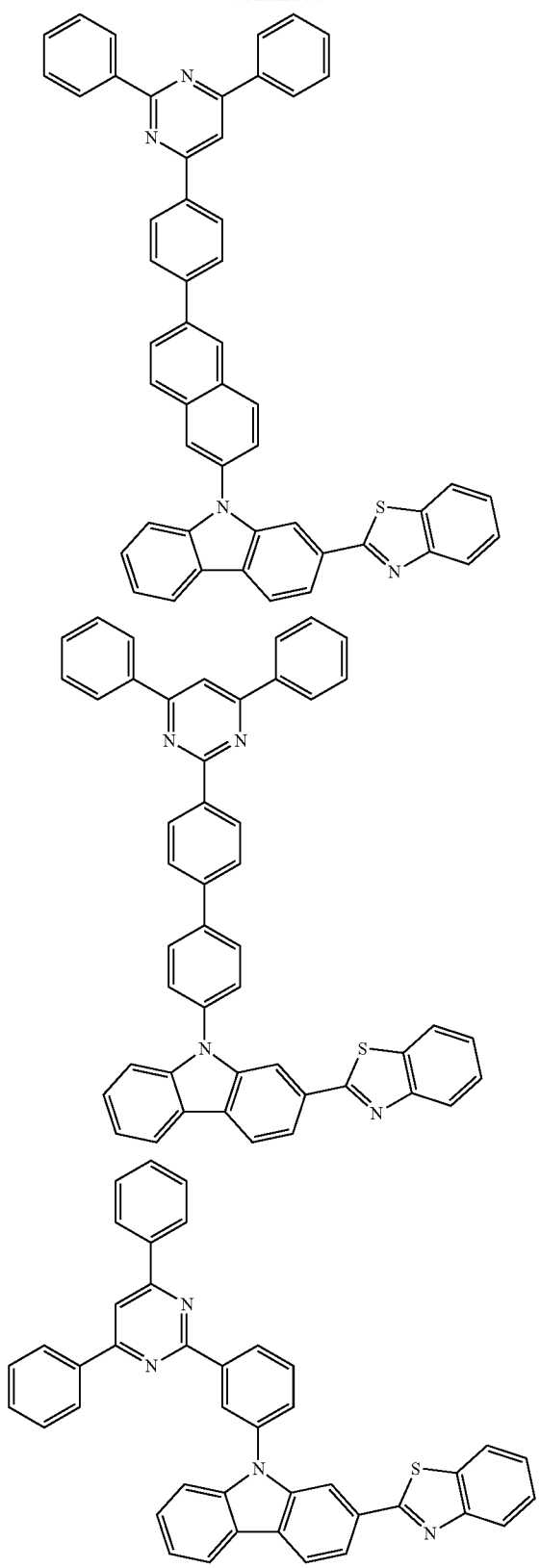
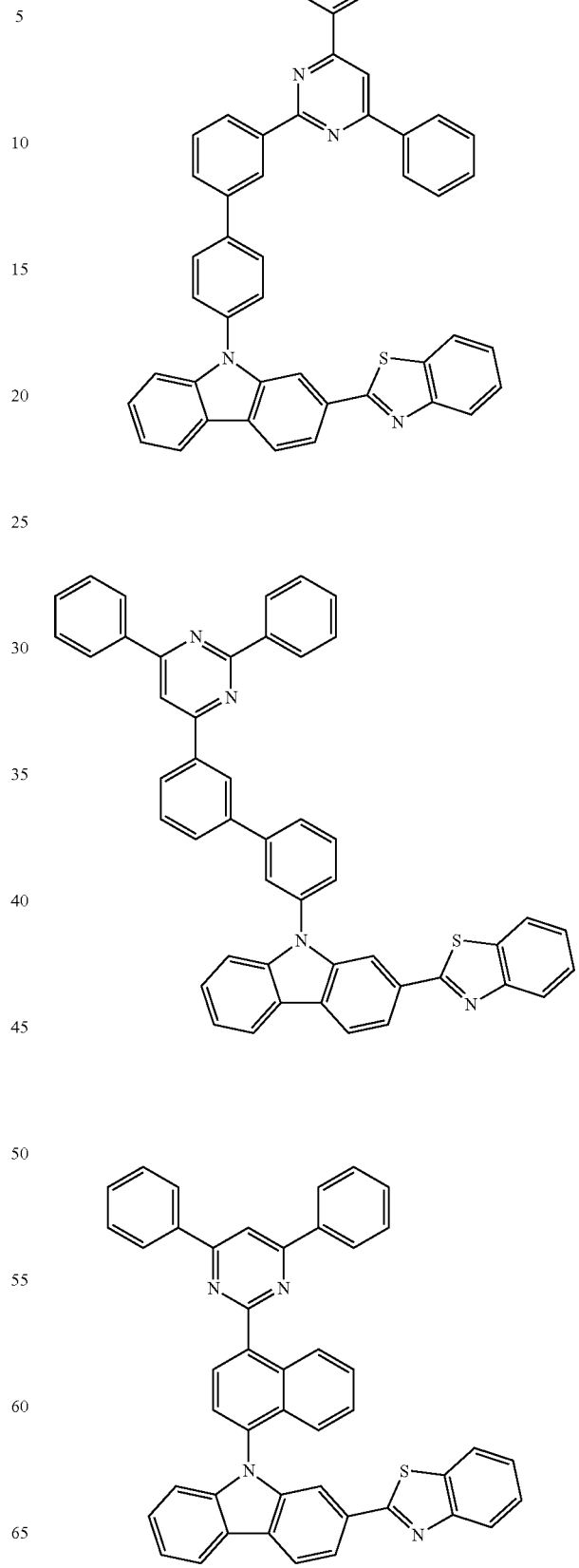

167
-continued
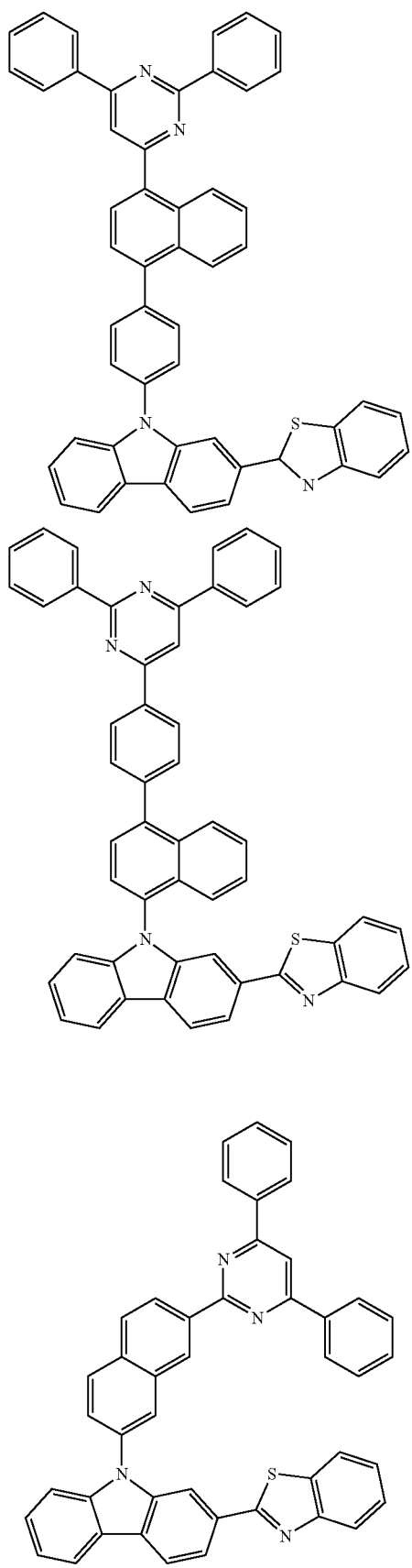
168
-continued
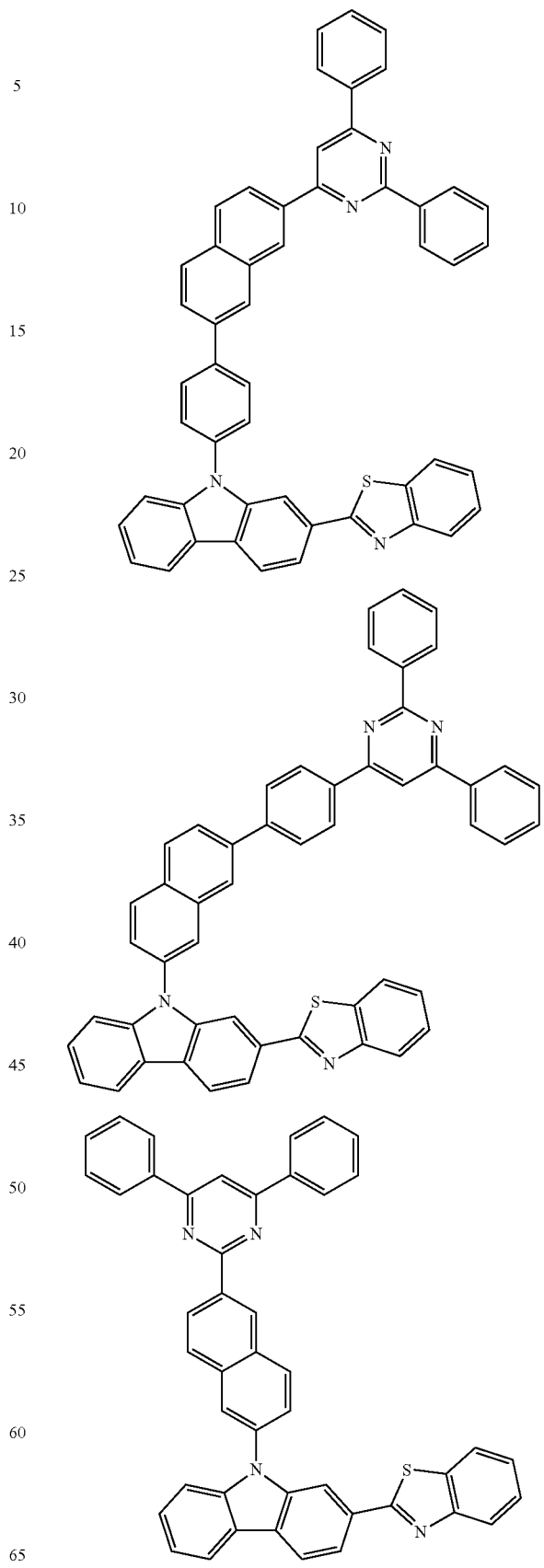

169
-continued
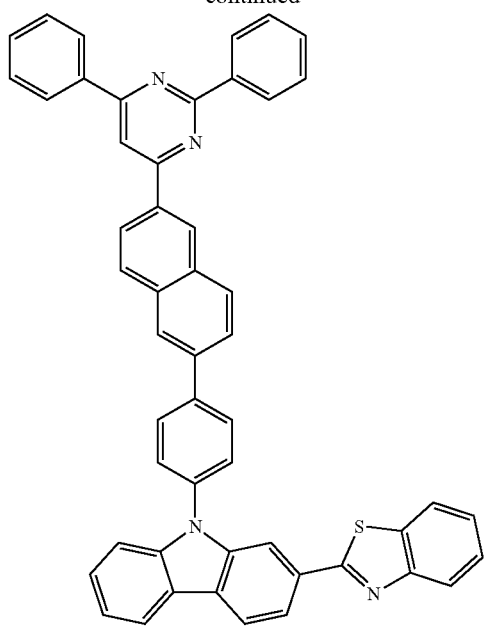
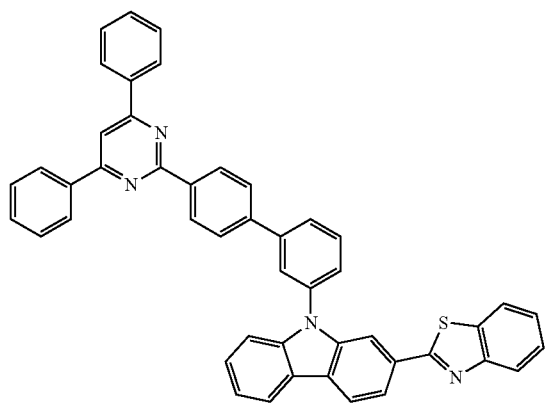
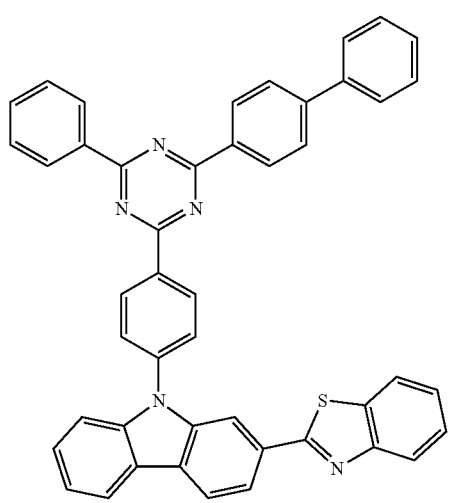
170
-continued
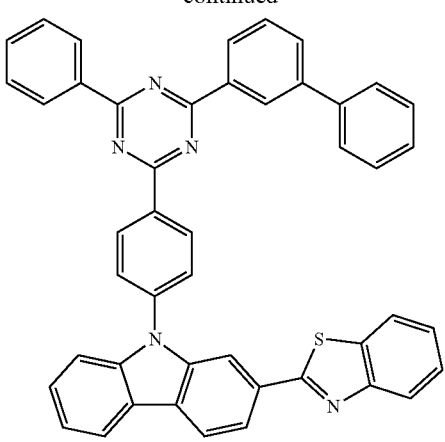
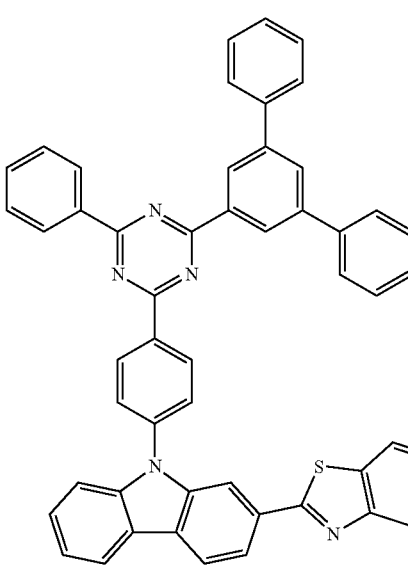
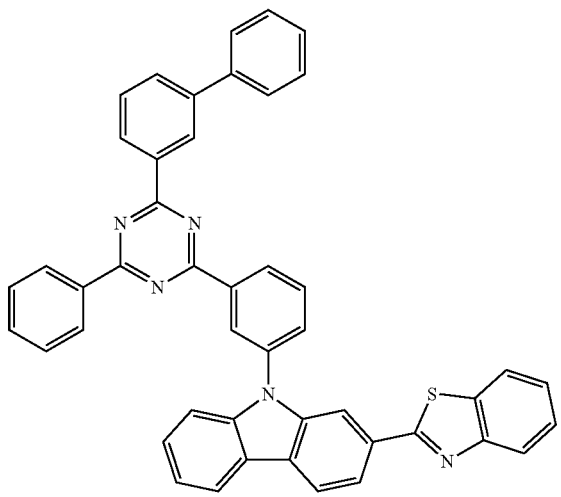

171
-continued
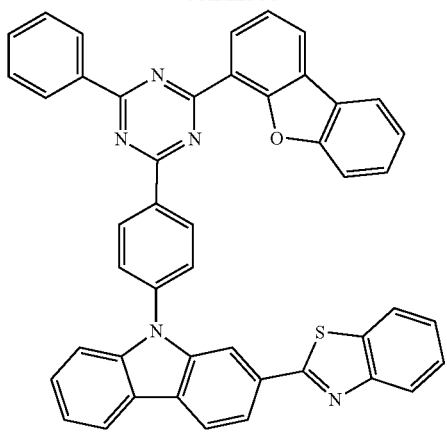
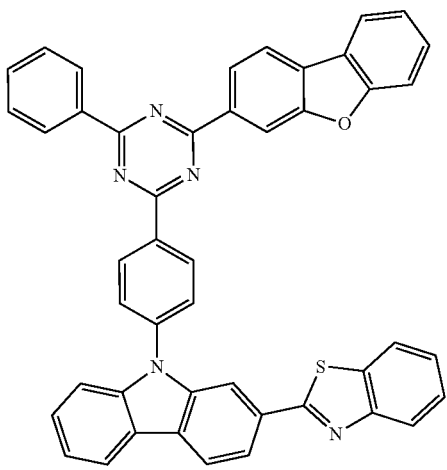
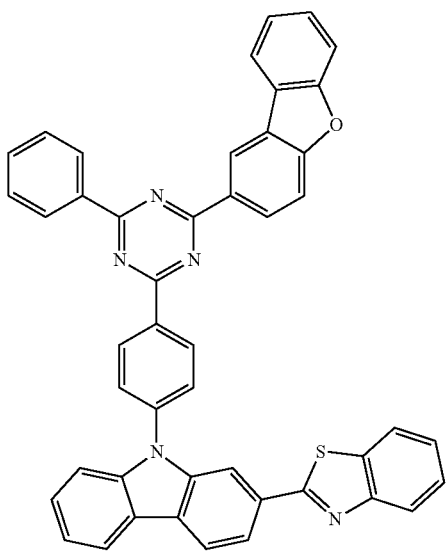
172
-continued
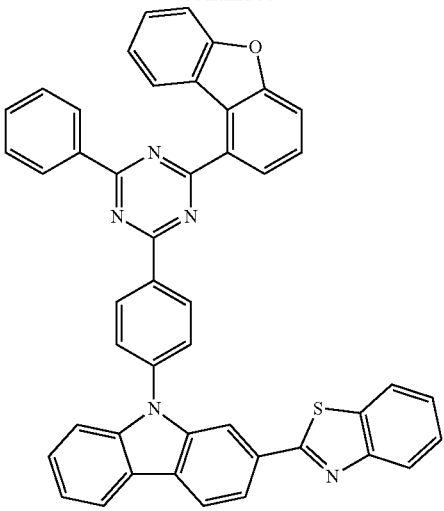
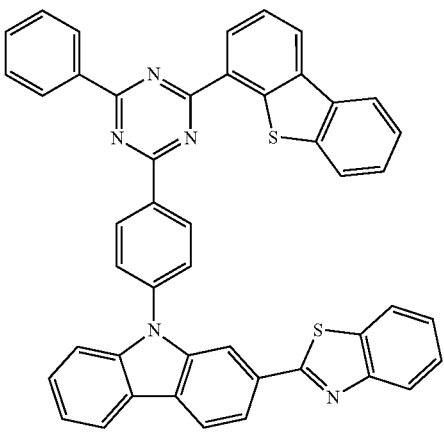
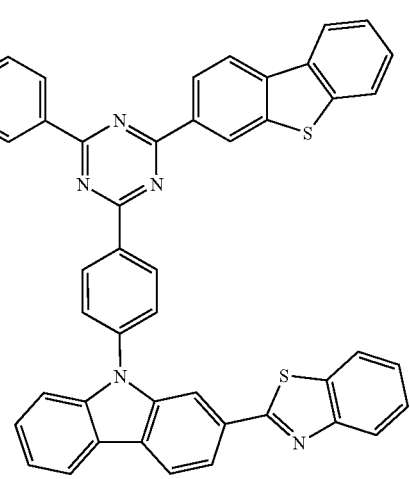

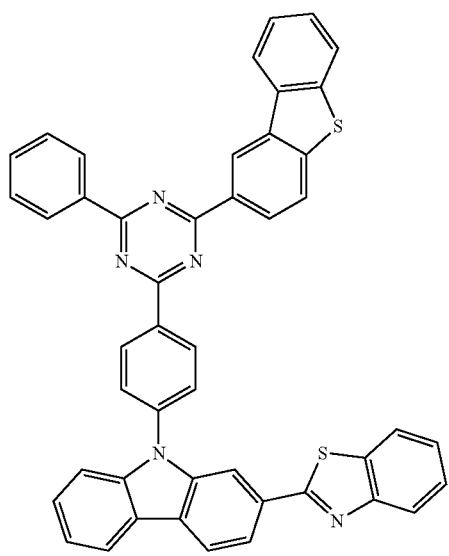
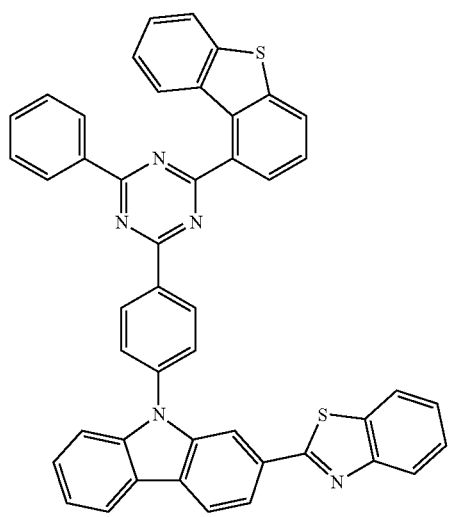
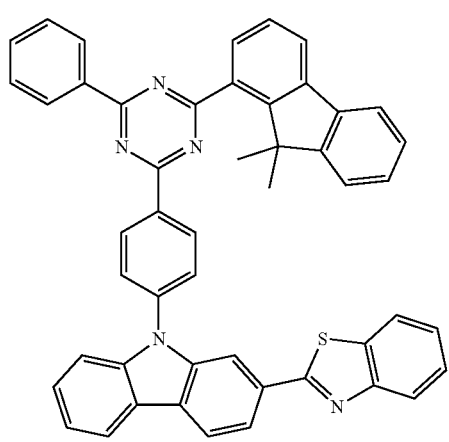
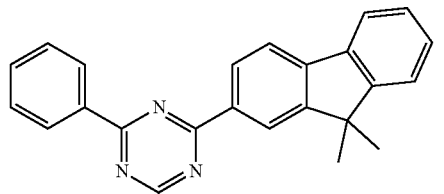
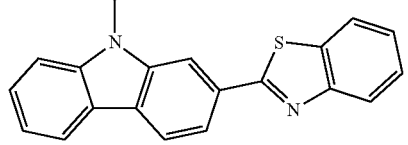
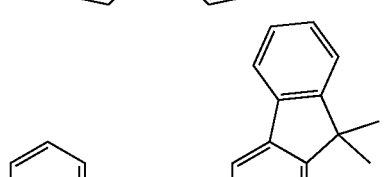
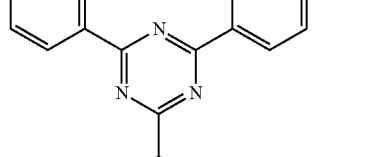
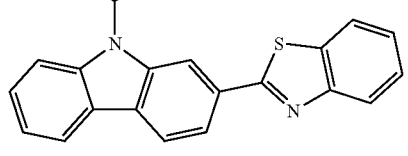
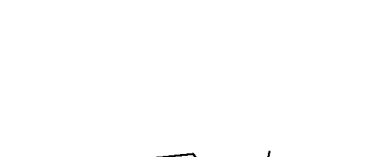
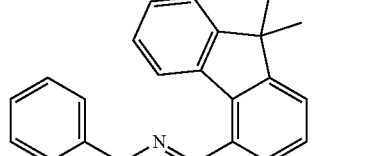
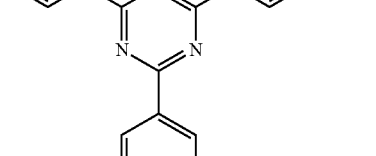
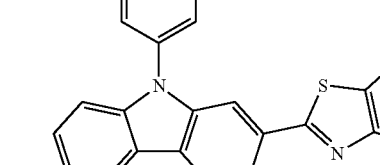
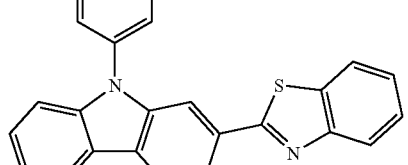

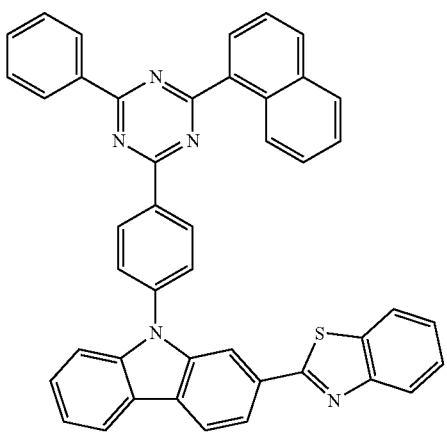
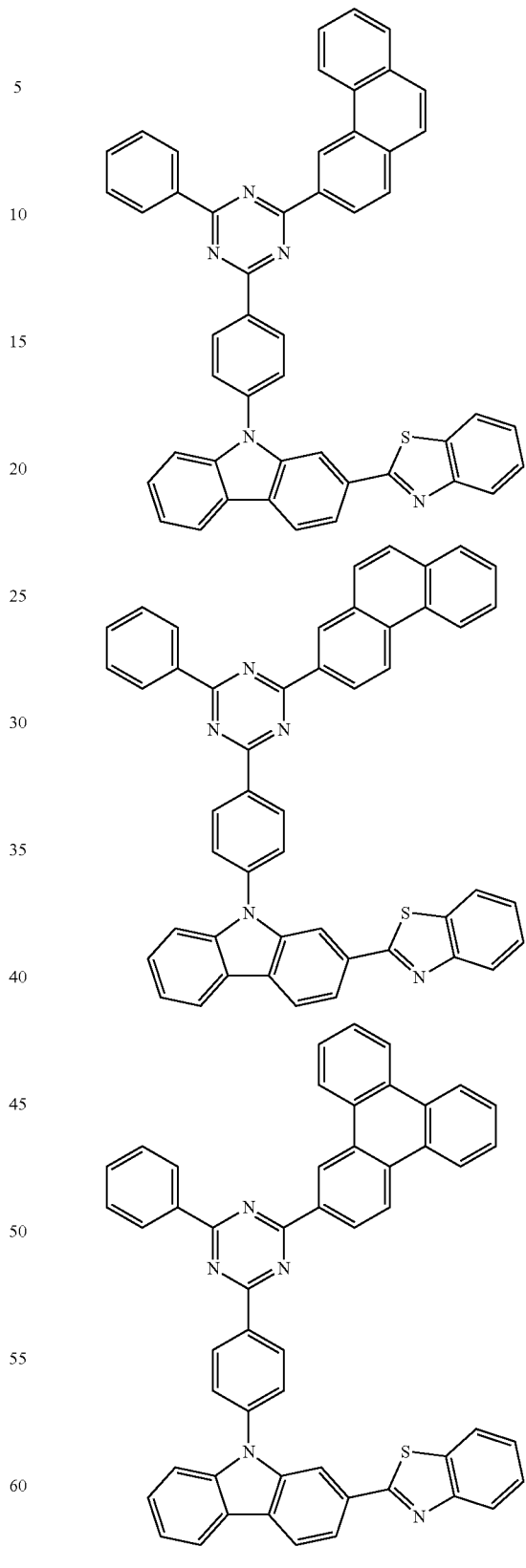

177
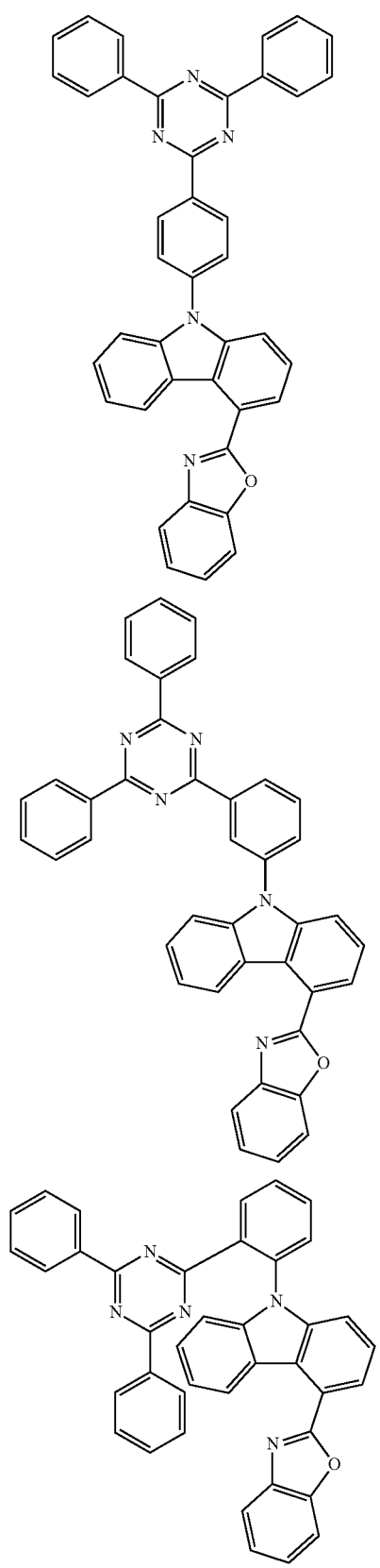
178
-continued

179
-continued
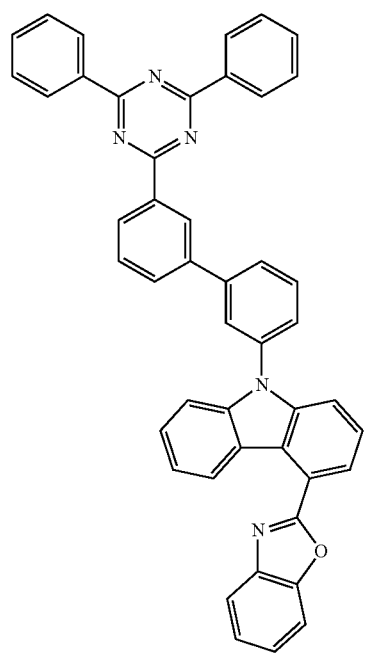
180
-continued
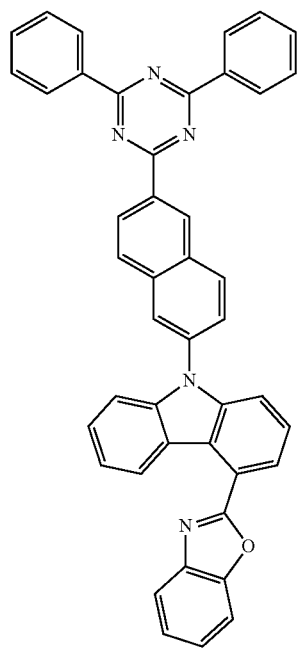
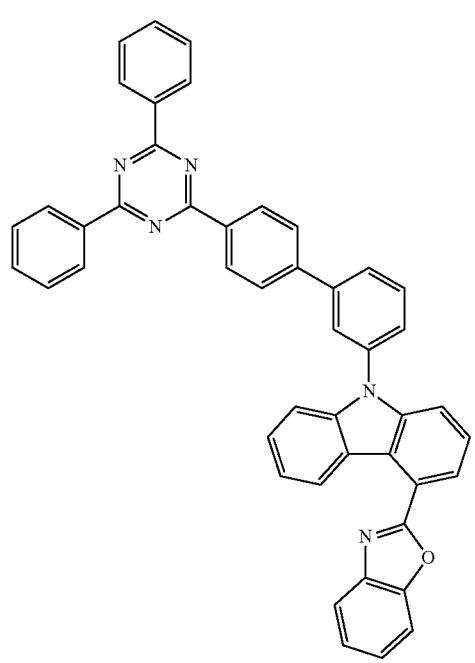
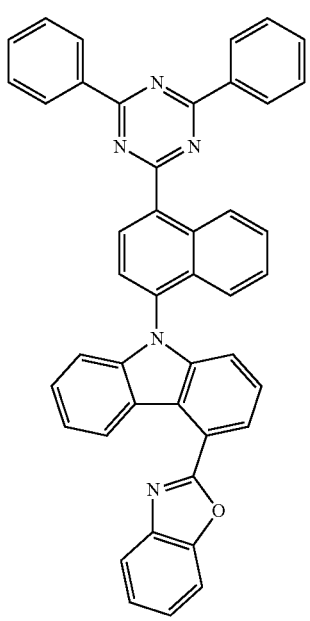

181
-continued
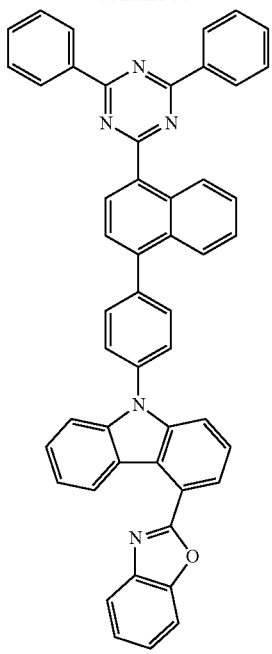
182
-continued
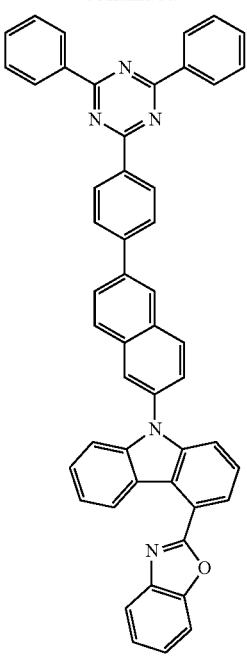
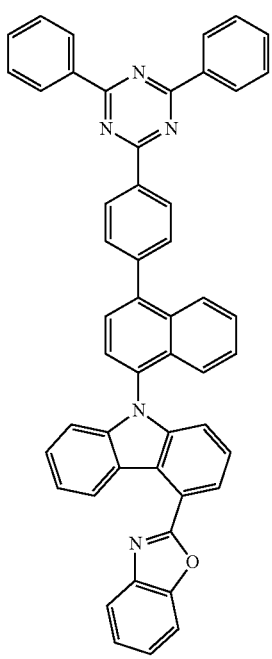
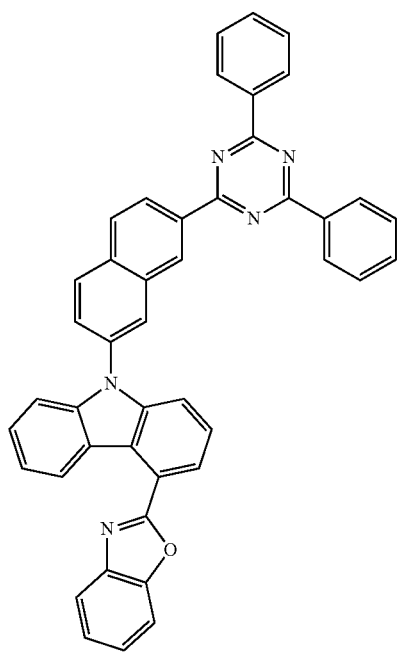

183
-continued
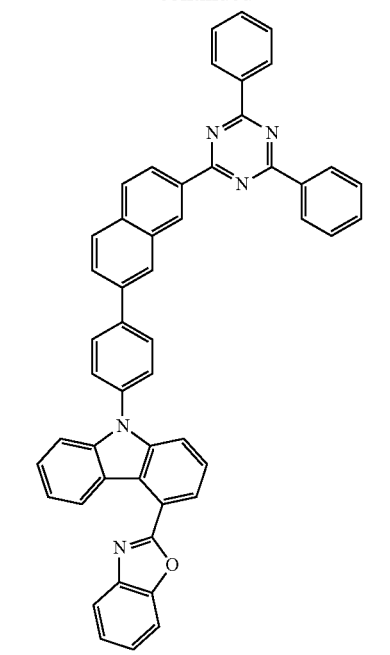
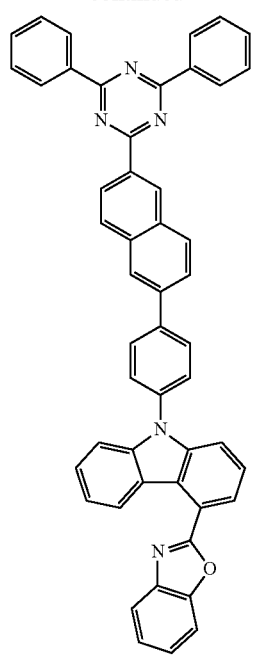 [SMILES: c1ccc(-c2nc(-c3ccccc3)nc(-c3ccc4cc(-c5ccc(-n6c7ccccc7c7c(-c8nc9ccccc9o8)cccc76)cc5)ccc4c3)n2)cc1]
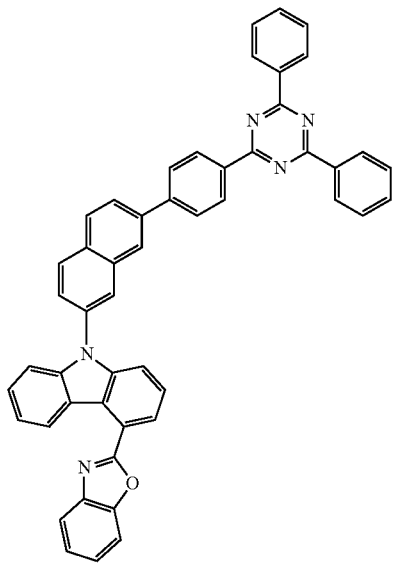
184
-continued
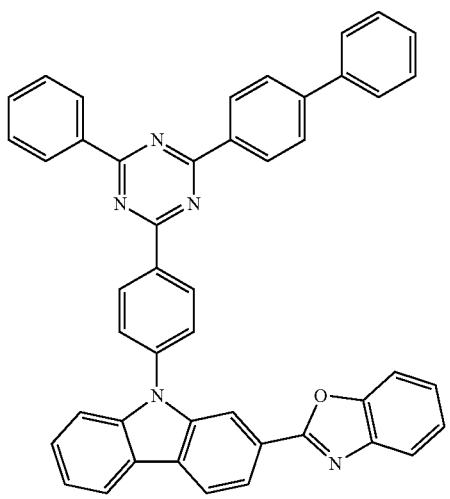
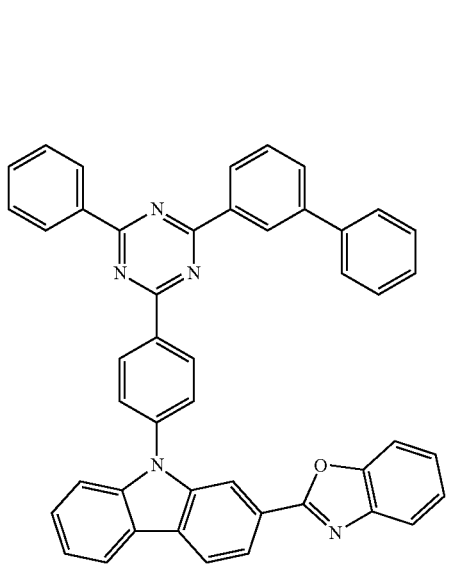

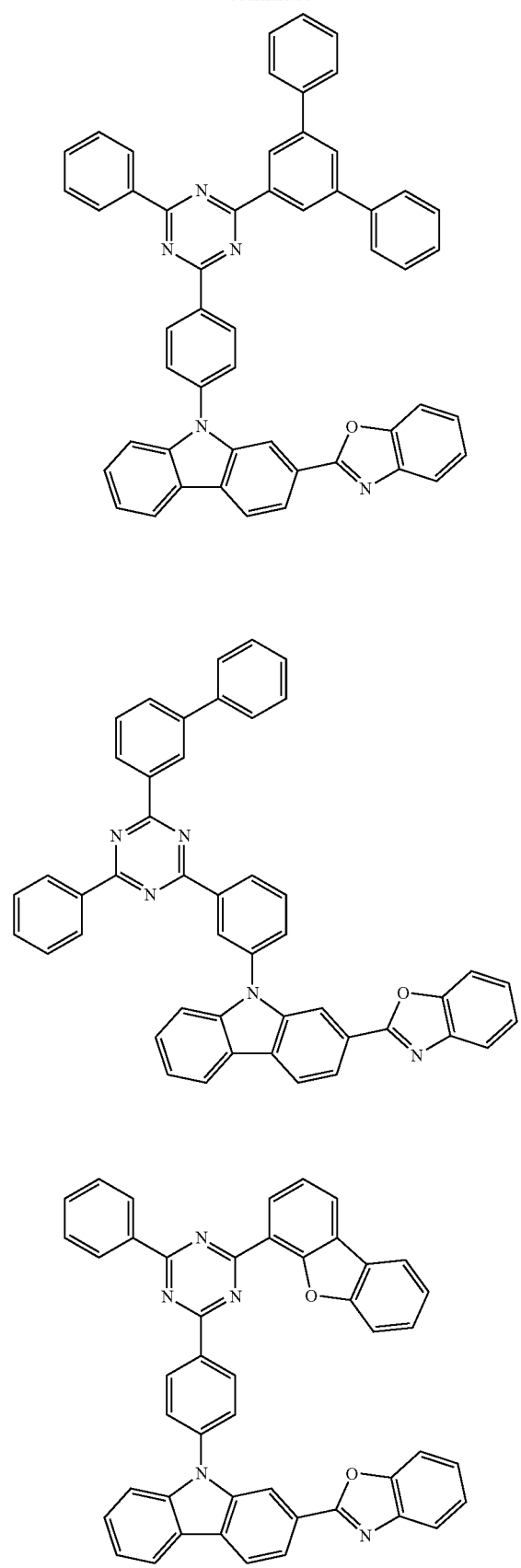
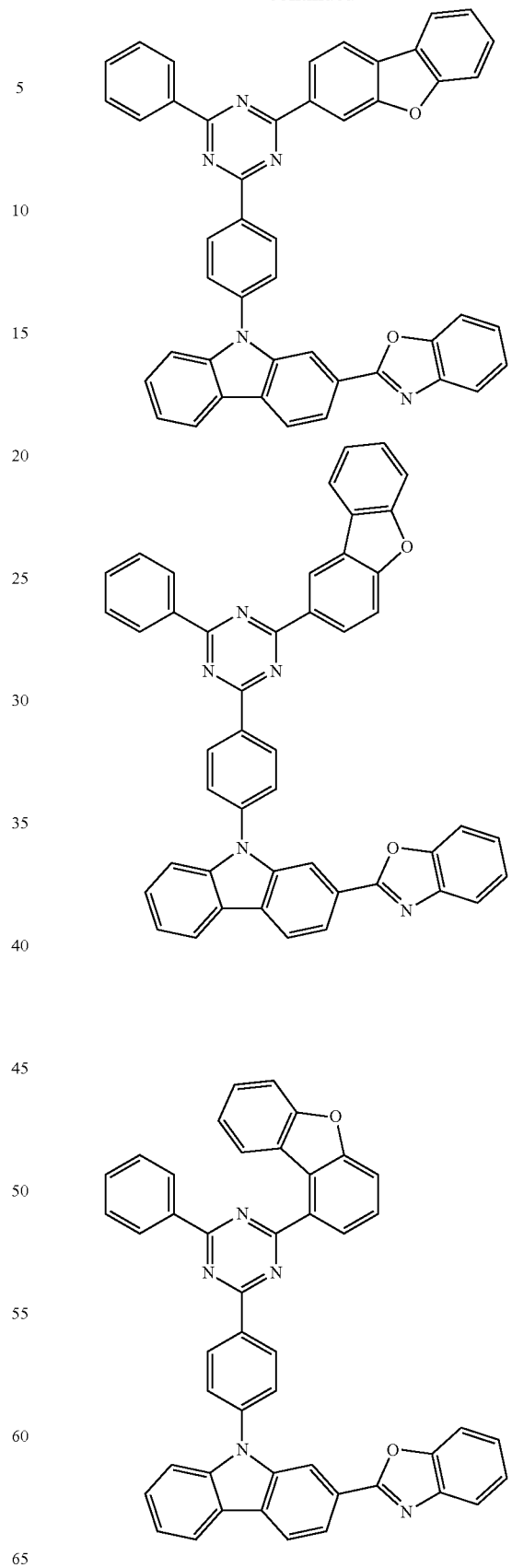

187
-continued
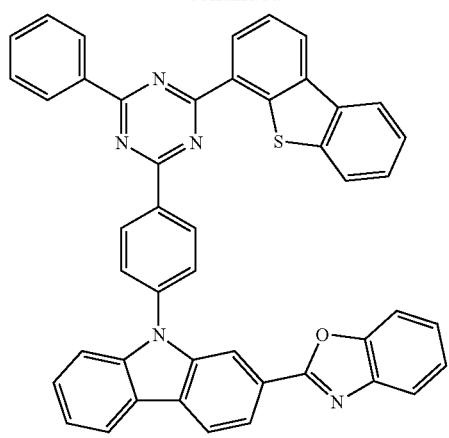
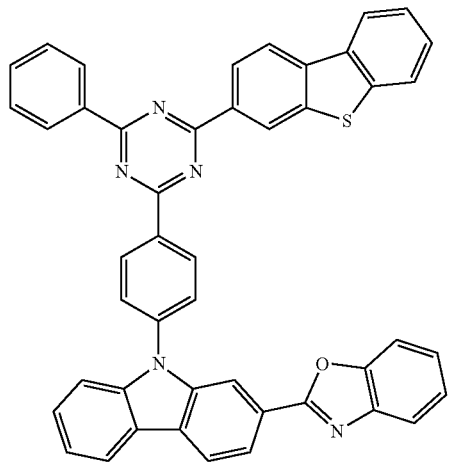
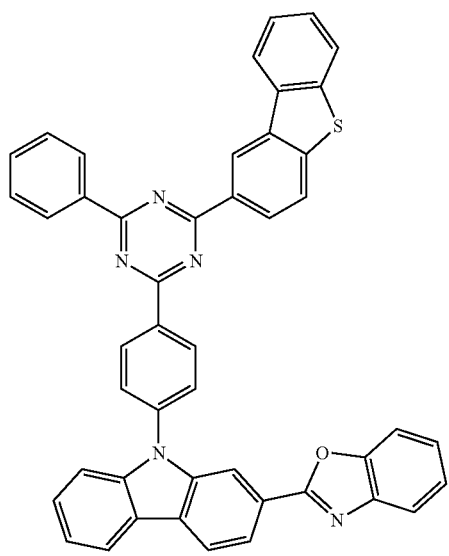
188
-continued
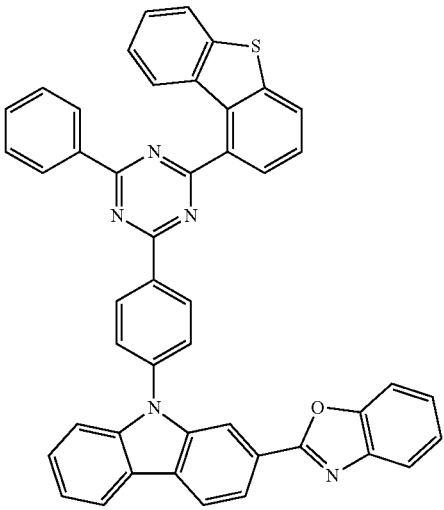
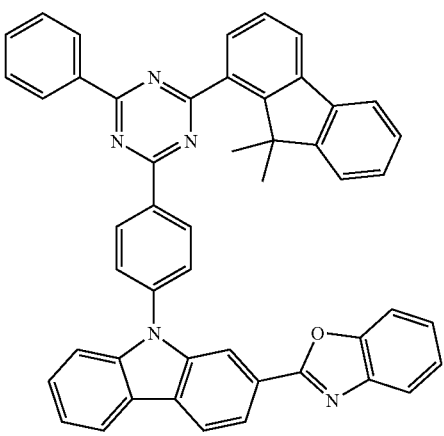
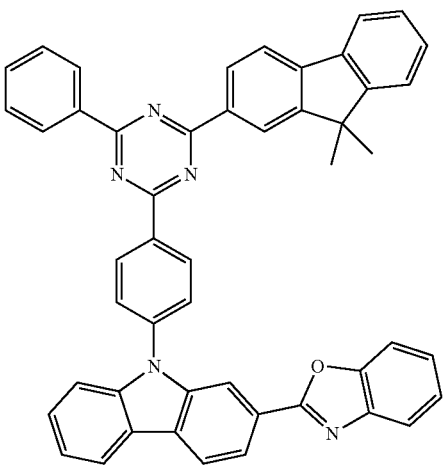

189
-continued
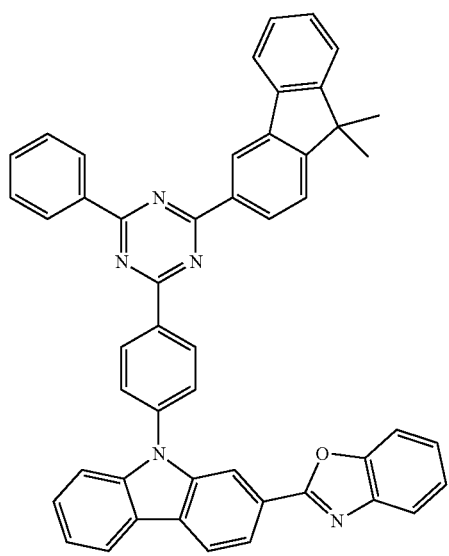
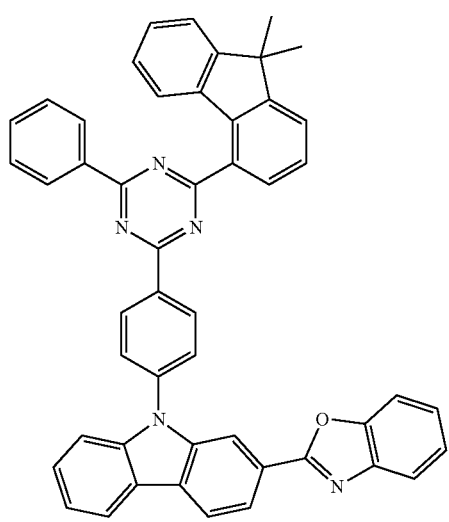
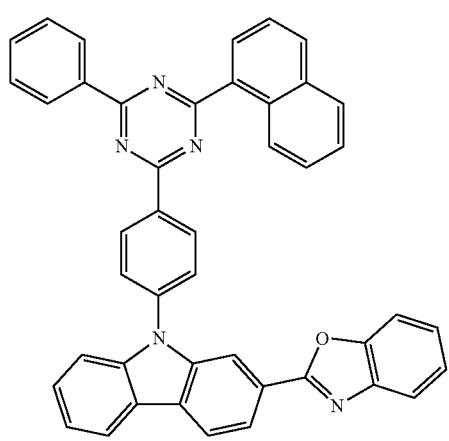
190
-continued
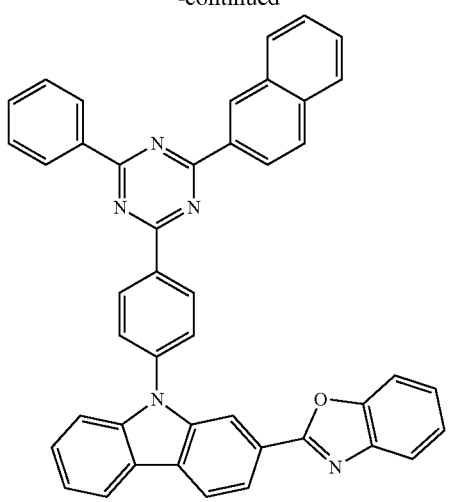
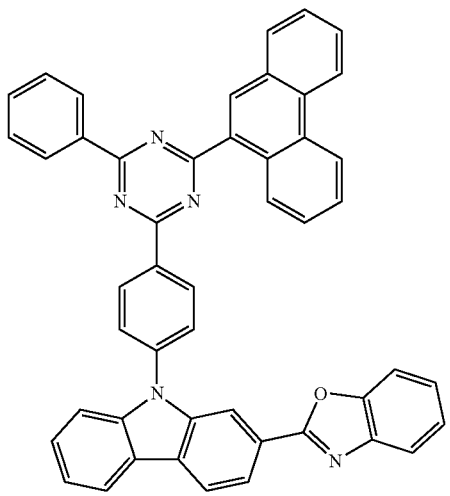
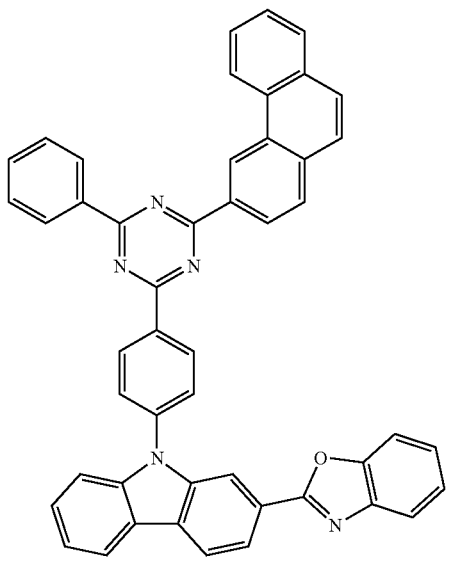

-continued
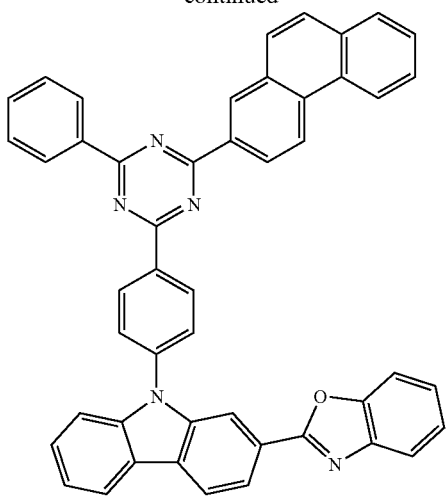
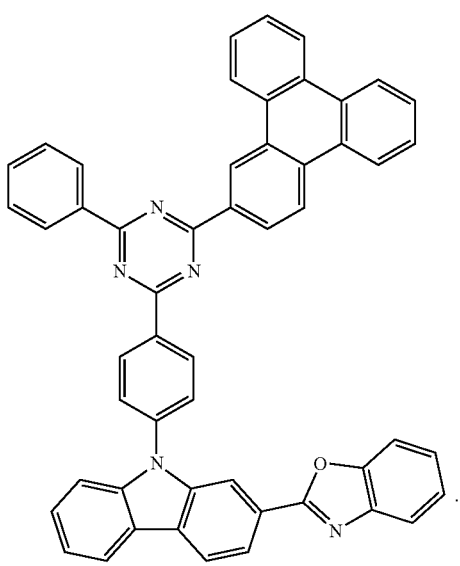 [SMILES: c1ccc(-c2nc(-c3ccc(-n4c5ccccc5c5ccc(-c6nc7ccccc7o6)cc54)cc3)nc(-c3ccc4c5ccccc5c5ccccc5c4c3)n2)cc1]
6. The organic light emitting device of claim 4, wherein the iridium-based dopant is selected from among the following compounds:
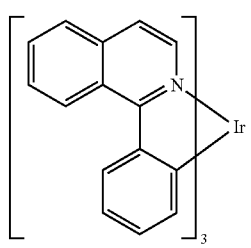
[Ir(piq)₃]
-continued
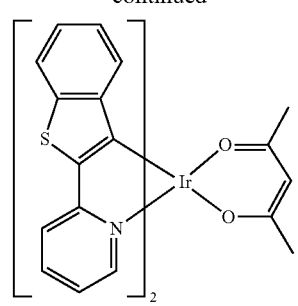
[Btp₂Ir(acac)]
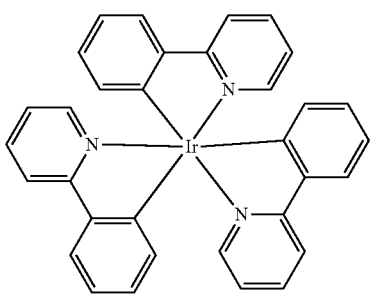
[Ir(ppy)₃]
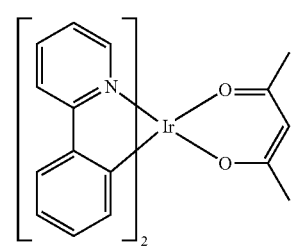
[Ir9ppy)₂(acac)]
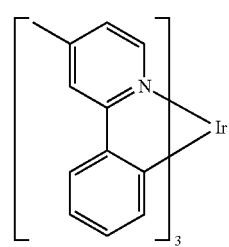
[Ir(mpyp)₃]
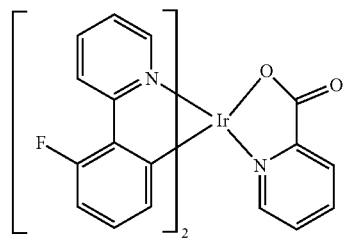
[F₂Irpic]

193
-continued
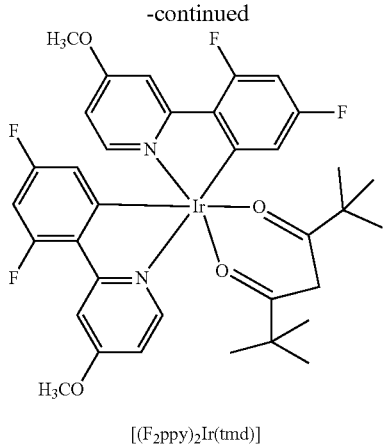
[(F₂ppy)₂Ir(tmd)]
194
-continued
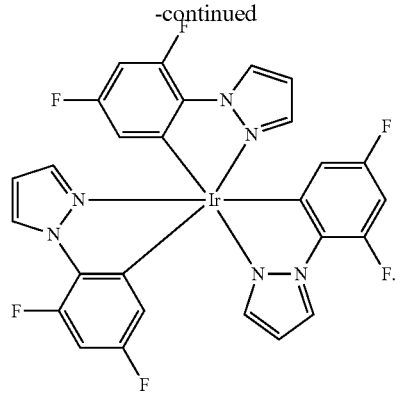
[Ir(dfppz)₃]
* * * * *

UNITED STATES PATENT AND TRADEMARK OFFICE
CERTIFICATE OF CORRECTION

PATENT NO. : 12,209,083 B2
APPLICATION NO. : 17/054687
DATED : January 28, 2025
INVENTOR(S) : Jung et al.

It is certified that error appears in the above-identified patent and that said Letters Patent is hereby corrected as shown below:

In the Claims

In Claim 3, at Column 116, the structure at Lines 20-35 should be deleted.
In Claim 3, at Column 128, the structure at Lines 20-35 should be deleted.
In Claim 5, at Column 177, before Line 1 the following compounds should be inserted:

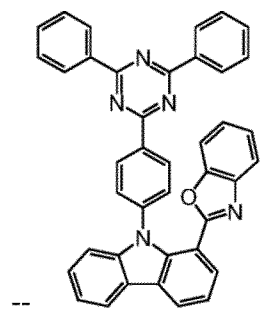 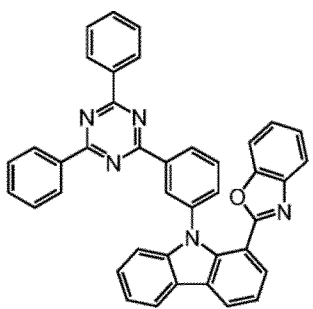 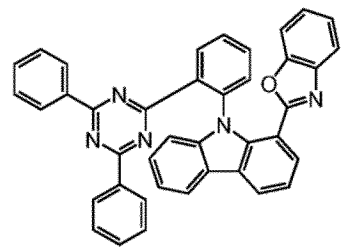

Signed and Sealed this
Fourth Day of March, 2025

Coke Morgan Stewart
*Acting Director of the United States Patent and Trademark Office*

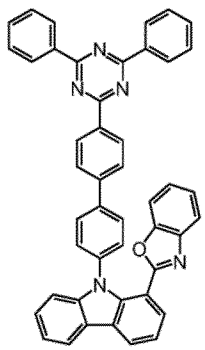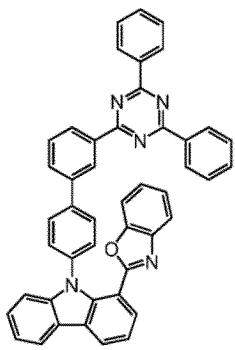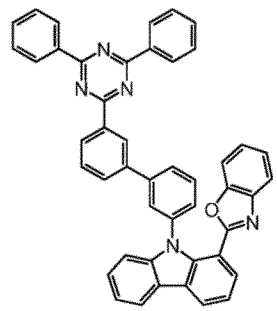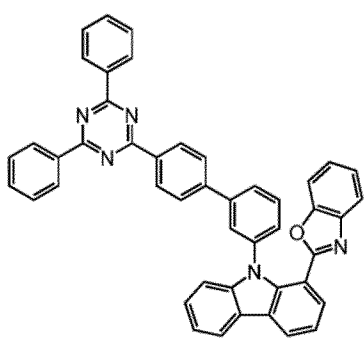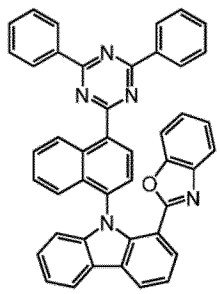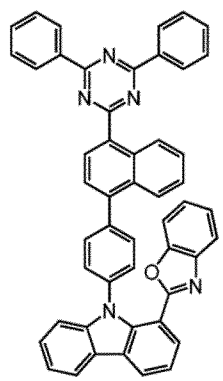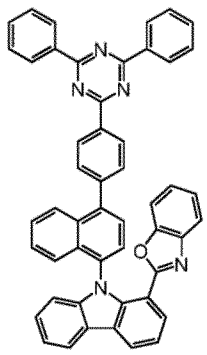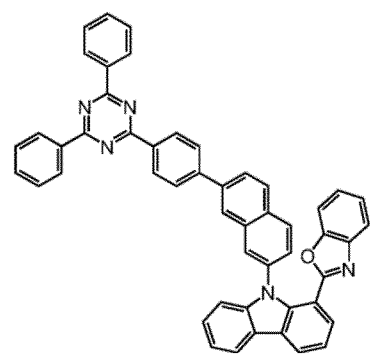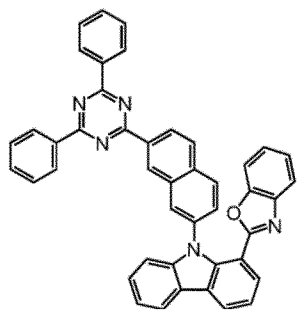

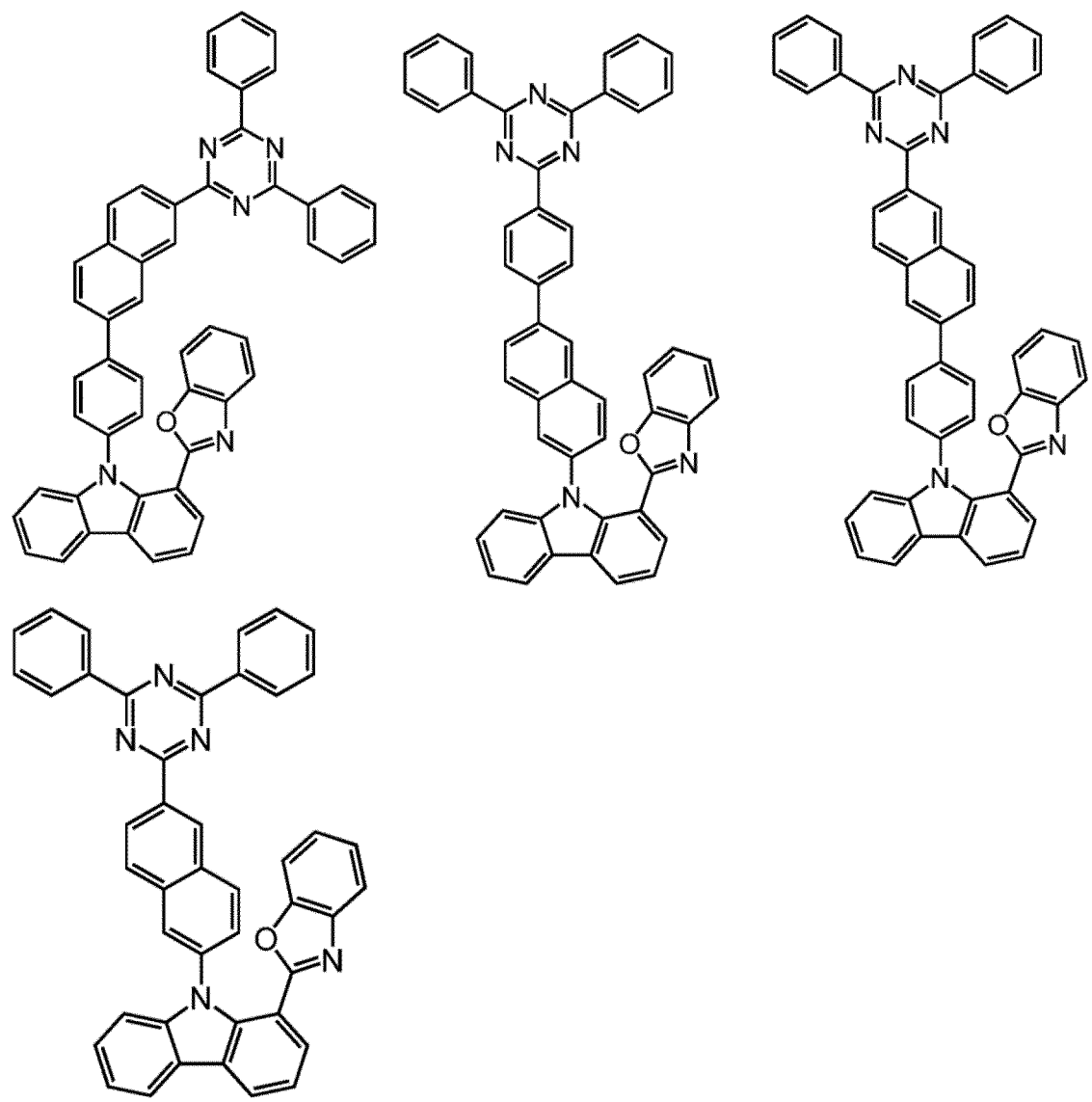

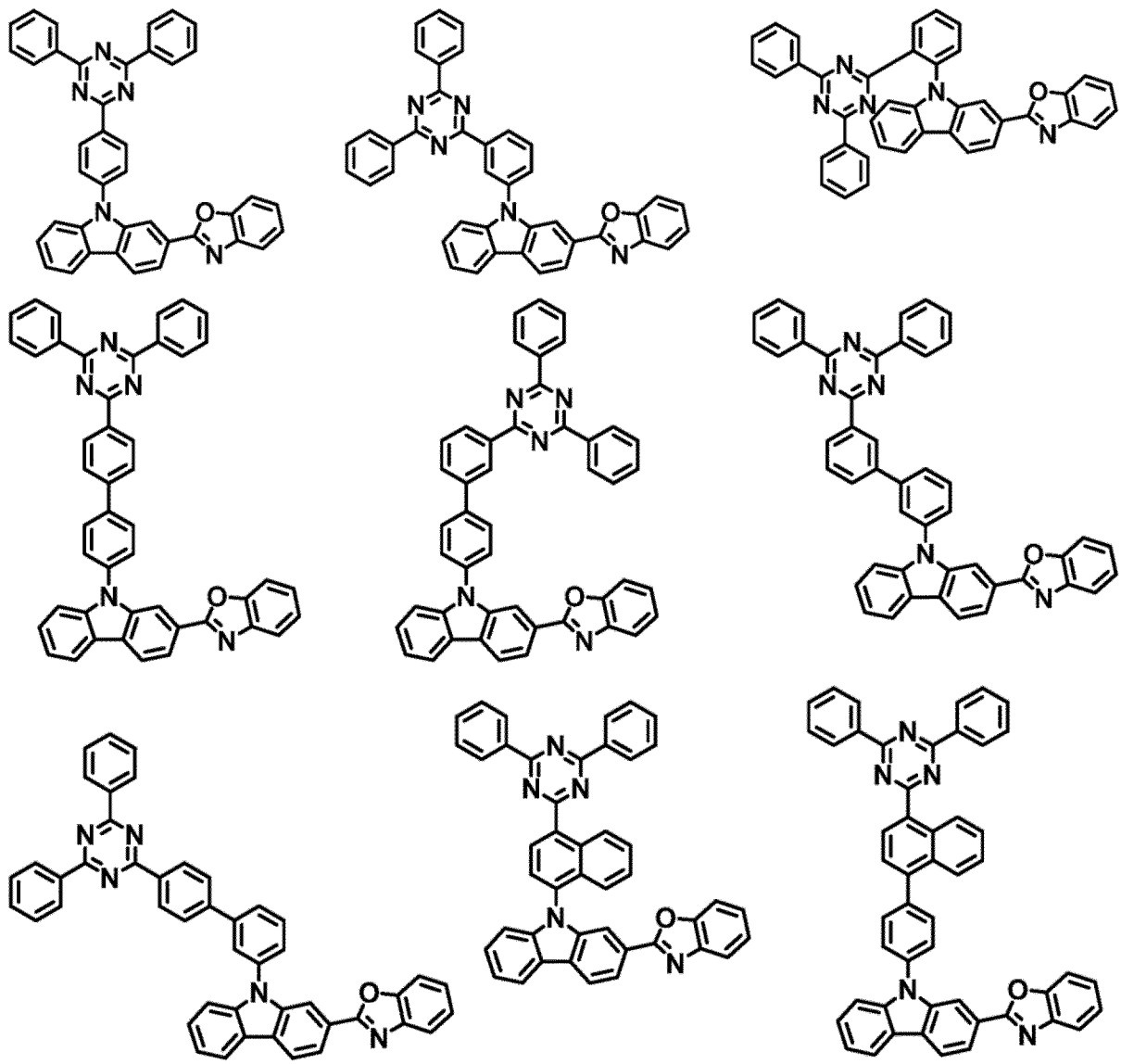

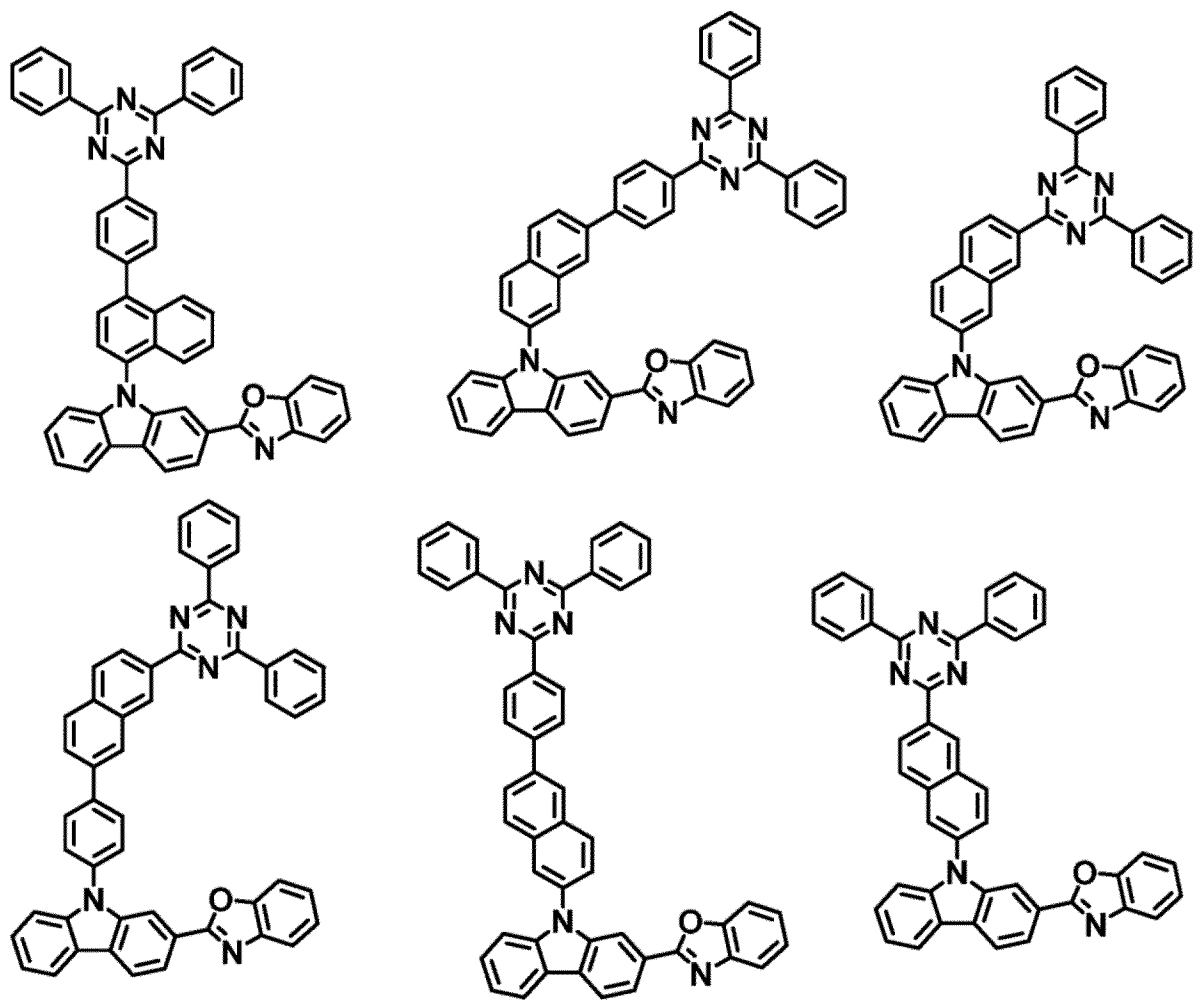

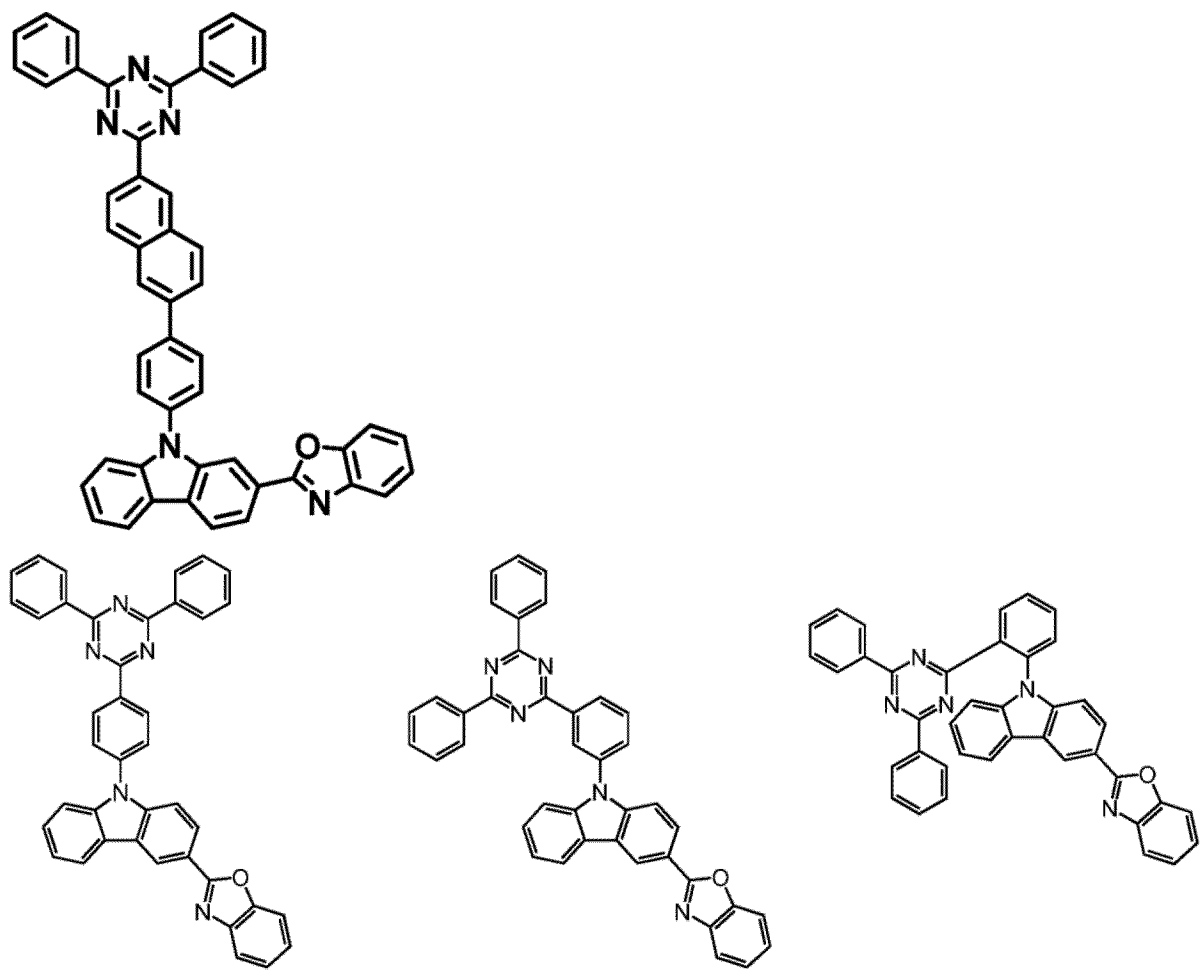

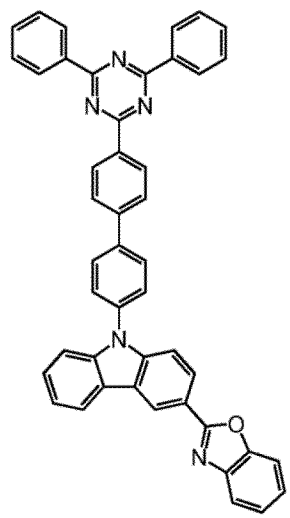 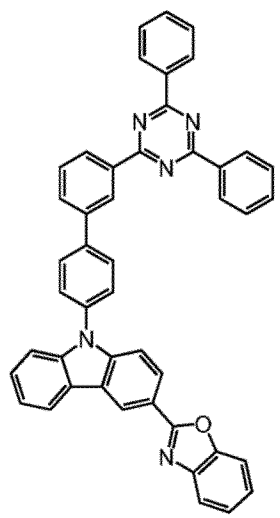 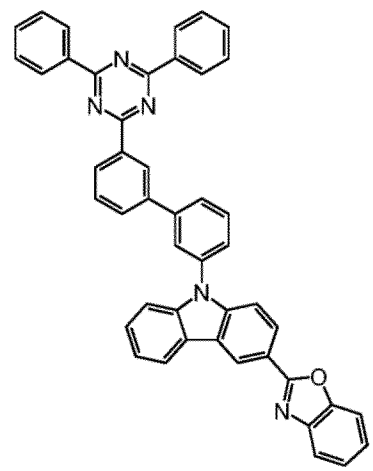
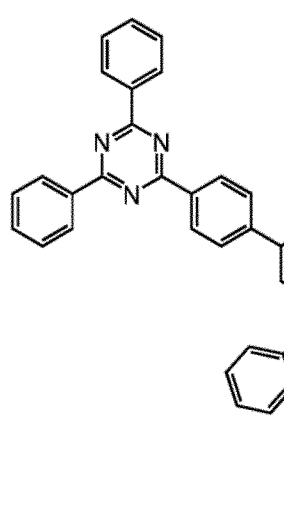 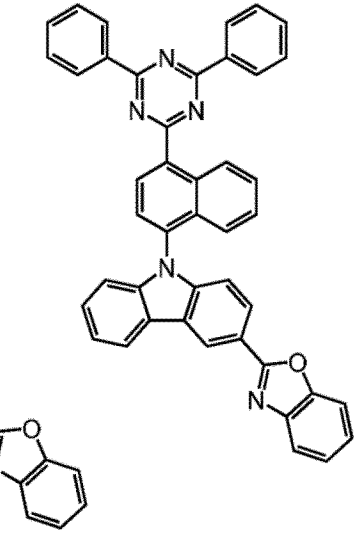 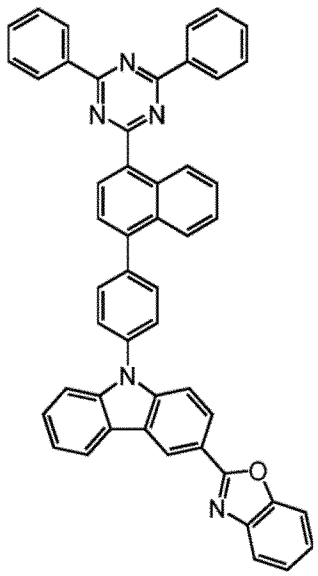

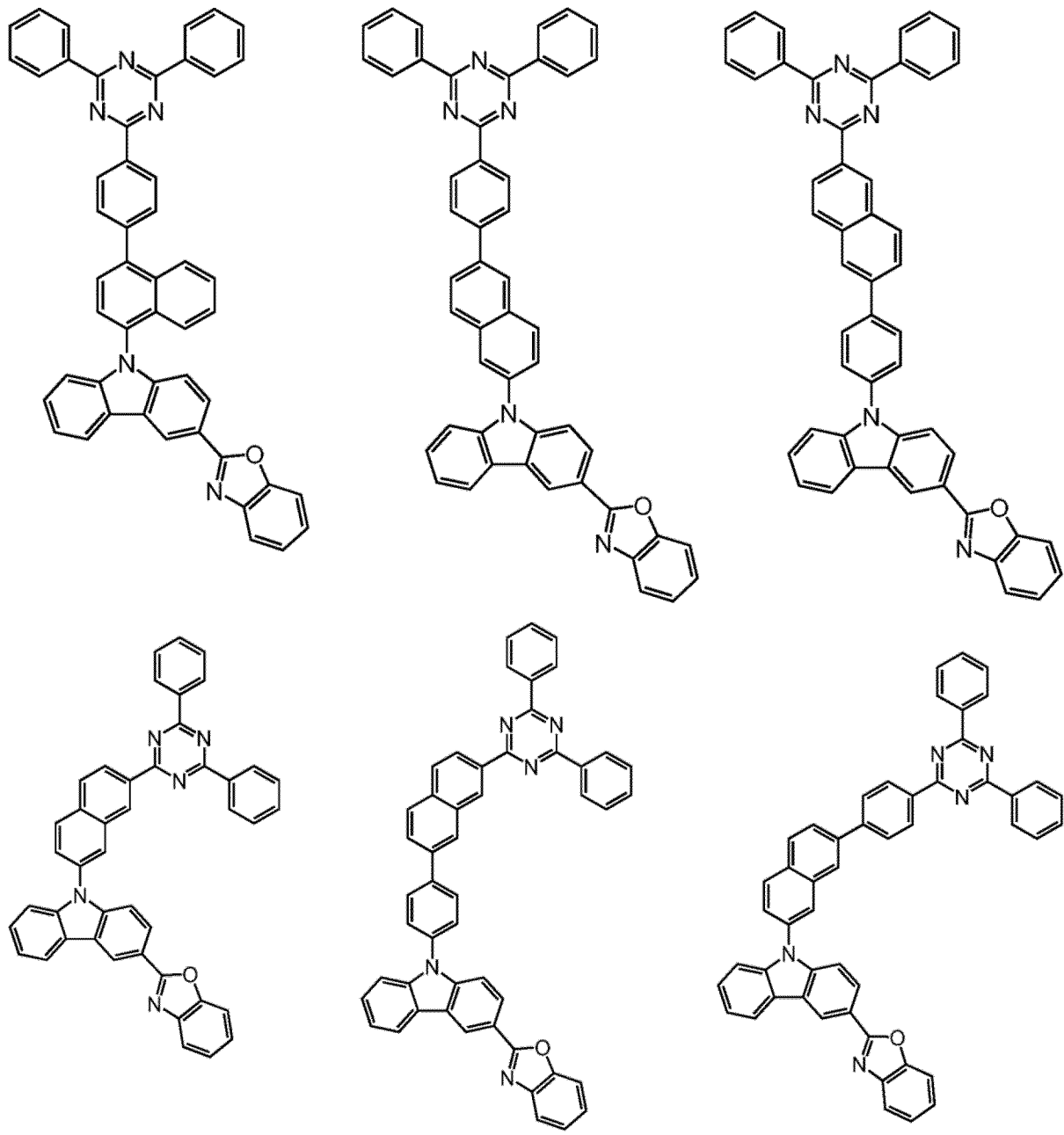

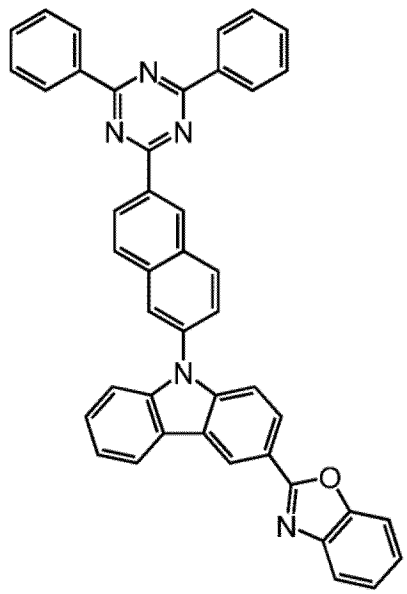
--
In Claim 5, at Column 184, at Line 27 between the first and second compound, the following compounds should be inserted:
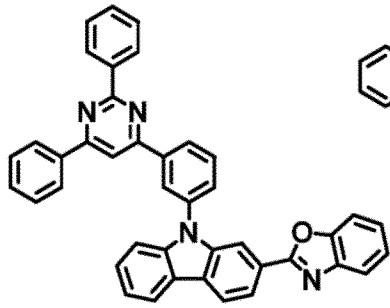 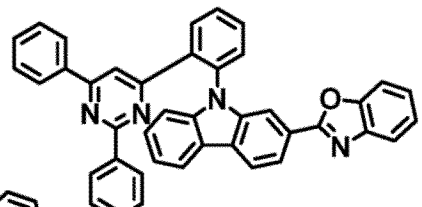 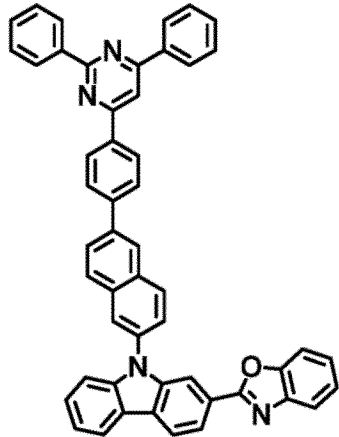
--

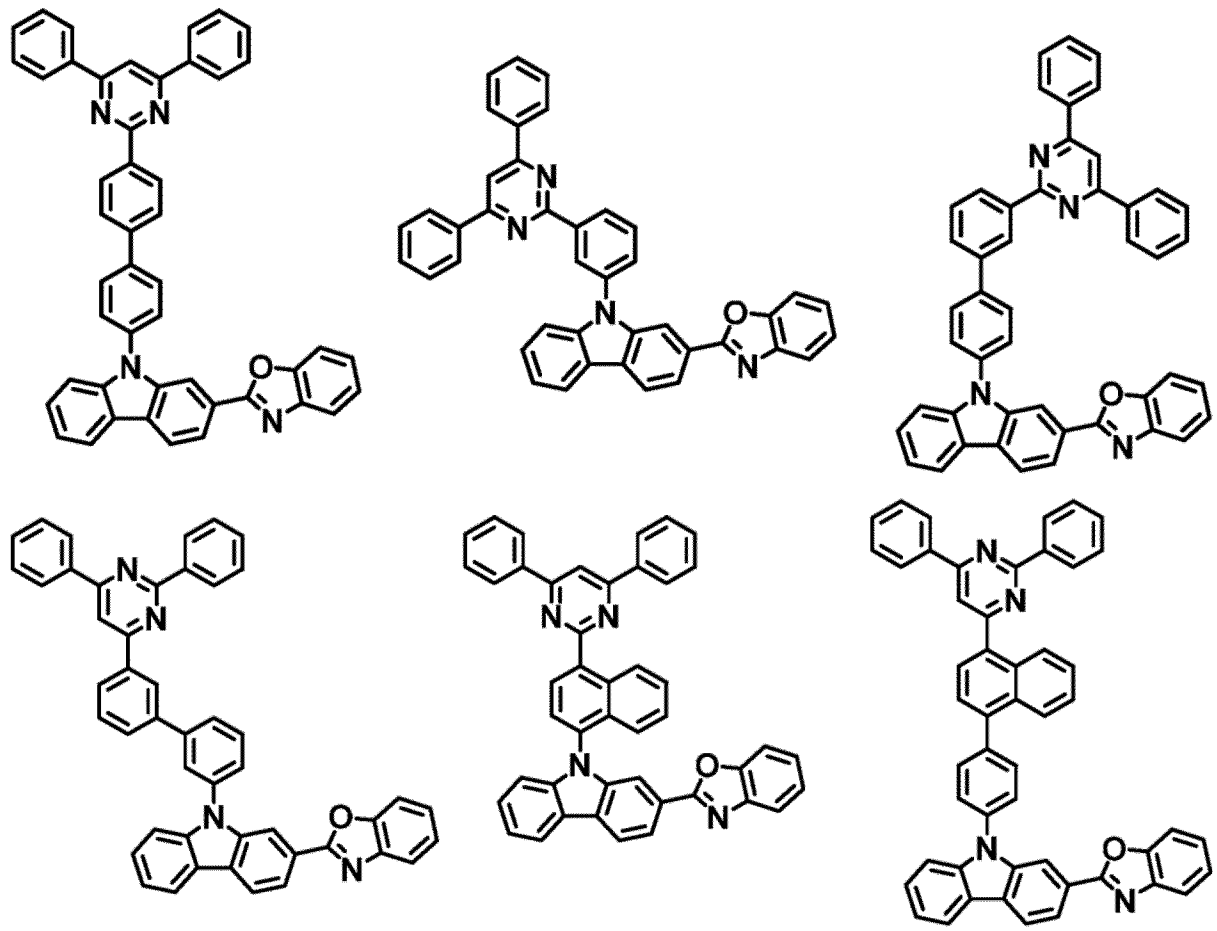

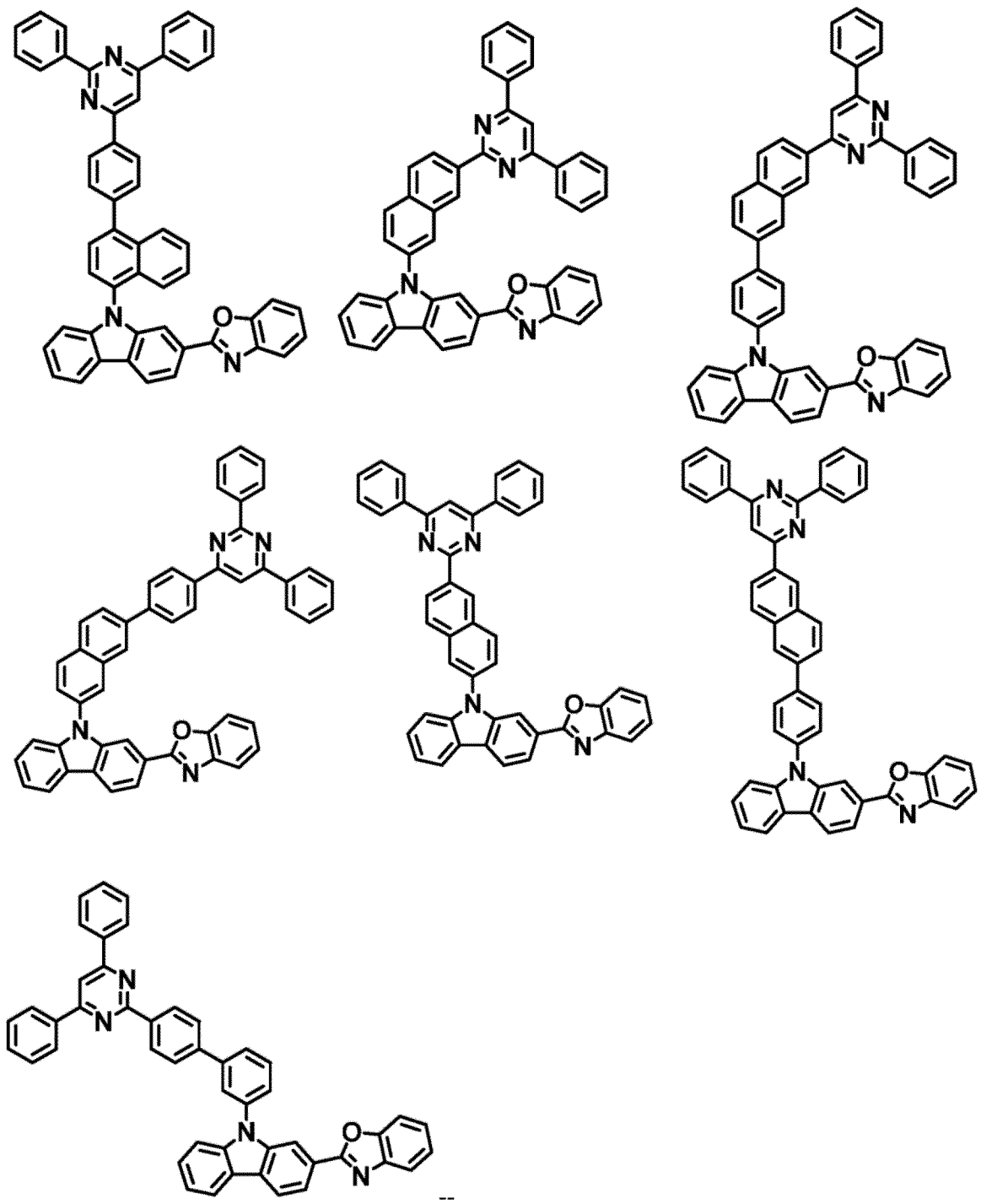
In Claim 6, Column 192, Line 38 should read: -- [Ir(ppy)$_2$(acac)] --